US007351728B2

(12) United States Patent
Brooks et al.

(10) Patent No.: US 7,351,728 B2
(45) Date of Patent: Apr. 1, 2008

(54) OXAZOLYL-ARYLOXYACETIC ACID DERIVATIVES AND THEIR USE AS PPAR AGONISTS

(75) Inventors: Dawn Alisa Brooks, Indianapolis, IN (US); Scott Eugene Conner, Elizabethtown, IN (US); Samuel James Dominianni, Indianapolis, IN (US); Alexander Glenn Godfrey, Mooresville, IN (US); Lynn Stacy Gossett, Indianapolis, IN (US); Christopher John Rito, Martinsville, IN (US); Allie Edward Tripp, Indianapolis, IN (US); Alan M. Warshawsky, Carmel, IN (US); Leonard Larry Winneroski, Jr., Greenwood, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 348 days.

(21) Appl. No.: 11/181,640

(22) Filed: Jul. 14, 2005

(65) Prior Publication Data
US 2005/0250825 A1 Nov. 10, 2005

Related U.S. Application Data

(62) Division of application No. 10/343,474, filed on Jan. 29, 2003, now Pat. No. 6,982,278.

(51) Int. Cl.
*A61K 31/421* (2006.01)
*C07D 263/32* (2006.01)
(52) U.S. Cl. ............... 514/374; 548/215; 548/235; 548/236
(58) Field of Classification Search .......... 548/215, 548/235, 236; 514/374
See application file for complete search history.

(56) References Cited

U.S. PATENT DOCUMENTS

| 5,089,514 A | 2/1992 | Hulin | |
|---|---|---|---|
| 5,232,945 A | 8/1993 | Hulin | |
| 5,306,726 A | 4/1994 | Hulin | |
| 5,902,726 A | 5/1999 | Kliewer et al. | |
| 5,994,554 A | 11/1999 | Kliewer et al. | |
| 6,414,001 B2 * | 7/2002 | Tomiyama et al. | 514/374 |
| 6,417,212 B1 * | 7/2002 | Brooks et al. | 514/374 |
| 6,610,696 B2 * | 8/2003 | Brooks et al. | 514/256 |
| 6,825,222 B2 * | 11/2004 | Brooks et al. | 514/365 |
| 6,930,120 B2 * | 8/2005 | Brooks et al. | 514/374 |
| 6,982,278 B2 * | 1/2006 | Brooks et al. | 514/374 |
| 7,176,224 B2 * | 2/2007 | Ardecky et al. | 514/374 |

FOREIGN PATENT DOCUMENTS

| EP | 0 930 299 A1 | 7/1999 |
|---|---|---|
| GB | 2 359 082 A | 8/2001 |
| WO | WO 97 28115 A1 | 8/1997 |
| WO | WO 97 31907 A1 | 9/1997 |
| WO | WO 99 46232 A1 | 9/1999 |
| WO | WO 01 16120 A1 | 3/2001 |
| WO | WO 02 16331 A1 | 2/2002 |
| WO | WO 02 16332 A1 | 2/2002 |

OTHER PUBLICATIONS

Bright et al (1997): STN International CAPLUS database (Columbus, Ohio), accession No. 1997:555602.*
Sarges, R., et al.: "*Glucose Transport-Enhancing and Hypoglycemic Activity of 2-Methyl-2-Phenoxy-3-Phenylpropanoic Acids*"; Journal of Medicinal Chemistry, vol. 39, No. 24, Nov. 22, 1996, pp. 4783-4803.
Cobb, J. E., et al.: "*N- (2-Benzoylphenyl) -L-Tyrosine PPARGamma Agonists. 3. Structure-Activity Relationship and Optimization of the N-Aryl Substituent*"; Journal of Medicinal Chemistry, vol. 41, No. 25, Dec. 3, 1998, pp. 5055-5069.
Bright, S. W., et. al. : "*Competitive Particle Concentration Fluorescence Immunoassays for Measuring Anti-Diabetic Drug Levels in Mouse Plasma*"; Journal of Immunological Methods, vol. 207, No. 1, Aug. 22, 1997, pp. 23-31.
Brooks, D. , et al. : "*Design and Synthesis of 2-methyl-2-{4-'2-'5-methyl-2-aryloxazol-4-yl) ethoxylphenoxy}propionic acids: A New Class of Dual PPARAlpha/Gamma Agonists*"; Journal of Medicinal Chemistry, vol. 44, No. 13, Jun. 21, 2001, pp. 2061-2064.
Shinkai, H. et al. : "*Isoxazolidine-3, 5-dione and Noncyclic 1,3-dicarbonyl Compounds as Hypoglycemic Agents*"; Journal of Medicinal Chemistry, vol. 41, No. 11, May 21, 1998, pp. 1927-1933.
Murugesan, N., et al. : "*Biphenylsulfonamide Endothelin Receptor Antogonists 2. Discovery of 4'-oxazoly-lbiphenylsulfonamides as a New Class of Poent, Highly Selective ET(A) Antagonists*"; Journal of Medicinal Chemistry, vol. 43, No. 16, Aug. 10, 2000, pp. 3111-3117.
Malamas, M.S., et al. : "*Azole Phenoxy Hydroxyureas as Selective and Orally Active Inhibitors fo 5-Lipoxygenase*"; Journal of Medicinal Chemistry, vol. 39, No. 1, Jan. 5, 1996, pp. 237-245.
Merguro, K., et al. : "*Studies on Antidiabetic Agents. VII. Synthesis and Hypoglycemic Activity fo 4-Oxazoleacetic Acid Derivatives*"; Chemical & Pharmaceutical Bulletin, vol. 34, No. 7, 1986, pp. 2840-2851.
Bright, et al. ; STN International CAPLUS database (Columbus, Ohio) ; accession No. 1997:555602 (1997).

(Continued)

Primary Examiner—Golam M. M. Shameem
(74) Attorney, Agent, or Firm—MaCharri Vorndran-Jones; Soonhee Jang

(57) ABSTRACT

Compounds represented by the following structural formula (I), and pharmaceutically acceptable salts, solvates and hydrates thereof, wherein R1 is an unsubstituted or substituted aryl, heteroaryl, cycloalkyl, aryl-alkyl, heteroarylalkyl or cycloalkyl-alkyl, R2 is H, alkyl or haloalkyl, the polymethylene chain (II), is saturated or may contain a carbon-carbon double bond, while n is 2, 3, 4, W is O or S, Y is an unsubstituted phenylene, naphthylene or 1, 2, 3, 4 tetrahydronaphthylene, R3 is II, alkyl or haloalkyl, R4 is II, alkyl, haloalkyl or a substituted or unsubstituted benzyl, are useful for modulating a peroxisome proliferator activated receptor, particularly in the treatment of diabetes mellitus.

4 Claims, No Drawings

OTHER PUBLICATIONS

Yanping Xu, et al., "Design and Synthesis of α-Aryloxy-α-methylhydrocinnamic Acids: A Novel Class of Dual Peroxisome Proliferator-Activated Receptor α/m Agonists," J. Med. Chem, 47, pp. 2422-2425 (2004).

* cited by examiner

OXAZOLYL-ARYLOXYACETIC ACID DERIVATIVES AND THEIR USE AS PPAR AGONISTS

This application is a divisional application of U.S. patent application Ser. No. 10/343,474, filed Jan. 29, 2003 now U.S. Pat. No. 6,982,278 which claims the benefit of U.S. Provisional Application No. 60/227,233, filed Aug. 23, 2000, the entire teachings of which are incorporated herein by reference.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include PPARα, PPARγ and PPARδ.

The PPARα receptor subtypes are reported to be activated by medium and long-chain fatty acids. They are involved in stimulating beta-oxidation of fatty acids and with the activity of fibrates which reportedly produce a substantial reduction in plasma triglycerides and moderate reduction in low density lipoprotein (LDL) cholesterol. The PPARγ receptor subtypes are reportedly involved in activating the program of adipocyte differentiation and are not involved in stimulating peroxisome proliferation in the liver.

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL which are risk factors in cardiovascular diseases. The constellation of symptoms which includes hyperinsulemia combined with hypertension, elevated body weight, elevated triglycerides and elevated LDL is known as Syndrome X.

Current treatment for diabetes mellitus generally first involves treatment with diet and exercise. However, compliance can be poor and as the disease progresses treatment with hypoglycemics, typically sulfonylureas, is often necessary. Sulfonylureas stimulate the β cells of the liver to secrete more insulin. However, the response of the β cells eventually fails and treatment with insulin injection is necessary. In addition, both sulfonylurea treatment and insulin injection have the life threatening side effect of hypoglycemic coma. Therefore, patients using these treatments must carefully control dosage.

Thiazolidinediones are a class of compounds which have been shown to increase the sensitivity of insulin sensitive cells. Increasing insulin sensitivity rather than the amount of insulin in the blood reduces the likelihood of hypoglycemic coma. Thiazolidinediones have been shown to increase insulin sensitivity by binding to PPARγ receptors. However, side effects associated with treatment with thiazolidinediones include weight gain, and, for troglitazone, liver toxicity.

PPARα and PPARγ receptors have been implicated in diabetes mellitus, cardiovascular disease, obesity, and gastrointestinal disease, such as, inflammatory bowel disease. There exists a need for new pharmaceutical agents which modulate these receptors to prevent, treat and/or alleviate these diseases or conditions while ameliorating side effects of current treatments.

SUMMARY OF THE INVENTION

The present invention is directed to compounds represented by Structural Formula I and pharmaceutically acceptable salts, solvates and hydrates thereof:

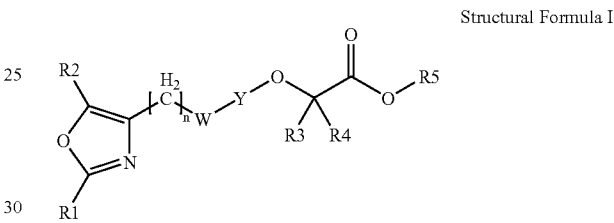

Structural Formula I

In Structural Formula I, R1 is an unsubstituted or substituted group selected from aryl, heteroaryl, cycloalkyl, aryl-C1-C4 alkyl, heteroaryl-C1-C4 alkyl or cycloalkyl-C1-C4 alkyl. R2 is H, C1-C4 alkyl or C1-C4 haloalkyl. The polymethylene chain,

is saturated or may contain a carbon-carbon double bond, while n is 2, 3, or 4. W is O or S. Y is an unsubstituted or substituted group selected from phenylene, naphthylene or 1,2,3,4 tetrahydronaphthylene. R3 is H, C1-C6 alkyl or C1-C6 haloalkyl. R4 is H, C1-C10 alkyl, C1-C10 haloalkyl, or a substituted or unsubstituted benzyl. However, when R3 and R4 are H, R2 is C1-C4 alkyl or C1-C4 haloalkyl. R5 is H, C1-C4 alkyl or aminoalkyl.

In one embodiment, the present invention also relates to pharmaceutical compositions which comprising at least one compound of the present invention, or a pharmaceutically acceptable salt, solvate, hydrate or prodrug thereof, and a pharmaceutically acceptable carrier.

In another embodiment, the present invention relates to a method of modulating a peroxisome proliferator activated receptor by contacting the receptor with at least one compound represented by Structural Formula I, and pharmaceutically acceptable salts, solvates and hydrates thereof In a further embodiment, the present invention relates to a method of making a compound represented by Structural Formula I.

The compounds of the present invention and pharmaceutically acceptable salts, solvates and hydrates thereof are believed to be effective in treating Syndrome X, Type II diabetes, hyperglycemia, hyperlipidemia, obesity, coagaulopathy, hypertension, atherosclerosis, and other disorders related to Syndrome X and cardiovascular diseases because they lower one or more of the following in mammals: glucose, insulin, triglycerides, fatty acids and/or cholesterol. In addition, the compounds exhibit fewer side effects than compounds currently used to treat these conditions.

DETAILED DESCRIPTION OF THE INVENTION

The terms used to describe the instant invention have the following meanings herein.

As used herein, alkyl groups include straight chained or branched C1-C6 hydrocarbons, which are saturated or unsaturated.

Cycloalkyl groups, as used herein, include C3-C8 hydrocarbons, which are partially or completely saturated.

As used herein, aryl groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl).

Heteroaryl groups, as used herein, is an aromatic ring system having at least one heteroatom such as nitrogen, sulfur or oxygen. Heteroaryl groups include thienyl (also referred to herein as "thiophenyl"), pyridyl, pyrrolyl, benzofuranyl, isoxazolyl, and pyrimidinyl.

An aryl-C1-C4-alkyl group, as used herein, is an aryl substituent that is linked to a compound by a saturated or unsaturated alkyl group having from one to four carbon atoms.

A heteroaryl-C1-C4-alkyl group, as used herein, is a heteroaryl substituent that is linked to a compound by a saturated or unsaturated alkyl group having from one to four carbon atoms.

A cycloalkyl-C1-C4-alkyl group, as used herein, is a cycloalkyl substituent that is linked to a compound by a saturated or unsaturated alkyl group having from one to four carbon atoms.

An aminoalkyl group is an alkyl group having from one to six carbon atoms which is substituted with at least one amine represented by —NR12R12 in which each R12 are, independently, a C1-C6 alkyl or both R12 taken together with the nitrogen to which they are attached form a five or six membered heterocycloalkyl.

A heterocycloalkyl is a non-aromatic ring which contains one or more oxygen, nitrogen or sulfer (e.g., morpholine, piperidine, piperazine, pyrrolidine, and thiomorpholine). The preferred heterocycloalkyl group is morpholine.

Substituents for aryl, heteroaryl and cycloalkyl groups include halo, hydroxy, carboxy, saturated or unsaturated C1-C4 alkyl, C1-C4 alkoxy, C1-C4 haloalkyl, C1-C4 haloalkoxy, cyano, carbamoyl, dioxaborolan-2-yl, benzoyl, or a substituted or unsubstituted group selected from aryl-C1-C4-alkyl, aryloxy, cycloalkyl, cycloalkyloxy or heterocyclo-oxy. Substituents for heteroaryl groups further include biphenyl. Preferred substituents for aryl are independently selected from CF$_3$, carboxy, saturated or unsaturated C1-C4 alkyl, C1-C4 alkoxy, C1-C4 haloalkyl, C1-C4 haloalkoxy, cyano, carbamoyl, dioxaborolan-2-yl, benzoyl, or a substituted or unsubstituted group selected from aryl-C1-C4-alkyl, aryloxy, cycloalkyl, cycloalkyloxy or heterocyclo-oxy.

Substituents for the phenylene, naphthylene or 1,2,3,4 tetrahydronaphthylene groups include halo, C1-C6 alkyl, C1-C6 alkoxy, C1-C6 haloalkyl, C1-C6 haloalkoxy, cycloalkyl-C1-C4 alkyl, or aryl-C1-C4 alkyl.

Preferably, the compounds of the present invention, and with their respective pharmaceutical composiions, have a structure represented by Structural Formula II:

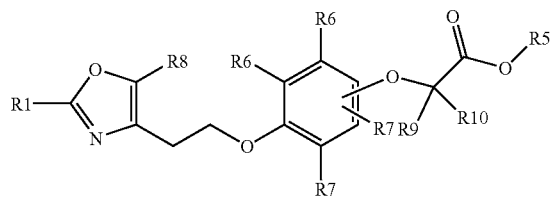

Structural Formula II and IIa

Structural Formula IIa:

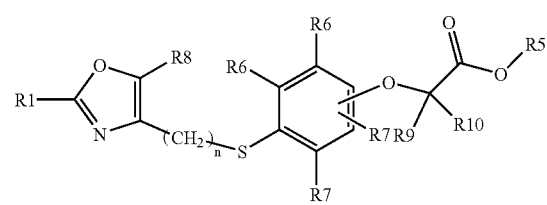

In Structural Formula II and IIa, R1 and R5 are as defined for Structural Formula I. R6 are each, independently, H, halo, C1-C6 alkyl, C1-C6 alkoxy, C1-C6 haloalkyl, C1-C6 haloalkoxy, cycloalkyl, cycloalkyl-C1-C4 alkyl, aryl-C1-C4 alkyl, or together with the phenyl to which they are bound form naphthyl or 1,2,3,4-tetrahydronaphthy. R7 are each, independently, H, halo, C1-C6 alkyl, C1-C6 alkoxy, C1-C6 haloalkyl, C1-C6 haloalkoxy, cycloalkyl-C1-C4 alkyl, or aryl-C1-C4 alkyl or C1-C6alkoxybenzyl, C1-C6alkoxyaryl or a group of the formula

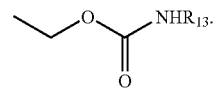

R8 is C1-C4 alkyl or C1-C4 haloalkyl. R9 is C1-C6 alkyl or C1-C6 haloalkyl. R10 is C1-C10 alkyl, C1-C10 haloalkyl, or a substituted or unsubstituted benzyl. R13 is selected from the group consisting of benzyl, substituted benzyl, C1-C6 cycloalkyl, C1-C6 alkyl.

Substituents for benzyl include, for example, C1-C4 alkyl, C1-C4 alkyloxy, C1-C4 haloalkyl, C1-C4 haloalkoxy or phenyl.

Examples of compounds having Structural Formula II include, for instance, the compounds described in Examples 1-2, 6-7, 9-32, 37-39HH and Examples 45, 46, 48-63. Examples of compounds having structural Formula IIa include, for instance, the compounds described in Examples 40, 41, 42, 43, 44 and 47.

More preferably, the compounds of the present invention, and with their respective pharmaceutical compositions, have a structure represented by Structural Formula III:

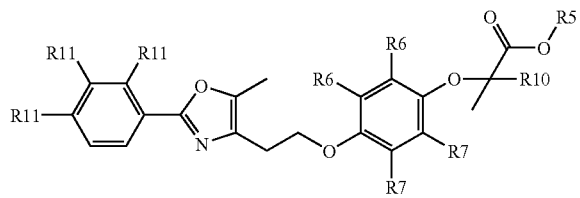

Structural Formula III

In Structural Formula III, R5, R6, R7 and R10 are as defined for Structural Formulas I and II while R11 is halo, hydroxy, carboxy, saturated or unsaturated C1-C4 alkyl, C1-C4 alkoxy, C1-C4 haloalkyl, C1-C4 haloalkoxy, cyano, carbamoyl, dioxaborolan-2-yl, benzoyl, or a substituted or unsubstituted group selected from aryl-C1-C4-alkyl, aryloxy, cycloalkyl, cycloalkyloxy or heterocyclo-oxy.

In another preferred embodiment, the compounds of the present invention, and with their respective pharmaceutical compositions, have a structure represented by Structural Formula IV:

Structural Formal IV

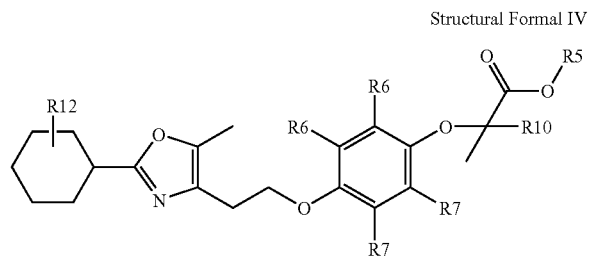

In Structural Formula IV, R5, R6, R7 and R10 are as defined for Structural Formulas I and II while R12, which is a substituent at the 1, 2, 3 or 4 carbon position of the cyclohexyl, is H, aryl or C1-C4 alkyl.

The compounds of Structural Formula I may contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may exist in more than one crystal form. Polymorphs of compounds represented by Structural Formula I form part of this invention and may be prepared by crystallization of a compound of Structural Formula I under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of Structural Formula I followed by gradual or fast cooling. The presence of polymorphs may be determined by solid probe nmr spectroscopy, ir spectroscopy, differential scanning calorimetry, powder X-ray diffraction or such other techniques.

Certain compounds of Structural Formula I and their salts may exist in more than one crystal form and the present invention includes each crystal form and mixtures thereof.

Certain compounds of Structural Formula I and their salts may also exist in the form of solvates, for example hydrates, and the present invention includes each solvate and mixtures thereof.

"Pharmaceutically-acceptable salt" refers to salts of the compounds of the Structural Formula I which are substantially non-toxic to mammals. Typical pharmaceutically-acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

By virtue of its acidic moiety, a compound of Structural Formula I forms salts with pharmaceutically acceptable bases. Some examples of base addition salts include metal salts such as aluminum; alkali metal salts such as lithium, sodium or potassium; and alkaline earth metal salts such as calcium, magnesium, ammonium, or substituted ammonium salts. Examples of substituted ammonium salts include, for instance, those with lower alkylamines such as trimethylamine, triethylamine; hydroxyalkylamines such as 2-hydroxyethylamine, bis-(2-hydroxyethyl)-amine or tri-(2-hydroxyethyl)-amine, cycloalkylamines such as bicyclohexylamine or dibenzylpiperidine, N-benzyl-β-phenethylamine, dehydroabietylamine, N,N'-bisdehydro-abietylamine, glucamine, N-methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of Structural Formula I, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)- tartrates or mixtures thereof including racemic mixtures], succinates, benzoates and salts with amino acids such as glutamic acid.

These salts may be prepared by methods known to those skilled in the art.

Certain compounds of Structural Formula I and their salts may also exist in the form of solvates, for example hydrates, and the present invention includes each solvate and mixtures thereof.

Prodrugs are compounds of the present invention, which have chemically or metabolically cleavable groups and become by solvolysis or under physiological conditions the compounds of the invention which are pharmaceutically active in vivo. Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl) oxy)alkyl esters. Particularly preferred esters as prodrugs are methyl, ethyl, propyl, isopropyl, n-butyl, isobutyl, tert-butyl, morpholinoethyl, and N,N-diethylglycolamido.

Methyl ester prodrugs may be prepared by reaction of the acid form of a compound of Formula I in a medium such as methanol with an acid or base esterification catalyst (e.g., NaOH, $H_2SO_4$). Ethyl ester prodrugs are prepared in similar fashion using ethanol in place of methanol. Morpholinylethyl ester prodrugs may be prepared by reaction of the sodium salt of a compound of Structural Formula I (in a medium such as dimethylformamide) 4-(2-chloroethyl)morphine hydrochloride (available from Aldrich Chemical Co., Milwaukee, Wis. USA, Item No. C4,220-3).

The term, "active ingredient" means the compounds generically described by Structural Formula I as well as the salts, solvates, and prodrugs of such compounds.

The term "pharmaceutically acceptable" means that the carrier, diluent, excipients and salt must be compatible with the other ingredients of the composition, and not deleterious to the recipient thereof. Pharmaceutical compositions of the present invention are prepared by procedures known in the art using well known and readily available ingredients.

"Preventing" refers to reducing the likelihood that the recipient will incur or develop any of the pathological conditions described herein.

"Treating" refers to mediating a disease or condition and preventing, or mitigating, its further progression or ameliorate the symptoms associated with the disease or condition.

"Pharmaceutically-effective amount" means that amount of a compound, or of its salt, solvate, hydrate or prodrug thereof, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a PPAR receptor, such as a PPARα or PPARγ receptor, which mediate a disease or condition. Conditions mediated by PPARα or PPARγ receptors include diabetes mellitus, cardiovascular disease, Syndrome X, obesity and gastrointestinal disease.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The human to whom the compounds and compositions of the present invention are administered has a disease or condition in which control blood glucose levels are not adequately controlled without medical intervention, but wherein there is endogenous insulin present in the human's blood. Non-insulin dependent diabetes mellitus (NIDDM) is a chronic disease or condition characterized by the presence of insulin in the blood, even at levels above normal, but resistance or lack of sensitivity to insulin action at the tissues. The compounds and compositions of the present invention are also useful to treat acute or transient disorders in insulin sensitivity, such as sometimes occur following surgery, trauma, myocardial infarction, and the like. The compounds and compositions of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof and/or a pharmaceutically acceptable solvate thereof to a hyperglycemic human or non-human mammal in need thereof.

They are useful as therapeutic substances in preventing or treating Syndrome X, diabetes mellitus and related endocrine and cardiovascular disorders and diseases in human or non-human animals.

The invention also relates to the use of a compound of Formula I as described above, for the manufacture of a medicament for treating a PPARα or PPARγ mediated condition, separately or in combination.

A therapeutically effective amount of a compound of Structural Formula I can be used for the preparation of a medicament useful for treating Syndrome X, diabetes, treating obesity, lowering tryglyceride levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention (1) typically reduces serum glucose levels, or more specifically HbA1c, of a patient by about 0.7% or more; (2) typically reduces serum triglyceride levels of a patient by about 20% or more, and (3) increases serum HDL levels in a patient. Preferably, HDL levels will be increased by about 30% or more.

Additionally, an effective amount of a compound of Structural Formula I and a therapeutically effective amount of one or more active agents selected from a group consisting of: antihyperlipidemic agent, plasma HDL-raising agents, antihypercholesterolemic agents, fibrates, vitamins, aspirin, insulin secretogogues, insulin and the like can be used together for the preparation of a medicament useful for the above-described treatments.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage formulation which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salts, solvates and hydrates thereof, have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient which is a compound of the present invention.

Preferably, the pharmaceutical composition is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

For oral administration, the compounds can be formulated readily by combining the active compounds with pharmaceutically acceptable carriers well known in the art. Such carriers enable the compounds of the invention to be formulated as tablets, pills, powders, sachets, granules, dragees, capsules, liquids, elixers, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid, or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

When a dosage unit form is a capsule, it may contain, in addition to materials of the above type, a liquid carrier such as a fatty oil.

Solid form formulations include powders, tablets and capsules. A solid carrier can be one or more substance which may also act as flavoring agents, lubricants, solubilisers, suspending agents, binders, tablet disintegrating agents and encapsulating material.

In powders, the carrier is a finely divided solid which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration the compounds of the present invention, or salts thereof, can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks's solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

The following pharmaceutical formulations 1 through 8 are illustrative only and are not intended to limit the scope of the invention in any way. "Active Ingredient", refers to a compound according to Structural Formula I or salts thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active Ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
| --- | --- |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| Active Ingredient | 225 mg |
| --- | --- |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| Active Ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active Ingredient | 100 mg |
| --- | --- |
| Isotonic saline | 1,000 ml |

The solution of the above materials generally is administered intravenously to a subject at a rate of 1 ml per minute.

In yet another embodiment of the compounds of the present invention, the compound is radiolabelled, such as with carbon-14, or tritiated. Said radiolabelled or tritiated compounds are useful as reference standards for in vitro assays to identify new PPARα and PPARγ agonists.

SYNTHESIS

Compounds of the present invention have been formed by reacting a 2-(R1-substituted)-5-R2-substituted-oxazol-4-yl ethyl sulfonyl ester with a 2-R4-substituted-(4-phenoxy)-alkanoic acid ester. Generally, the sulfonyl ester chemical intermediates have been synthesized through two different routes, shown in Schemes IA and IB, while Scheme II is typical of the synthethic method used to make the propionic acid chemical intermediate. The formation of the compounds of the present invention from these chemical intermediates is shown in Scheme III.

In Scheme IA, the first step is a condensation of a dionemonooxime represented by Structural Formula IA-1 with a R1-substituted aldehyde represented by Structural Formula IA-2 in the presence of an acid such as aqueous concentrated hydrochloric acid or, preferably, acetic acid which is saturated with hydrogen chloride gas. Typically, hydrogen chloride is bubbled through a solution of the dionemonooxime and the R1-substituted aldehyde in acetic acid, which is held at a constant temperature of about 0° C. to about 20° C. for about 15 minutes to about 1 hour. The product of the condensation is an oxazole n-oxide represented by Structural Formula IA-3.

The oxazole n-oxide is then treated with phosphorous oxyhalide, such as phosphorous oxychloride or phosphorous oxybromide in an inert solvent such as dichloromethane or chloroform to form a 2-(R1-substituted)-4-halomethyl-oxazole represented by Structural Formula IA-4. The reaction typically is carried out at the reflux temperature of the solvent used and is complete in about 15 minutes to about 1 hour.

The 2-(R1-substituted)-4-chloromethyl-oxazole is then treated with a cyanide and an iodide salt to form a 2-(R1-substituted)-4-cyanomethyl-oxazole represented by Structural Formula IA-5. The reaction is typically carried out in a polar, aprotic solvent such as dimethylformamide at a temperature of about 80° C. to about 120° C. for about 1 hour to about 6 hours. Preferably, the cyanide and iodide salts are potassium cyanide and potassium iodide.

The cyano group of the a 2-(R1-substituted)-4-cyanomethyl-oxazole is converted to a carboxylic acid group by treatment with a alkali metal hydroxide to form a 2-(R1-substituted)-4-carboxymethyl-oxazole represented by Structural Formula IA-6. The reaction is generally carried out in an aqueous solution at about 80° C. to about 100° C. The concentration of the alkali metal hydroxide in the aqueous solution is typically about 25% to about 85% (weight/volume). Preferably, the alkali metal hydroxide is potassium hydroxide.

The 2-(R1-substituted)-4-carboxymethyl-oxazole is then treated with a carboxylic acid reducing agent, such as borane or lithium aluminum hydride, to form the 2-(R1-substituted)-4-(2-hydroxyethyl)-oxazole intermediate represented by Structural Formula IA-7. The reaction is typically carried out under anhydrous conditions in an ether solvent such as tetrahydrofuran (THF), dioxane, or ethyl ether. When borane is the reducing agent used, it typically forms a complex with the ether solvent such as a $BH_3$-THF complex. A solution having a concentration of about 0.5 M to about 1.5 M borane complex in the ether solvent is added dropwise to a solution of 0.1 M to 1.3 M of the 2-(R1-substituted)-4-carboxymethyl-oxazole in the ether solvent. The reaction temperature is about 20° C. to about 40° C. Typically, the reaction is complete in about 1 hour to about 5 hours.

The chemical intermediate, represented by Structural Formula IA-7, is then converted into a 2-(R1-substituted-oxazol-4-yl)ethyl sulfonyl ester represented by Structural Formula IA-8 by treatment with a sulfonyl anhydride, such as tosyl anhydride or mesyl anhydride, or a sulfonyl halide, such as tosyl chloride or mesyl chloride, in the presence of a base. The reaction is typically carried out in an aprotic solvent such as methylene chloride in the presence of aprotic bases such as pyridine and N,N-dimethylaminopyridine (DMAP). The reaction is complete in about 0.5 hours to about 5 hours.

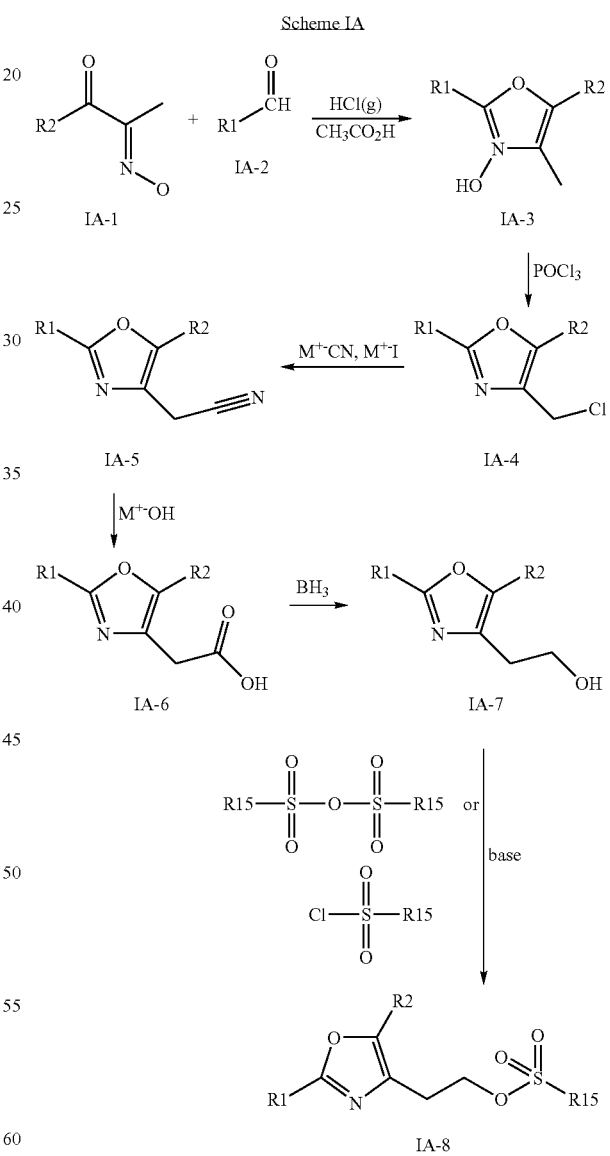

In Scheme IB, the first step is a condensation of β-methyl L-aspartate represented by Structural Formula IB-1 with a R1-substituted acid chloride in the presence of mild base to form the amide represented by Structural Formula IB-3. Typically, the reaction is carried out in an acetone/water media in the presence of a carbonate base, such as potassium or sodium carbonate. The R1-substituted acid chloride is added to a solution of β-methyl L-aspartate in acetone/water at about 0° C. to about 10° C. and the reaction warms to ambient temperature for about 60 minutes to 2 hours.

The acid is then treated with a base such as pyridine and an anhydride such as acetic, n-propyl or trifluoro-acetic anhydride to form the R2-substituted ketone represented by Structural Formula IB-4. The reaction is typically carried out at 90° C. and is complete in about 90 minutes to about 2 hours.

Cyclo-dehydration of the R2-substituted ketone is completed with a protic acid such as sulfuric acid in the presence of acetic anhydride to form the 2-(R1-substituted)-5-(R2-substituted)-oxazole represented by Structural Formula IB-5. Alternatively, the ketone can be treated with a phosphorus oxyhalide, such as phosphorous oxychloride or phosphorous oxybromide in a polar, aprotic solvent such as dimethylformamide. In both methods, the reaction is heated to about 90° C. and is complete in about 15 minutes to 30 minutes.

The 2-(R1-substituted)-5-(R2-substituted)-oxazole is treated with aqueous base, such as aqueous sodium hydroxide in an alcohol solvent at about 25° C. to about 45° C. for about 30 minutes to form the corresponding acid. The acid is treated with a carboxylic acid reducing agent, such as borane or lithium aluminum hydride, to form the 2-(R1-substituted)-4-(2-hydroxyethyl)-oxazole intermediate represented by Structural Formula IA-7. The reaction is typically carried out as described for the formation of the intermediate represented by Structural Formula IA-7 in Scheme IA.

Formula IIA-1) is reacted with a phenol (Structural Formula IIA-2) in the presence of cesium carbonate to form a 2-(3-{2-[2-(bromophenyl)-5-substituted-oxazol-4-yl]ethoxy}-2-phenoxy)-alkanoic acid ester (Structural Formula IIA-3).

In Structural Formula IIA-3, $R_2$, $R_3$ and $R_4$ are terms are as previously defined for Structural Formulas I-III. The reaction is typically carried out in a polar, aprotic solvent such as dimethylformamide at about 40° C. to about 70° C. and is allowed to proceed for about 10 hours to about 24 hours. The reactants IIA-1 and IIA-2 are present in about equal molar amounts or with about 0.1M to about 0.5M excess of the sulfonyl ester compound. The cesium carbonate is present in about one molar equivalent to about 1.5 molar equivalents with respect to the sulfonyl ester.

The 2-(3-{2-[2-(bromophenyl)-5-substituted-oxazol-4-yl]ethoxy}-2-phenoxy)-alkanoic acid ester can be treated with a substituted or unsubstituted alkenyl or alkynyl tributyl tin in the presence of Pd(PPh$_3$)$_4$ to form 2-(3-{2-[2-(alkenylphenyl)-5-substituted-oxazol-4-yl]ethoxy}-2-phenoxy)-alkanoic acid ester or 2-(3-{2-[2-(alkynylphenyl)-5-substituted-oxazol-4-yl]ethoxy}-2-phenoxy)-alkanoic acid ester. The reaction is typically carried out at reflux temperature in a polar, aprotic solvent such as THF, and is complete in about 10 hours to about 20 hours. Optionally, the saturated functionality of the R11 substitution can be reduced by hydrogen in the presence of a palladium on carbon catalyst to form the intermediate represented by Structural Formula IIA-5, where R13 is C1-C4 alkyl, substituted or unsubstituted aryl-C1-C4 alkyl or heteroaryl-C1-C4 alkyl.

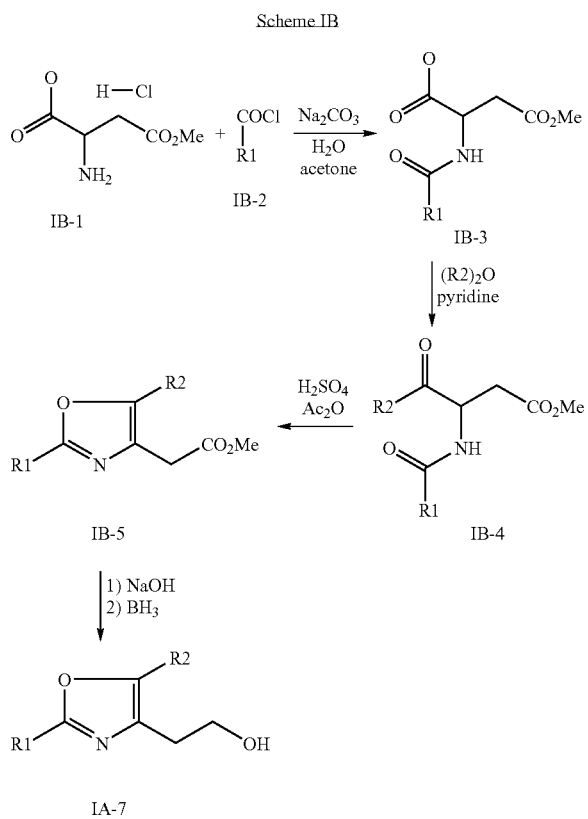

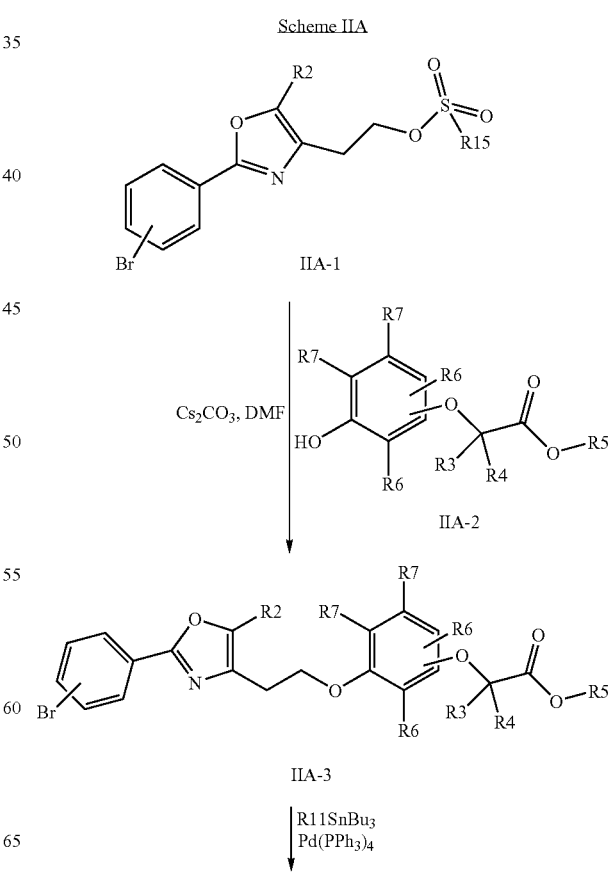

In one method, shown in Scheme IIA, a 2-(bromophenyl-5-R2-substituted-oxazol-4-yl)ethyl sulfonyl ester (Structural

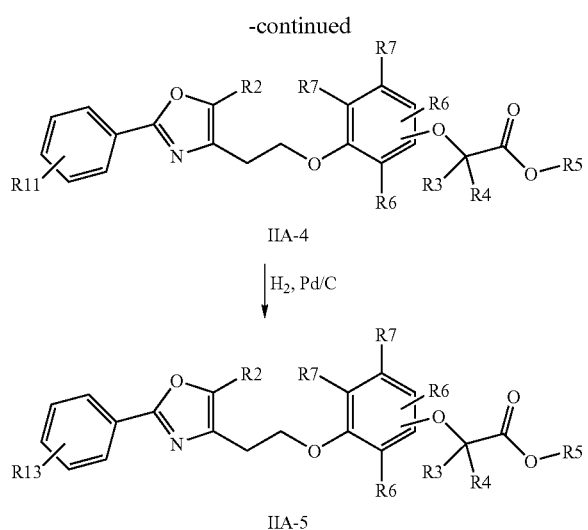

IIA-4

↓ H₂, Pd/C

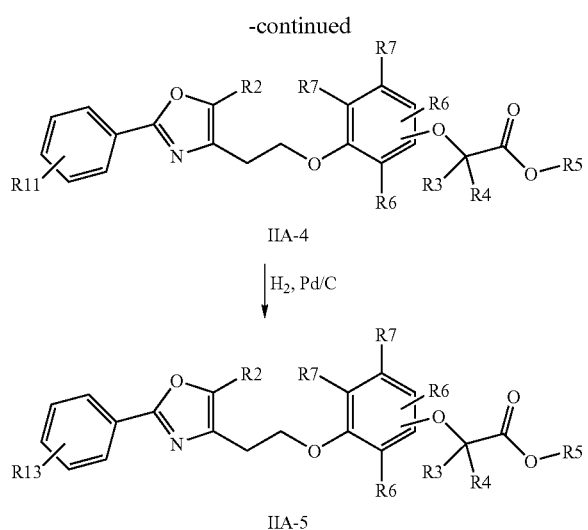

IIA-5

In a second method, shown in Scheme IIB, the 2-(3-{2-[2-(bromophenyl)-5-substituted-oxazol-4-yl]ethoxy}-2-phenoxy)-alkanoic acid ester can be treated with an arylalcohol in the presence of palladium aectate, 2-(di-tert-butylphosphino)biphenyl and potassium phosphonate to form a 2-(3-{2-[2-(aryloxyphenyl)-5-substituted-oxazol-4-yl]ethoxy}-2-phenoxy)-alkanoic acid ester. The reaction is typically carried out in a nonpolar solvent such as toluene at reflux temperature for about 2 hours to about six hours.

Scheme IIB

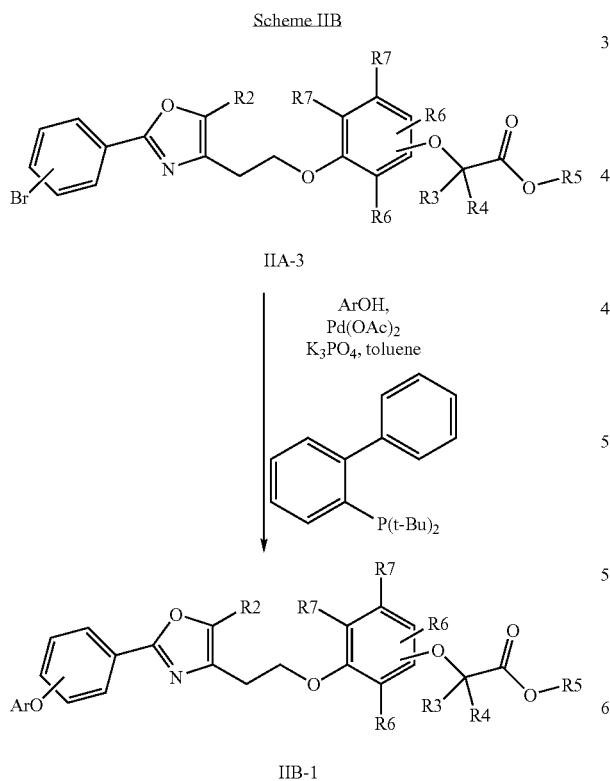

In a third method, shown in Scheme IIC, a 2-(3-{2-[2-(benzyloxyphenyl)-5-substituted-oxazol-4-yl]ethoxy}-2-phenoxy)-alkanoic acid ester, formed as described in Scheme IA and Scheme IIA, is treated to form the phenol represented by Structural Formula IIC-2. The phenol is then treated with an alkyliodide in the presence of a base, such as aqueous sodium hydroxide, and a phase transfer catalyst, such as tetrabutylammonium bromide, to form an alkoxyphenol represented by Structural Formula IIC-3 where R14 is C1-C6 alkyl, cycloalkyl, aryl-C1-C4 alkyl or 1,2,3,4-tetrahydronaphthyl. An alternative method uses an alcohol in the presence of triphenylphosphine and diisopropylazodicarboxylate.

Scheme IIC

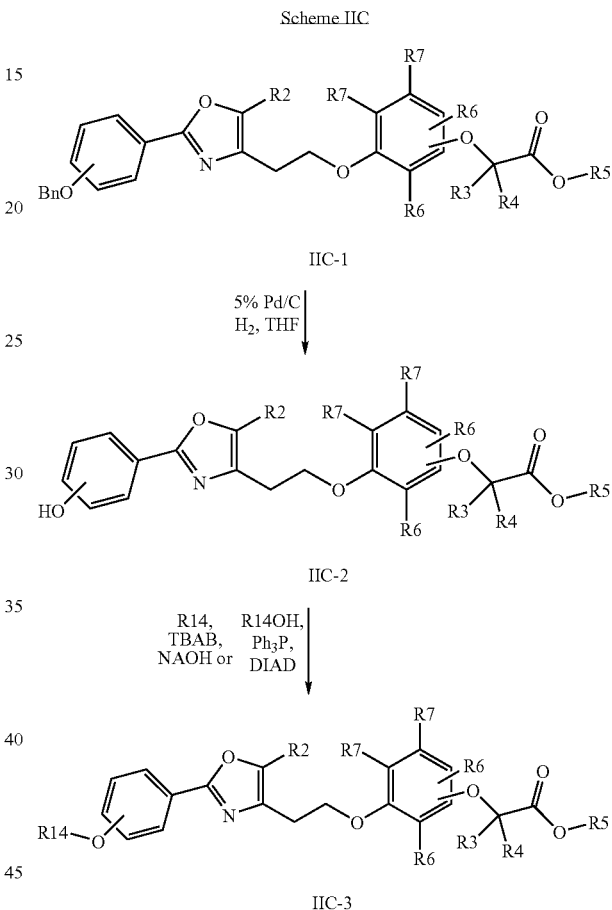

The compound represented by Structural Formula IIA-2 can be prepared by the method depicted in Scheme III. In this method, the benzyloxyphenol represented by Structural Formula III-1 is reacted with a α-haloester represented by Structural Formula III-2 in the presence of cesium carbonate to form a compound represented by Structural Formula III-3. The reaction is carried out under anhydrous conditions in a polar, aprotic solvent such as dimethylformamide at about 40° C. to about 80° C. The α-haloester and the cesium carbonate are present in about 1.5 to about 2.5 molar equivalents with respect to the benzyloxyphenol. Typically, the reaction is complete in about 10 hours to about 24 hours. The R4 substitution is introduced by formation of the enolate with a lithium alkylamide base, such as LDA, at −78° C. followed by addition of an unsubstituted or substituted alkyl or benzyl halide and TBAI to form the intermediate represented by Structural Formula III-4.

The compound represented by Structural Formula III-4 is then treated to remove the benzyl protecting group to form the phenol represented by Structural Formula IIA-2. Methods of removing a benzyl protecting group from a phenol can be found in Green, et al., *Protective Groups in Organic Synthesis*, 2$^{nd}$ edition, (1991), John Wiley & Sons, Inc., New York, pages 156-158, the entire teachings of which are incorporated herein by reference. A preferred method of removing a benzyl protecting group is by treating the compound represented by Structural Formula III-4 with hydrogen in the presence of palladium on carbon (Pd—C) catalyst.

When it is desired to prepare a compound represented by Structural Formula IIA-2 in which at least one R6 or R7 group is other than hydrogen, the compound can be prepared by the method depicted in Scheme IV. A benzyloxy-hydroxybenzaldehyde is treated with a Wittig reagent to form an alkenyl-benzyloxyphenol represented by Structural Formula XXVIII. R16 of the Wittig reagent is a C1-C5 alkyl, an aryl-C1-C5-alkyl, a cycloalkyl-C1-C3-alkyl, or a cycloalkyl. Conditions for carrying out a Wittig reaction are known to those skilled in the art. The alkenyl-benzyloxyphenol is then reacted as described in Scheme III to form the compound represented by Structural Formula IV-4.

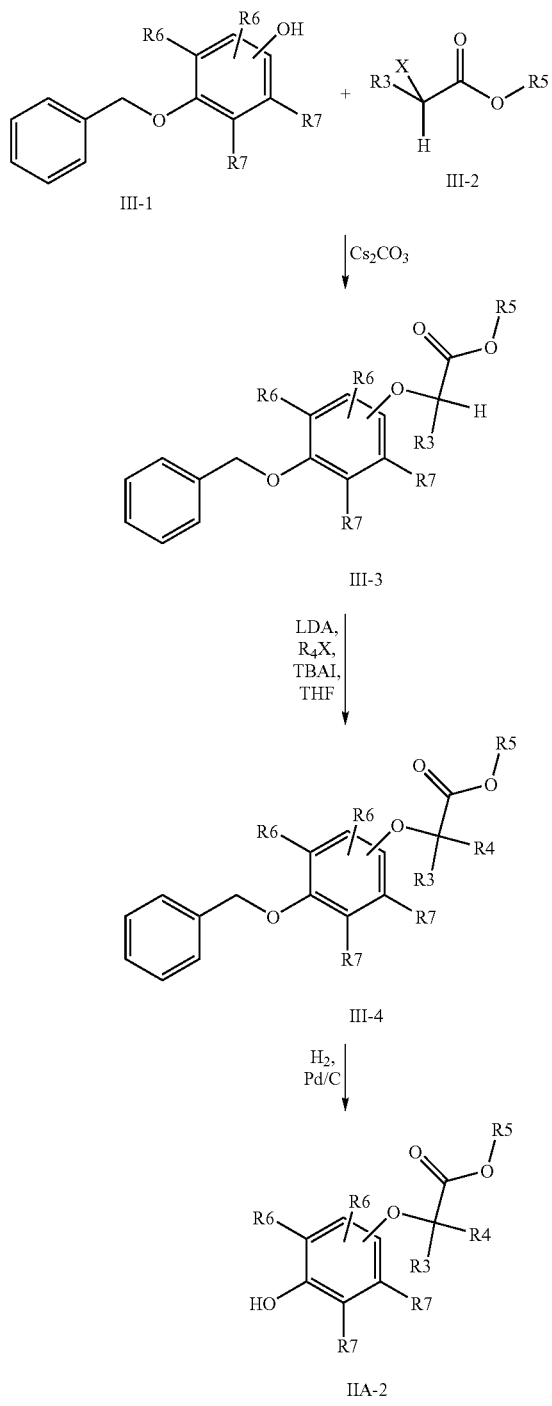

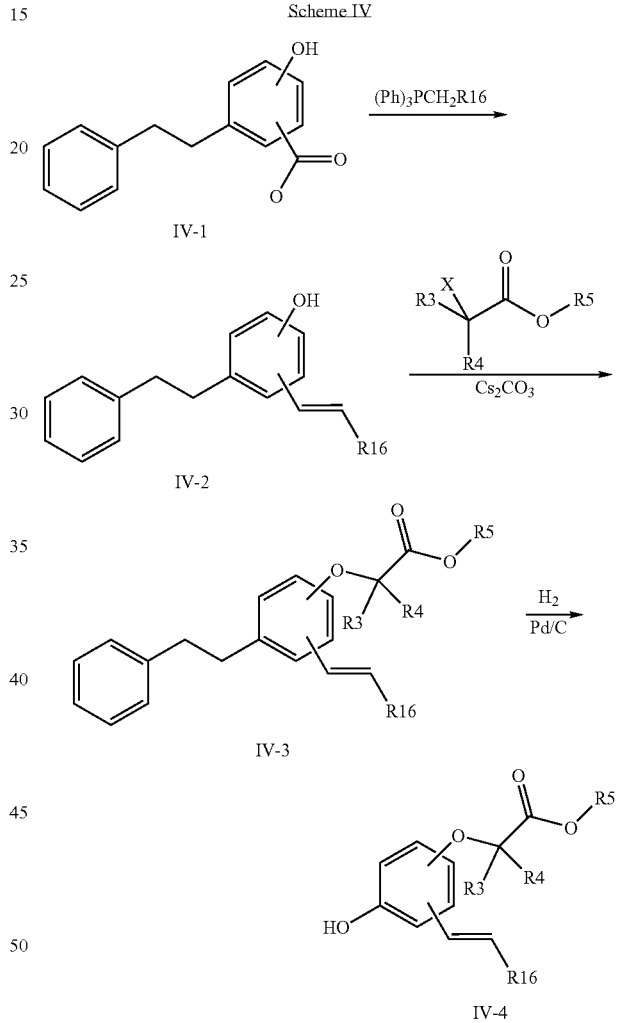

Hydrolysis of alkanoic acid esters are typically carried out in an alcohol solvent in the presence of an excess of aqueous alkali metal hydroxide. The reaction is heated at about 50° C. to about 60° C. and is allowed to proceed for about 10 hours to about 24 hours to form the alkanoic acids of the present invention.

EXEMPLIFICATION

Instrumental Analysis

Infrared spectra were recorded on a Perkin Elmer 781 spectrometer. $^1$H NMR spectra were recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR were recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses were performed by Eli Lilly & Company Microanalytical Laboratory. High resolution mass spectra were obtained on VG ZAB 3F or VG 70 SE spectrometers. Analytical thin layer chromatography was performed on EM Reagent 0.25 mm silica gel 60-F plates. Visualization was accomplished with UV light.

EXAMPLE 1

2-Methyl-2-{4-[2-(5-methyl-2-phenyloxazol-4-yl)ethoxy]phenoxy}propionic acid

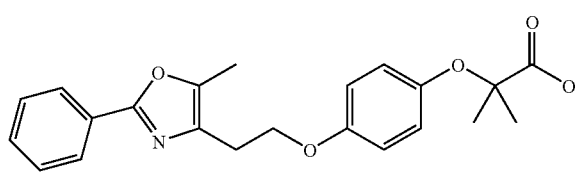

Step A

2-Methyl-2-{4-[2-(5-methyl-2-phenyloxazol-4-yl)ethoxy]phenoxy}propionic acid ethyl ester

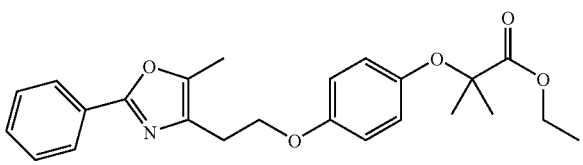

A mixture of the toluene-4-sulfonic acid 2-(5-methyl-2-phenyl-oxazol-4-yl)-ethyl ester (See Japan Tobacco Inc International Application WO 9518125) (24 g, 66.9 mmol), 2-(4-hydroxyphenoxy)-2-methylpropanoic acid ethyl ester (See American Home Products U.S. Pat. No. 3,795,691) (12.5 g, 55.71 mmol) and Cs$_2$CO$_3$ (22.7 g, 69.6 mmol) was heated at 55° C. in DMF (45 mL) for 18 h. The reaction was partitioned between EtOAc (160 mL) and H$_2$O (180 mL), and the aqueous phase extracted with EtOAc (150 mL). The combined organic phases were dried (MgSO$_4$) and concentrated under reduced pressure to an oil which was purified by column chromatography (1500 mL SiO$_2$, 10% EtOAc/hexanes to 20% EtOAc/hexanes) to provide 2-methyl-2-{4-[2-(5-methyl-2-phenyloxazol-4-yl)ethoxy]phenoxy}propionic acid ethyl ester (17.8 g, 78%) as a colorless, viscous oil: Rf=0.48 in 35% EtOAc/hexanes; $^1$H NMR (400 MHz, CDCl$_3$) δ 7.99-7.96 (m, 2H), 7.43-7.40 (m, 3H), 6.83-6.75 (m, 4H), 4.22 (q, J=9.2 Hz, 2H), 4.18 (t, J=8.8 Hz, 2H), 2.95 (t, J=8.8 Hz, 2H), 2.36 (s, 3H), 1.52 (s, 6H), 1.27 (t, J=9.2 Hz, 3H).

Step B

2-Methyl-2-{4-[2-(5-methyl-2-phenyloxazol-4-yl)ethoxy]phenoxy}propionic acid

2-Methyl-2-{4-[2-(5-methyl-2-phenyloxazol-4-yl)ethoxy]phenoxy}propionic acid ethyl ester (6.4 g, 15.6 mmol) was dissolved in MeOH (200 mL) and 2N NaOH (150 mL) was added. The resulting cloudy solution became clear after 30 min and the reaction was stirred vigorously overnight. The solution was concentrated under reduced pressure, diluted with H$_2$O (100 mL) and acidified to pH=1 with 5N HCl. The mixture was extracted with EtOAc (2×200 mL), dried (MgSO$_4$), and concentrated under reduced pressure to provide a white solid. The compound was recrystallized from CH$_3$CN (85 mL) to afford the product (4.50 g, 75%) as colorless needles after drying at 50° C. under vacuum for 6 h: Rf=0.14 in 35% EtOAc/hexanes; mp 129-130° C.; $^1$H NMR (400 MHz, CDCl$_3$) δ 7.98-7.96 (m, 2H), 7.44-7.41 (m, 3H), 6.91-6.79 (m, 4H), 4.16 (t, J=8.8 Hz, 2H), 2.99 (t, J=8.8 Hz, 2H), 2.38 (s, 3H), 1.53 (s, 6H); $^{13}$C (100 MHz, CDCl$_3$) δ 177.2, 159.7, 154.7, 148.3, 145.3, 132.4, 130.1, 128.7, 127.2, 126.1, 122.1, 114.9, 79.9, 67.0, 26.1, 25.1, 10.2; IR (CHCl$_3$) 2991, 1775, 1718, 1554, 1506, 1469, 1237, 1145, 1023 cm$^{-1}$; HRMS (TOF) m/e calcd. for C$_{22}$H$_{24}$NO$_5$ (M$^+$+1) 382.1654, found 382.1628.

EXAMPLE 2

2-{4-[2-(5-Methyl-2-phenyloxazol-4-yl)ethoxy]phenoxy}butyric acid

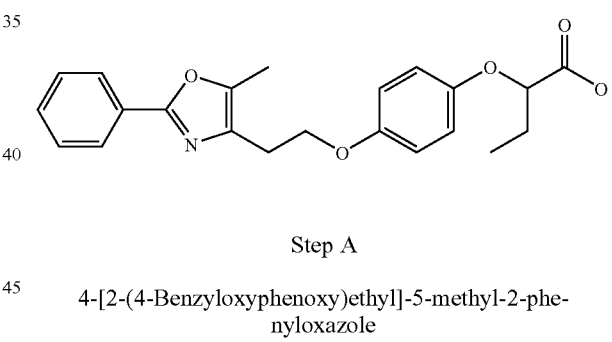

Step A

4-[2-(4-Benzyloxyphenoxy)ethyl]-5-methyl-2-phenyloxazole

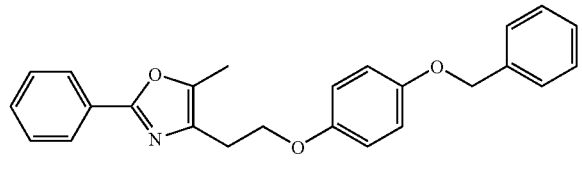

2-(5-Methyl-2-phenyloxazol-4-yl)ethanol [Hulin, et al., J. Med. Chem. (1992) 35(10), 1853-64] (7.42 g, 36.0 mmol), 4-benzyloxyphenol (7.3 g, 36.0 mmol) and triphenylphosphine (9.57 g, 36.0 mmol) were dissolved in anhydrous THF (500 mL) and treated with dropwise addition of diisopropyl azodicarboxylate (7.18 mL, 36.0 mmol). The reaction mixture was stirred at 20° C. for 18 h under a positive-pressure atmosphere of N$_2$. The reaction was partitioned between EtOAc (100 mL) and 0.1 N NaOH (100 mL), and the organic phase washed with water (100 mL) and brine (100 mL). The organic layer was dried with Na₂SO₄ and concentrated to a residue which was purified by gradient column chromatography (silica column, 100% hexanes to 20% EtOAc/hexanes) to provide a white solid (10.5 g, 76%). R$_f$=0.3 (10% EtOAc/hexanes) $^1$H NMR (250 MHz, DMSO-d$_6$) δ 7.86 (d, 2H), 7.41-7.48 (m, 3H), 7.22-7.38 (m, 5H), 6.86 (d, 2H), 6.80 (d, 2H), 4.97 (s, 2H), 4.07 (t, 2H), 2.84 (t, 2H), 2.30 (s, 3H).

Step B

4-[2-(5-methyl-2-phenyloxazol-4-yl)ethoxy]phenol

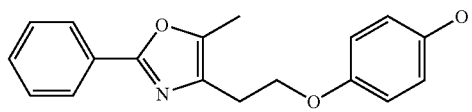

4-[2-(4-Benzyloxyphenoxy)ethyl]-2-phenyloxazole (7.0 g, 18.8 mmol) was dissolved in methanol (150 mL) and treated with palladium on carbon (1.0 g, 10 mol %) and ammonium formate (20.0 g, 0.32 mol). The suspension was heated at reflux for 8 h and then cooled to ambient temperature. The resultant suspension was filtered through Celite with a methanol wash, and the filtrate was concentrated to provide a colorless oil (3.72 g, 70%). $^1$H NMR (250 MHz, CDCl₃) δ 8.84 (s, 1H), 7.81-7.87 (m, 2H), 7.41-7.49 (m, 3H), 6.72 (d, 2H), 6.59 (d, 2H), 4.04 (t, 2H), 2.81 (t, 2H), 2.30 (s, 3H); MS(EI): 282 (M+H), 280 (M−H).

Step C

2-{4-[2-(5-Methyl-2-phenyloxazol-4-yl)ethoxy]phenoxy}butyric acid ethyl ester

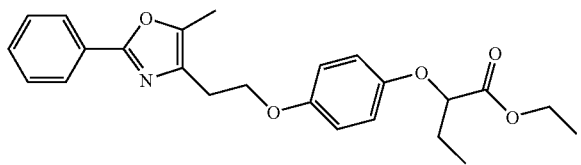

A solution of 4-[2-(5-methyl-2-phenyloxazol-4-yl)ethoxy]phenol in dry DMF (3.0 mL) under argon was treated with Cs₂CO₃ (483 mg, 1.5 mmol) then 2-bromobutyric acid ethyl ester (350 μL, 2.4 mmol). The reaction mixture was stirred at 55° C. for 18 h, was allowed to cool to room temperature, diluted with H₂O, saturated with NaCl, and partitioned with ethyl acetate. The organic layer was washed with NaHCO₃ then brine, dried (Na₂SO₄), and concentrated in vacuo to give a yellow oil (394 mg). The product was purified by radial chromatography using a 1 mm plate and 0-2% ethyl acetate in CH₂Cl₂ to give a yellow oil (216 mg, 88%). $^1$H NMR (400 MHz, CDCl₃) δ 1.07 (t, 3H, J=7.33 Hz), 1.22-1.26 (m, 3H), 1.91-1.99 (m, 2H), 2.37 (s, 3H), 2.96 (t, 2H, J=6.60 Hz), 4.18-4.25 (m, 5H), 4.44 (t, 1H, J=6.35 Hz), 6.81 (s, 4H), 7.42-7.48 (m, 3H), 7.98-8.00 (m, 2H); MS (ES) m/e 410.2 (M+1).

The following compounds were prepared by the same procedure using the appropriate bromoester:

2-{4-[2-(5-Methyl-2-phenyloxazol-4-yl)ethoxy]phenoxy}propionic acid methyl ester

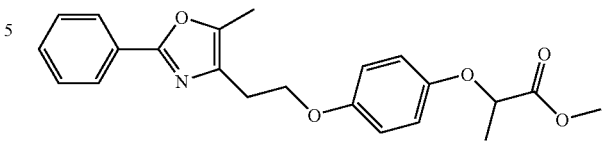

colorless oil: $^1$H NMR (400 MHz, CDCl₃) δ 1.60 (d, 3H, J=6.8 Hz), 2.43 (s, 3H), 3.10 (brt, 2H, J=5.9 Hz), 4.19 (brt, 2H, J=5.6 Hz), 4.66 (q, 1H, J=6.8 Hz), 6.75 (d, 2H, J=9.3 Hz), 6.81 (d, 2H, J=9.3 Hz), 7.42-7.53 (m, 3H), 8.18 (d, 2H, J=6.4 Hz).

2-{4-[2-(5-Methyl-2-phenyloxazol-4-yl)ethoxy]phenoxy}-3-phenyl-propionic acid ethyl ester:

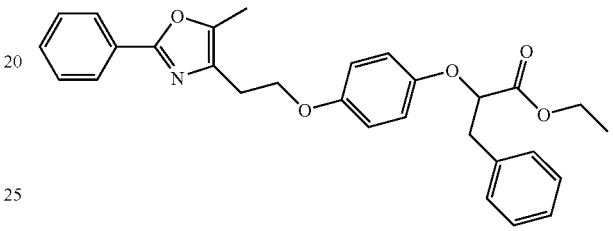

$^1$H NMR (400 MHz, CDCl₃) 1.13 (t, 3H, J=6.8 Hz), 2.31 (s, 3H), 2.89 (t, 2H, J=6.8 Hz), 3.14-3.20 (m, 2H), 4.61-4.64 (m, 4H), 4.63 (dd, 1H, J=5.6, 7.6 Hz), 6.70 (d, 2H, J=8.8 Hz), 6.71 (d, 2H, J=9.8 Hz), 7.17-7.25 (m, 5H), 7.35-7.40 (m, 3H), 7.92-7.94 (m, 2H).

Step D

2-{4-[2-(5-Methyl-2-phenyloxazol-4-yl)ethoxy]phenoxy}butyric acid

Under N₂, a solution of 2-{4-[2-(5-methyl-2-phenyloxazol-4-yl)ethoxy]phenoxy}butyric acid ethyl ester (216 mg, 0.53 mmol) in ethanol (2.5 mL) and THF (2.5 mL) was treated with 2.0 N NaOH (2.0 mL). The reaction mixture was stirred at 55° C. for 1 h and concentrated in vacuo. The resulting slurry was suspended in ethyl acetate, acidified to pH 1 with 1N HCl, and partitioned. The organic layer was washed with brine, dried (Na₂SO₄), and concentrated in vacuo to give a white solid (155 mg, 77%): 1H NMR (400 MHz, CDCl₃) δ 1.05 (t, 3H, J=7.57 Hz), 1.92-1.96 (m, 2H), 2.35 (s, 3H), 2.94 (t, 2H, J=6.35 Hz), 4.16 (t, 21H, J=6.60 Hz), 4.41 (t, 1H, J=6.11 Hz), 6.76-6.83 (m, 4H), 7.39-7.41 (m, 3H), 7.97-7.99 (m, 2H); MS (ES) m/e 382.0 (M+1).

The following compounds were prepared by the same procedure:

Example 2A

2-{4-[2-(5-Methyl-2-phenyloxazol-4-yl)ethoxy]phenoxy}propionic acid:

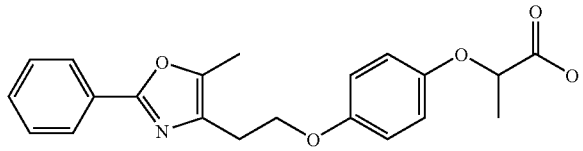

mp 135° C.; $^1$H NMR (400 MHz, CDCl₃) δ 1.57 (d, 3H, J=6.8 Hz), 2.37 (s, 3H), 2.98 (t, 2H, J=6.4 Hz), 3.73 (s, 3H), 4.20 (t, 2H, J=6.4 Hz), 4.63 (q, 1H, J=6.8 Hz), 6.80 (s, 4H), 7.42-7.45 (m, 3H), 8.00-8.03 (m, 2H); MS (FIA) m/e 368.1 (M+1). $^1$H NMR (400 MHz, CDCl$_3$) δ 2.28 (s, 3H), 2.87 (t, 2H, J=6.3 Hz), 3.18 (d, 2H, J=6.8 Hz), 3.88-3.97 (m, 2H), 4.63 (t, 1H, J=6.4 Hz), 6.59 (d, 2H, J=9.3 Hz), 6.68 (d, 2H, J=8.8 Hz), 7.13-7.26 (m, 5H), 7.34-7.35 (m, 3H), 7.85-7.87 (m, 2H); MS (FIA) m/e 444.2 (M+1). Anal. Calcd. for C$_{27}$H$_{25}$NO$_5$: C, 73.12; H, 5.68; N, 3.16. Found: C, 73.06; H, 5.99; N, 3.25.

Example 2B

2-{4-[2-(5-Methyl-2-phenyloxazol-4-yl)ethoxy]-phenoxy}phenylacetic acid:

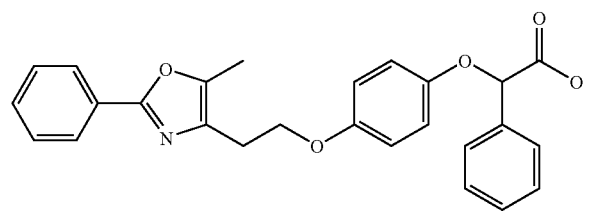

MS (ES+) m/e 430.1 (M+1), (ES−) m/e 428.2 (M−1)

Example 2C

2-{4-[2-(5-Methyl-2-phenyloxazol-4-yl)ethoxy]phenoxy}acetic acid:

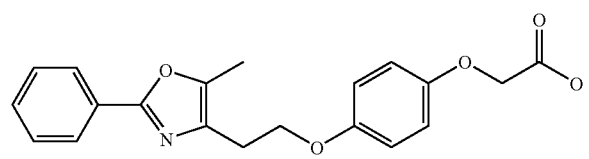

MS (ES+) m/e 354.1 (M+1), (ES−) m/e 352.1 (M−1)

Example 2D

2-{4-[2-(5-Methyl-2-phenyloxazol-4-yl)ethoxy]phenoxy}-3-methylbutyric acid:

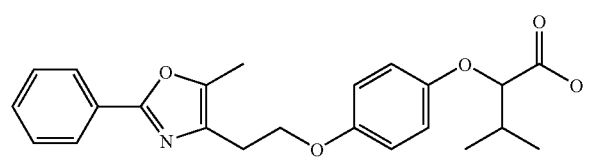

MS (ES+) m/e 382.1 (M+1), 396.1 (M+NH$_4$).

Example 2E

2-{4-[2-(5-Methyl-2-phenyloxazol-4-yl)ethoxy]phenoxy}hexanoic acid:

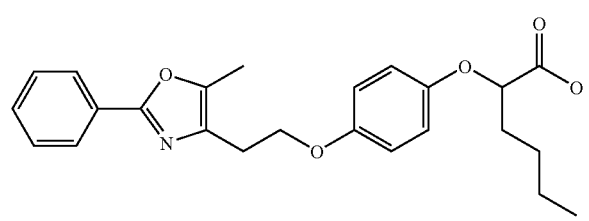

MS (ES+) m/e 409.1 (M+1), 424.2 (M+NH$_4$).

Example 2F

2-{4-[2-(5-Methyl-2-phenyloxazol-4-yl)ethoxy]-phenoxy}octanoic acid:

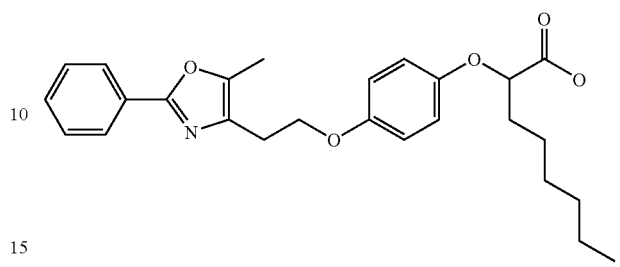

MS (ES+) m/e 438.1 (M+1), 452.2 (M+NH$_4$).

Example 2G

2-{4-[2-(5-Methyl-2-phenyloxazol-4-yl)ethoxy]-phenoxy}dodecanoic acid:

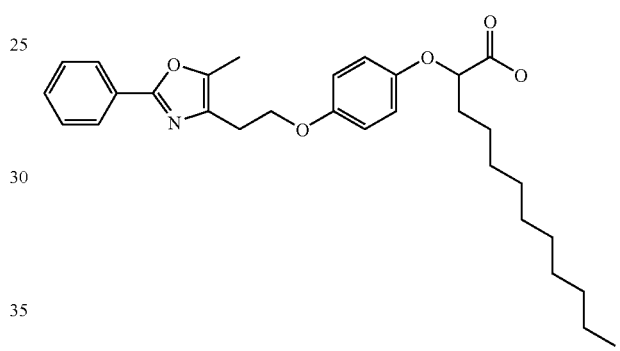

MS (ES+) m/e 494.1 (M+1), 508.3 (M+NH$_4$).

EXAMPLE 3

Sodium 2-methyl-2-{4-[2-(2-phenyloxazol-4-yl)ethoxy]phenoxy}propionate

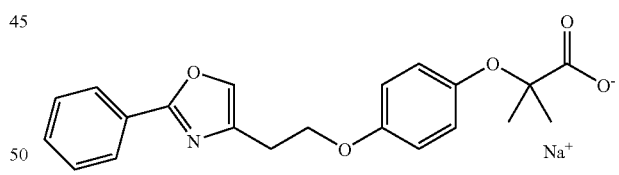

Step A

4-[2-(2-Phenyloxazol-4-yl)ethoxy]phenol

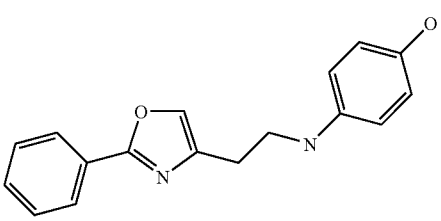

Made from 4-[2-(4-benzyloxyphenoxy)ethyl]-2-phenyloxazole (Eli Lilly & Company, WO9613264) using the procedure described in Example 2, Step A. $^1$H NMR (250 MHz, CDCl$_3$) δ 8.92 (s, 1H), 8.03 (s, 1H), 7.90-8.02 (m, 2H), 7.48-7.56 (m, 3H), 6.78 (d, 2H), 6.66 (d, 2H), 4.15 (t, 2H), 2.94 (t, 2H). MS(EI): 190 (M+H), 188 (M−H).

Step B

2-Methyl-2-{4-[2-(2-phenyloxazol-4-yl)ethoxy]phenoxy}propionic acid, ethyl ester

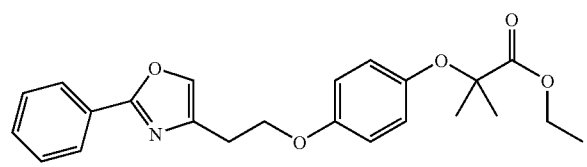

4-[2-(2-Phenyloxazol-4-yl)ethoxy]phenol (3.7 g, 13.0 mmol) and cesium carbonate (4.71 g, 14.5 mmol) were suspended in anhydrous DMF (100 mL) and treated with dropwise addition of ethyl 2-bromoisobutyrate (2.54 g, 13.0 mmol, 1.93 mL). The reaction mixture was stirred at ambient temperature for 24 h and then partitioned between ether (200 mL) and 1.0 N HCl (200 mL). The organic layer was washed with water (100 mL), dried over MgSO$_4$ and concentrated to a brown oil, which was purified by gradient column chromatography (200 mL SiO$_2$, 100% hexanes to 20% EtOAc/hexanes) to provide 2-methyl-2-{4-[2-(2-phenyloxazol-4-yl)ethoxy]phenoxy}propionic acid, ethyl ester (2.54 g,

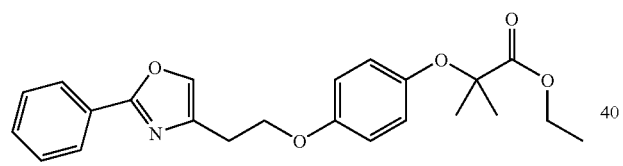

50%) as a colorless, viscous oil: R$_f$=0.5 in 20% EtOAc/hexanes; $^1$H NMR (250 MHz, CDCl$_3$) δ 7.96-8.02 (m, 2H), 7.37-7.46 (m, 3H), 6.81 (s, 4H), 4.32 (q, 2H), 4.20 (t, 2H), 3.03 (t, 2H), 1.52 (s, 6H), 1.27 (t, 3H).

Step C

Sodium 2-methyl-2-{4-[2-(2-phenyloxazol-4-yl)ethoxy]phenoxy}propionate

2-Methyl-2-{4-[2-(2-phenyloxazol-4-yl)ethoxy]phenoxy}propionic acid, ethyl ester 2.5 g, 63.2 mmol) was dissolved in MeOH (200 mL) and 2N NaOH (100 mL) was added. The resulting cloudy solution became clear after 30 min and the reaction was stirred vigorously for 6 h. The solvents were removed, and the residual solids were triturated with water. The suspended solids were then collected and triturated with pentane to produce a white solid (2.38 g, 97%). mp 199-200° C.; $^1$H NMR (300 MHz, DMSO-d$_6$) δ 7.90-7.93 (m, 2H), 7.46-7.49 (m, 3H), 6.73 (d, J=9.0 Hz, 2H), 6.69 (d, J=9.0 Hz, 2H), 4.12 (t, J=6.4 Hz, 2H), 2.91 (t, J=6.4 Hz, 2H), 1.26 (s, 3H); MS(EI): 390 (M+H), 366 (M−Na).

EXAMPLE 4

2-Methyl-2-[4-(5-methyl-2-phenyloxazol-4-ylmethoxy)phenoxy]propionic acid

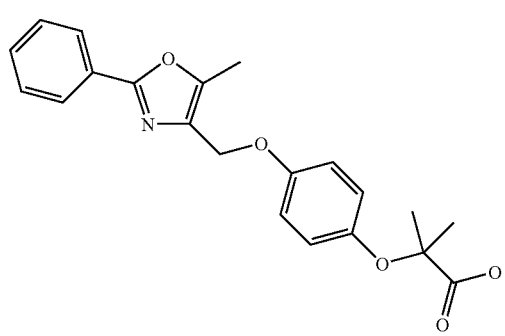

Step A

2-Methyl-2-[4-(5-methyl-2-phenyloxazol-4-ylmethoxy)phenoxy]propionic acid, ethyl ester

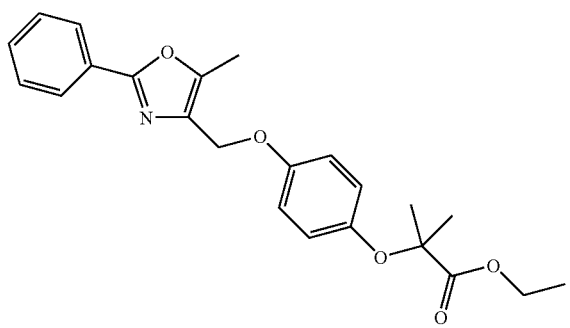

Made from (5-methyl-2-phenyloxazol-4-yl)methanol [Overman, et al., J. Org. Chem. (1979), 44(13), 2323-25] and ethyl 2-(4-hydroxyphenoxy)-2-methylpropanoate (American Home Products, U.S. Pat. No. 3,795,691) via an analogous procedure to that reported for Example 2, Step A: $^1$H NMR (300 MHz, CDCl$_3$) δ 8.03-8.09 (m, 2H), 7.45-7.52 (m, 3H), 6.94 (d, 2H), 6.88 (d, 2H), 4.99 (s, 2H), 4.37 (q, 2H), 2.47 (s, 3H), 1.60 (s, 6H), 1.33 (t, 3H).

Step B

2-Methyl-2-[4-(5-methyl-2-phenyloxazol-4-ylmethoxy)phenoxy]propionic acid

Hydrolysis of 2-methyl-2-[4-(5-methyl-2-phenyloxazol-4-ylmethoxy)-phenoxy]propionic acid, ethyl ester was carried out in the manner described in Example 2, Step D: mp 136-138° C.; $^1$H NMR (300 MHz, DMSO-d$_6$) δ 7.88-7.91 (m, 2H), 7.46-7.49 (m, 3H), 6.90 (d, J=8.8 Hz, 2H), 6.78 (d, J=8.8 Hz, 2H), 4.89 (s, 2H), 2.39 (s, 3H), 1.40 (s, 6H); MS(EI): 368 (M+1), 366 (M−1).

EXAMPLE 5

2-Methyl-2-{4-[3-(5-methyl-2-phenyloxazol-4-yl)allyloxy]phenoxy}propionic acid

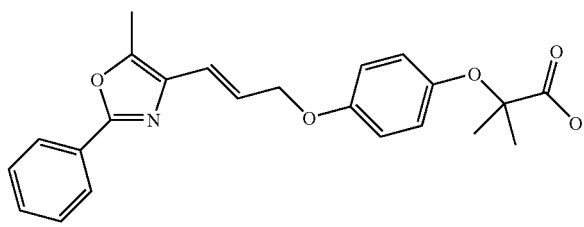

Step A 3-(5-Methyl-2-phenyloxazol-4-yl)-acrylic acid, ethyl ester

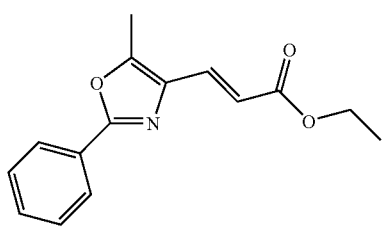

5-Methyl-2-phenyloxazole-4-carbaldehyde [Hulin, et al., J. Med. Chem. (1992) 35(10), 1853-64] (5.62 g, 30 mmol), triethylphosphonoacetate (6.55 mL, 33 mmol), and LiOH (1.38 g, 33 mmol) were dissolved in anhydrous THF (150 mL) and stirred for 18 h at ambient temperature under an atmosphere of nitrogen. The reaction mixture was then diluted with ether (100 mL) and washed with saturated NH$_4$Cl solution (100 mL), then water (100 mL). The aqueous layers were back-extracted with ether (100 mL) and the combined organic layers were again washed with water (100 mL). The ether layer was dried over MgSO$_4$ and concentrated. The resultant residual solids were purified by column chromatography (250 mg silica, 100% hexanes to 10% EtOAc/hexanes) to provide a white crystalline solid (3.46 g, 45%): R$_f$=0.55 (50% hexanes/EtOAc); $^1$H NMR (400 MHz, CDCl$_3$) δ 7.97-8.05 (m, 2H), 7.50 (d, 1H), 7.40-7.44 (m, 3H), 6.63 (d, 2H) 4.26 (q, 2H), 2.43 (s, 3H), 1.33 (t, 3H); MS(EI): 258 (M+1).

Step B 3-(5-Methyl-2-phenyloxazol-4-yl)-prop-2-en-1-ol

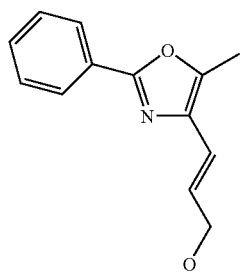

Lithium aluminum hydride (480 mg, 12.6 mmol) was slurried in anhydrous THF (15 mL) and treated with dropwise addition of a solution of 3-(5-methyl-2-phenyloxazol-4-yl)-acrylic acid, ethyl ester (2.60 g, 10.1 mmol) at 0° C. The reaction mixture was stirred for 1.5 h at this temperature and then treated with dropwise addition of isopropanol (1.0 mL) followed by water (10 mL). The biphasic suspension was acidified with 0.1 N HCl (10 mL), diluted with ether (20 mL) and partitioned. The aqueous layer was extracted once with ether (15 mL) and the combined organic layers dried over MgSO$_4$ and concentrated to provide a colorless oil (1.13 g, 52%): R$_f$=0.18 (50% hexanes/EtOAc); $^1$H NMR (300 MHz, CDCl$_3$) δ 7.99-8.03 (m, 2H), 7.42-7.48 (m, 3H), 6.60 (dt, 1H), 6.47 (d, 1H), 4.35 (m, 2H), 3.76 (b, 1H), 2.37 (s, 3H); MS(EI): 216 (M+1).

Step C

2-Methyl-2-{4-[3-(5-methyl-2-phenyloxazol-4-yl)allyloxy]phenoxy}propionic acid, ethyl ester

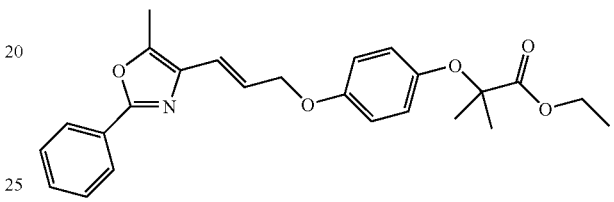

Synthesized from 3-(5-methyl-2-phenyloxazol-4-yl)-prop-2-en-1-ol and ethyl 2-(4-hydroxyphenoxy)-2-methyl-propanoate (American Home Products, U.S. Pat. No. 3,795,691) via an analogous procedure to that reported for Example 2, Step A:

$^1$H NMR (300 MHz, CDCl$_3$) δ 7.95-7.99 (m, 2H), 7.36-7.43 (m, 3H), 6.80 (s, 4H), 6.61 (dt, 1H), 6.49 (d, 1H), 4.62 (d, 2H), 4.18 (q, 2H), 2.37 (s, 3H), 1.49 (s, 6H), 1.23 (t, 3H); MS (EI): 422 (M+1).

Step D

2-Methyl-2-{4-[3-(5-methyl-2-phenyloxazol-4-yl)allyloxy]phenoxy}propionic acid

Hydrolysis of 2-methyl-2-{4-[3-(5-methyl-2-phenyloxazol-4-yl)allyloxy]-phenoxy}propionic acid, ethyl ester was carried out in the manner described in Example 2, Step D: $^1$H NMR (300 MHz, DMSO-d$_6$) δ 7.87-7.93 (m, 2H), 7.41-7.48 (m, 3H), 6.85 (d, 2H), 6.77 (d, 2H), 6.64 (d, 1H), 6.41 (dt, 1H), 4.62 (d, 2H), 2.38 (s, 3H), 1.37 (s, 6H); MS (EI): 394 (M+1), 392 (M−1).

EXAMPLE 6

2-Methyl-2-{4-[2-(5-methyl-2-phenyloxazol-4-yl)ethoxy]phenoxy}-3-phenylpropionic acid

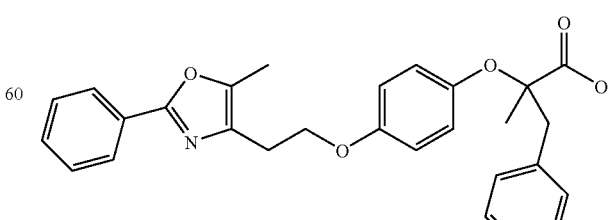

Step A

2-2-(4-Benzyloxyphenoxy)-2-methyl-3-phenylpropionic acid, ethyl ester

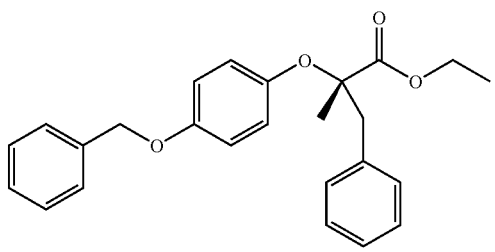

2-(4-Benzyloxyphenoxy)propionic acid, ethyl ester [American Cyanamid, U.S. Pat. No. 4,209,651] (2.0 g, 6.66 mmol) dissolved in anhydrous THF (16 mL) was cooled to −78° C. under an atmosphere of nitrogen, and treated with dropwise addition of lithium diisopropylamide (4.16 mL of a 2.0M in THF). After 15 min, benzyl bromide (1.03 mL, 8.66 mmol) was added dropwise rapidly followed immediately by addition of tetrabutylammonium iodide (246 mg, 0.7 mmol). The cooling bath was removed and the reaction mixture allowed to stir for 14 h while gradually warming to ambient temperature. The crude reaction mixture was partitioned between EtOAc (15 mL) and saturated aqueous NH$_4$Cl (15 mL), and the aqueous layer extracted once with ether (20 mL). The combined organic layers were washed with brine (25 mL), dried over MgSO$_4$ and concentrated to an oily residue. This material was purified by gradient column chromatography (100 g SiO$_2$, 100% hexanes to 20% EtOAc/hexanes) to provide a colorless oil (2.22 g, 85%): R$_f$=0.45 (20% EtOAc/hexanes); $^1$H NMR (300 MHz, CDCl$_3$) δ 7.10-7.40 (m, 10H), 6.80 (d, 2H), 6.76 (d, 2H), 4.97 (s, 2H), 4.18 (q, 2H), 3.26 (d, 1H), 3.13 (d, 1H), 1.28 (s, 3H), 1.21 (t, 3H); MS (EI): 391 (M+1).

Step B

2-(4-Hydroxyphenoxy)-2-methyl-3-phenylpropionic acid, ethyl ester

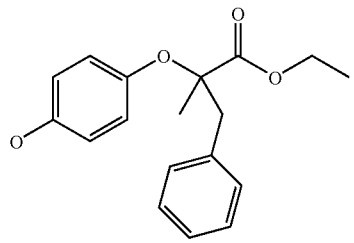

Debenzylation of 2-(4-benzyloxyphenoxy)-2-methyl-3-phenylpropionic acid, ethyl ester was achieved in the manner described in Example 2, Step B. $^1$H NMR (300 MHz, CDCl$_3$) δ 7.20-7.28 (m, 5H), 6.73 (d, 2H), 6.66 (d, 2H), 4.71 (b, 1H), 4.11 (q, 2H), 3.26 (d, 1H), 3.12 (d, 1H), 1.30 (s, 3H), 1.24 (t, 3H); MS (EI): 301 (M+1), 299 (M−1).

Step C

2-Methyl-2-{4-[2-(5-methyl-2-phenyloxazol-4-yl)ethoxy]phenoxy}-3-phenylpropionic acid, ethyl ester

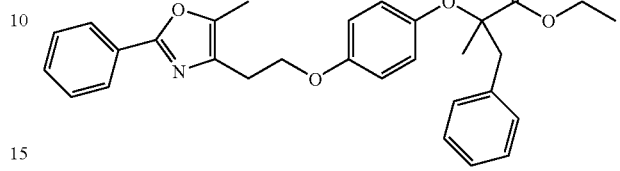

Mitsunobu coupling of 2-(4-hydroxyphenoxy)-2-methyl-3-phenylpropionic acid, ethyl ester and 2-(5-methyl-2-phenyloxazol-4-yl)ethanol [Hulin, et al., J. Med. Chem. (1992) 35(10), 1853-64] in the manner described in Example 2, Step A. $^1$H NMR (300 MHz, CDCl$_3$) δ 7.89-7.93 (m, 2H), 7.33-7.41 (m, 3H), 7.19-7.23 (m, 5H), 6.74 (d, 2H), 6.70 (d, 2H), 4.17 (q, 2H), 4.13 (t, 2H), 3.24 (d, 1H), 3.09 (d, 1H), 2.91 (t, 2H), 2.32 (s, 3H), 1.25 (s, 3H), 1.21 (t, 3H); MS(EI): 486 (M+1).

Step D

2-Methyl-2-{4-[2-(5-methyl-2-phenyloxazol-4-yl)ethoxy]phenoxy}-3-phenylpropionic acid Hydrolysis of 2-methyl-2-{4-[2-(5-methyl-2-phenyloxazol-4-yl)ethoxy]phenoxy}-3-phenyl propionic acid ethyl ester was carried out in the manner described in Example 2, Step D. $^1$H NMR (300 MHz, DMSO-d$_6$) δ 13.0 (b, 1H), 7.88-7.93 (m, 2H), 7.48-7.55 (m, 3H), 7.22-7.32 (m, 5H), 6.83 (d, 2H), 6.74 (d, 2H), 4.13 (t, 2H), 3.20 (d, 1H), 3.08 (d, 1H), 2.91 (t, 2H), 2.34 (s, 3H), 1.21 (s, 3H); MS (EI): 458 (M+1).

EXAMPLE 7

2-Methyl-2-{4-[2-(2-phenyl-5-propyloxazol-4-yl)ethoxy]phenoxy}propionic acid

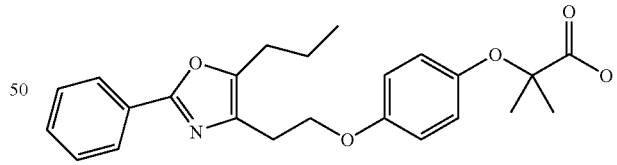

Step A

4-(2-Benzyloxyethyl)-2-phenyloxazole

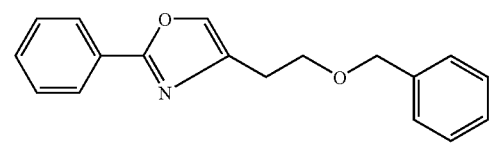

To a solution of 2-(2-phenyloxazol-4-yl)-ethanol (Eli Lilly and Co. WO 9613264) (500 mg, 2.64 mmol) in THF (8 mL) was added NaH (215 mg, 5.28 mmol), followed by tetrabutylammonium iodide (96 mg, 0.26 mmol). After 10 min, benzyl bromide (677 mg, 3.96 mmol, 0.47 mL) was added via syringe. After 3 h, the reaction was partitioned between H$_2$O (20 mL) and diethyl ether (20 mL). The organic phase was washed with brine and then the combined aqueous phases were back extracted with ether (50 mL). The organic phases were dried (MgSO$_4$), filtered and concentrated. The product was purified by flash chromatography (80 mL SiO$_2$, 25% EtOAc/hexanes) and obtained as a colorless oil (690 mg, 93%): Rf=0.46 in 25% EtOAc/hexanes; $^1$H NMR (500 MHz, CDCl$_3$) δ 8.03-8.01 (m, 2H), 7.52 (t, J=1.0 Hz, 1H), 7.45-7.41 (m, 3H), 7.34-7.33 (m, 3H), 7.29-7.26 (m, 1H), 4.57 (s, 2H), 3.80 (t, J=7.0 Hz, 2H), 2.93 (t, J=7.0 Hz, 2H); $^{13}$C (125 MHz, CDCl$_3$) δ 161.3, 139.3, 138.2, 135.0, 130.1, 128.7, 128.4, 127.7, 127.6, 126.3, 73.0, 68.5, 27.3.

Step B 4-(2-Benzyloxyethyl)-2-phenyl-5-propyloxazole

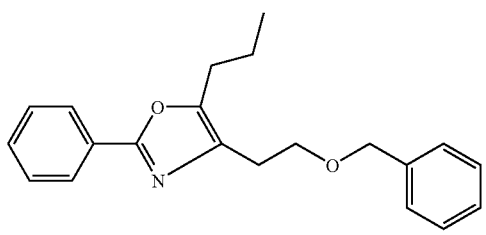

4-(2-Benzyloxyethyl)-2-phenyloxazole (670 mg, 239 mmol) was dissolved in THF (10 mL) and cooled to −78° C. before adding n-butyllithium (1.15 mL of a 2.5 M solution in hexanes). The resulting orange solution was warmed to −65° C., stirred 45 min, and then propyl iodide (1.22 g, 7.17 mmol, 0.70 mL) was added via syringe. The solution was warmed to ambient temperature and stirred 90 min. The mixture was concentrated and the product purified by flash chromatography (100 mL SiO$_2$, hexanes to 20% EtOAc/hexanes) and obtained as a colorless oil (340 mg, 44%): Rf=0.49 in 20% EtOAc/hexanes; $^1$H NMR (500 MHz, CDCl$_3$) δ 8.00-7.96 (m, 2H), 7.42-7.26 (m, 8H), 4.54 (s, 2H), 3.76 (t, J=7.0 Hz, 2H), 2.83 (t, J=7.0 Hz, 2H), 2.64 (t, J=7.0 Hz, 2H) 1.68 (sextet, J=7.0 Hz, 2H), 0.96 (t, J=7.0 Hz, 3H).

Step C 2-(2-Phenyl-5-propyloxazol-4-yl)ethanol

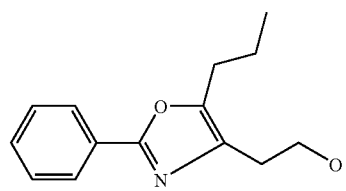

4-(2-Benzyloxyethyl)-2-phenyl-5-propyloxazole (340 mg, 1.05 mmol) was dissolved in THF (5 mL) and treated with Pearlman's catalyst (170 mg). The solution was stirred vigorously under a hydrogen atmosphere (1 atm) for 90 min, and then the mixture was filtered through celite. The celite was rinsed with CH$_2$Cl$_2$ and the solution dried (MgSO$_4$), filtered and concentrated to a clear, colorless oil: Rf=0.25 in 60% EtOAc/hexanes; $^1$H NMR (300 MHz, CDCl$_3$) δ 8.00-7.96 (m, 2H), 7.44-7.22 (m, 2H), 3.92 (br s, 2H), 2.73 (t, J=5.5 Hz, 2H), 2.65 (t, J=7.0 Hz, 2H) 1.70 (sextet, J=7.0 Hz, 2H), 0.98 (t, J=7.0 Hz, 3H).

Step D

2-Methyl-2-{4-[2-(2-phenyl-5-propyloxazol-4-yl) ethoxy]phenoxy}propionic acid ethyl ester

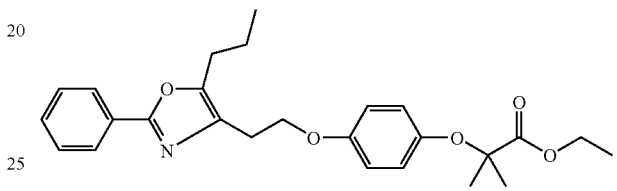

2-(2-Phenyl-5-propyloxazol-4-yl)ethanol (225 mg, 0.97 mmol) and triethyl amine (167 mg, 1.65 mmol, 0.23 mL) were dissolved in CH$_2$Cl$_2$ (3.5 mL) at 0° C. and treated with methane sulfonyl chloride (167 mg, 1.46 mmol, 0.11 mL). After 1 h, NH$_4$Cl (25 mL of a 10% aqueous solution) was added and then the organic phase was dried (MgSO$_4$), filtered and concentrated to an oil. The intermediate mesylate was combined with Cs$_2$CO$_3$ (383 mg, 1.18 mmol), and 2-(4-hydroxyphenoxy)-2-methylpropanoic acid ethyl ester (American Home Products U.S. Pat. No. 3,795,691) (190 mg, 0.84 mmol) in DMF (4 mL) and heated to 55° C. After 18 h, the reaction mixture was partitioned between H$_2$O (25 mL) and EtOAc (25 mL) and then the organic phase washed with H$_2$O (2×), dried (MgSO$_4$), filtered and concentrated. The product was purified by flash chromatography (70 mL SiO$_2$, hexanes to 20% EtOAc/hexanes) and obtained as a colorless oil (170 mg, 46%): Rf=0.49 in 20% EtOAc/hexanes; $^1$H NMR (500 MHz, CDCl$_3$) δ 8.00-7.96 (m, 2H), 7.42-7.38 (m, 3H), 6.83-6.76 (m, 4H), 4.22 (q, J=7.0 MHz, 2H), 4.19 (t, J=7.0 Hz, 2H), 2.95 (t, J=7.0 Hz, 2H), 2.67 (t, J=7.0 Hz, 2H) 1.71 (sextet, J=7.0 Hz, 2H), 1.52 (s, 6H), 1.26 (t, J=7.0 Hz, 3H), 0.96 (t, J=7.0 Hz, 3H).

Step E

2-Methyl-2-{4-[2-(2-phenyl-5-propyloxazol-4-yl) ethoxy]phenoxy}propionic acid

2-Methyl-2-{4-[2-(2-phenyl-5-propyloxazol-4-yl) ethoxy]phenoxy}propionic acid ethyl ester (170 mg, 0.39 mmol) was hydrolyzed as described in Example 1 to provide the product as a pale yellow oil: $^1$H NMR (400 MHz, CDCl$_3$) δ 10.85 (br s, 1H), 8.04-8.00 (m, 2H), 7.44-7.42 (m, 3H), 6.91-6.72 (m, 4H), 4.16 (t, J=6.1 Hz, 2H), 3.04 (t, J=6.1 Hz, 2H), 2.70 (t, J=7.0 Hz, 2H) 1.73 (sextet, J=7.0 Hz, 2H), 1.53 (s, 6H), 1.01 (t, J=7.0 Hz, 2H).

EXAMPLE 8

2-(4-{2-[2-(3,5-Di-tert-butyl-4-hydroxyphenyl)ox-azol-4-yl]ethoxy}phenoxy)-2-methylpropionic acid

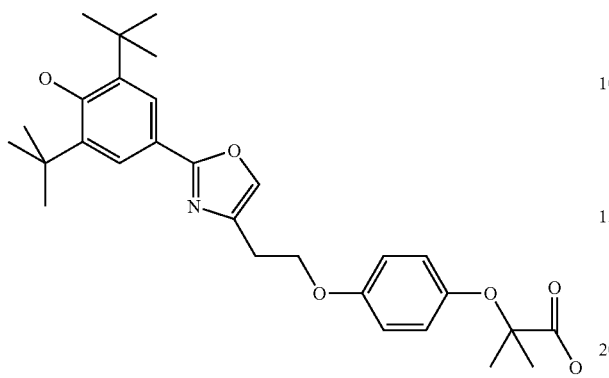

Step A 2-(4-{2-[2-(3,5-Di-tert-butyl-4-hydroxyphenyl)ox-azol-4-yl]ethoxy}phenoxy)-2-methylpropionic acid ethyl ester

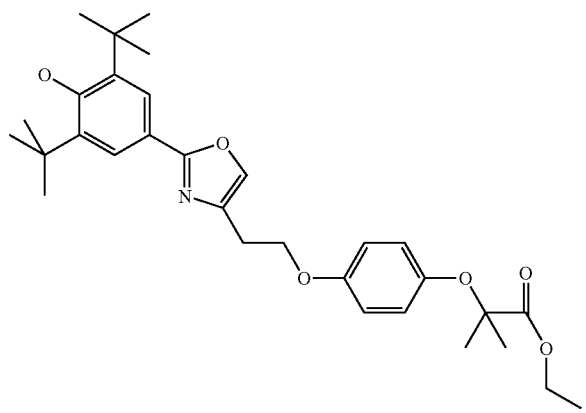

Toluene-4-sulfonic acid 2-[2-(3,5-di-tert-butyl-4-hydroxyphenyl)oxazol-4-yl]ethyl ester (Eli Lilly and Co, Eur. Pat. Appl. 98-308063) (490 mg, 1.04 mmol) was coupled to 2-(4-hydroxyphenoxy)-2-methylpropanoic acid ethyl ester (American Home Products U.S. Pat. No. 3,795,691) (203 mg, 0.90 mmol) following the procedure described in Example 1 to provide the product (330 mg, 70%) as a clear, colorless oil:

Rf=0.55 in 35% EtOAc/hexanes; $^1$H NMR (500 MHz, CDCl$_3$) δ 7.84 (s, 2H), 7.49 (s, 1H), 6.83-6.80 (m, 4H), 5.50 (s, OH), 4.23 (q, J=7.0 MHz, 2H), 4.22 (t, J=6.0 Hz, 2H), 3.04 (t, J=6.0 Hz, 2H), 1.53 (s, 6H), 1.48 (s, 18H), 1.27 (t, J=7.0 Hz, 3H).

Step B 2-(4-{2-[2-(3,5-Di-tert-butyl-4-hydroxyphenyl)ox-azol-4-yl]ethoxy}phenoxy)-2-methylpropionic acid 2-(4-{2-[2-(3,5-Di-tert-butyl-4-hydroxyphenyl)oxazol-4-yl]ethoxy}phenoxy)-2-methylpropionic acid ethyl ester (320 mg, 0.61 mmol) was hydrolyzed following the procedure described in Example 1 to provide the product (191 mg, 63%) as a white solid: Rf=0.07 in 40% EtOAc/hexanes; $^1$H NMR (500 MHz, CDCl$_3$) δ 7.83 (s, 2H), 7.50 (s, 1H), 6.92-6.80 (m, 4H), 5.51 (s, OH), 4.19 (t, J=6.5 Hz, 2H), 3.07 (t, J=6.5 Hz, 2H), 1.53 (s, 6H), 1.48 (s, 18H).

EXAMPLE 9

2-(4-{2-[2-(4-Bromophenyl)-5-methyloxazol-4-yl]ethoxy}phenoxy)-2-methylpropionic acid

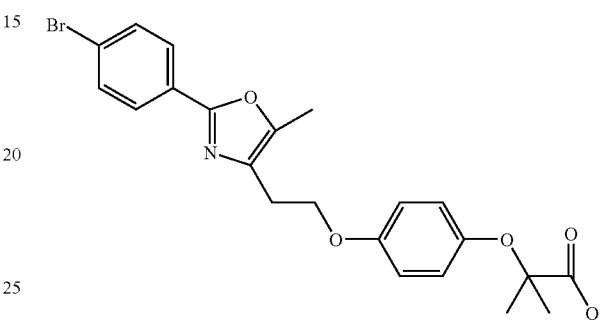

Step A 2-(4-Bromophenyl)-4,5-dimethyloxazole-3-oxide

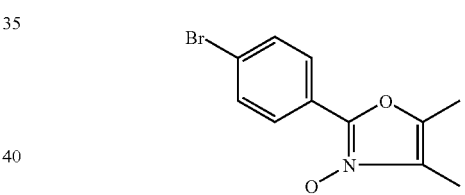

A solution of 2,3-butanedione monooxime (50 g, 0.49 mol) and 4-bromobenzaldehyde (101 g, 0.54 mol) in acetic acid (500 mL) was cooled to 0° C. and then gaseous HCl was bubbled through the solution for 35 min while the reaction was stirred in an ice bath. Diethyl ether (500 mL) was then added to the reaction to precipitate the product and the resultant slurry stirred 45 min at 0° C. before being filtered. The solids were rinsed with Et$_2$O (50 mL), taken up in water (1 L) and conc. NH$_4$OH (60 mL) added to the slurry. This mixture was extracted with CHCl$_3$, the organic layer was dried (MgSO$_4$), and the solvent removed in vacuo to give 97.4 g (74%) of 2-(4-bromophenyl)-4,5-dimethyloxazole-3-oxide as a white solid. The compound should be used directly with 24-48 h: $^1$H NMR (500 MHz, CDCl$_3$) δ 8.34 (d, J=9.0 Hz, 2H), 7.61 (d, J=9.0 Hz, 2H), 2.35 (s, 3H), 2.20 (s, 3H); $^{13}$C (125 MHz, CDCl$_3$) δ 142.1, 131.9, 129.5, 126.3, 124.1, 122.2, 11.1, 6.2; IR (KBr) 1685, 1529, 1418, 1377, 1233, 1165 cm$^{-1}$; UV (EtOH) λ$_{max}$ 307 nm (ε 24371); HRMS (TOF) m/z calc'd for C$_{11}$H$_{11}$$^{79}$BrNO$_2$: 267.997, found 267.9951.

Using 3-bromobenzaldehyde, 2-thiophenecarboxaldehyde, and 4-benzyloxybenzaldehyde, respectively, the following compounds were prepared by the same procedure:

2-(3-Bromophenyl)-4,5-dimethyloxazole-3-oxide:

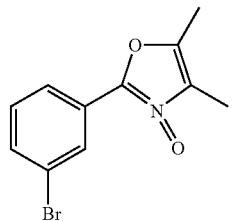

¹H NMR (300 MHz, CDCl₃) δ 8.06 (s, 1H), δ 8.40 (d, J=8.0 Hz, 1H), 7.55 (d, J=8.0 Hz, 1H), 7.38 (d, J=8.0 Hz, 1H), 2.39 (s, 3H), 2.20 (s, 3H).

2-(4-Benzyloxy-phenyl)-4,5-dimethyl-oxazole-N-oxide:

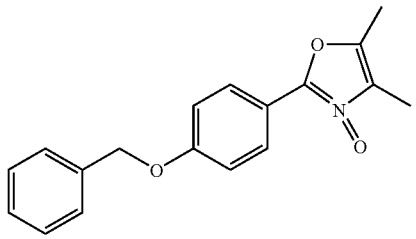

¹H NMR (500 MHz, CDCl₃) δ 8.40-8.38 (m, 2H), 7.40-7.29 (m, 5H), 7.05-7.02 (m, 2H), 5.07 (s, 2H), 2.29 (s, 3H), 2.16 (s, 3H).

Step B 2-(4-Bromophenyl)-4-(chloromethyl)-5-methyloxazole

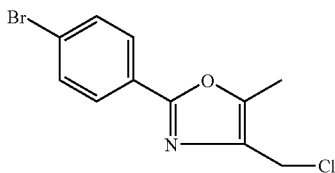

A solution of 2-(4-bromophenyl)-4,5-dimethyl-oxazole-3-oxide

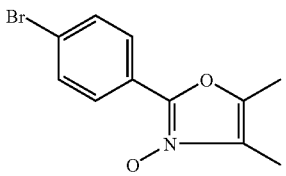

(96.6 g, 0.36 mol) in CHCl₃ (0.90 L) was treated dropwise with phosphorous oxychloride (61.1 g, 0.40 mol) allowing the reaction to exotherm and then stir at reflux for 30 min. The reaction was then cooled to rt and washed with water (2×1 L). The combined aqueous washes were back extracted with CH₂Cl₂ (2×400 mL). The organic layers were dried (MgSO₄), and the solvent removed in vacuo to give crude product that was recrystallized from hot hexanes (300 mL), decanting the hot supernate away from a dark oily material. The remaining dark oil was agitated in additional hot hexanes (200 mL) and the combined supernates were cooled to 0° C. to crystallize the product which was isolated by filtration to give 74.2 g (72%) of 2-(4-bromophenyl)-4-(chloromethyl)-5-methyloxazole as a lime-green powder: Rf=0.39 in 20% EtOAc/hexanes; ¹H NMR (500 MHz, CDCl₃) δ 7.88-7.86 (m, 2H), 7.59-7.56 (m, 2H), 4.54 (s, 2H), 2.42 (s, 3H); ¹³C (125 MHz, CDCl₃) δ 159.2, 146.9, 133.2, 132.0, 127.6, 126.1, 124.7, 37.1, 11.5; IR (KBr) 2970, 1633, 1599, 1481, 1401, 1258, 1117, 1008 cm⁻¹; UV (EtOH) λ$_{max}$ 281 nm (ε 21349); HRMS (FAB) m/z calc'd for C₁₁H₁₀⁷⁹BrClNO: 285.9634, found 285.9641. Anal. Calc'd for C₁₁H₉ClBrNO: C, 46.11; H, 3.17; N, 4.89; Cl, 12.37; Br, 27.88. Found: C, 46.28; H, 3.07; N, 4.81; Cl, 12.36; Br, 27.88.

The following compounds were also prepared by this procedure:

2-(3-Bromophenyl)-4-(chloromethyl)-5-methyloxazole:

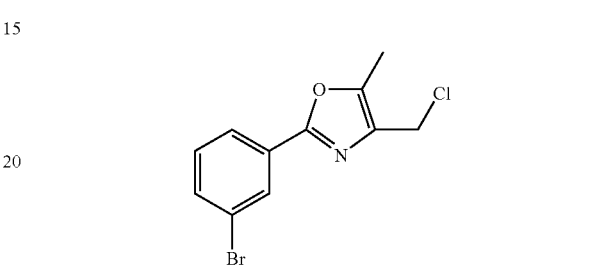

¹H NMR (300 MHz, d₆-DMSO) δ 8.19 (s, 1H), 7.93 (d, J=8.0, 1H), 7.58 (d, J=8.0 Hz, 1H), 7.35 (t, J=8.0 Hz, 1H), 4.45 (s, 2H), 2.41 (s, 3H).

2-(4-Benzyloxy-phenyl)-4-chloromethyl-5-methyl-oxazole

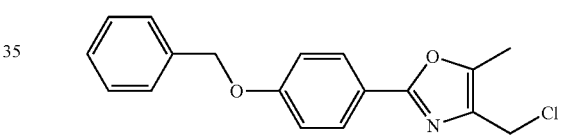

¹H NMR (500 MHz, CDCl₃) δ 7.92-7.90 (m, 2H), 7.42-7.31 (m, 5H), 7.00-6.98 (m, 2H), 5.08 (s, 2H), 4.51 (s, 2H), 2.37 (s, 3H); ¹³C (125 MHz, CDCl₃) δ 160.6, 145.9, 136.5, 132.5, 128.9, 128.5, 128.1, 127.9, 127.5, 120.1, 115.1, 70.1, 37.2, 11.2; IR (CHCl₃) 1637, 1611, 1499, 1454, 1246, 1168, 1010, 1004, 836, 750, 696 cm⁻¹; UV (EtOH) λ$_{max}$ 2825 nm (ε 32622); HRMS (ES⁺) m/z exact mass calcd for C₁₈H₁₇NO₂Cl 314.0948, found 314.0939. Anal. Calc'd for C₁₆H₁₆NO₂Cl: C, 68.90; H, 5.14; N, 4.46; Cl, 11.30. Found: C, 68.70; H, 5.00; N, 3.97; Cl, 11.32.

Step C 2-(4-Bromophenyl)-5-methyl-4-oxazoleacetic acid

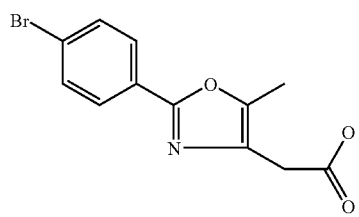

To a solution of 2-(4-bromophenyl)-4-(chloromethyl)-5-methyloxazole

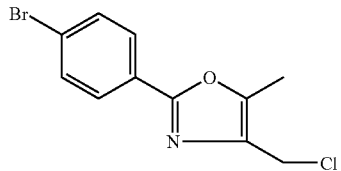

(64.8 g, 0.23 mol) in DMF (400 mL) was added powdered potassium cyanide (22.1 g, 0.34 mol) and potassium iodide (28.6 g, 0.17 mol) and the resultant mixture heated to 85° C. for 3.5 h. The reaction mixture was then cooled to rt. Potassium carbonate (5 g) was dissolved in water (800 mL) and added dropwise to the reaction to precipitate the product (stir vigorously 15 min following addition) which was isolated by filtration and washed with water (2×400 mL). The crude [2-(4-bromophenyl)-5-methyloxazole-4-yl]-acetonitrile was carried on as is in the next step without purification. $^1$H NMR (300 MHz, CDCl$_3$) δ 7.85 (m, 2H), 7.58 (m, 2H), 3.64 (s, 2H), 2.43 (s, 3H).

The crude [2-(4-bromophenyl)-5-methyloxazole-4-yl]-acetonitrile

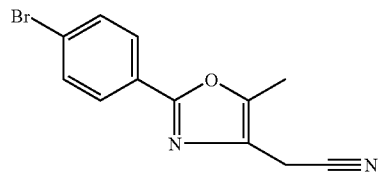

(assume 0.22 mol) was combined with 2-methoxyethanol (630 mL) and 85% solid KOH (74.6 g, 1.33 mol) in water (360 mL) was added to the reaction. The mixture was heated to reflux for 3 h, cooled, quenched with 2 M HCl (500 mL), and extracted with CH$_2$Cl$_2$. The organic layer was dried (MgSO$_4$), and the solvent removed in vacuo, using toluene to azeotropically remove residual 2-methoxyethanol. The crude product (57.3 g) was recrystallized from toluene (450 mL) to give 39.8 g (60%) of 2-(4-bromophenyl)-5-methyl-4-oxazoleacetic acid as an off-white powder: Rf=0.23 in 10% MeOH/CH$_2$Cl$_2$; $^1$H NMR (500 MHz, CDCl$_3$) δ 9.00 (br s, 1H), 7.85-7.83 (m, 2H), 7.58-7.56 (m, 2H), 3.62 (s, 2H), 2.36 (s, 3H); $^{13}$C (125 MHz, CDCl$_3$) δ 173.8, 159.0, 146.2, 132.0, 129.1, 127.6, 125.9, 124.7, 31.5, 10.2; IR (CHCl$_3$) 2923, 1699, 1641, 1481, 1428, 1306, 1234, 1010, 829, 727 cm$^{-1}$.

The following compounds were prepared by the same procedure.

[2-(3-Bromophenyl)-5-methyloxazole-4-yl]-acetonitrile

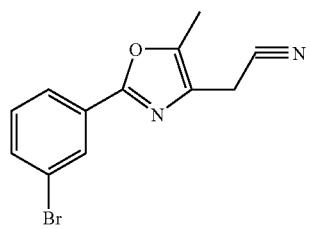

$^1$H NMR (300 MHz, d$_6$-DMSO) δ 8.00 (t, J=1.83 Hz, 1H), 7.90 (dt, J=8.2, 1.2 Hz, 1H), 7.70 (ddd, J=8.0, 1.8, 1.2 Hz, 1H), 7.48 (t, J=7.9 Hz, 1H), 4.01 (s, 2H), 2.41 (s, 3H).

2-(3-Bromophenyl)-5-methyl-4-oxazoleacetic acid

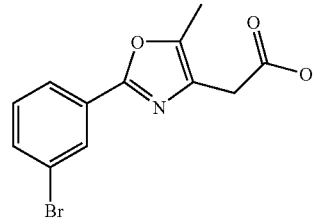

$^1$H NMR (300 MHz, d$_6$-DMSO) δ 7.99 (t, J=1.83 Hz, 1H), 7.88 (dt, J=8.1, 1.5 Hz, 1H), 7.65 (ddd, J=8.1, 1.8, 1.5 Hz, 1H), 7.45 (t, J=8.1 Hz, 1H), 3.50 (s, 2H), 2.35 (s, 3H).

(5-Methyl-2-thiophen-2-yl-oxazol-4-yl)-acetonitrile. mp 82-84° C.; $^1$H NMR (500 MHz, CDCl$_3$) δ 7.60 (m, 1H), 7.40 (m, 1H), 7.08 (m, 1H), 3.60 (s, 2H) 2.40 (s, 3H).

(5-Methyl-2-thiophen-2-yl-4-oxazoleacetic acid. mp 185° C.; $^1$H NMR (500 MHz, CDCl$_3$) δ 7.65 (m, 1H), 7.40 (m, 1H), 7.08 (m, 1H), 3.60 (s, 2H), 2.31 (s, 3H). [2-(4-Benzyloxyphenyl)-5-methyl-oxazol-4-yl]-acetic acid

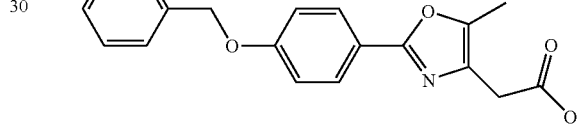

$^1$H NMR (500 MHz, CDCl$_3$) δ 7.91 (d, 2H, J=8.21 Hz), 7.45-7.27 (m, 5H), 7.03 (d, 2H, J=8.21 Hz), 5.11 (s, 2H), 3.60 (s, 3H), 2.34 (s, 3H); $^{13}$C (125 MHz, CDCl$_3$) δ 171.5, 159.8, 158.2, 144.9, 136.6, 129.9, 128.4, 127.9, 127.7, 127.1, 119.9, 115.2, 69.4, 31.6, 9.7; IR (CHCl$_3$) 1711, 1611, 1501, 1293, 1257, 1216, 834, 742 cm$^{-1}$; UV (EtOH) λ$_{max}$ 285 nm (ε 25018); HRMS (ES$^+$) m/z exact mass calcd for C$_{19}$H$_{18}$NO$_4$ 324.1236, found 324.1265; Anal. Calc'd for C$_{19}$H$_{17}$NO$_4$: C, 70.58; H, 5.30; N, 4.33. Found: C, 69.69; H, 5.26; N, 4.34

Step D 2-(4-Bromophenyl)-5-methyl-4-oxazoleethanol

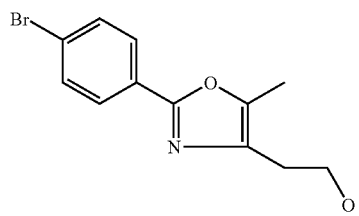

A solution of 2-(4-bromophenyl)-5-methyl-4-oxazoleacetic acid (39.1 g, 0.13 mol) in dry THF (175 mL) was treated dropwise with borane-THF complex (227 mL of a 1.0 M solution in THF, 1.3 mol) over 2 h (reaction temperature to 35° C.). After stirring 2 h at rt under N$_2$, the reaction was quenched with slow addition of methanol (60 mL) and stirred overnight at rt. The reaction was diluted with 1 N NaOH (50 mL) and extracted with $CH_2Cl_2$ (2×200 mL). The organic layer was washed with $H_2O$ (3×100 mL), dried ($MgSO_4$), and the solvent removed in vacuo to give 38.7 g of crude product that was recrystallized from toluene (200 mL, wash solid with cold hexanes) to give 26.9 g (72%) of 2-(4-bromophenyl)-5-methyl-4-oxazoleethanol as a white powder: Rf=0.37 in 10% $MeOH/CH_2Cl_2$; $^1H$ NMR (500 MHz, $CDCl_3$) δ 7.84-7.82 (m, 2H), 7.57-7.55 (m, 2H), 3.91 (q, J=5.5 Hz, 2H), 3.14 (t, J=6.0 Hz, OH), 2.72 (t, J=5.5 Hz, 2H), 2.33 (s, 3H); $^{13}C$ (125 MHz, $CDCl_3$) δ 158.7, 144.5, 134.2, 131.9, 127.4, 126.4, 124.3, 61.8, 28.1, 10.1; IR (KBr) 3293, 2948, 1642, 15985, 1480, 1472, 1401, 1053, 1003, 836, 734 $cm^{-1}$; Anal. Calc'd for $C_{12}H_{12}BrNO_2$: C, 51.09; H, 4.29; N, 4.96; Br, 28.32. Found: C, 51.31; H 4.06; N, 4.90; Br, 28.19.

The following compounds were prepared by the same procedure.

2-(3-Bromophenyl)-5-methyl-4-oxazoleethanol

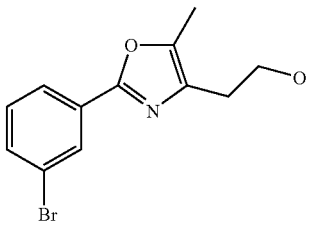

mp 92-93° C.; $^1H$ NMR (300 MHz, $d_6$-DMSO) δ 7.99 (s, 1H), 7.88 (d, J=7.7 Hz, 1H), 7.64 (d, J=7.7 Hz, 1H), 7.44 (t, J=7.7 Hz, 1H), 4.61 (t, J=5.5 Hz, OH), 3.63 (q, J=5.5 Hz, 2H), 2.60 (t, J=6.6 Hz, 2H), 2.32 (s, 3H).

2-(5-Methyl-2-thiophen-2-yl-4-oxazoleethanol

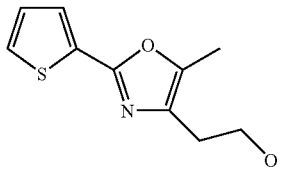

mp 71° C.; $^1H$ NMR (500 MHz, $CDCl_3$): δ 7.54 (m, 1H), 7.33 (m, 1H), 7.03 (m, 1H), 3.87 (t, J=5.8 Hz, 2H), 3.5 (s, 1H), 2.67 (t, J=5.8 Hz, 2H), 2.25 (s, 3H).

2-[2-(4-Benzyloxy-phenyl)-5-methyl-oxazol-4-yl]-ethanol

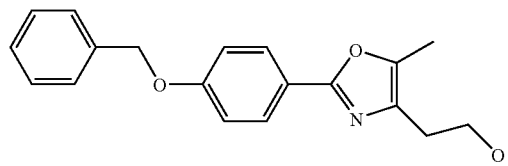

$^1H$ NMR (500 MHz, $CDCl_3$) δ 7.91 (d, 2H, J=8.60 Hz), 7.45-34 (m, 5H), 7.02 (d, 2H, J=8.60 Hz), 5.11 (s, 2H), 3.91 (t, 2H, J=5.7 Hz), 2.71 (t, 2H, J=5.7 Hz), 2.31 (s, 3H); MS ($ES^+$) Calc'd for $C_{19}H_{20}NO_3$: Found m/e 310 (M+1, 100%)

Step E

Toluene-4-sulfonic acid 2-[2-(4-bromophenyl)-5-methyloxazol-4-yl]ethyl ester

To a solution of 2-(4-bromophenyl)-5-methyl-4-oxazoleethanol

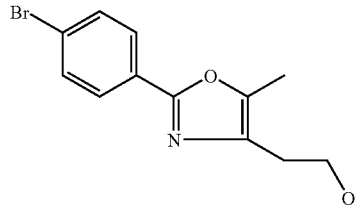

(8.89 g, 31.5 mmol) in $CH_2Cl_2$ (150 mL) at rt under $N_2$ was added pyridine (8.74 g, 110 mmol, 8.9 mL) and DMAP (0.97 g, 7.88 mmol) followed by portionwise addition of tosyl anhydride (12.7 g, 37.8 mmol). The reaction exothermed to 32° C. and was stirred 1 h before 1N HCl (200 mL) was added. The mixture was stirred vigorously 15 min, and then the organic phase was dried ($MgSO_4$) and filtered through a pad of silica gel (200 mL, packed with $CH_2Cl_2$). After rinsing the silica gel with EtOAc (100 mL) the solution was concentrated to toluene-4-sulfonic acid 2-[2-(4-bromophenyl)-5-methyloxazol-4-yl]ethyl ester which was used without further purification (mp 136° C.).

Using the corresponding alcohols, the following compounds were prepared by the same procedure:

Toluene-4-sulfonic acid 2-[2-(3-bromophenyl)-5-methyloxazol-4-yl]ethyl ester.

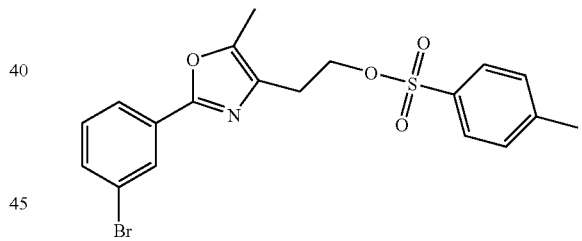

$^1H$ NMR (300 MHz, $CDCl_3$) δ 7.99 (s, 1H), 7.80 (d, J=8.0 Hz, 1H), 7.64 (d, J=8.0 Hz, 1H), 7.51 (d, J=9.0 Hz, 1H), 7.30 (t, J=8.0 Hz, 1H), 7.20 (d, J=9.0 Hz, 1H), 4.30 (t, J=7.0 Hz, 2H), 2.80 (t, J=7.0 Hz, 2H), 2.30 (s, 3H), 2.23 (s, 3H).

Toluene-4-sulfonic acid 2-(5-methyl-2-thiophen-2-yloxazol-4-yl)ethyl ester.

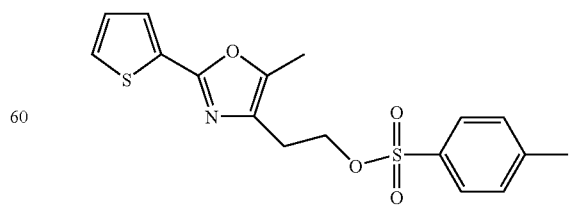

mp 107-109° C.; $^1H$ NMR (400 MHz, $CDCl_3$): δ 7.67 (d, J=8.3 Hz, 2H), 7.51 (dd, J=3.8, 1.4 Hz, 1H), 7.37 (dd, J=4.9, 1.2 Hz, 1H), 7.21 (d, J=7.9 Hz, 2H), 7.08 (dd, J=4.8, 3.5 Hz, 1H), 4.28 (t, J=6.3 Hz, 2H), 2.80 (t, J=6.3 Hz, 2H), 2.28 (s, 3H), 2.26 (s, 3H).

Toluene-4-sulfonic acid 2-[2-(4-benzyloxy-phenyl)-5-methyl-oxazol-4-yl]-ethyl ester. $^1$H NMR (500 MHz, CDCl$_3$) δ 7.80-7.78 (m, 2H), 7.67-7.65 (m, 2H), 7.45-7.34 (m, 5H), 7.25-7.17 (m, 2H), 7.02-6.99 (m, 2H), 5.12 (s, 2H), 4.29 (t, 2H, J=6.45 Hz), 2.80 (t, 2H, J=6.45 Hz), 2.27 (s, 3H), 2.22 (s, 3H); $^{13}$C (125 MHz, CDCl$_3$) δ 160.25, 144.8, 144.6, 136.5, 132.8, 130.6, 130.2, 129.6, 128.6, 128.1, 127.8, 127.6, 127.4, 127.0, 115.1, 70.1, 68.9, 25.9, 21.4, 10.0; IR (KBr) 1645, 1613, 1499, 1351, 1248, 1190, 1173, 900, 665, 556 cm$^{-1}$; UV (EtOH) $\lambda_{max}$ 286 nm (ε 22658); HRMS (ES$^+$) m/z exact mass calcd for C$_{26}$H$_{26}$NO$_5$S 464.1532, found 464.1531. Anal. Calc'd for C$_{26}$H$_{25}$NO$_5$S: C, 67.37; H, 5.44; N, 3.02. Found: C, 66.59; H, 5.33; N, 3.06.

Step F 2-(4-{2-[2-(4-Bromophenyl)-5-methyloxazol-4-yl]ethoxy}phenoxy)-2-methylpropionic acid ethyl ester

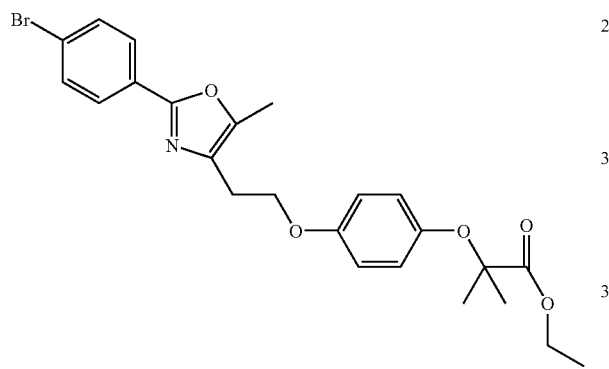

A mixture of toluene-4-sulfonic acid 2-[2-(4-bromophenyl)-5-methyloxazol-4-yl]ethyl ester (prepared as described in E above), 2-(4-hydroxyphenoxy)-2-methylpropanoic acid ethyl ester (American Home Products U.S. Pat. No. 3,795,691) (7.06 g, 31.5 mmol) and Cs$_2$CO$_3$ (13.3 g, 41.0 mmol) was heated at 55° C. in DMF (45 mL) for 18 h. The reaction was partitioned between EtOAc (250 mL) and H$_2$O (250 mL), and the aqueous phase extracted with EtOAc (2×100 mL). The combined organic phases were dried (MgSO$_4$) and concentrated under reduced pressure to an oil which was purified by column chromatography (1500 mL SiO$_2$, hexanes to 10% EtOAc/hexanes) to provide 2-(4-{2-[2-(4-Bromophenyl)-5-methyloxazol-4-yl]ethoxy}phenoxy)-2-methyl propionic acid ethyl ester (6.81 g, 44%) as a off-white solid: Rf=0.48 in 35% EtOAc/hexanes; mp 78-79° C.; $^1$H NMR (300 MHz, CDCl$_3$) δ 7.85-7.82 (m, 2H), 7.57-7.53 (m, 2H), 6.83-6.75 (m, 4H), 4.22 (q, J=7.0 Hz, 2H), 4.18 (t, J=6.6 Hz, 2H), 2.94 (t, J=6.7 Hz, 2H), 2.36 (s, 3H), 1.52 (s, 6H), 1.27 (t, J=7.0 Hz, 3H) and by-product 2-(4-Bromophenyl)-5-methyl-4-vinyloxazole (1.81 g, 22%) as a white solid: $^1$H NMR (300 MHz, CDCl$_3$) δ 7.92-7.87 (m, 2H), 7.58-7.55 (m, 2H), 6.54 (dd, J=17.3, 10.8 Hz, 1H), 5.94 (dd, J=17.0, 1.8 Hz, 1H), 5.30 (dd, J=10.8, 1.8 Hz, 1H), 2.41 (s, 3H).

The following compounds were prepared by the same procedure using toluene-4-sulfonic acid 2-[2-(3-bromophenyl)-5-methyloxazol-4-yl]ethyl ester and toluene-4-sulfonic acid 2-[2-(4-benzyloxy-phenyl)-5-methyl-oxazol-4-yl]-ethyl ester, respectively:

2-(4-{2-[2-(3-Bromophenyl)-5-methyloxazol-4-yl]ethoxy}phenoxy)-2-methyl-propionic acid ethyl ester

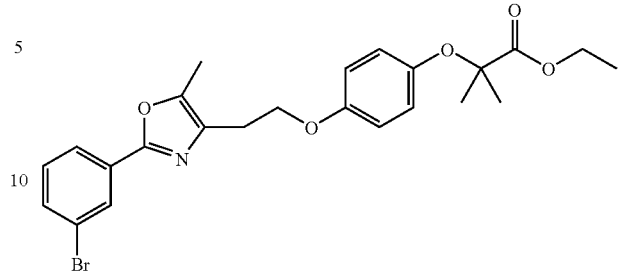

Rf=0.39 in 1:4 EtOAc:hexanes; $^1$H NMR (400 MHz, CDCl$_3$) δ 8.11 (t, J=1.6 Hz, 1H), 7.89-7.86 (m, 1H), 7.49 (ddd, J=8.0, 2.0, 1.2 Hz, 1H), 7.27 (t, J=8.0 Hz, 1H), 6.80-6.72 (m, 4H), 4.20 (q, J=7.2 Hz, 2H), 4.15 (t, J=6.6 Hz, 2H), 2.92 (t, J=6.6 Hz, 2H), 2.34 (s, 3H), 1.49 (s, 6H), 1.24 (t, J=7.2 Hz, 3H); MS (EI) 510.1 (M+Na)$^+$, 488.1 (M+H)$^-$.

2-Methyl-2-{4-[2-(5-methyl-2-thiophen-2-yl-oxazol-4-yl)ethoxy]phenoxy}propionic acid ethyl ester. MS (ES) m/e 416.2 (M+1).

2-(4-{2-[2-(4-Benzyloxy-phenyl)-5-methyl-oxazol-4-yl]ethoxy}-phenoxy)-2-methyl-propionic acid ethyl ester

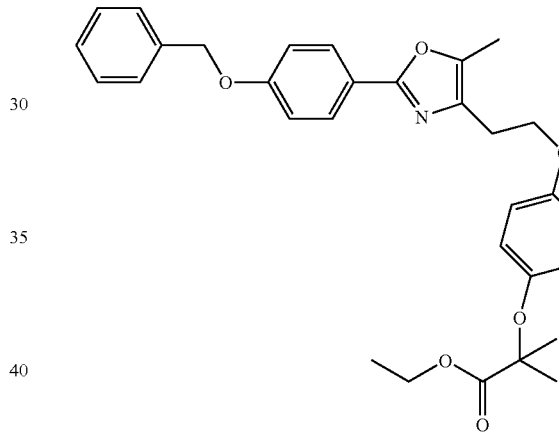

$^1$H NMR (500 MHz, CDCl$_3$) δ 7.91 (d, 2H, J=8.60 Hz), 7.45-7.33 (m, 5H), 7.01 (d, 2H, J=9.0 Hz), 6.83-6.69 (m, 4H), 5.10 (s, 2H), 4.25-4.09 (m, 4H), 2.94 (t, 2H, J=6.65 Hz), 2.34 (s, 3H), 1.52 (s, 6H), 1.29 (t, 3H, J=9.2 Hz); $^{13}$C (125 MHz, CDCl$_3$) δ 174.3, 160.3, 159.5, 154.4, 148.9, 144.5, 136.5, 132.1, 128.6, 128.1, 127.7, 127.5, 121.9, 121.6, 115.7, 115.1, 114.9, 79.7, 70.1, 67.0, 61.2, 26.3, 25.3, 14.1, 10.1; IR (KBr) 2987, 2874, 1729, 1614, 1505, 1287, 1245, 1228, 1171, 1142, 1022, 838 cm$^{-1}$; UV (EtOH) $\lambda_{max}$ 286 nm (ε 24476); HRMS (ES$^+$) m/z exact mass calcd for C$_{31}$H$_{34}$NO$_6$ 516.2386, found 516.2362. Anal. Calc'd for C$_{31}$H$_{33}$NO$_6$: C, 72.21; H, 6.45; N, 2.71. Found: C, 71.90; H, 6.62; N, 2.51.

Step G 2-(4-{2-[2-(4-Bromophenyl)-5-methyloxazol-4-yl]ethoxy}phenoxy)-2-methylpropionic acid 2-(4-{2-[2-(4-Bromophenyl)-5-methyloxazol-4-yl]ethoxy}phenoxy)-2-methylpropionic acid ethyl ester was hydrolyzed as described in Example 1 to provided the product: $^1$H NMR (300 MHz, CDCl$_3$) δ 7.85-7.82 (m, 2H), 7.57-7.53 (m, 2H), 6.83-6.75 (m, 4H), 4.18 (t, J=6.6 Hz, 2H), 2.94 (t, J=6.7 Hz, 2H), 2.36 (s, 3H), 1.52 (s, 6H).

The following compounds were hydrolyzed by the same procedure:

Example 9A 2-(4-{2-[2-(3-Bromophenyl)-5-methyloxazol-4-yl]ethoxy}phenoxy)-2-methylpropionic acid

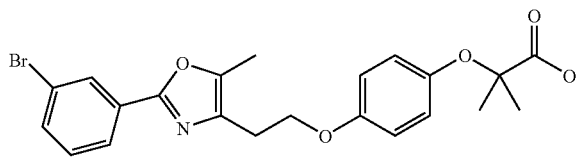

mp 158-159° C.; Rf=0.1 in 6:4 EtOAc:hexanes; $^1$H NMR (400 MHz, CDCl$_3$) δ 8.10 (S, 1H), 7.88 (d, 1H), 7.47 (d, 1H) 7.31 (t, 1H), 6.86-6.76 (m, 4H), 4.17 (t, 2H), 2.97 (t, 2H), 2.35 (s, 3H), 1.46 (s, 6H); MS (EI) 461.0 (M+H)$^+$.

Example 9B 2-(4-{2-[2-(4-Benzyloxy-phenyl)-5-methyl-oxazol-4-yl]-ethoxy}-phenoxy)-2-methyl-propionic acid

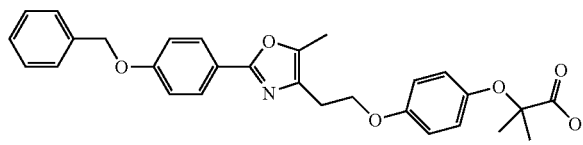

$^1$H NMR (500 MHz, CDCl$_3$) δ 7.94 (d, 2H, J=7.82 Hz), 7.44-7.34 (m, 5H), 7.01 (d, 2H, J=8.60 Hz), 6.90-6.84 (m, 2H), 6.80-6.74 (m, 2H), 5.10 (s, 2H), 4.19 (t, 2H, J=6.65 Hz), 2.934 (t, 2H, J=6.65 Hz), 2.37 (s, 3H), 1.52 (s, 6H); HRMS (ES$^+$) m/z exact mass calcd for C$_{29}$H$_{30}$NO$_6$ 488.2073, found 488.2058.

EXAMPLE 10

2-(4-{2-[2-(3-Ethynylphenyl)-5-methyloxazol-4-yl]ethoxy}phenoxy)-2-methylpropionic acid

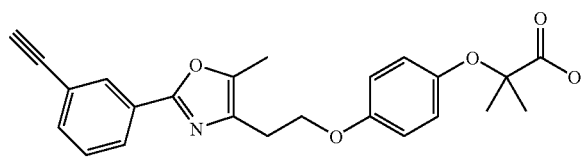

Step A 2-(4-{2-[2-(3-Ethynylphenyl)-5-methyloxazol-4-yl]ethoxy}phenoxy)-2-methylpropionic acid ethyl ester

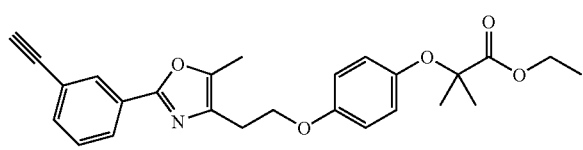

A solution of 2-(4-{2-[2-(3-bromophenyl)-5-methyloxazol-4-yl]ethoxy}-phenoxy)-2-methylpropionic acid ethyl ester (780 mg, 1.6 mmol), tributyl-(ethynyl)stannane (1.02 g, 3.2 mmol, 0.934 mL), and Pd(PPh$_3$)$_4$ (92 mg, 0.08 mmol) in THF (80 mL) was heated at reflux for 18 h. The reaction mixture was cooled to rt, concentrated to a dark green paste, and filtered through a plug of silica gel (50 g, 1:4 EtOAc:hexanes). The material was further purified by two iterations of column chromatography (40 g SiO$_2$, 1:4 EtOAc:hexanes) to provide the product (550.6 mg, 79%) as a faintly green oil: Rf=0.30 in 1:4 EtOAc:hexanes; $^1$H NMR (400 MHz, CDCl$_3$) δ 8.08 (s, 1H), 7.92 (d, 1H), 7.44 (d, 1H), 7.36 (t, 1H), 6.81-6.72 (m, 4H), 4.22-4.12 (m, 4H), 3.09 (s, 1H), 2.91 (t, 2H), 2.32 (s, 3H), 1.44 (s, 6H), 1.22 (t, 3H); MS (EI) 456.2 (M+Na)$^+$, 434.2 (M+H)$^+$.

Using tributyl(vinyl)tin and tributyl(phenylethynyl)tin, respectively, the following compounds were prepared by the same procedure:

2-Methyl-2-(4-{2-[5-methyl-2-(3-vinylphenyl)oxazol-4-yl]ethoxy}phenoxy)propionic acid ethyl ester

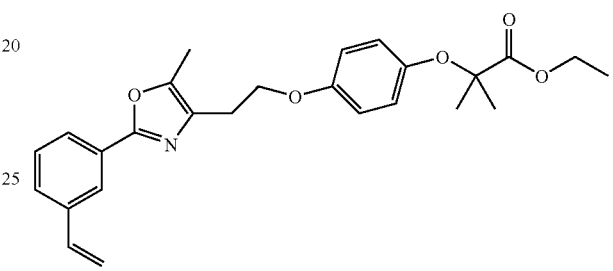

Rf=0.29 in 1:4 EtOAc:hexanes; $^1$H NMR (400 MHz, CDCl$_3$) δ 7.99 (s, 1H), 7.85-7.81 (m, 1H), 7.50-7.34 (m, 3H), 6.80-6.69 (m, 4H), 5.82 (d, 1H), 5.28 (d, 1H), 4.22-4.10 (m, 4H), 2.92 (t, 2H), 2.33 (s, 3H), 1.44 (s, 6H), 1.24 (t, 3H); MS (EI) 436.2 (M+H)$^+$.

2-Methyl-2-(4-{2-[5-methyl-2-(3-phenylethynylphenyl)oxazol-4-yl]ethoxy}phenoxy)propionic acid ethyl ester

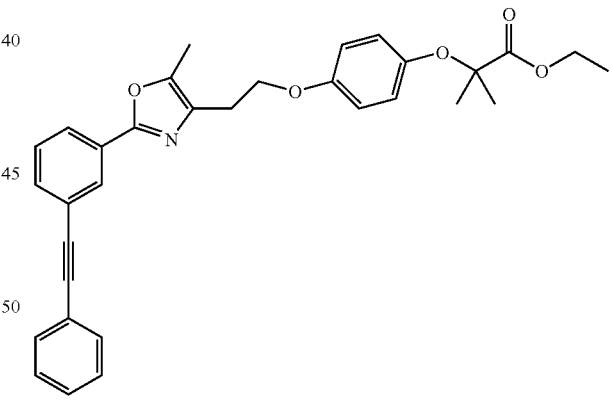

Rf=0.46 in 1:4 EtOAc:hexanes; $^1$H NMR (400 MHz, CDCl$_3$) δ 8.14 (s, 1H), 7.90 (d, 1H), 7.53-7.49 (m, 3H), 7.40-7.28 (m, 4H), 6.81-6.72 (m, 4H), 4.21-4.14 (m, 4H), 2.93 (t, 2H), 2.32 (s, 3H), 1.48 (s, 6H), 1.23 (t, 3H); MS (EI) 532.2 (M+Na)$^+$, 510.2 (M+H)$^+$.

Step B 2-(4-{2-[2-(3-Ethynylphenyl)-5-methyloxazol-4-yl]ethoxy}phenoxy)-2-methyl propionic acid 2-(4-{2-[2-(3-Ethynylphenyl)-5-methyloxazol-4-yl]ethoxy}phenoxy)-2-methyl propionic acid ethyl ester (94.7 mg, 0.218 mmol) was hydrolyzed according to the procedure in Example 2, Step D to provide the product (67.2 mg, 76%) as a white solid: Rf=0.10 in 6:4 EtOAc:hexanes; mp=131-134° C.; $^1$H NMR (400 MHz, CDCl$_3$) δ 8.09 (s, 1H), 7.93 (d, 1H), 7.44 (d, 1H), 7.36 (t, 1H), 6.83-6.74 (m, 4H), 4.18 (t, 2H), 3.07 (s, 1H), 2.96 (t, 2H), 2.35 (s, 3H), 1.46 (s, 6H); MS (EI) 428.1 (M+Na)$^+$, 406.2 (M+H)$^+$.

The corresponding esters were hydrolyzed according to the aforementioned procedure:

Example 10A

2-Methyl-2-(4-{2-[5-methyl-2-(3-vinylphenyl)oxazol-4-yl]ethoxy}phenoxy)propionic acid

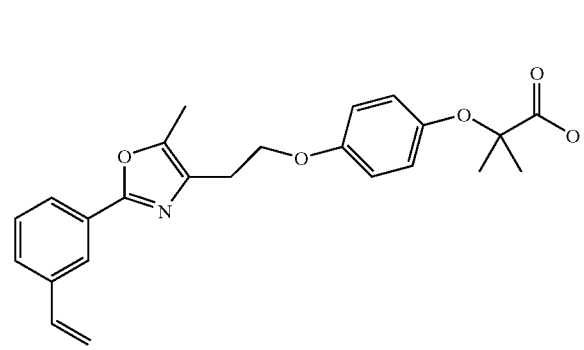

Rf=0.19 in 6:4 EtOAc:hexanes; mp=137-139° C.; $^1$H NMR (400 MHz, CDCl$_3$) δ 7.98 (s, 1H), 7.86-7.80 (m, 1H), 7.46-7.38 (m, 3H), 6.88-6.77 (m, 4H), 5.82 (d, 1H), 5.24 (d, 1H), 4.18 (t, 2H), 2.96 (t, 2H), 2.38 (s, 3H), 1.42 (s, 6H); MS (EI) 430.2 (M+Na)$^+$, 408.2 (M+H)$^+$.

Example 10B

2-Methyl-2-(4-{2-[5-methyl-2-(3-phenylethynylphenyl)oxazol-4-yl]ethoxy}phenoxy)propionic acid

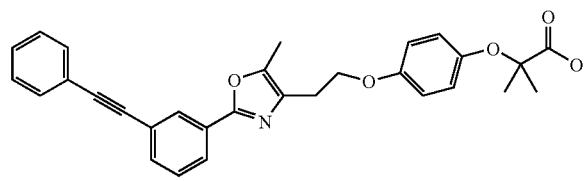

Rf=0.15 in 6:4 EtOAc:hexanes; $^1$H NMR (400 MHz, CDCl$_3$) δ 8.13 (s, 1H), 7.90 (d, J=8.0 Hz, 1H), 7.55-7.43 (m, 3H), 7.39 (t, J=8.0 Hz, 1H), 7.35-7.31 (m, 3H), 6.89-6.76 (m, 4H), 4.15 (t, J=6.6 Hz, 2H), 2.96 (t, J=6.6 Hz, 2H), 2.36 (s, 3H), 1.49 (s, 6H); MS (EI) 504.1 (M+Na)$^+$, 482.1 (M+H)$^+$.

EXAMPLE 11

2-(4-{2-[2-(4-Ethynylphenyl)-5-methyloxazol-4-yl]ethoxy}phenoxy)-2-methylpropionic acid

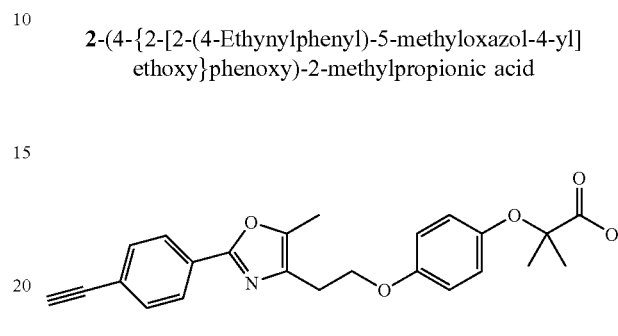

Step A 2-(4-{2-[2-(4-Ethynylphenyl)-5-methyloxazol-4-yl]ethoxy}phenoxy)-2-methylpropionic acid ethyl ester

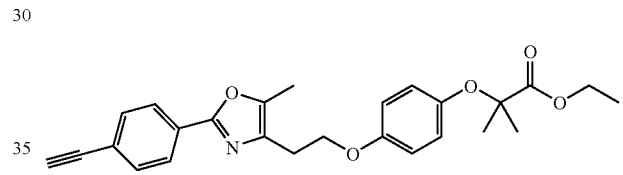

2-(4-{2-[2-(4-Bromophenyl)-5-methyloxazol-4-yl]ethoxy}phenoxy)-2-methyl-propionic acid ethyl ester (298 mg, 0.610 mmol) was coupled with tributyl(ethynyl)stannane according to the procedure in Example 10 Step A, to provide the product (224.6 mg, 49%) as an off-white solid: Rf=0.43 in 1:4 EtOAc:hexanes; $^1$H NMR (400 MHz, CDCl$_3$) δ 7.88 (d, 2H), 7.43 (d, 2H), 6.80-6.68 (m, 4H), 4.20-4.11 (m, 4H), 3.12 (s, 1H), 2.88 (t, 2H), 2.32 (s, 3H), 2.46 (s, 6H), 1.21 (t, 3H); MS (EI) 456.2 (M+Na)$^+$, 434.2 (M+H)$^+$.

The following compound was prepared by the same procedure, using tributyl(phenylethynyl)stannane:

2-Methyl-2-(4-{2-[5-methyl-2-(4-phenylethynylphenyl)oxazol-4-yl]ethoxy}-phenoxy)propionic acid ethyl ester

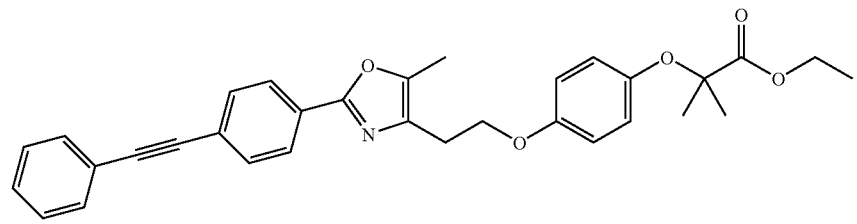

Rf=0.38 in 1:4 EtOAc:hexanes; ¹H NMR (400 MHz, CDCl₃) δ 7.93 (d, 2H), 7.56 (d, 2H) 7.48, (m, 2H), 7.33-7.32 (m, 3H) 6.81-6.74 (m, 4H), 4.21-4.15 (m, 4H), 2.93 (t, 2H), 2.34 (s, 3H), 1.53 (s, 6H), 1.24 (t, 3H); MS (EI) 532.2 (M+Na)⁺, 510.2 (M+H)⁺.

Step B 2-(4-{2-[2-(4-Ethynylphenyl)-5-methyloxazol-4-yl]ethoxy}phenoxy)-2-methylpropionic acid 2-(4-{2-[2-(4-Ethynylphenyl)-5-methyloxazol-4-yl]ethoxy}phenoxy)-2-methyl-propionic acid ethyl ester (53.2 mg, 0.123 mmol) was hydrolyzed according to the procedure in Example 2, Step D to provide the product (31.7 mg, 64%) as a white solid: Rf=0.11 in 6:4 EtOAc:hexanes; mp=137-139° C.; ¹H NMR (400 MHz, CDCl₃) δ 7.92 (d, 2H), 7.50 (d, 2H), 6.86-6.78 (m, 4H), 4.17 (t, 2H), 3.18 (s, 1H), 2.97 (t, 2H), 2.37 (s, 6H), 1.51 (s, 6H); MS (EI) 428.1 (M+Na)⁺, 406.1 (M+H)⁺.

The following compound was prepared by the same procedure:

Example 11A

2-Methyl-2-(4-{2-[5-methyl-2-(4-phenylethynylphenyl)oxazol-4-yl]ethoxy}-phenoxy)propionic acid

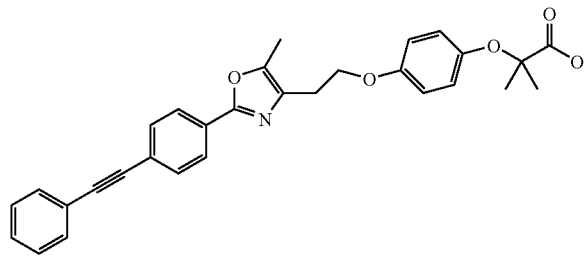

Rf=0.12 in 6:4 EtOAc:hexanes; MS (EI) 504.2 (M+Na)⁺, 482.2 (M+H)⁺.

EXAMPLE 12

2-(4-{2-[2-(3-Ethylphenyl)-5-methyloxazol-4-yl]ethoxy}phenoxy)-2-methylpropionic acid

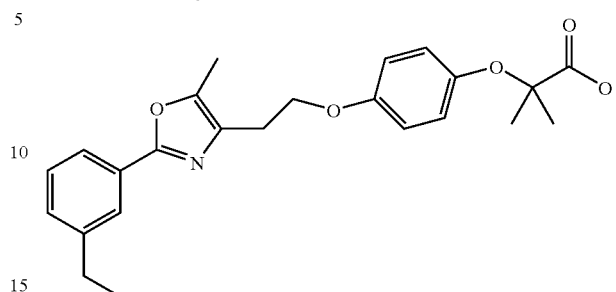

Step A 2-(4-{2-[2-(3-Ethylphenyl)-5-methyloxazol-4-yl]ethoxy}phenoxy)-2-methylpropionic acid ethyl ester

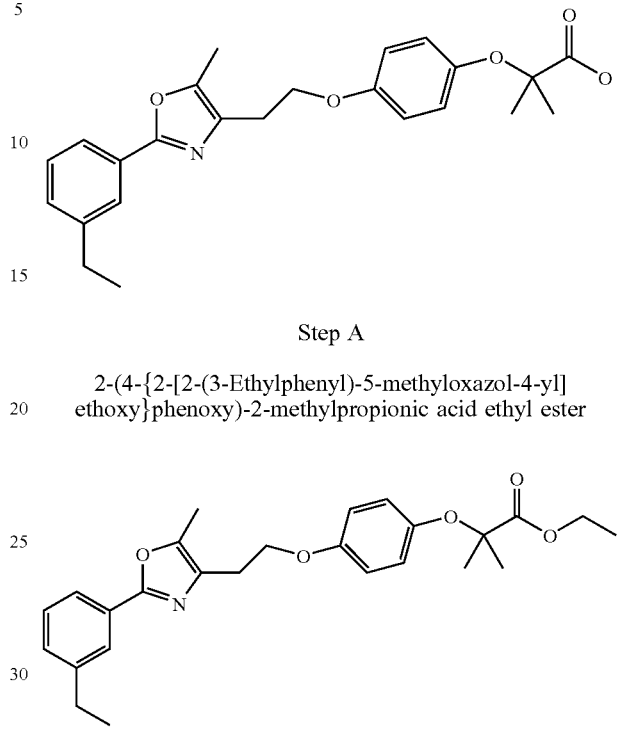

In a 250 mL thick-walled flask, a magnetically stirred solution of 2-(4-{2-[2-(3-ethynylphenyl)-5-methyloxazol-4-yl]ethoxy}phenoxy)-2-methylpropionic acid ethyl ester (4.72 g, 10.9 mmol) in EtOH:EtOAc (136 mL of a 9:1 solution) was purged with nitrogen (3×), then treated with 10% Pd/C (630 mg, 0.592 mmol Pd). The mixture was purged with H₂ (3×), followed by application of H₂ at 50 p.s.i. for 14 h. After a subsequent nitrogen purge (3×), the mixture was filtered through celite and concentrated to an oil, which was purified by column chromatography (350 g SiO₂, 1:9 EtOAc:hexanes to 1:4 EtOAc:hexanes) to provide the product (3.36 g, 70%) as a colorless oil: Rf=0.34 in 1:4 EtOAc:hexanes; ¹H NMR (400 MHz, CDCl₃) δ 7.81 (s, 1H), 7.76 (d, J=7.6 Hz, 1H), 7.31 (t, J=7.6 Hz, 1H), 7.21 (d, J=7.6 Hz, 1H), 6.80-6.73 (m, 4H), 4.20 (q, J=6.8 Hz, 2H), 4.16 (t, J=6.4 Hz, 2H), 2.93 (t, J=6.4 Hz, 2H), 2.67 (q, J=7.2 Hz, 2H), 2.34 (s, 3H), 1.49 (s, 6H), 1.26-1.23 (m, 6H); MS (EI) 460.2 (M+Na)⁺, 438.2 (M+H)⁺.

The following compound was prepared by the same procedure, using 2-methyl-2-(4-{2-[5-methyl-2-(3-phenylethynylphenyl)oxazol-4-yl]ethoxy}phenoxy)propionic acid ethyl ester:

2-Methyl-2-(4-{2-[5-methyl-2-(3-phenethylphenyl)oxazol-4-yl]ethoxy}phenoxy)-propionic acid ethyl ester

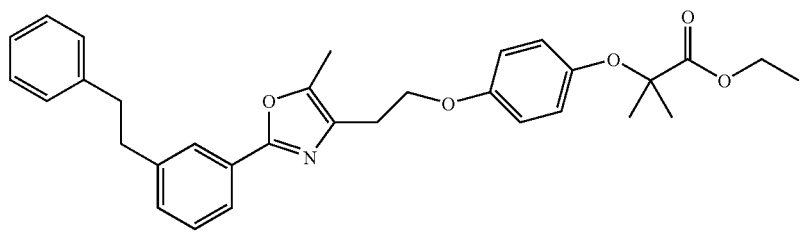

Rf=0.36 in 1:4 EtOAc:hexanes; $^1$H NMR (400 MHz, CDCl$_3$) δ 7.82 (s, 1H), 7.79 (d, 1H), 7.32-7.20 (m, 3H), 7.19-7.13 (m, 4H), 6.80-6.72 (m, 4H), 4.23-4.16 (m, 4H), 2.94-2.86 (m, 6H), 2.34 (s, 3H), 1.43 (s, 6H), 1.24-1.19 (m, 6H); MS (EI) 536.2 (M+Na)$^+$, 514.2 (M+H)$^+$.

Step B

2-(4-{2-[2-(3-Ethylphenyl)-5-methyloxazol-4-yl]ethoxy}phenoxy)-2-methylpropionic acid 2-(4-{2-[2-(3-Ethylphenyl)-5-methyloxazol-4-yl]ethoxy}phenoxy)-2-methyl-propionic acid ethyl ester (3.36 g, 7.86 mmol) was hydrolyzed according to the procedure in Example 2, Step D to provide the product (2.78 g, 89%) as a white solid: Rf=0.12 in 6:4 EtOAc:hexanes; mp=134-135° C.; $^1$H NMR (400 MHz, CDCl$_3$) δ 7.83 (s, 1H), 7.78 (d, J=8 Hz, 1H), 7.32 (t, J=8 Hz, 1H), 7.25 (d, J=8 Hz, 1H), 6.88-6.77 (m, 4H), 4.18 (t, J=6.8 Hz, 2H), 2.97 (t, J=6.8 Hz, 2H), 2.67 (q, J=8 Hz, 2H), 2.36 (s, 3H), 1.49 (s, 6H) 1.24 (t, J=8 Hz, 3H); MS (EI) 432.1 (M+Na)$^+$, 410.1 (M+H)$^+$.

The following compound was prepared according to the same procedure:

Example 12A

2-Methyl-2-(4-{2-[5-methyl-2-(3-phenethylphenyl)oxazol-4-yl]ethoxy}phenoxy)-propionic acid

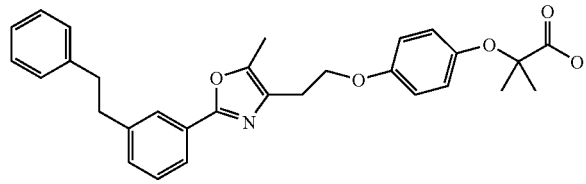

Rf=0.2 in 6:4 EtOAc:hexanes; mp=124-125° C.; $^1$H NMR (400 MHz, CDCl$_3$) δ 7.83 (s, 1H), 7.98 (d, 1H), 7.32-7.21 (m, 3H), 7.20-7.16 (m, 4H), 6.88-6.76 (m, 4H), 4.16 (t, 2H), 2.99 (t, 2H), 2.92 (m, 4H), 2.36 (s, 3H), 1.51 (s, 6H); MS (EI) 508.2 (M+Na)$^+$, 486.3 (M+H)$^+$.

EXAMPLE 13

2-(4-{2-[2-(4-Ethylphenyl)-5-methyloxazol-4-yl]ethoxy}phenoxy)-2-methylpropionic acid

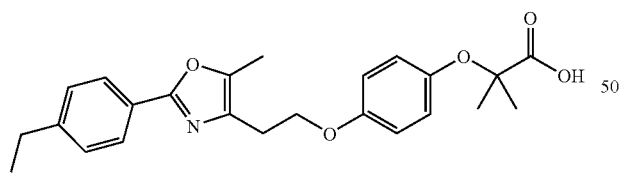

Step A

2-(4-{2-[2-(4-Ethylphenyl)-5-methyloxazol-4-yl]ethoxy}phenoxy)-2-methylpropionic acid ethyl ester

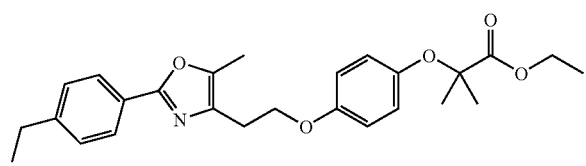

2-(4-{2-[2-(4-Ethynylphenyl)-5-methyloxazol-4-yl]ethoxy}phenoxy)-2-methyl propionic acid ethyl ester was hydrogenated according to the procedure in Example 12, Step A to provide the product (196 mg, 87%) as a colorless oil:

Rf=0.35 in 1:4 EtOAc:hexanes; $^1$H NMR (400 MHz, CDCl$_3$) δ 7.83 (d, 2H), 7.21 (d, 2H), 6.80-6.74 (m, 4H), 4.22-4.18 (m, 4H), 2.93 (t, 2H), 2.63 (q, 2H), 2.32 (s, 3H), 1.48 (s, 6H), 1.24-1.19 (m, 6H); MS (EI) 460.2 (M+Na)$^+$, 438.2 (M+H)$^+$.

By the same procedure, the following compound was prepared from 2-methyl-2-(4-{2-[5-methyl-2-(4-phenyl-ethynylphenyl)-oxazol-4-yl]ethoxy}phenoxy)propionic acid ethyl ester:

2-Methyl-2-(4-{2-[5-methyl-2-(4-phenethylphenyl)oxazol-4-yl]ethoxy}phenoxy)-propionic acid ethyl ester

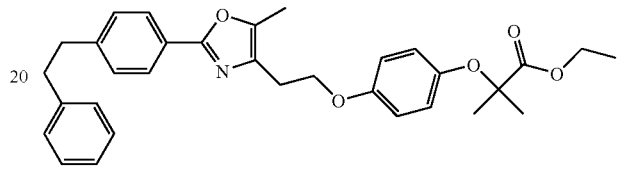

Rf=0.38 in 1:4 EtOAc:hexanes; $^1$H NMR (400 MHz, CDCl$_3$) δ 7.82 (d, 2H), 7.24-7.16 (m, 7H), 6.82-6.74 (m, 4H), 4.22-4.16 (m, 4H), 2.95-2.86 (m, 6H), 2.31 (s, 3H), 1.50 (s, 6H), 1.24-1.20 (m, 6H); MS (EI) 536.2 (M+Na)$^+$, 514.2 (M+H)$^+$.

Step B

2-(4-{2-[2-(4-Ethylphenyl)-5-methyloxazol-4-yl]ethoxy}phenoxy)-2-methyl-propionic acid 2-(4-{2-[2-(4-Ethylphenyl)-5-methyloxazol-4-yl]ethoxy}phenoxy)-2-methyl-propionic acid ethyl ester (196 mg, 0.449 mmol) was hydrolyzed according to the procedure in Example 2, Step D to provide the product (162 mg, 88%) as a white solid: Rf=0.08 in 6:4 EtOAc:hexanes; $^1$H NMR (400 MHz, CDCl$_3$) δ 8.23 (d, 2H), 7.22 (d, 2H), 6.84-6.70 (m, 4H), 4.18 (t, 2H), 2.98 (t, 1H), 2.64 (t, 2H), 2.36 (s, 3H), 1.52 (s, 6H), 1.22 (t, 3H); MS (EI) 432.2 (M+Na)$^+$, 410.2 (M+H)$^+$.

The following compound was prepared according to the same procedure:

Example 13A

2-Methyl-2-(4-{2-[5-methyl-2-(4-phenethylphenyl)oxazol-4-yl]ethoxy}phenoxy)-propionic acid

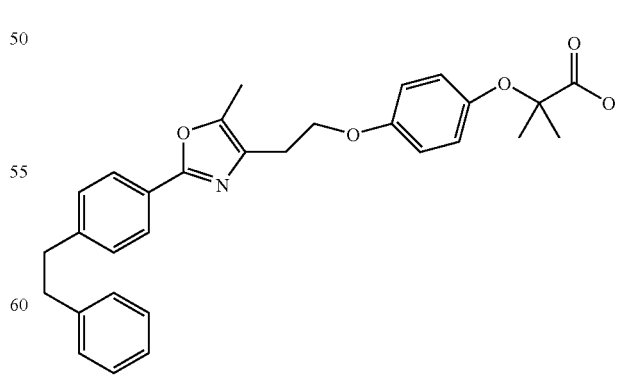

Rf=0.18 in 6:4 EtOAc:hexanes; $^1$H NMR (400 MHz, CDCl$_3$) δ 7.83 (d, 2H), 7.22-7.10 (m, 7H), 6.88-6.78 (m, 4H), 4.18 (t, 2H), 2.99 (t, 2H), 2.92 (m, 4H), 2.38 (s, 3H), 1.47 (s, 6H); MS (EI) 508.2 (M+Na)$^+$, 486.2 (M+H)$^+$.

EXAMPLE 14

2-(4-{2-[2-(4-Carbamoylphenyl)-5-methyloxazol-4-yl]ethoxy}phenoxy)-2-methylpropionic acid

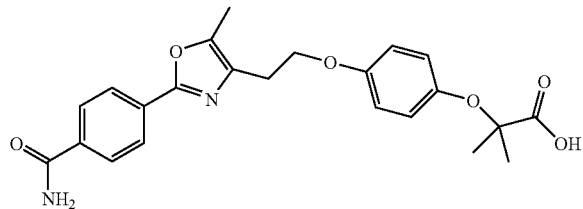

Step A 2-(4-{2-[2-(4-Cyanophenyl)-5-methyloxazol-4-yl]ethoxy}phenoxy)-2-methylpropionic acid ethyl ester

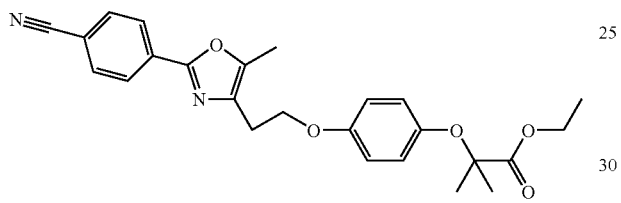

2-(4-{2-[2-(4-Bromophenyl)-5-methyloxazol-4-yl]ethoxy}phenoxy)-2-methylpropionic acid ethyl ester (170 mg, 0.35 mmol), copper (I) cyanide (96 mg, 1.07 mmol), and copper (I) iodide (120 mg, 0.63 mmol) were dissolved in dimethylformamide (1.5 mL) and heated to 150° C. for 20 h. The mixture was cooled ambient temperature and partitioned between EtOAc (20 mL) and saturated aqueous FeCl$_3$ (20 mL). The organic phase was washed with FeCl$_3$ solution, H$_2$O, brine and then dried (MgSO$_4$), filtered and concentrated. The product was purified by flash chromatography (15 mL SiO$_2$, 40% EtOAc/hexanes) and obtained as a clear, colorless oil (132 mg, 87%). Rf=0.32 in 35% EtOAc/hexanes; $^1$H NMR (400 MHz, CDCl$_3$) δ 8.04 (d, J=8.4 Hz, 2H), 7.69 (d, J=8.4 Hz, 2H), 6.81-6.76 (m, 4H), 4.21 (q, J=6.4 Hz, 2H), 4.18 (t, J=6.4 Hz, 2H), 2.95 (t, J=6.4 Hz, 2H), 2.38 (s, 3H), 1.51 (s, 6H), 1.26 (t, J=7.2 Hz, 3H); MS (EI) 457.2 (M+Na)$^+$; 435.2 (M+H)$^+$.

Step B 2-(4-{2-[2-(4-Carbamoylphenyl)-5-methyloxazol-4-yl]ethoxy}phenoxy)-2-methylpropionic acid ethyl ester

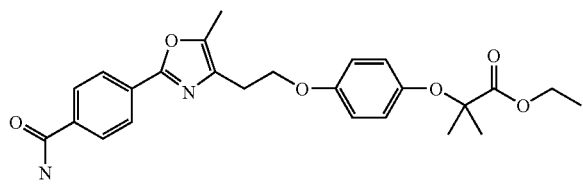

2-(4-{2-[2-(4-Cyanophenyl)-5-methyloxazol-4-yl]ethoxy}phenoxy)-2-methylpropionic acid ethyl ester (60 mg, 0.14 mmol) and potassium carbonate (30 mg, excess) were dissolved in dimethylsulfoxide (1 mL). After cooling to 0° C., the mixture was treated with hydrogen peroxide (120 •L of a 30% aqueous solution) and then warmed to ambient temperature. After stirring for 1 h, the mixture was partitioned between EtOAc (15 mL) and H$_2$O. The aqueous phase was extracted with EtOAc (3×), and then the combined organic phases were dried (MgSO$_4$), filtered and concentrated to provide the product as a white solid (58 mg, 93%): mp 112° C.; $^1$H NMR (400 MHz, CDCl$_3$) δ 8.05 (d, J=8.4 Hz, 2H), 7.87 (d, J=8.4 Hz, 2H), 6.81-6.77 (m, 4H), 6.12 (br s, 1H), 5.66 (br s, 1H), 4.22 (q, J=6.8 Hz, 2H), 4.18 (t, J=6.4 Hz, 2H), 2.95 (t, J=6.4 Hz, 2H), 2.38 (s, 3H), 1.52 (s, 6H), 1.27 (t, J=7.2 Hz, 3H); MS (EI) 475.2 (M+Na)$^+$, 453.2 (M+H)$^+$.

Step C 2-(4-{2-[2-(4-Carbamoylphenyl)-5-methyloxazol-4-yl]ethoxy}phenoxy)-2-methylpropionic acid ethyl ester was hydrolyzed was described in Example 1 to provide the product as a white solid (42 mg, 90%): Rf=0.7 in 100% EtOAc; mp 126-127° C.; $^1$H NMR (400 MHz, CDCl$_3$) δ 8.05 (br s, 1H), 7.93 (m, 4H), 7.42 (br s, 1H), 6.77 (m, 4H), 4.10 (t, J=6.4 Hz, 2H), 2.86 (t, J=6.4 Hz, 2H), 2.32 (s, 3H), 1.37 (s, 6H); MS (EI) 448.2 (M+Na)$^+$, 425.1 (M+H)$^+$.

EXAMPLE 15

2-(4-{2-[2-(4-Cyanophenyl)-5-methyloxazol-4-yl]ethoxy}phenoxy)-2-methylpropionic acid <image>
2-(4-{2-[2-(4-Cyanophenyl)-5-methyloxazol-4-yl]ethoxy}phenoxy)-2-methylpropionic acid ethyl ester (prepared as described in Example 14) was hydrolyzed according to the procedure in Example 1 to provide the product as a white solid: $^1$H NMR (400 MHz, d$_6$-DMSO) δ 7.98 (d, J=8.0 Hz, 1H), 7.89 (d, J=8.0 Hz, 1H), 6.75-6.74 (m, 4H), 4.09 (t, J=6.4 Hz, 2H), 2.86 (t, J=6.4 Hz, 2H), 2.31 (s, 3H), 1.34 (s, 6H); MS (EI) 407 (M+H)$^+$.

EXAMPLE 16

2-Methyl-2-(4-{2-[5-methyl-2-(4-phenoxy-phenyl)-oxazol-4-yl]-ethoxy}-phenoxy)-propionic acid A mixture of 2-(4-{2-[2-(4-bromo-phenyl)-5-methyloxazol-4-yl]-ethoxy}-phenoxy)-2-methyl-propionic acid ethyl ester

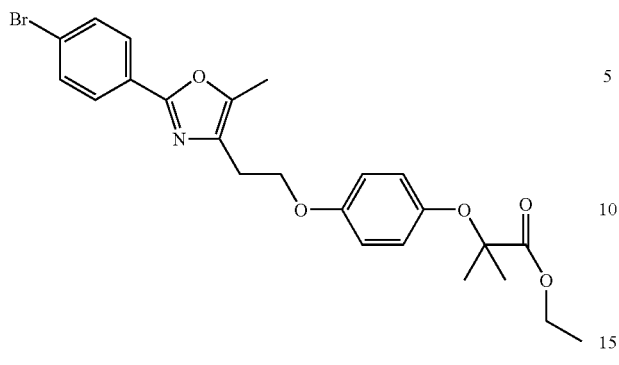

(0.30 g, 0.614 mmol), potassium phosphate (0.26 g, 1.22 mmol), 2-(di-tert-butylphosphino)biphenyl (0.014 g, 0.0469 mmol) and phenol (0.069 g, 0.733 mmol) in toluene (6 mL) was degassed three times by successive application of vacuum to the reaction vessel followed by nitrogen purge. Palladium (II) acetate (0.007 g, 0.0312 mmol) was added to the reaction and the mixture heated to reflux under nitrogen for 3 h. The reaction was cooled to room temperature, diluted with Et$_2$O, and extracted with water then 1 N NaOH (10 mL). The organic layer was dried (MgSO$_4$) and the solvent removed in vacuo to give 0.316 g of crude 2-methyl-2-(4-{2-[5-methyl-2-(4-phenoxy-phenyl)-oxazol-4-yl]-ethoxy}-phenoxy)-propionic acid ethyl ester.

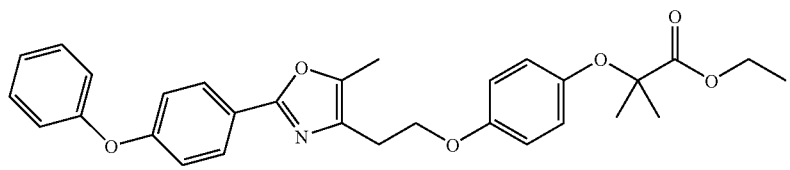

MS (ES$^+$) Calc'd for C$_{30}$H$_{31}$NO$_6$: Found m/e 502.3 (M+1, 100%).

The crude 2-methyl-2-(4-{2-[5-methyl-2-(4-phenoxy-phenyl)-oxazol-4-yl]-ethoxy}-phenoxy)-propionic acid ethyl ester (0.316 g, 0.614 mmol) was combined with 5 N NaOH (0.61 mL, 3.05 mmol) in absolute EtOH (20 mL) and heated to reflux for 3 h. The reaction mixture was cooled, filtered through hyflo, and the solvent removed in vacuo from the filtrate. The residue was acidified with 1 N HCl (3.2 mL) and then extracted with EtOAc and water. The organic layer was dried (MgSO$_4$) and the solvent removed in vacuo to give 0.282 g of crude 2-methyl-2-(4-{2-[5-methyl-2-(4-phenoxy-phenyl)-oxazol-4-yl]-ethoxy}-phenoxy)-propionic acid. Approximately ⅓ of this material was purified by LCMS to afford 0.014 g of analytically pure 2-methyl-2-(4-{2-[5-methyl-2-(4-phenoxy-phenyl)-oxazol-4-yl]-ethoxy}-phenoxy)-propionic acid: $^1$H NMR (500 MHz, CDCl$_3$) δ 7.90 (d, 2H, J=8.80 Hz), 7.36-7.32 (m, 2H), 7.18-7.12 (m, 1H), 7.03-6.99 (m, 3H), 6.88-6.86 (m, 2H), 6.79-6.77 (m, 3H), 4.16 (t, 2H, J=6.84 Hz), 2.94 (t, 2H, J=6.84 Hz), 2.34 (s, 3H), 1.44 (s, 6H). HRMS (ES$^+$) m/z exact mass calcd for C$_{28}$H$_{28}$NO$_6$ 474.1917, found 474.1929.

The following compounds were prepared by the same procedure using 4-methoxyphenol, 4-hydroxybenzotrifluoride, o-cresol, guaiacol, 3-tert-butylphenol, and 3-methoxyphenol, respectively:

Example 16A

2-[4-(2-{2-[4-(4-Methoxy-phenoxy)-phenyl]-5-methyl-oxazol-4-yl}-ethoxy)-phenoxy]-2-methyl-propionic acid

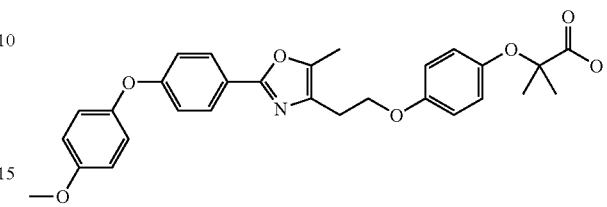

$^1$H NMR (500 MHz, CDCl$_3$) δ 7.92 (d, 2H, J=8.80 Hz), 7.00-6.96 (m, 4H), 6.91-6.85 (m, 4H), 6.77 (d, 2H, J=8.80 Hz), 4.17 (t, 2H, J=5.87 Hz), 3.80 (s, 3H), 3.04 (t, 2H, J=5.87 Hz), 2.40 (s, 3H), 1.47 (s, 6H). HRMS (ES$^+$) m/z exact mass calcd for C$_{29}$H$_{30}$NO$_7$ 504.2022, found 504.2046.

Example 16B

2-Methyl-2-[4-(2-{5-methyl-2-[4-(4-trifluoromethyl-phenoxy)-phenyl]-oxazol-4-yl}-ethoxy)-phenoxy]-propionic acid

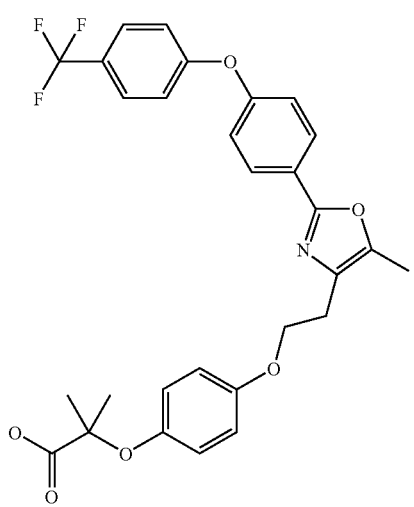

$^1$H NMR (500 MHz, CDCl$_3$) δ 7.98 (d, 2H, J=8.80 Hz), 7.61 (d, 2H, J=8.80 Hz), 7.11-7.08 (m, 4H), 6.87-6.86 (m, 2H), 6.78-6.75 (m, 2H), 4.17 (t, 2H, J=5.87 Hz), 3.04 (t, 2H,

J=5.87 Hz), 2.41 (s, 3H), 1.48 (s, 6H). HRMS (ES⁺) m/z exact mass calcd for $C_{29}H_{27}NO_6F_3$ 542.1790, found 542.1806.

Example 16C

2-Methyl-2-(4-{2-[5-methyl-2-(4-o-tolyloxy-phenyl)-oxazol-4-yl]-ethoxy}-phenoxy)-propionic acid

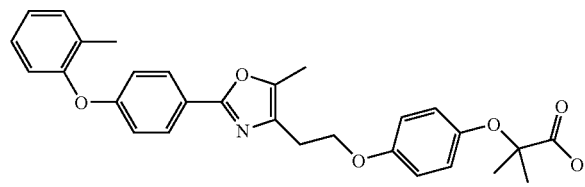

¹H NMR (500 MHz, CDCl₃) δ 7.84 (d, 2H, J=8.80 Hz), 7.21-7.04 (m, 3H), 6.90-6.80 (m, 5H), 6.72-6.70 (m, 2H), 4.09 (t, 2H, J=6.60 Hz), 2.90 (t, 2H, J=6.60 Hz), 2.29 (s, 3H), 2.14 (s, 3H), 1.45 (s, 6H). HRMS (ES⁺) m/z exact mass calcd for $C_{29}H_{30}NO_6$ 488.2073, found 488.2072.

Example 16D

2-[4-(2-{2-[4-(2-Methoxy-phenoxy)-phenyl]-5-methyl-oxazol-4-yl}-ethoxy)-phenoxy]-2-methyl-propionic acid

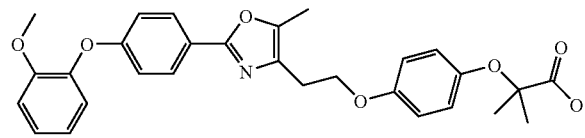

¹H NMR (500 MHz, CDCl₃) δ 7.94 (d, 2H, J=9.0 Hz), 7.20-7.18 (m, 1H), 7.07-6.85 (m, 5H), 6.87-6.85 (m, 2H), 6.77-6.75 (m, 2H), 4.17 (t, 2H, J=5.87 Hz), 3.76 (s, 3H), 3.06 (t, 2H, J=5.87 Hz), 2.41 (s, 3H), 1.48 (s, 6H). HRMS (ES⁺) m/z exact mass calcd for $C_{29}H_{30}NO_7$ 504.2022, found 504.2021.

Example 16E

2-[4-(2-{2-[4-(3-tert-Butyl-phenoxy)-phenyl]-5-methyl-oxazol-4-yl}-ethoxy)-phenoxy]-2-methyl-propionic acid

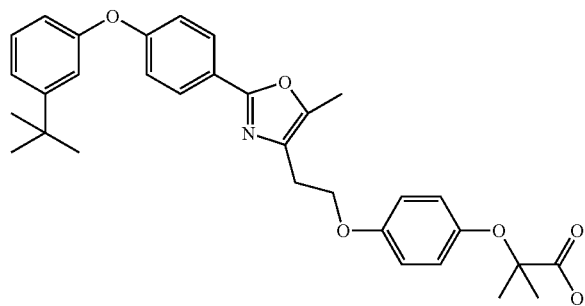

¹H NMR (500 MHz, CDCl₃) δ 7.97 (d, 2H, J=8.60 Hz), 7.30-7.27 (m, 1H), 7.23-7.18 (m, 1H), 7.08-7.02 (m, 3H), 6.88-6.82 (m, 3H), 6.78-6.75 (m, 2H), 4.18 (t, 2H, J=5.87 Hz), 3.06 (t, 2H, J=5.87 Hz), 2.41 (s, 3H), 1.48 (s, 6H), 1.29 (s, 9H). HRMS (ES⁺) m/z exact mass calcd for $C_{32}H_{36}NO_6$ 530.2543, found 530.2538.

Example 16F

2-[4-(2-{2-[4-(3-Methoxy-phenoxy)-phenyl]-5-methyl-oxazol-4-yl}-ethoxy)-phenoxy]-2-methyl-propionic acid

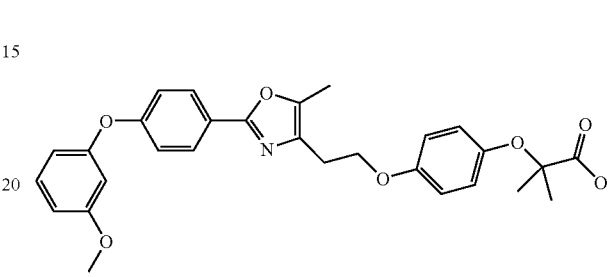

¹H NMR (500 MHz, CDCl₃) δ 7.98 (d, 2H, J=9.0 Hz), 7.31-7.24 (m, 1H), 7.08 (d, 2H, J=8.60 Hz), 6.89 (d, 2H, J=9.0 Hz), 6.79-6.77 (m, 3H), 6.76-6.62 (m, 2H), 4.19 (t, 2H, J=5.87 Hz), 3.80 (s, 3H), 3.10 (t, 2H, J=5.87 Hz), 2.45 (s, 3H), 1.50 (s, 6H). HRMS (ES⁺) m/z exact mass calcd for $C_{29}H_{30}NO_7$ 504.2022, found 504.2009.

EXAMPLE 17

2-Methyl-2-(4-{2-[5-methyl-2-(3-phenoxy-phenyl)-oxazol-4-yl]-ethoxy}-phenoxy)-propionic acid

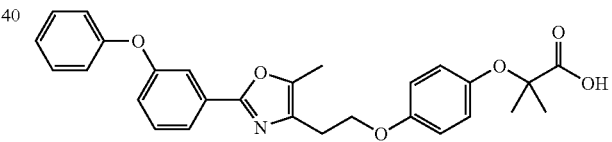

Step A

2-Methyl-2-(4-{2-[5-methyl-2-(3-phenoxy-phenyl)-oxazol-4-yl]-ethoxy}-phenoxy)-propionic acid ethyl ester

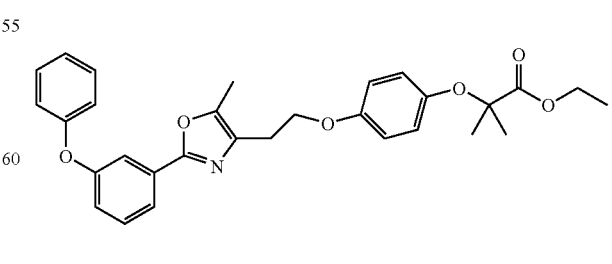

A solution of 2-(4-{2-[2-(3-bromophenyl)-5-methyloxazol-4-yl]ethoxy}phenoxy)-2-methylpropionic acid ethyl ester

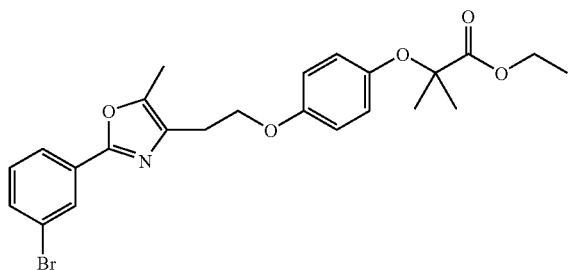

(303 mg, 0.620 mmol), phenol (116.7 mg, 1.24 mmol), potassium phosphate (276.4 mg, 1.302 mmol), palladium acetate (13.9 mg, 0.062 mmol), and 2-(di-t-butylphosphino) biphenyl (27.8 mg, 0.093 mmol) were combined under $N_2$, to which toluene (6.2 mL) was added. The mixture was heated at reflux for 4 h. After cooling to rt, the mixture was partitioned between $Et_2O$ (20 mL) and $H_2O$ (10 mL). The layers were separated, and the organic phase was washed with 1M NaOH (10 mL), which was then dried over $Na_2SO_4$, and concentrated to a brown residue. The product was purified by silica gel chromatography (20 g $SiO_2$, 1:4 EtOAc:hexanes) to yield 104.9 mg (34%) as an oil. Rf=0.45 in 1:4 EtOAc:hexanes; $^1$H NMR (400 MHz, $CDCl_3$) δ 7.98-7.96 (m, 1H), 7.74-7.71 (m, 1H), 7.63-7.62 (m, 1H), 7.43-7.33 (m, 3H), 7.14-7.10 (m, 1H), 7.06-7.01 (m, 2H), 6.82-6.74 (m, 4H), 4.23 (q, J=8.0 Hz, 2H), 4.16 (t, J=6.4 Hz, 2H), 2.93 (t, J=6.4 Hz, 2H), 2.34 (s, 3H), 1.52 (s, 6H), 1.28-1.24 (t, J=8.0 Hz, 3H); MS (EI) 540.0 (M+K)$^+$, 502.0 (M+H)$^+$.

The following compound was prepared by the same procedure, using 2-methylphenol:

2-Methyl-2-(4-{2-[5-methyl-2-(3-o-tolyloxy-phenyl)-oxazol-4-yl]-ethoxy}-phenoxy)-propionic acid ethyl ester

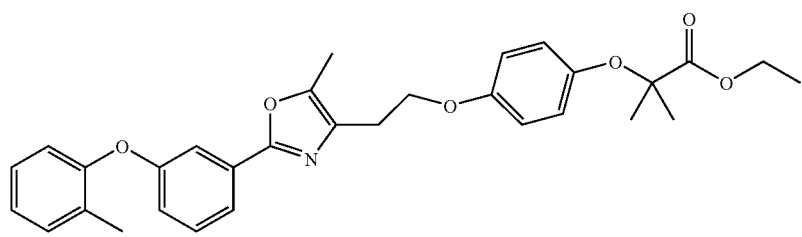

Rf=0.45 in 1:4 EtOAc:hexanes; MS (EI) 554.1 (M+K)$^+$, 516.1 (M+H)$^+$.

Step B

2-Methyl-2-(4-{2-[5-methyl-2-(3-phenoxy-phenyl)-oxazol-4-yl]-ethoxy}-phenoxy)-propionic acid 2-Methyl-2-(4-{2-[5-methyl-2-(3-phenoxy-phenyl)-oxazol-4-yl]-ethoxy}-phenoxy)propionic acid ethyl ester (104.9 mg, 0.209 mmol) was hydrolyzed according to the procedure in Example 2, Step D to provide the crude product, which was purified by LC/MS to yield the product (3.8 mg, 3.8%) as a lyophilized solid.

Rf=0.10 in 6:4 EtOAc:hexanes $^1$H NMR (400 MHz, $CDCl_3$) δ 7.78-7.61 (m, 1H), 7.69-7.66 (m, 1H), 7.42-7.29 (m, 3H), 7.13-6.97 (m, 3H), 6.86-6.74 (m, 4H), 4.13 (t, J=6.2 Hz, 2H), 2.94 (s, J=6.2 Hz, 2H), 2.33 (s, 3H), 1.46 (s, 6H); MS (EI) 474.1 (M+H)$^+$.

The following compound was prepared by the same procedure, using 2-Methyl-2-(4-{2-[5-methyl-2-(3-o-tolyloxy-phenyl)-oxazol-4-yl]-ethoxy}-phenoxy)propionic acid ethyl ester

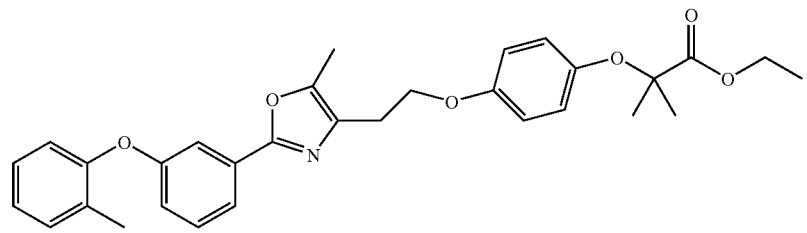

Example 17A

2-Methyl-2-(4-{2-[5-methyl-2-(3-o-tolyloxy-phenyl)-oxazol-4-yl]-ethoxy}-phenoxy)-propionic acid

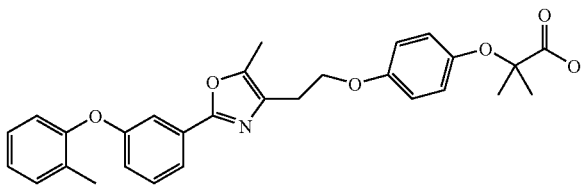

Rf=0.11 in 6:4 EtOAc:hexanes; $^1$H NMR (400 MHz, $CDCl_3$) δ 7.63-7.62 (m, 1H), 7.47-7.46 (m, 1H), 7.35-7.31

(m, 1H), 7.23 (s, 1H), 7.17-7.12 (m, 1H) 7.07-7.03 (m, 1H) 6.94-6.82 (m, 4H), 6.75-6.72 (m, 2H) 4.11 (t, J=6.4 Hz, 2H), 2.96 (t, J=6.4 Hz, 2H), 2.33 (s, 3H), 2.19 (s, 3H), 1.47 (s, 6H); MS (EI) 488.1 (M+H)+.

EXAMPLE 18

2-[4-(2-{2-[4-(4-Benzoyl-phenoxy)-phenyl]-5-methyl-oxazol-4-yl}-ethoxy)-phenoxy]-2-methyl-propionic acid

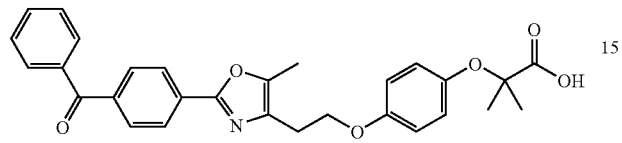

A mixture of 2-(4-{2-[2-(4-bromo-phenyl)-5-methyl-oxazol-4-yl]-ethoxy}-phenoxy)-2-methyl-propionic acid ethyl ester (0.20 g, 0.410 mmol), phenyl boronic acid (0.055 g, 0.451 mmol), powdered K$_2$CO$_3$ (0.169 g, 1.22 mmol), potassium iodide (0.20 g, 1.20 mmol), 1,1'-bis(diphenylphosphino)ferrocene (0.023 g, 0.0414 mmol) and palladium (II) chloride (0.007 g, 0.0395 mmol) in anisole (4 mL) and then carbon monoxide was bubbled through the reaction mixture to saturate the mixture. The reaction was then heated at 80° C. in an oil bath under a carbon monoxide balloon for 2 h. The reaction was cooled, diluted with Et$_2$O, and extracted with water and brine. The organic layer was dried (MgSO$_4$) and the solvent removed in vacuo to give an oil that passed over a plug of silica gel to remove most of the anisole (98:2 ratio CH$_2$Cl$_2$:MeOH). The resultant oil was dissolved in EtOH (8 mL) and treated with 5 N NaOH (0.1 mL) at reflux for 1 h. The reaction mixture was cooled, acidified with 1 N HCl (1 mL) and the reaction mixture extracted with EtOAc and water to give 0.061 g of crude 2-[4-(2-{2-[4-(4-benzoyl-phenoxy)-phenyl]-5-methyl-oxazol-4-yl}-ethoxy)-phenoxy]-2-methyl-propionic acid that was purified by LCMS to afford 0.017 g of 2-[4-(2-{2-[4-(4-benzoyl-phenoxy)-phenyl]-5-methyl-oxazol-4-yl}-ethoxy)-phenoxy]-2-methyl-propionic acid.

$^1$H NMR (500 MHz, CDCl$_3$) δ 8.10 (d, 2H, J=8.21 Hz), 7.90 (d, 2H, J=8.21 Hz), 7.80 (d, 2H, J=8.21 Hz), 7.63-7.60 (m, 1H), 7.53-7.49 (m, 2H), 6.90 (d, 2H, J=9.0 Hz), 6.80 (d, 2H, J=8.60), 4.21 (t, 2H, J=5.87 Hz), 3.07 (t, 2H, J=5.87 Hz), 2.45 (s, 3H), 1.52 (s, 6H). HRMS (ES$^+$) m/z exact mass calcd for C$_{29}$H$_{28}$NO$_6$ 486.1917, found 486.1904.

EXAMPLE 19

2-(4-{2-[2-(4-Hydroxy-phenyl)-5-methyl-oxazol-4-yl]-ethoxy}-phenoxy)-2-methyl-propionic acid

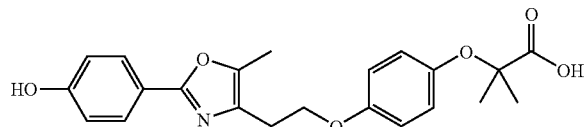

Step A 2-(4-{2-[2-(4-Hydroxy-phenyl)-5-methyl-oxazol-4-yl]-ethoxy}-phenoxy)-2-methyl-propionic acid ethyl ester

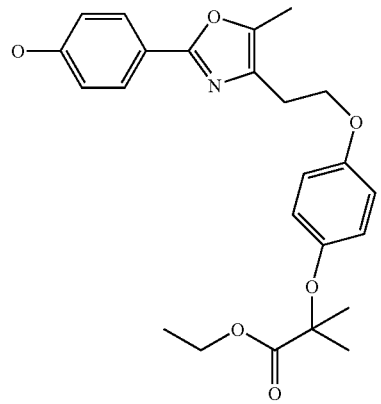

A mixture of 2-(4-{2-[2-(4-benzyloxy-phenyl)-5-methyl-oxazol-4-yl]-ethoxy}-phenoxy)-2-methyl-propionic acid ethyl ester (8.16 g, 15.8 mmol) and 5% palladium on carbon (1.63 g) in tetrahydrofuran (100 mL) and methanol (100 mL) was purged successively with nitrogen then hydrogen, and then stirred under a hydrogen balloon at room temperature for 18 h. The reaction mixture was filtered through hyflo and solvent was removed from the filtrate in vacuo to give an oil which was dissolved in EtOAc and dried (MgSO$_4$). The solvent was removed in vacuo to afford 6.40 g (95%) of 2-(4-{2-[2-(4-hydroxy-phenyl)-5-methyl-oxazol-4-yl]-ethoxy}-phenoxy)-2-methyl-propionic acid ethyl ester. $^1$H NMR (500 MHz, CDCl$_3$) δ 8.25 (bs, 1H), 7.32 (d, 2H, J=8.79 Hz), 6.75-6.67 (m, 4H), 6.65 (d, 2H, J=8.79 Hz), 4.17 (q, 2H, J=6.84 Hz), 4.09 (t, 2H, J=6.35 Hz), 2.88 (t, 2H, J=6.35 Hz), 2.30 (s, 3H), 1.45 (s, 6H), 1.21 (t, 3H, J=6.84 Hz); $^{13}$C (125 MHz, CDCl$_3$) δ 174.4, 160.2, 159.0, 154.3, 148.9, 144.7, 131.5, 128.1, 122.0, 121.6, 118.7, 115.9, 115.7, 114.9, 79.8, 66.8, 61.3, 25.9, 25.2, 14.1, 10.1; IR (KBr) 2985, 2941, 2809, 2606, 1742, 1731, 1507, 1442, 1277, 1233, 1213, 1170, 1137 cm$^{-1}$; UV (EtOH) λ$_{max}$ 285 nm (ε 21145), 219 nm (• 15842); HRMS (ES$^+$) m/z exact mass calcd for C$_{24}$H$_{28}$NO$_6$ 426.1917, found 426.1896. Anal. Calc'd for C$_{24}$H$_{27}$NO$_6$: C, 67.75; H, 6.40; N, 3.29. Found: C, 67.22; H, 6.50; N, 2.79.

Step B 2-(4-{2-[2-(4-Hydroxy-phenyl)-5-methyl-oxazol-4-yl]-ethoxy}-phenoxy)-2-methyl-propionic acid A mixture of 2-(4-{2-[2-(4-benzyloxy-phenyl)-5-methyl-oxazol-4-yl]-ethoxy}-phenoxy)-2-methyl-propionic acid (0.238 g, 0.490 mmol) and 5% palladium on carbon (0.10 g)

in tetrahydrofuran (10 mL) and methanol (10 mL) was purged successively with nitrogen then hydrogen, and then stirred under a hydrogen balloon at room temperature for 18 h. The reaction mixture was filtered through hyflo and solvent was removed from the filtrate in vacuo to give an oil which was dissolved in $CH_2Cl_2$ and dried ($MgSO_4$). The solvent was removed in vacuo to give a crude oil which was purified by flash chromatography (9/1 $CH_2Cl_2$/MeOH) to afford 0.072 g (37%) 2-(4-{2-[2-(4-hydroxy-phenyl)-5-methyl-oxazol-4-yl]-ethoxy}-phenoxy)-2-methyl-propionic acid. $^1H$ NMR (500 MHz, DMSO-$d_6$) δ 10.08 (bs, 1H), 7.70 (d, 2H, J=8.60 Hz), 6.84-6.72 (m, 6H), 4.08 (t, 2H, J=6.65 Hz), 2.83 (t, 2H, J=6.65 Hz), 2.28 (s, 3H), 1.33 (s, 6H); MS (ES$^+$) Calc'd for $C_{22}H_{23}NO_6$: Found m/e 398 (M+1, 100%)

EXAMPLE 20

2-(4-{2-[2-(4-Methoxy-phenyl)-5-methyl-oxazol-4-yl]-ethoxy}-phenoxy)-2-methyl-propionic acid

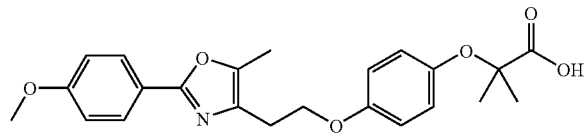

Step A 2-(4-{2-[2-(4-Methoxy-phenyl)-5-methyl-oxazol-4-yl]-ethoxy}-phenoxy)-2-methyl-propionic acid ethyl ester

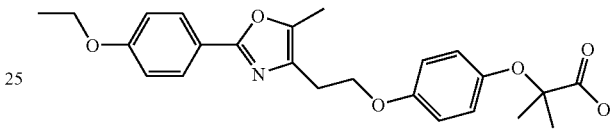

A solution of 2-(4-{2-[2-(4-hydroxy-phenyl)-5-methyl-oxazol-4-yl]-ethoxy}-phenoxy)-2-methyl-propionic acid ethyl ester (0.15 g, 0.352 mmol), methyl iodide (0.15 g, 1.06 mmol), tetrabutylammonium bromide (0.023 g, 0.0713) mmol) in $CH_2Cl_2$ (8 mL) was treated with a 50% weight solution of NaOH (0.1 mL), and stirred at room temperature. The reaction mixture was extracted with water and more $CH_2Cl_2$ and the organic layer dried ($MgSO_4$). The solvent was removed in vacuo to give a crude oil which was purified by flash chromatography (2/1 hexanes/EtOAc) to afford 0.038 g (25%) 2-(4-{2-[2-(4-methoxy-phenyl)-5-methyl-oxazol-4-yl]-ethoxy}-phenoxy)-2-methyl-propionic acid ethyl ester. $^1H$ NMR (500 MHz, CDCl$_3$) δ 7.87-7.85 (m, 2), 6.90-6.88 (m, 2H), 6.78-6.71 (m, 4H), 4.21-4.06 (m, 4H), 3.80 (s, 3H), 2.88 (t, 2H, J=6.60 Hz), 2.29 (s, 3H), 1.47 (s, 6H), 1.23 (t, 3H, J=7.33 Hz); MS (ES$^+$) Calc'd for $C_{25}H_{30}NO_6$: Found m/e 440 (M+1, 100%).

Step B 2-(4-{2-[2-(4-Methoxy-phenyl)-5-methyl-oxazol-4-yl]-ethoxy}-phenoxy)-2-methyl-propionic acid A solution of 2-(4-{2-[2-(4-methoxy-phenyl)-5-methyl-oxazol-4-yl]-ethoxy}-phenoxy)-2-methyl-propionic acid ethyl ester (0.036 g, 0.0819 mmol) in ethanol (5 mL) was treated with 5 N NaOH (0.1 mL) and the reaction heated to reflux for 1 h. The reaction mixture was cooled and the solvent removed in vacuo. The resultant oil was acidified with 1 N HCl and extracted with EtOAc and water. The organic layer was dried ($MgSO_4$) and the solvent removed in vacuo to afford 0.034 g (100%) of 2-(4-{2-[2-(4-methoxy-phenyl)-5-methyl-oxazol-4-yl]-ethoxy}-phenoxy)-2-methyl-propionic acid. $^1H$ NMR (500 MHz, CDCl$_3$) δ 7.93 (d, 2H, J=8.60 Hz), 6.94 (d, 2H, J=8.60 Hz), 6.90-6.87 (m, 2H), 6.79-6.77 (m, 2H), 4.17 (t, 2H, J=6.45 Hz), 3.85 (s, 3H), 2.98 (t, 2H, J=6.45 Hz), 2.36 (s, 3H), 1.52 (s, 6H); HRMS (ES$^+$) m/z exact mass calcd for $C_{23}H_{26}NO_6$ 412.1760, found 412.1783 The following compounds were prepared following the same procedure using ethyl iodide, 2-iodopropane, 1-iodopropane, and 1-iodohexane, respectively:

Example 20A 2-(4-{2-[2-(4-Ethoxy-phenyl)-5-methyl-oxazol-4-yl]-ethoxy}-phenoxy)-2-methyl-propionic acid

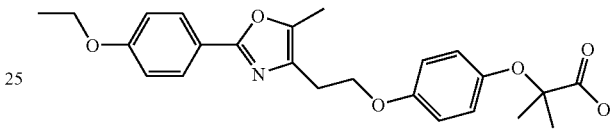

$^1H$ NMR (500 MHz, CDCl$_3$) δ 7.90-7.88 (m, 2H), 6.93-6.88 (m, 4H), 6.80-6.77 (m, 2H), 4.16 (t, 2H, J=6.65 Hz), 4.07 (q, 2H, J=6.65 Hz), 2.96 (t, 2H, J=6.65 Hz), 2.35 (s, 3H), 1.52 (s, 6H), 1.43 (t, 3H, J=6.65 Hz); HRMS (ES$^+$) m/z exact mass calcd for $C_{24}H_{28}NO_6$ 426.1917, found 426.1945

Example 20B 2-(4-{2-[2-(4-Isopropoxyphenyl)-5-methyl-oxazol-4-yl]-ethoxy}-phenoxy)-2-methyl-propionic acid

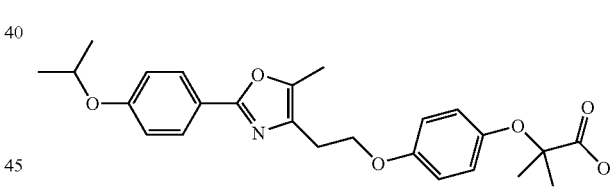

$^1H$ NMR (500 MHz, CDCl$_3$) δ 7.82-7.80 (m, 2H), 6.85-6.80 (m, 4H), 6.71-6.69 (m, 2H), 4.53 (septet, 1H, J=6.25 Hz), 4.07 (t, 2H, J=6.65 Hz), 2.89 (t, 2H, J=6.65 Hz), 2.28 (s, 3H), 1.46 (s, 6H), 1.28 (d, 6H, J=6.25 Hz); HRMS (ES$^+$) m/z exact mass calcd for $C_{25}H_{30}NO_6$ 440.2073, found 440.2104

Example 20C

2-Methyl-2-(4-{2-[5-methyl-2-(4-propoxy-phenyl)-oxazol-4-yl]-ethoxy}-phenoxy)-propionic acid

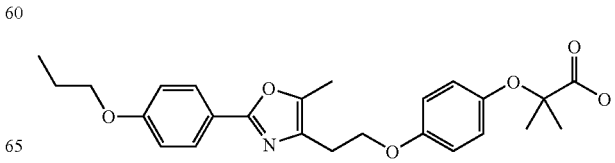

$^1$H NMR (500 MHz, CDCl$_3$) δ 7.83-7.80 (m, 2H), 6.87-6.81 (m, 4H), 6.73-6.71 (m, 2H), 4.09 (t, 2H, J=6.65 Hz), 3.89 (t, 2H, J=6.65 Hz), 2.88 (t, 2H, J=6.65 Hz), 2.28 (s, 3H), 1.78-1.73 (m, 2H), 1.45 (s, 6H), 0.98 (t, 3H, J=7.43 Hz); HRMS (ES$^+$) m/z exact mass calcd for C$_{25}$H$_{30}$NO$_6$ 440.2073, found 440.2047

Example 20D 2-(4-{2-[2-(4-Hexyloxy-phenyl)-5-methyl-oxazol-4-yl]-ethoxy}-phenoxy)-2-methyl-propionic acid

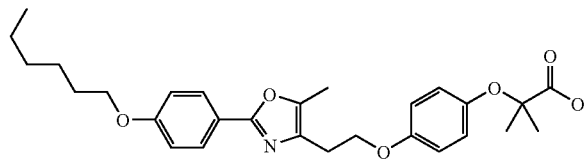

$^1$H NMR (500 MHz, CDCl$_3$) δ 7.82 (d, 2H, J=8.21 Hz), 6.86-6.81 (m, 4H), 6.71 (m, 2H, J=9.00 Hz), 4.09 (t, 2H, J=6.65 Hz), 3.92 (t, 2H, J=6.65 Hz), 2.90 (t, 2H, J=6.65 Hz), 2.28 (s, 3H), 1.74-1.68 (m, 2H), 1.45 (s, 6H), 1.43-1.35 (m, 2H), 1.33-1.25 (m, 4H), 0.88-0.71 (m, 3H); HRMS (ES$^+$) m/z exact mass calcd for C$_{28}$H$_{36}$NO$_6$ 482.2543, found 482.2552

EXAMPLE 21

2-(4-{2-[2-(4-Cyclohexyloxy-phenyl)-5-methyl-oxazol-4-yl]-ethoxy}-phenoxy)-2-methyl-propionic acid

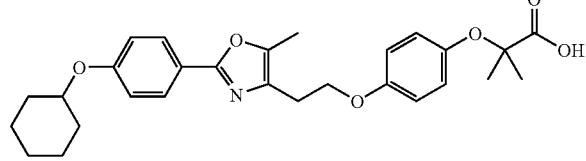

Step A 2-(4-{2-[2-(4-Cyclohexyloxy-phenyl)-5-methyl-oxazol-4-yl]-ethoxy}-phenoxy)-2-methyl-propionic acid ethyl ester To a 0° C. solution of 2-(4-{2-[2-(4-hydroxy-phenyl)-5-methyl-oxazol-4-yl]-ethoxy}-phenoxy)-2-methyl-propionic acid ethyl ester (0.60 g, 1.41 mmol), cyclohexanol (0.212 g, 2.11 mmol) and triphenyl phosphine (0.55 g, 2.10 mmol) in THF (18 mL) was added diisopropyl azodicarboxylate (0.43 g, 2.12 mmol) in THF (2 mL). The reaction was warmed to room temperature and stirred under N$_2$ for 18 h. Silica gel was added directly to the reaction mixture and the solvent removed in vacuo to absorb the crude product onto the silica gel. The crude product was then purified by flash chromatography (3/1 hexanes/EtOAc) to afford 0.339 g (47%) 2-(4-{2-[2-(4-cyclohexyloxy-phenyl)-5-methyl-oxazol-4-yl]-ethoxy}-phenoxy)-2-methyl-propionic acid ethyl ester. $^1$H NMR (500 MHz, CDCl$_3$) δ 7.94-7.85 (m, 2H), 6.92 (d, 2H, J=9.0 Hz), 6.82-6.75 (m, 4H), 4.32-4.23 (m, 1H), 4.21-4.16 (m, 4H), 2.98-2.90 (m, 2H), 2.39 (s, 3H), 2.05-1.95 (m, 2H), 1.85-1.78 (m, 2H), 1.62-1.51 (m, 3H), 1.52 (s, 6H), 1.42-1.25 (m, 3H), 1.27 (t, 3H, J=7.23 Hz); MS (ES$^+$) Calc'd for C$_{30}$H$_{38}$NO$_6$: Found m/e 508.3 (M+1, 100%).

Step B 2-(4-{2-[2-(4-Cyclohexyloxy-phenyl)-5-methyl-oxazol-4-yl]-ethoxy}-phenoxy)-2-methyl-propionic acid A solution of 2-(4-{2-[2-(4-cyclohexyloxy-phenyl)-5-methyl-oxazol-4-yl]-ethoxy}-phenoxy)-2-methyl-propionic acid ethyl ester (0.339 g, 0.667 mmol) in ethanol (40 mL) was treated with 5 N NaOH (0.8 mL) and the reaction heated to reflux for 1 h. The reaction mixture was cooled and the solvent removed in vacuo. The resultant oil was acidified with 1 N HCl and extracted with EtOAc and water. The organic layer was dried (MgSO$_4$) and the solvent removed in vacuo to afford 0.304 g (95%) of 2-(4-{2-[2-(4-cyclohexyloxy-phenyl)-5-methyl-oxazol-4-yl]-ethoxy}-phenoxy)-2-methyl-propionic acid. $^1$H NMR (500 MHz, CDCl$_3$) δ 7.94-7.85 (m, 2H), 6.89-6.73 (m, 4H), 6.71 (d, 2H, J=9.28 Hz), 4.30-4.23 (m, 1H), 4.14-4.05 (m, 2H), 2.95-2.85 (m, 2H), 2.29 (s, 3H), 1.98-1.85 (m, 2H), 1.80-1.75 (m, 2H), 1.58-1.40 (m, 8H), 1.38-1.20 (m, 4H); HRMS (ES$^+$) m/z exact mass calcd for C$_{28}$H$_{34}$NO$_6$ 480.2386, found 480.2381
The following compound was prepared using tetrahydro-2H-pyran-4-ol:

Example 21A

2-Methyl-2-[4-(2-{5-methyl-2-[4-(tetrahydro-pyran-4-yloxy)-phenyl]-oxazol-4-yl}-ethoxy)-phenoxy]-propionic acid

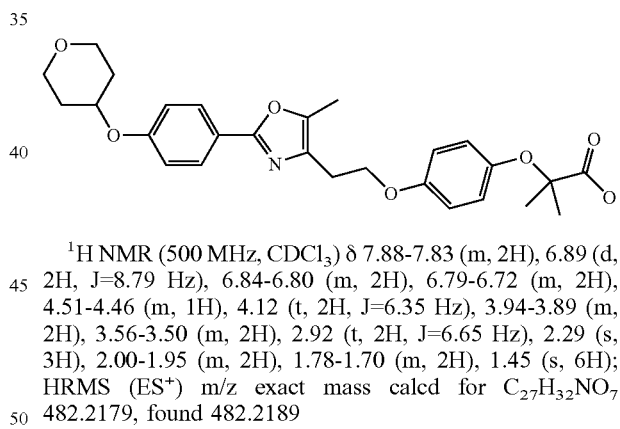

$^1$H NMR (500 MHz, CDCl$_3$) δ 7.88-7.83 (m, 2H), 6.89 (d, 2H, J=8.79 Hz), 6.84-6.80 (m, 2H), 6.79-6.72 (m, 2H), 4.51-4.46 (m, 1H), 4.12 (t, 2H, J=6.35 Hz), 3.94-3.89 (m, 2H), 3.56-3.50 (m, 2H), 2.92 (t, 2H, J=6.65 Hz), 2.29 (s, 3H), 2.00-1.95 (m, 2H), 1.78-1.70 (m, 2H), 1.45 (s, 6H); HRMS (ES$^+$) m/z exact mass calcd for C$_{27}$H$_{32}$NO$_7$ 482.2179, found 482.2189

EXAMPLE 22

2-Methyl-2-[4-(2-{5-methyl-2-[4-(4,4,5,5-tetramethyl-[1,3,2]dioxaborolan-2-yl)-phenyl]-oxazol-4-yl}-ethoxy)-phenoxy]-propionic acid

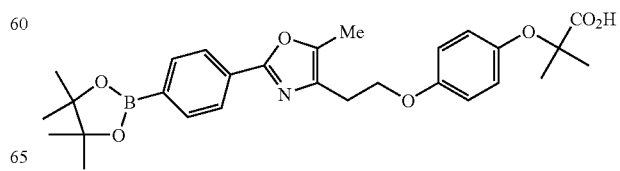

Step A

2-Methyl-2-[4-(2-{5-methyl-2-[4-(4,4,5,5-tetramethyl-[1,3,2]dioxaborolan-2-yl)-phenyl]-oxazol-4-yl}-ethoxy)-phenoxy]-propionic acid ethyl ester

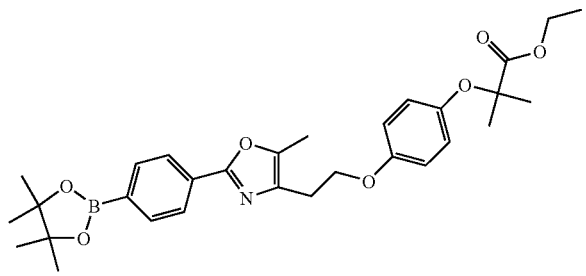

A flask charged with 2-(4-{2-[2-(4-bromophenyl)-5-methyl-oxazol-4-yl]-ethoxy}-phenoxy)-2-methyl-propionic acid ethyl ester (3.00 g, 6.155 mmol), KOAc (1.81 g, 18.466 mmol), and bis(pinacolato)diboron (1.87 g, 7.387 mmol) in DMSO (31.2 mL) was flushed and purged with $N_2$ three times. [1,1'-Bis(diphenylphosphino)-ferrocene]dichloro palladium(II), complex with dichloromethane (1:1) (905 mg, 1.108 mmol) was then added. After being stirred at 80° C. for 2 h, the reaction was checked by HPLC. The product was extracted with $CH_2Cl_2$ (60 mL) and washed with $H_2O$. The aqueous layer was back extracted with $CH_2Cl_2$ (60 mL). The combined organic layers were washed with $H_2O$ (50 mL), dried over NaCl, and solvent removed in vacuo. Flash chromatography using hexanes, 10% EtOAc, 20% EtOAc, then 40% EtOAc provided product in quantitative yield: $^1$H NMR (400 MHz, $CDCl_3$) δ 7.94 (d, 2 H), 7.82 (d, 2 H), 6.76 (d, 2 H), 6.73 (d, 2 H), 4.22 (q, 2 H), 4.18 (t, 2 H), 2.93 (t, 2 H), 2.33 (s, 3 H), 1.47 (s, 6 H), 1.31 (s, 12 H), 1.21 (t, 3 H); MS (EI) 536.3 $(M+H)^+$.

Step B

2-Methyl-2-[4-(2-{5-methyl-2-[4-(4,4,5,5-tetramethyl-[1,3,2]dioxaborolan-2-yl)-phenyl]-oxazol-4-yl}-ethoxy)-phenoxy]-propionic acid A sample of 2-methyl-2-[4-(2-{5-methyl-2-[4-(4,4,5,5-tetramethyl-[1,3,2]dioxaborolan-2-yl)-phenyl]-oxazol-4-yl}-ethoxy)-phenoxy]-propionic acid ethyl ester (55 mg, 0.103 mmol) was dissolved in 10 mL of EtOH with 3 mL of 5 N NaOH. This mixture was allowed to stir at 60° C. for 1 h. The mixture was cooled to room temperature and then acidified to pH 2 by the dropwise addition of 5 N HCl. This acidic mixture was diliuted with 10 mL of $H_2O$ and then extracted with $CH_2Cl_2$ (2×25 mL). The organic layers were combined, dried over NaCl, and solvent removed in vacuo which provided 49 mg (94%) of desired acid: $^1$H NMR (400 MHz, $CDCl_3$) δ 8.32 (d, 2 H), 7.95 (d, 2 H), 6.82 (d, 2 H), 6.74 (d, 2 H), 4.35 (t, 2 H), 3.25 (t, 2 H), 2.50 (s, 3 H), 1.44 (s, 6 H), 1.32 (s, 12 H); MS (EI) 508.0 $(M+H)^+$.

EXAMPLE 23

2-methyl-2-{3-[2-(5-methyl-2-phenyloxazol-4-yl)ethoxy]phenoxy}propionic acid

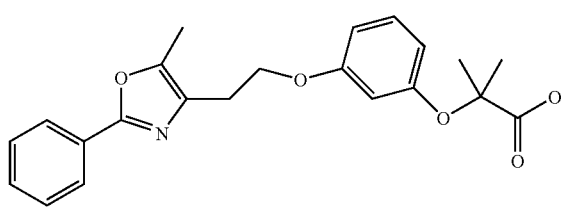

Step A

Toluene-4-sulfonic acid 2-(2-phenyl-4-yl-5-methyloxazol-4-yl)ethyl ester

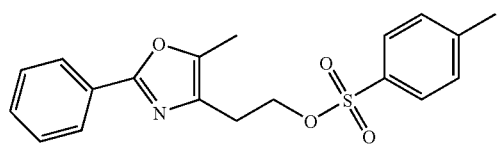

2-phenyl-5-methyl-4-oxazoleethanol was converted to toluene-4-sulfonic acid 2-(2-phenyl-4-yl-5-methyloxazol-4-yl)ethyl ester following the procedure described in Example 9, Step E (mp 132-134° C.)

Step B

2-Methyl-2-{3-[2-(5-methyl-2-phenyloxazol-4-yl)ethoxy]phenoxy}propionic acid ethyl ester

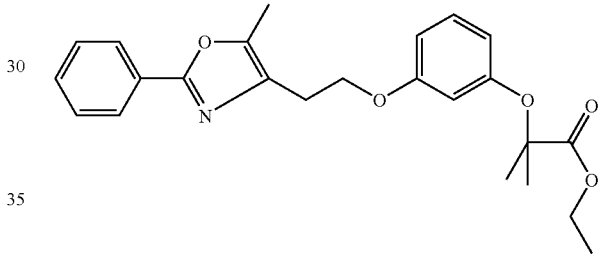

Toluene-4-sulfonic acid 2-(2-phenyl-4-yl-5-methyloxazol-4-yl)ethyl ester (382 mg, 1.07 mmol) and 2-(3-hydroxyphenoxy)-2-methylpropanoic acid ethyl ester (Columbia University WO 9731530) (200 mg, 0.89 mmol) were coupled following the procedure described in Example 1 to provide the product (276 mg, 76%) as a colorless oil: Rf=0.59 in 20% EtOAc/hexanes; $^1$H NMR (400 MHz, $CDCl_3$) δ 7.94 (m, 2H) 7.40-7.38 (m, 3H), 7.06 (t, J=8.0 Hz), 6.51 (d, J=8.0 Hz, 1H), 6.41 (s, 1H), 6.36 (d, 8.0 Hz), 4.22-4.15 (m, 4H), 2.93 (t, J=6.8 Hz, 2H), 2.34 (s, 3H), 1.55 (s, 6H), 1.21 (t, J=9.4 Hz, 3H); MS (EI) 410.1 $(M+H)^+$.

Step C

2-Methyl-2-{3-[2-(5-methyl-2-phenyloxazol-4-yl)ethoxy]phenoxy}propionic acid 2-Methyl-2-{3-[2-(5-methyl-2-phenyloxazol-4-yl)ethoxy]phenoxy}propionic acid ethyl ester (276 mg) was hydrolyzed following the procedure in Example 2 to provide the product (4.30 g, 99%) as a white solid: mp 140-141° C.;

Rf=0.11 in 60% EtOAc/hexanes; $^1$H NMR (400 MHz, $CDCl_3$) δ 7.95 (m, 2H), 7.43-7.41 (m, 3H), 7.14 (t, J=8.0 Hz, 1H), 6.71 (s, 1H), 6.62 (d, J=8.0 Hz, 1H), 6.53 (d, J=8.0 Hz, 1H), 4.19 (t, J=7.4 Hz, 2H), 2.91 (t, J=7.4 Hz, 2H), 2.35 (s, 3H), 1.58 (s, 6H); MS (EI) 381.9 $(M+H)^+$.

EXAMPLE 24

2-Methyl-2-{2-methyl-4-[2-(5-methyl-2-phenyloxazol-4-yl)ethoxy]phenoxy}propionic acid

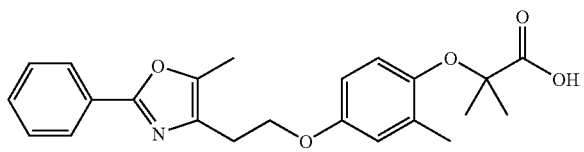

Step A 2-(4-Benzyloxy-2-formylphenoxy)-2-methyl propionic acid ethyl ester

5-Benzyloxy-2-hydroxy-benzaldehyde (Kappe, T.; Witoszynskyj, T. Arch. Pharm., 1975, 308 (5), 339-346) (2.28 g, 10.0 mmol), ethyl bromoisobutyrate (2.2 mL, 15 mmol), and cesium carbonate (3.26 g, 10.0 mmol) in dry DMF (25 mL) were heated at 80° C. for 18 h. The reaction mixture was cooled and partitioned between water (30 mL) and ether (75 mL). The organic layer was washed with brine (15 mL). The aqueous layers were back-extracted with ethyl acetate (30 mL), and the organic layer was washed with brine (20 mL). The combined organic layers were dried ($Na_2SO_4$) and concentrated to a brown oil. The crude product was purified by flash chromatography using hexanes:ethyl acetate (2.5:1) to give a pale yellow solid (3.04 g, 89%): mp 65° C.; $^1$H NMR (400 MHz, $CDCl_3$) δ 1.24 (t, 3H, J=7.1 Hz), 1.62 (s, 6H), 4.23 (q, 2H, J=7.1 Hz), 6.81 (d, 1H, J=8.8 Hz), 7.10 (dd, 1H, J=4.6, 9.0 Hz), 7.30-7.43 (m, 6H); MS (ES) m/e 343.1 [M+1].

Step B 2-(4-Hydroxy-2-methyl-phenoxy)-2-methyl-propionic acid ethyl ester

2-Methyl-2-{2-methyl-4-[2-(5-methyl-2-phenyloxazol-4-yl)ethoxy]phenoxy}propionic acid (9.00 g, 26.3 mmol) in ethanol (250 mL) was treated with 5% Pd/C (1.25 g) and hydrogen (60 psi, rt, overnight). Additional 5% Pd/C (1.25 g) was added, and the reaction was continued for 6 h at 40° C. The mixture was filtered and concentrated to a tan oil (6.25 g). This oil contained 9 mol % of 2-(4-Hydroxy-2-hydroxymethyl-phenoxy)-2-methyl-propionic acid ethyl ester.

$^1$H NMR (400 MHz, $CDCl_3$) δ 1.26 (t, 3H, J=7.3 Hz), 1.51 (s, 6H), 2.14 (s, 3H), 4.24 (q, 2H, J=7.3 Hz), 5.68 (brs, 1H), 6.47 (dd, 1H, J=3.4, 8.8 Hz), 6.59 (d, 1H, J=8.3 Hz), 6.60 (brs, 1H).

Step C

2-Methyl-2-{2-methyl-4-[2-(5-methyl-2-phenyloxazol-4-yl)ethoxy]phenoxy}propionic acid ethyl ester A mixture of 2-(4-hydroxy-2-methyl-phenoxy)-2-methyl-propionic acid ethyl ester (4.50 g, 18.9 mmol), toluene-4-sulfonic acid 2-(5-methyl-2-phenyl-oxazol-4-yl)ethyl ester (Japan Tobacco Inc WO 9518125) (8.43 g, 23.6 mmol), and $Cs_2CO_3$ (7.68 g, 23.6 mmol) was heated at 55° C. in DMF (45 mL) for 20 h. Additional toluene-4-sulfonic acid 2-(5-methyl-2-phenyl-oxazol-4-yl)ethyl ester (2.81 g, 7.86 mmol) and $Cs_2CO_3$ (2.56 g, 7.86 mmol) were added, and the mixture was heated at 55° C. in DMF (45 mL) for 6 h. The reaction mixture cooled and partitioned between EtOAc (200 mL) and $H_2O$ (100 mL). The organic layer was washed with brine (50 mL). The aqueous layers were extracted further with EtOAc (200 mL). The combined organic layers were dried ($Na_2SO_4$) and concentrated. The crude product was purified by flash chromatography using hexanes:ethyl acetate (6:1 to 4:1) to give an oil (5.81 g, 73%): $^1$H NMR (400 MHz, $CDCl_3$) δ 1.27 (t, 3H, J=7.1 Hz), 1.51 (s, 6H), 2.18 (s, 3H), 2.36 (s, 3H), 2.95 (t, 2H, J=6.6 Hz), 4.17 (t, 2H, J=6.6 Hz), 4.24 (q, 2H, J=7.1 Hz), 6.57 (dd, 1H, J=2.9, 8.8 Hz), 6.65 (d, 1H, J=9.3 Hz), 6.69 (d, 1H, J=2.9 Hz), 7.38-7.45 (m, 3H), 7.98-8.00 (m, 2H); MS (ES) m/e 424.2 [M+1].

Step D

2-Methyl-2-{2-methyl-4-[2-(5-methyl-2-phenyloxazol-4-yl)ethoxy]phenoxy}propionic acid A solution of 2-methyl-2-{2-methyl-4-[2-(5-methyl-2-phenyloxazol-4-yl)ethoxy]phenoxy}propionic acid ethyl ester (5.00 g, 11.8 mmol) in THF (30 mL) and MeOH (60 mL) was treated with 5N aqueous NaOH (20 mL). The solution was heated at 55° C. for 1 h, cooled to ambient temperature, and concentrated in vacuo. The residue was treated with ice water (20 mL), acidified with 5N aqueous HCl (25 mL), and extracted with ethyl acetate (200 mL). The organic layer was washed with brine (40 mL), dried ($Na_2SO_4$), and concentrated to a white solid (4.46 g, 96%): mp 117° C.; $^1$H NMR (400 MHz, $CDCl_3$) δ 1.53 (s, 6H), 2.19 (s, 3H), 2.38 (s, 3H), 2.98 (t, 2H, J=6.6 Hz), 4.15 (t, 2H, J=6.6 Hz), 6.58 (dd, 1H, J=3.4, 8.8 Hz), 6.70 (d, 1H, J=2.9 Hz), 6.80 (d, 1H, J=8.8 Hz), 7.38-7.45 (m, 3H), 7.97-8.00 (m, 2H); MS (FIA) m/e 394.2 [M−1].

EXAMPLE 25

{2-Methyl-4-[2-(5-methyl-2-phenyloxazol-4-yl)ethoxy]phenoxy}acetic acid

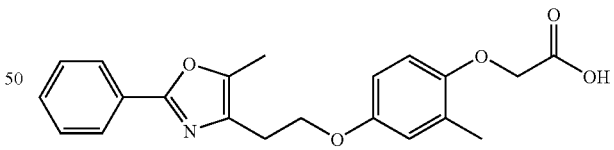

Step A (4-Benzyloxy-2-formylphenoxy)acetic acid ethyl ester (4-Benzyloxy-2-formylphenoxy)acetic acid ethyl ester was prepared from ethyl bromoacetate following the procedure described in Example 24, Step A. $^1$H NMR (400 MHz, $CDCl_3$) δ 1.29 (t, 3H, J=7.1 Hz), 4.27 (q, 2H, J=7.0 Hz), 4.71 (s, 2H), 5.06 (s, 2H), 6.85 (d, 1H, J=9.3 Hz), 7.17 (dd, 2H, J=3.2, 9.0 Hz), 7.46-7.33 (m, 5H), 10.54 (s, 1H); MS (ES) m/e 315 (M+1).

Step B (4-Hydroxy-2-methylphenoxy)acetic acid ethyl ester (4-Benzyloxy-2-formylphenoxy)acetic acid ethyl ester was debenzylated following the procedure described in Example 24, Step B. $^1$H NMR (400 MHz, CDCl3) δ 1.28 (t, 3H, J=7.1 Hz), 2.24 (s, 3H), 4.25 (q, 2H, J=7.1 Hz), 4.55 (s, 2H), 6.56 (dd, 1H, J=2.7, 8.5 Hz), 6.61 (d, 1H, J=8.3 Hz), 6.65 (d, 2H, J=2.9 Hz).

Step C

{2-Methyl-4-[2-(5-methyl-2-phenyloxazol-4-yl)ethoxy]phenoxy}acetic acid ethyl ester (4-Hydroxy-2-methylphenoxy)acetic acid ethyl ester and toluene-4-sulfonic acid 2-(5-methyl-2-phenyl-oxazol-4-yl)ethyl ester were coupled as described in Example 24, Step C.

$^1$H NMR (400 MHz, CDCl$_3$) δ 1.28 (t, 3H, J=7.0 Hz), 2.25 (s, 3H), 2.36 (s, 3H), 2.94 (t, 2H, J=6.8 Hz), 4.17 (t, 2H, J=6.6 Hz), 4.23 (q, 2H, J=7.0 Hz), 4.55 (s, 2H), 6.65 (s, 2H), 6.72 (s, 1H), 7.38-7.44 (m, 3H), 7.94-7.97 (m, 2H); MS (ES) m/e 396.2 (M+1).

Step D

{2-Methyl-4-[2-(5-methyl-2-phenyloxazol-4-yl)ethoxy]phenoxy}acetic acid

{2-Methyl-4-[2-(5-methyl-2-phenyloxazol-4-yl)ethoxy]phenoxy}acetic acid ethyl ester was hydrolyzed as described in Example 24, Step D. mp 133° C.; $^1$H NMR (300 MHz, CDCl$_3$) δ 2.24 (s, 3H), 2.39 (s, 3H), 3.00 (t, 2H, J=6.2), 4.16 (t, 2H, J=6.587), 4.58 (s, 2H), 6.60 (dd, 1H, J=2.9, 9.0), 6.72 (d, 1H, J=8.8), 6.72 (d, 1H, J=2.9), 7.42-7.48 (m, 3H), 7.98-8.03 (m, 2H); MS (FIA) m/e 368.2 (M+1).

EXAMPLE 26

{4-[2-(5-methyl-2-phenyl-oxazol-4-yl)ethoxy]-2-propylphenoxy}acetic acid

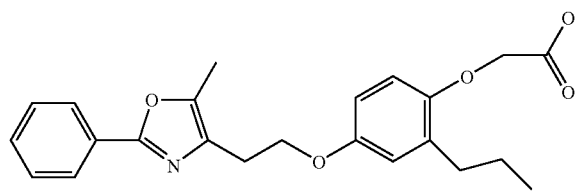

Step A

4-Benzyloxy-2-propylphenol

2-Allyl-4-benzyloxyphenol (WO 9728137 A1 19970807, Adams, A. D. et al.) (5.00 g, 20.8 mmol) in ethyl acetate (40 mL) was treated with 5% Pd/C (0.25 g) and hydrogen (1 atm) at ambient temperature for 18 h. The mixture was filtered and concentrated. The crude product was purified on a Biotage medium pressure chromatography system using a 40 L normal phase cartridge and eluted with 10% ethyl acetate in hexanes to give a tan solid (2.8 g, 56%). Rf=0.33 (25% EtOAc/Hexanes); $^1$H NMR (400 MHz, CDCl$_3$) δ 7.44-7.31 (m, 5H), 6.78 (s, 1H), 6.69 (d, J=1.5 Hz, 2H), 5.00 (s, 2H), 4.31 (s, 1H), 2.55 (t, J=7.6 Hz, 2H), 1.64 (q, J=7.5 Hz, 2H), 0.97 (t, J=7.3 Hz, 3H).

Step B (4-Benzyloxy-2-propylphenoxy)acetic acid ethyl ester

A solution of 4-benzyloxy-2-propylphenol (0.50 g, 1.94 mmol) in dry DMF (7 mL) was cooled in an ice bath and treated with NaH (0.15 g, 3.8 mmol, 60% oil dispersion). The ice bath was removed, ethyl bromoacetate (0.43 mL, 3.9 mmol) was added, and the mixture was placed in an oil bath (T=85° C.). After 18 h, the reaction mixture was cooled and concentrated in vacuo. The residue was diluted with EtOAc, washed with brine (2×), dried (Na$_2$SO$_4$), and concentrated. The crude product was purified by radial chromatography using 10% ethyl acetate in hexanes to give a tan solid (0.62 g, 97%). $^1$H NMR (400 MHz, CDCl$_3$) δ 7.44-7.31 (m, 5H), 6.82 (d, J=2.9 Hz, 1H), 6.72 (dd, J=8.8, 2.9 Hz, 1H), 6.66 (d, J=8.8 Hz, 1H), 5.00 (s, 2H), 4.57 (s, 2H), 4.25 (q, J=7.0 Hz, 2H), 2.63 (t, J=7.6 Hz, 2H), 1.64 (q, J=7.5 Hz, 2H), 1.29 (t, J=7.1 Hz, 3H), 0.95 (t, J=7.3 Hz, 3H); MS (FIA) m/e 329 (M+1).

Step C (4-Hydroxy-2-propylphenoxy)acetic acid ethyl ester

A solution of (4-benzyloxy-2-propylphenoxy)acetic acid ethyl ester (0.60 g, 1.83 mmol) in THF (15 mL) was treated with 5% Pd/C (75 mg) and hydrogen (60 psi) at ambient temperature for 24 h. The mixture was filtered and concentrated. The crude product was purified by radial chromatography using 15% ethyl acetate in hexanes to give a tan solid (0.25 g, 57%). $^1$H NMR (400 MHz, CDCl$_3$) δ 6.66 (d, J=2.9 Hz, 1H), 6.62 (d, J=8.8 Hz, 1H), 6.57 (dd, J=8.8, 2.9 Hz, 1H), 4.56 (s, 1H), 4.40 (s, 1H), 4.25 (q, J=7.2 Hz, 2H), 2.61 (t, J=7.6 Hz, 2H), 1.63 (q, J=7.5 Hz, 2H), 1.29 (t, J=7.1 Hz, 3H), 0.95 (t, J=7.3 Hz, 3H); MS (FIA) m/e 239 (M+1).

Step D

{4-[2-(5-Methyl-2-phenyloxazol-4-yl)ethoxy]-2-propylphenoxy}acetic acid ethyl ester A mixture of (4-hydroxy-2-propylphenoxy)acetic acid ethyl ester (0.23 g, 0.965 mmol), toluene-4-sulfonic acid 2-(5-methyl-2-phenyloxazol-4-yl)ethyl ester (Japan Tobacco Inc WO 9518125) (0.41 g, 1.16 mmol), and cesium carbonate (0.41 g, 1.25 mmol) was heated at 55° C. in DMF (45 mL) for 18 h. The reaction mixture cooled, concentrated in vacuo, and partitioned between EtOAc (60 mL) and H$_2$O (40 mL). The organic layer was washed with brine, dried (Na$_2$SO$_4$), and concentrated. The crude product was purified by radial chromatography using 15% ethyl acetate in hexanes to give a tan solid (0.25 g, 61%). $^1$H NMR (400 MHz, CDCl$_3$) δ 7.97, (dd, J=8.3, 2.0 Hz, 2H), 7.45-7.39 (m, 3H), 6.73 (s, 3H), 6.65 (d, J=1.5 Hz, 2H), 4.55 (s, 2H), 4.24 (q, J=7.2 Hz, 2H), 4.18 (t, J=6.8 Hz, 2H), 2.61 (t, J=7.8 Hz, 2H), 2.37 (s, 3H), 1.62 (q, J=7.5 Hz, 2H), 1.52 (s, 6H), 1.27 (t, J=7.1 Hz, 3H), 1.08 (t, J=7.3 Hz, 3H); MS (FIA) m/e 424 (M+1).

The following compound was prepared by the same procedure using ethyl bromoisobutyrate in step B:

2-Methyl-2-{4-[2-(5-methyl-2-phenyloxazol-4-yl) ethoxy]-2-propylphenoxy}propionic acid ethyl ester: ¹H NMR (400 MHz, CDCl₃) δ 7.97 (dd, J=8.3, 2.4 Hz, 2H), 7.43-7.41 (m, 3H), 6.70 (d, J=2.9 Hz, 1H), 6.63-6.58 (m, 2H), 4.23 (q, J=7.2 Hz, 2H), 4.18 (t, J=6.6 Hz, 2H), 2.95 (t, J=6.6 Hz, 2H), 2.54 (t, J=7.6 Hz, 2H), 2.36 (s, 3H), 1.59 (q, J=7.5 Hz, 2H), 1.53 (s, 6H), 1.26 (t, J=7.1 Hz, 3H), 0.93 (t, J=7.3 Hz, 3H); MS (FIA) m/e 452 (M+1).

Step E

{4-[2-(5-methyl-2-phenyloxazol-4-yl)-ethoxy]-2-propylphenoxy}acetic acid

A solution of 2-methyl-2-{4-[2-(5-methyl-2-phenyloxazol-4-yl)ethoxy]-2-propylphenoxy}propionic acid ethyl ester (0.21 g, 0.5 mmol) in MeOH (10 mL) was treated with 2.5N aqueous NaOH (1.2 mL). The solution was heated at 55° C. for 1.5 h, cooled to ambient temperature, and concentrated in vacuo. The residue was diluted with EtOAc (30 mL) and water (30 mL) and acidified to pH=1 with 5N aqueous HCl. The organic layer was washed with brine (40 mL), dried (Na₂SO₄), and concentrated to a white solid (0.17 g, 86%). ¹H. NMR (400 MHz, CDCl₃) δ 7.97 (dd, J=7.4, 2.4 Hz, 2H), 7.44-7.41 (m, 3H), 6.72 (d, J=2.9 Hz, 1H), 6.68-6.59 (m, 2H), 4.59 (s, 2H), 4.14 (t, J=6.6 Hz, 2H), 2.97 (t, J=6.6 Hz, 2H), 2.59 (t, J=7.6 Hz, 2H), 2.38 (s, 3H), 1.61 (q, J=7.7 Hz, 2H), 0.94 (t, J=7.6 Hz, 3H); MS (ES) m/e 396 (M+1).

The following compound was also prepared from the corresponding ester:

Example 26A

2-Methyl-2-{4-[2-(5-methyl-2-phenyloxazol-4-yl) ethoxy]-2-propylphenoxy}propionic acid

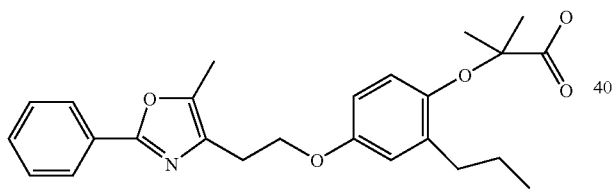

¹H NMR (400 MHz, CDCl₃) δ 7.97 (dd, J=8.3, 2.9 Hz, 2H), 7.44-7.40 (m, 3H), 6.77 (d, J=8.8 Hz, 1H), 6.71 (d, J=2.9 Hz, 1H), 6.59 (dd, J=8.8, 2.9 Hz, 1H), 4.15 (q, J=6.6 Hz, 2H), 2.98 (t, J=6.6 Hz, 2H), 2.52 (t, J=7.6 Hz, 2H), 2.37 (s 3H), 1.59 (q, J=7.5 Hz, 2H), 1.54 (s, 6H), 0.93 (t, J=7.3 Hz, 3H); MS (ES) m/e 424 (M+1).

EXAMPLE 27

{4-[2-(5-Methyl-2-phenyloxazol-4-yl)ethoxy]-3-propylphenoxy}acetic acid

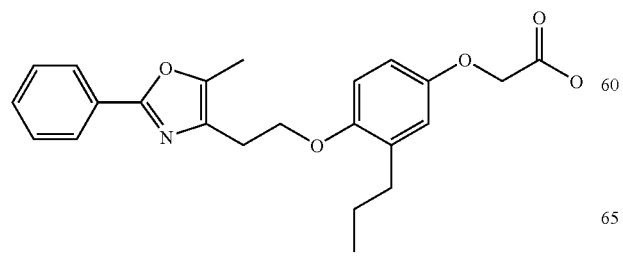

Step A

4-[2-(4-Benzyloxy-2-propylphenoxy)ethyl]-5-methyl-2-phenyloxazole

A solution of 4-benzyloxy-2-propylphenol (1.00 g, 4.13 mmol), 2-(5-methyl-2-phenyloxazol-4-yl)ethanol (Japan Tobacco Inc WO 9518125) (0.84 g, 4.13 mmol), and triphenylphosphine (1.41 g, 5.37 mmol) in THF (17 mL) was treated dropwise at ambient temperature with diisopropyl azodicarboxylate (0.96 mL, 5.0 mmol). After 18 h, the reaction mixture was concentrated in vacuo. The residue was diluted with EtOAc, washed with brine (40 mL), dried (Na₂SO₄), and concentrated. The crude product was purified by radial chromatography using 10-15% ethyl acetate in hexanes to give the product (1.2 g, 68%). ¹H. NMR (400 MHz, CDCl₃) δ 7.98 (dd, J=7.8, 2.4 Hz, 2H), 7.45-7.30 (m, 8H), 6.78-6.69 (m, 3H), 4.99 (s, 2H), 4.19 (t, J=6.6 Hz, 2H), 2.96 (t, J=6.4 Hz, 2H), 2.50 (t, J=7.6 Hz, 2H), 2.38 (s, 3H), 1.53 (q, J=7 Hz, 2H), 0.88 (t, J=7 Hz, 3H); MS (FIA) m/e 42.8 (M+1).

Step B

4-[2-(5-Methyl-2-phenyloxazol-4-yl)ethoxy]-3-propylphenol

A solution of 4-[2-(4-benzyloxy-2-propylphenoxy)ethyl]-5-methyl-2-phenyloxazole. (1.2 g, 2.8 mmol) in THF (50 mL) was treated with 5% Pd/C (0.15 g) and hydrogen (60 psi) at ambient temperature for 18 h. The mixture was filtered and concentrated. The crude product was purified by radial chromatography using 15% ethyl acetate in hexanes to give a tan solid (0.74 g, 78%): ¹H. NMR (400 MHz, CDCl₃) δ 7.99 (dd, J=7.8 Hz, 2.4 Hz, 2H), 7.44-7.39 (m, 3H), 6.65-6.47 (m, 3H), 4.11 (t, J=6.4 Hz, 2H), 2.95 (t, J=6.4 Hz, 2H), 2.43 (t, J=7.8 Hz, 2H), 2.39 (s, 3H), 1.46 (q, J=7.2 Hz, 2H), 0.85 (t, J=7 Hz, 3H).

Step C

{4-[2-(5-Methyl-2-phenyl-oxazol-4-yl)ethoxy)]-3-propylphenoxy}acetic acid ethyl ester

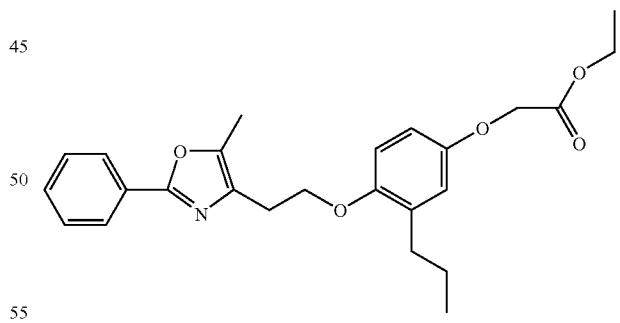

A solution of 4-[2-(5-methyl-2-phenyloxazol-4-yl) ethoxy]-3-propylphenol (0.37 g, 1.10 mmol) in dry DMF (4 mL) was cooled in an ice bath and treated with NaH (0.13 g, 3.3 mmol, 60% oil dispersion). After 10 min, ethyl bromoacetate (0.37 mL, 3.3 mmol) was added. The ice bath was removed, and the mixture was placed in an oil bath (T=85° C.). After 18 h, the reaction mixture was cooled and concentrated in vacuo. The residue was partitioned between EtOAc (70 mL) and water (40 mL). The organic layer was dried (Na₂SO₄) and concentrated. The crude product was purified by radial chromatography using 5% ethyl acetate in dichloromethane to give a white solid (0.34 g, 73%). ¹H NMR (400 MHz, CDCl₃), δ 7.97 (dd, J=7.8, 2.4 Hz, 2H), 7.41-7.39 (m, 3H), 6.77-6.73 (m, 2H), 6.61-6.63 (m, 1H, 4.54 (s, 1H), 4.28-4.24 (m, 2H), 2.96 (t, J=6.4 Hz, 2H), 2.50 (t, J=7.1 Hz, 2H), 2.37 (s, 3H), 1.51 (q, J=7.6 Hz, 2H), 1.31-1.29 (m, 5H), 0.84 (t, J=7.0 Hz, 3H); MS (FIA) m/e 424 (M+1).

Step D

{4-[2-(5-Methyl-2-phenyloxazol-4-yl)-ethoxy]-3-propylphenoxy}acetic acid

A solution of {4-[2-(5methyl-2-phenyloxazol-4-yl)ethoxy]-3-propylphenoxy}acetic acid ethyl ester (0.10 g, 0.24 mmol) in MeOH (5 mL) was treated with 2.5 N aqueous NaOH (0.52 mL). The solution was heated at 55° C. for 2 h, cooled to ambient temperature, and concentrated in vacuo. The residue was diluted with EtOAc (40 mL) and water (40 mL) and acidified to pH=1 with 5N aqueous HCl. The organic layer was washed with brine (40 mL), dried (Na₂SO₄), and concentrated to give a white solid (0.080 g, 86%). ¹H NMR (400 MHz, CDCl₃), δ 7.97 (dd, J=7.8, 2.9 Hz, 2H), 7.44-7.40 (m, 3H), 6.76 (d, J=2.9 Hz, 1H), 6.72 (d, J=8.8 Hz, 1H), 6.64 (dd, J=8.8, 2.9 Hz, 1H), 4.58 (s, 2H), 4.14 (t, J=6.4 Hz, 2H), 2.99 (t, J=6.4 Hz, 2H), 2.39 (s, 3H), 1.51 (q, J=7.5 Hz, 2H), 0.88 (t, J=7.3 Hz, 3H); MS (FIA) m/e 396 (M+1).

The following compound was also prepared by the same procedure using ethyl bromoisobutyrate in step C:

Example 27A

2-Methyl-2-{4-[2-(5-methyl-2-phenyloxazol-4-yl)ethoxy]-3-propylphenoxy}propionic acid

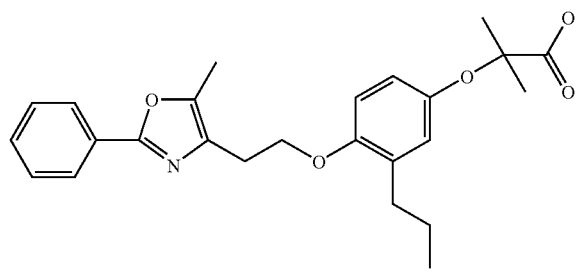

¹H NMR (400 MHz, CDCl₃) δ 7.97 (dd, J=8.3, 2.4 Hz, 2H), 7.43-7.40 (m, 3H), 6.75-6.72 (m, 3H), 4.18 (t, J+6.4 Hz, 2H), 3.00 (t, J=6.4 Hz, 2H), 2.49 (t, J=7.6 Hz, 2H), 2.39 (s, 3H), 1.53-1.48 (m, 8H), 0.87 (t, J=7.3 Hz, 3H); Rf=0.59 (20% MeOH/CH₂Cl₂).

EXAMPLE 28

{4-[2-(5-Methyl-2-phenyl-oxazol-4-yl)-ethoxy]-2,6-dipropyl-phenoxy}acetic acid

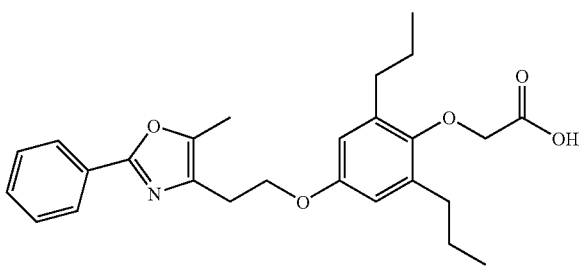

Step A

2-Allyl-1-allyloxy-4-benzyloxy-benzene

A mixture of 2-allyl-4-benzyloxy-phenol (ER2-YYR-17) (35.56 g, 148 mmol), allyl bromide (21.5 g, 178 mmol), cesium carbonate (58 g, 178 mmol) and methyl ethyl ketone (400 mL) was refluxed with stirring in a 1 L round bottomed flask. After 23 h, the reaction was cooled and concentrated. The residue was partitioned between water (500 mL) and EtOAc (400 mL). The organic layer was dried (MgSO₄) and concentrated to a tan oil, 39.37 (95%) ER0-LKW-190A: ¹H NMR (CDCl₃) δ 3.45 (dd, 2H), 4.54 (dd, 2H), 5.04 (s, 2H), 5.18 (m, 2H), 5.29 (dd, 1H), 5.46 (dd, 1H), 5.94-6.18 (m, 2H), 6.81 (s, 2H), 6.88 (s, 1H), 7.30-7.48 (m, 5H), MS (ES) m/e 281 [M+1].

Step B 2,6-Diallyl-4-benzyloxy-phenol

A mixture of 2-allyl-1-allyloxy-4-benzyloxy-benzene (5.45 g, 19.44 mmol) and N,N-dimethylaniline (DMA) (5 mL) was heated at reflux for 5 h. The reaction was cooled and 1N H₂SO₄ (50 mL) was added. The product was extracted into EtOAc (100 mL) and washed with 1N H₂SO₄ (2×100 mL). The organic layer was dried (MgSO₄) and concentrated to a dark brown oil 5.45 g. The crude product was purified by flash chromatography (300 g silica gel/6% EtOAc/hexane) to give a yellow oil 3.10 (57%): ¹H NMR (CDCl₃) δ 3.44 (dd, 4H), 4.83 (s, 1H), 5.04 (s, 2H), 5.19 (dd, 4H), 5.97-6.14 (m, 2H), 6.72 (s, 2H), 7.33-7.52 (m, 5H), MS (ES) m/e 281 [M+1].

Step C (2,6-Diallyl-4-benzyloxy-phenoxy)-acetic acid ethyl ester 2,6-Diallyl-4-benzyloxy-phenol (1.507 g, 5.37 mmol), ethyl bromoacetate (0.89 mL, 8.0 mmol), and cesium carbonate (1.75 g, 5.37 mmol) in dry DMF (15 mL) were heated at 85° C. for 18 h. The reaction mixture was cooled and partitioned between water (25 mL) and ethyl acetate (75 mL). The organic layer was washed with brine (25 mL), dried (Na₂SO₄), and concentrated to an oil (2.08 g, 105%): ¹H NMR (400 MHz, CDCl₃) δ 1.32 (t, 3H, J=7.3 Hz), 3.41 (d, 2H, J=6.3 Hz), 4.28 (q, 2H, J=7.3 Hz), 4.34 (s, 2H), 4.98 (s, 2H), 5.02-5.09 (m, 4H), 5.94 (ddt, 2H, J=5.1, 10.3, 16.6 Hz), 6.68 (s, 2H), 7.29-7.42 (m, 5H).

The following compound was prepared by the same procedure: 2-(2,6-Diallyl-4-benzyloxy-phenoxy)-2-methyl-propionic acid ethyl ester: ¹H NMR (400 MHz, CDCl₃) δ 1.30 (t, 3H, J=7.3 Hz), 1.41 (s, 6H), 3.29 (d, 4H, J=6.8 Hz), 4.23 (q, 2H, J=7.1 Hz), 4.92 (s, 2H), 5.02-5.06 (m, 2H), 5.06 (s, 2H), 5.80-5.90 (m, 2H), 6.61 (s, 2H), 7.27-7.38 (m, 5H).

Step D (4-Hydroxy-2,6-dipropyl-phenoxy)-acetic acid ethyl ester (2,6-Diallyl-4-benzyloxy-phenoxy)-acetic acid ethyl ester (2.07 g, 5.65 mmol) in ethanol (35 mL) was treated with 5% Pd/C (0.25 g) and hydrogen (60 psi, rt, 6 h). The mixture was filtered and concentrated to a viscous colorless oil (1.21 g, 76%): ¹H NMR (400 MHz, CDCl₃) δ 0.95 (t, 6H, J=7.3 Hz), 1.28 (t, 4H, J=7.3 Hz), 1.61 (sextet, 4H, J=7.3 Hz), 2.53-2.57 (m, 4H), 4.29 (q, 2H, J=7.2 Hz), 4.33 (s, 2H), 4.46 (brs, 1H), 6.49 (s, 2H).

The following compound was prepared by the same procedure: 2-(4-Hydroxy-2,6-dipropyl-phenoxy)-2-methyl-propionic acid ethyl ester: 623 mg (80%).

Step E

{4-[2-(5-Methyl-2-phenyl-oxazol-4-yl)-ethoxy]-2,6-dipropyl-phenoxy}-acetic acid ethyl ester A mixture of (4-hydroxy-2,6-dipropyl-phenoxy)-acetic acid ethyl ester (240 mg, 0.89 mmol), toluene-4-sulfonic acid 2-(5-methyl-2-phenyl-oxazol-4-yl)ethyl ester (Japan Tobacco Inc WO 9518125) (400 mg, 1.12 mmol), and $Cs_2CO_3$ (360 mg, 1.10 mmol) was heated at 55° C. in DMF (5 mL) for 20 h. The reaction mixture cooled and partitioned between EtOAc (30 mL) and $H_2O$ (10 mL). The organic layer was washed with brine (15 mL). The organic layer was dried ($Na_2SO_4$) and concentrated. The crude product was purified by radial chromatography using hexanes:ethyl acetate (8:1 to 6:1) to give an oil (244 mg, 59%): $^1$H NMR (400 MHz, $CDCl_3$) δ 0.94 (t, 6H, J=7.3 Hz), 1.32 (t, 3H, J=7.0 Hz), 1.60 (sextet, 4H, J=7.6 Hz), 2.39 (s, 3H), 2.53-2.56 (m, 4H), 3.05 (brt, 2H), 4.20 (brt, 2H), 4.28 (q, 2H, J=7.3 Hz), 4.30 (s, 2H), 6.54 (s, 2H), 7.45-7.50 (m, 3H), 8.02-8.09 (m, 2H).

The following compound was prepared by the same procedure: 2-Methyl-2-{4-[2-(5-methyl-2-phenyl-oxazol-4-yl)-ethoxy]-2,6-dipropyl-phenoxy}-propionic acid ethyl ester: $^1$H NMR (400 MHz, $CDCl_3$) δ 0.91 (t, 6H, J=7.3 Hz), 1.33 (t, 3H, J=7.1 Hz), 1.41 (s, 6H), 1.59 (sextet, 4H, J=7.3 Hz), 2.33 (s, 3H), 2.42-2.47 (m, 4H), 2.94 (t, 2H, J=6.6 Hz), 4.18 (t, 2H, J=6.8 Hz), 4.26 (q, 2H, J=7.3 Hz), 6.52 (s, 2H), 7.38-7.43 (m, 3H), 7.96 (dd, 2H, J=1.5, 7.8 Hz).

Step F

{4-[2-(5-Methyl-2-phenyl-oxazol-4-yl)-ethoxy]-2,6-dipropyl-phenoxy}-acetic acid

A solution of {4-[2-(5-methyl-2-phenyl-oxazol-4-yl)-ethoxy]-2,6-dipropyl-phenoxy}-acetic acid ethyl ester (244 mg, 0.524 mmol) in THF (3 mL) and MeOH (6 mL) was treated with 2.5N aqueous NaOH (2 mL). The solution was heated at 55° C. for 2.5 h, cooled to ambient temperature, and concentrated in vacuo. The residue was treated with ice water (1 mL) and acidified with 5N aqueous HCl (2 mL). The mixture with $CH_2Cl_2$ (3 mL) was transferred to a ChemElute cartridge (5 g) and eluted with $CH_2Cl_2$ (40 mL). The eluent was concentrated to a white foam (228 mg, 100%): $^1$H NMR (400 MHz, $CDCl_3$) δ 0.94 (t, 6H, J=7.3 Hz), 1.60 (sextet, 4H, J=7.6 Hz), 2.37 (s, 3H), 2.50-2.54 (m, 4H), 2.98 (brt, 2H), 4.19 (brt, 2H), 4.37 (s, 2H), 6.56 (s, 2H), 7.42-7.43 (m, 3H), 7.98-7.99 (m, 2H); MS (ES) m/e 438.2 [M+1].

The following compound was hydrolyzed by the same procedure:

Example 28A

2-Methyl-2-{4-[2-(5-methyl-2-phenyl-oxazol-4-yl)-ethoxy]-2,6-dipropyl-phenoxy}-propionic acid

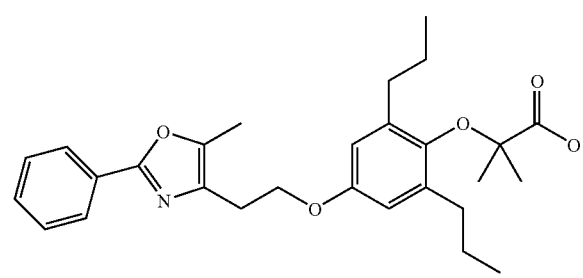

$^1$H NMR (300 MHz, DMSO-d6) δ 0.86 (t, 6H, J=7.3 Hz), 1.28 (s, 6H), 1.51 (sextet, 4H, J=7.3 Hz), 2.34 (s, 3H), 2.41-2.46 (m, 4H), 2.88 (t, 2H, J=6.6 Hz), 4.51 (t, 2H, J=6.8 Hz), 6.54 (s, 2H), 7.46-7.54 (m, 3H), 7.94-7.96 (m, 2H); MS (FIA) m/e 466.4 [M+1].

EXAMPLE 29

2-Methyl-2-{4-[2-(5-methyl-2-phenyl-oxazol-4-yl)-ethoxy]-3,5-dipropyl-phenoxy}-propionic acid

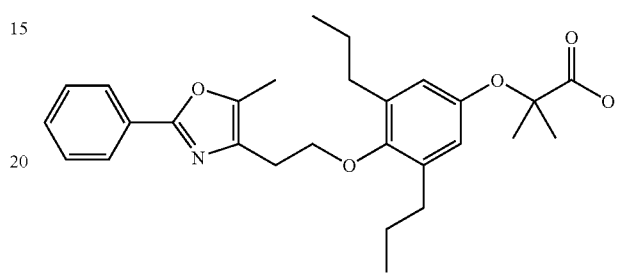

and 2-{4-[2-(2-Cyclohexyl-5-methyl-oxazol-4-yl)-ethoxy]-3,5-dipropyl-phenoxy}-2-methyl-propionic acid

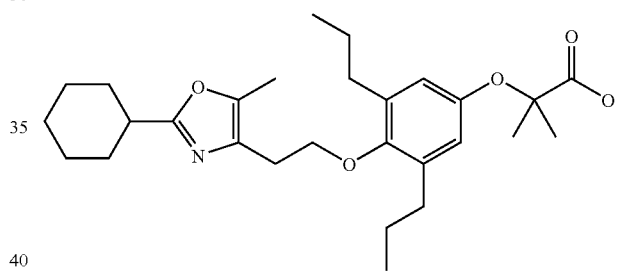

Step A

4-[2-(2,6-Diallyl-4-benzyloxy-phenoxy)-ethyl]-5-methyl-2-phenyl-oxazole

A mixture of 2,6-diallyl-4-benzyloxy-phenol (520 mg, 1.85 mmol), toluene-4-sulfonic acid 2-(5-methyl-2-phenyl-oxazol-4-yl)ethyl ester (Japan Tobacco Inc WO 9518125) (828 mg, 2.32 mmol), and $Cs_2CO_3$ (604 mg, 1.85 mmol) was heated at 55° C. in DMF (5 mL) for 20 h. Additional toluene-4-sulfonic acid 2-(5-methyl-2-phenyl-oxazol-4-yl) ethyl ester (300 mg, 0.839 mmol) and $Cs_2CO_3$ (200 mg, 0.614 mmol) were added, and the mixture was heated for 18 h. The reaction mixture was cooled and partitioned between EtOAc (40 mL) and $H_2O$ (10 mL). The organic layer was washed with brine (15 mL), dried ($Na_2SO_4$), and concentrated. The crude product was purified by radial chromatography using hexanes:ethyl acetate (8:1) to give a colorless oil (722 mg, 83%): $^1$H NMR (400 MHz, $CDCl_3$) δ 2.38 (s, 3H), 2.95 (t, 2H, J=6.3 Hz), 3.33 (d, 2H, J=6.3 Hz), 4.01 (t, 2H, J=6.3 Hz), 4.96 (s, 2H), 4.97-5.02 (m, 2H), 5.03 (s, 2H), 5.84-5.94 (m, 1H), 6.65 (s, 2H), 7.28-7.45 (m, 8H), 7.99 (dd, 2H, J=2.0, 7.8 Hz).

Step B

4-[2-(5-Methyl-2-phenyl-oxazol-4-yl)-ethoxy]-3,5-dipropyl-phenol and 4-[2-(2-cyclohexyl-5-methyl-oxazol-4-yl)-ethoxy]-3,5-dipropyl-phenol 4-[2-(2,6-Diallyl-4-benzyloxy-phenoxy)-ethyl]-5-methyl-2-phenyl-oxazole (722 mg, 1.54 mmol) in ethanol (35 mL) was treated with 5% Pd/C (0.90 g) and hydrogen (60 psi, rt, 18 h). The mixture was filtered and concentrated to a viscous colorless oil (377 mg, 76%) as a ~1:1 molar mixture of the title compounds: $^1$H NMR (400 MHz, CDCl$_3$) δ 0.86 (t, 3H, J=7.3 Hz), 0.88 (t, 3H, J=7.3 Hz), 1.20-1.40 (m, 1.5H), 1.45-1.58 (m, 6H), 1.65-1.75 (m, 1H), 1.78-1.82 (m, 1H), 1.98-2.05 (m, 1H), 2.26 (s, 1.5H), 2.39 (s, 1.5), 2.37-2.45 (m, 4H), 2.82-2.88 (m, 1H), 2.94 (t, 1H, J=6.3 Hz), 3.84 (t, 1H, J=6.3 Hz), 3.93 (t, 1H, J=6.3 Hz), 6.44 (brs, 2H), 7.38-7.42 (m, 1.5H), 7.98-8.00 (m, 1H).

Step C

2-Methyl-2-{4-[2-(5-methyl-2-phenyl-oxazol-4-yl)-ethoxy]-3,5-dipropyl-phenoxy}-propionic acid ethyl ester and 2-{4-[2-(2-Cyclohexyl-5-methyl-oxazol-4-yl)-ethoxy]-3,5-dipropyl-phenoxy}-2-methyl-propionic acid ethyl ester A mixture of 4-[2-(5-methyl-2-phenyl-oxazol-4-yl)-ethoxy]-3,5-dipropyl-phenol and 4-[2-(2-cyclohexyl-5-methyl-oxazol-4-yl)-ethoxy]-3,5-dipropyl-phenol (377 mg, 0.993 mmol), ethyl bromoisobutyrate (0.29 mL, 2.0 mmol), and Cs$_2$CO$_3$ (326 mg, 1.00 mmol) was heated at 55° C. in DMF (5 mL) for 16 h. Additional bromo ester (0.29 mL) and Cs$_2$CO$_3$ (326 mg) were added, and the mixture was heated for 7 h. The reaction mixture cooled and partitioned between EtOAc (30 mL) and H$_2$O (10 mL). The organic layer was washed with brine (10 mL), dried (Na$_2$SO$_4$), and concentrated. The crude product was purified by flash chromatography using hexanes:ethyl acetate (100:0 to 5:1) to give a colorless oil (450 mg, 92%), a ~1:1 molar ratio of the title compounds:

$^1$H NMR (400 MHz, CDCl$_3$) δ 0.86 (t, 3H, J=7.3 Hz), 0.88 (t, 3H, J=7.3 Hz), 1.24 (2t, 3H, J=7 Hz), 1.2-1.4 (m, 1.5H), 1.45-1.58 (m, 6H), 1.52 (s, 6H), 1.65-1.75 (m, 1H), 1.78-1.82 (m, 1H), 1.98-2.05 (m, 1H), 2.25 (s, 1.5H), 2.38 (s, 1.5), 2.37-2.45 (m, 4H), 2.82-2.88 (m, 1H), 2.94 (t, 1H, J=6 Hz), 3.85 (t, 1H, J=6 Hz), 3.95 (t, 1H, J=6 Hz), 4.18 (2q, 2H, J=7 Hz), 6.44 (s, 2H), 7.38-7.42 (m, 1.5H), 7.98-8.00 (m, 1H).

Step D

2-Methyl-2-{4-[2-(5-methyl-2-phenyl-oxazol-4-yl)-ethoxy]-3,5-dipropyl-phenoxy}-propionic acid and 2-{4-[2-(2-Cyclohexyl-5-methyl-oxazol-4-yl)-ethoxy]-3,5-dipropyl-phenoxy}-2-methyl-propionic acid A solution of 2-methyl-2-{4-[2-(5-methyl-2-phenyl-oxazol-4-yl)-ethoxy]-3,5-dipropyl-phenoxy}-propionic acid ethyl ester and 2-{4-[2-(2-cyclohexyl-5-methyl-oxazol-4-yl)-ethoxy]-3,5-dipropyl-phenoxy}-2-methyl-propionic acid ethyl ester (450 mg, 0.966 mmol) in THF (5 mL) and MeOH (12 mL) was treated with 2 N aqueous NaOH (3 mL). The solution was heated at 55° C. for 2 h, cooled to ambient temperature, and concentrated in vacuo. The residue was acidified with 5N aqueous HCl (1 mL) and partitioned between EtOAc (30 mL) and H$_2$O (5 mL). The organic layer was washed with brine (10 mL), dried (Na$_2$SO$_4$), and concentrated to a colorless oil (450 mg). The mixture was separated using HPLC to give the title compounds as white foams.

Example 29A

2-Methyl-2-{4-[2-(5-methyl-2-phenyl-oxazol-4-yl)-ethoxy]-3,5-dipropyl-phenoxy}-propionic acid $^1$H NMR (400 MHz, CDCl$_3$) δ 0.85 (t, 6H, J=7.3 Hz), 1.51 (s, 6H), 1.51 (sextet, 4H, J=7.8 Hz), 2.39 (s, 3H), 2.42-2.46 (m, 4H), 2.96 (t, 2H, J=6.4 Hz), 3.96 (t, 2H, J=6.4 Hz), 6.57 (s, 2H), 7.41-7.43 (m, 3H), 7.98-8.01 (m, 2H).

Example 29B

2-{4-[2-(2-Cyclohexyl-5-methyl-oxazol-4-yl)-ethoxy]-3,5-dipropyl-phenoxy}-2-methyl-propionic acid (482878) $^1$H NMR (400 MHz, CDCl$_3$) δ 0.86 (t, 6H, J=7.3 Hz), 1.20-1.40 (m, 3H), 1.24-1.60 (m, 6H), 1.52 (s, 6H), 1.68-1.71 (m, 1H), 1.78-1.83 (m, 2H), 2.00-2.03 (m, 2H), 2.26 (s, 3H), 2.40 (t, 4H, J=7.8 Hz), 2.70-2.80 (m, 1H), 2.86 (t, 2H, J=6.1 Hz), 3.86 (t, 2H, J=6 Hz), 6.56 (s, 2H).

EXAMPLE 30

{2-Ethyl-4-[2-(5-methyl-2-phenyloxazol-4-yl)ethoxy]phenoxy}acetic acid

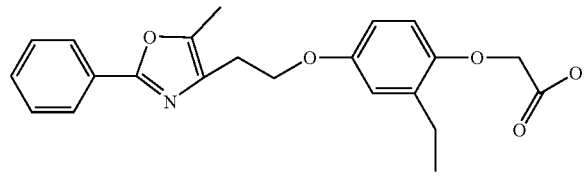

Step A

4-Benzyloxy-2-vinylphenol

To a flame dried 500 mL 3-neck flask under an atmosphere of argon, was charged methyltriphenylphosphonium bromide (43.8 mmol) dissolved in anhydrous THF (120 mL), followed by the dropwise addition of n-butyllithium (21.9 mL, 35.04 mmol). The dark red mixture was stirred at ambient temperature for 1 h. Next 5-benzyloxy-2-hydroxybenzaldehyde (2.0 g, 8.76 mmol) (Acta. Chem. Scand., Ser. B, B40(5), 400-1, (1986) was added followed by the addition of anhydrous dichloromethane (40 mL). The mixture was stirred at ambient temperature for 18 h. The solvents were removed in vacuo, and the residue was partitioned between EtOAc and water (500 mL each). The organic layer was washed with brine (500 mL), dried (Na$_2$SO$_4$), and concentrated in vacuo. The crude product was purified using the Biotage FlashElute chromatography system using a 65M normal phase cartridge, eluting with 15% EtOAc/Hexanes to give a yellow solid (1.75 g, 88%). $^1$H NMR (400 MHz, CDCl$_3$) δ 7.44-7.30, (m, 4H), 7.14 (d, J=2.9 Hz, 1H), 6.94-6.87 (m, 1H), 6.79 (dd, J=8.8, 2.9 Hz, 2H), 6.72 (d, J=8.8 Hz, 1H), 5.71 (dd, J=17.6, 1.5 Hz, 1H), 5.35 (dd, J=11.2, 0.98 Hz, 1H), 5.02 (s, 2H), 4.60 (s, 1H); MS (FIA) m/e 227 (M+1).

Step B

(4-Benzyloxy-2-vinylphenoxy)acetic acid ethyl ester

4-Benzyloxy-2-vinylphenol (0.40 g, 1.77 mmol) was dissolved in anhydrous DMF (4 mL), followed by the addition of ethyl bromoacetate (0.29 mL, 2.65 mmol), and cesium carbonate (0.75 g, 2.30 mmol). The mixture was then heated for 18 h (55° C.). The reaction mixture was then cooled and concentrated in vacuo. The crude residue was partitioned between EtOAc (70 mL) and water (40 mL). The organic layer was washed with brine, dried (Na$_2$SO$_4$), and removed in vacuo to give 0.56 g (100%) of a yellow solid: $^1$H NMR (400 MHz, CDCl$_3$) δ 7.44-7.31 (m, 4H), 7.13 (d, J=2.9 Hz, 1H), 7.10-7.06 (m, 1H), 6.82 (dd, J=8.8, 2.9 Hz, 1H), 6.73 (d, J=9.3 Hz, 1H), 5.76 (dd, J=17.1 Hz, 1.5 Hz, 1H), 5.30 (dd, J=11.2, 1.5 Hz, 1H), 5.03 (s, 2H), 4.58 (s, 2H), 4.26 (q, J=7.2 Hz, 2H), 1.30 (t, J=7.1 Hz, 3H); MS (FIA) m/e 313 (M+1).

Step C

(2-Ethyl-4-hydroxyphenoxy)acetic acid ethyl ester

A solution of (4-benzyloxy-2-vinylphenoxy)acetic acid ethyl ester (0.55 g, 1.77 mmol) in ethanol (15 mL) was treated with 5% Pd/C (70 mg) and hydrogen (60 psi) at ambient temperature for 18 h. The mixture was filtered and concentrated in vacuo to give a tan oil (0.31 g, 77%): $^1$H NMR (400 MHz, CDCl$_3$) δ 6.68 (d, J=2.9 Hz, 1H), 6.62 (d, J=8.8 Hz, 1H), 6.57 (dd, J=8.8, 2.9 Hz, 1H), 4.62 (s, 1H), 4.57 (s, 2H), 4.25 (q, J=7.2 Hz, 2H), 3.73 (q, J=7.0 Hz, 2H), 2.66 (q, J=7.7 Hz, 2H), 1.34-0.92 (m, 6H); MS (FIA) m/e 225 (M+1).

Step D

{2-Ethyl-4-[2-(5-methyl-2-phenyloxazol-4-yl)ethoxy]phenoxy}acetic acid ethyl ester

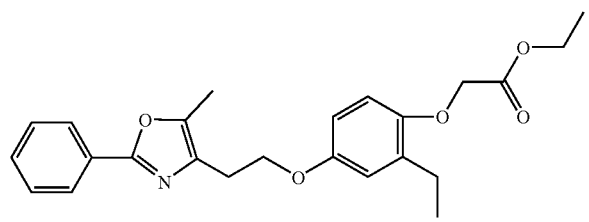

A mixture of (2-ethyl-4-hydroxyphenoxy)acetic acid ethyl ester (0.29 g, 1.29 mmol), toluene-4-sulfonic acid 2-(5-methyl-2-phenyloxazol-4-ly)ethyl ester (0.55 g, 1.55 mmol), and cesium carbonate (0.55 g, 1.7 mmol) in anhydrous DMF (4 mL) was heated for 18 h (55° C.). The mixture was concentrated in vacuo, and the residue was partitioned between EtOAc (100 mL) and water (50 mL), washed with brine (50 mL), dried (Na$_2$SO$_4$), and removed in vacuo to give a crude oil which was purified using radial chromatography eluting with 10-15% EtOAc/Hexanes to give 0.24 g (38%) of a white solid. $^1$H NMR (400 MHz, CDCl$_3$) δ 7.97 (dd, J=7.8, 2.4 Hz, 2H), 7.44-7.39 (m, 3H), 6.75 (s, 1H), 6.65 (d, J=1.5 Hz, 2H), 4.56 (s, 2H), 4.24 (q, J=7.2 Hz, 2H), 4.19 (t, J=6.6 Hz, 2H), 2.95 (t, J=6.8 Hz, 2H), 2.67 (q, J=7.5 Hz, 2H), 2.37 (s, 3H), 1.28 (t, J=7.1 Hz, 3H), 1.20 (t, J=7.6 Hz, 3H); MS (FIA) m/e 424 (M+1).

The following compounds were also prepared by this procedure:

2-{2-Ethyl-4-[2-(5-methyl-2-phenyloxazol-4-yl)ethoxy]phenoxy}2-methylpropionic acid ethyl ester, $^1$H NMR (400 MHz, CDCl$_3$) δ 7.97 (dd, J=7.8, 2.4 Hz, 2H), 7.44-7.39 (m, 3H), 6.72 (d, J=2.9 Hz, 1H), 6.64-6.52 (m, 2H), 4.24 (q, J=7.0 Hz, 2H), 4.18 (t, J=6.8 Hz, 2H), 2.95 (t, J=6.8 Hz, 2H), 2.60 (q, J=7.5 Hz, 2H), 2.36 (s, 3H), 1.53 (s, 6H), 1.26 (t, J=7.6 Hz, 3H), 1.17 (t, J=7.6 Hz, 3H); MS (FIA) m/e 438 (M+1).

{2-Isobutyl-4-[2-(5-methyl-2-phenyloxazol-4-yl)ethoxy]phenoxy}acetic acid ethyl ester, $^1$H NMR (400 MHz, CDCl$_3$) δ 7.98 (dd, J=7.8, 2.0 Hz, 2H), 7.45-7.39 (m, 3H), 6.69-6.62 (m, 3H), 4.54 (s, 2H), 4.20 (q, J=7.5 Hz, 2H), 4.11 (t, J=7.1 Hz), 2.96 (t, J=6.6 Hz, 2H), 2.50 (t, 6.1 Hz, 2H), 2.37 (s, 3H), 1.87-2.00 (m, 1H), 1.24 (t, J=7.5 Hz, 3H), 0.87 (d, J=7 Hz, 6H); MS (ES) m/e 438 (M+1).

2-{2-Isobutyl-4-[2-(5-methyl-2-phenyloxazol-4-yl)ethoxy]phenoxy}-2-methylpropionic acid ethyl ester, $^1$H NMR (400 MHz, CDCl$_3$) δ 7.97 (dd, J=7.8, 2.0 Hz, 2H), 7.45-7.39 (m, 3H), 6.66 (d, J=2.4 Hz, 1H), 6.18-6.53 (m, 2H), 4.22 (q, J=7.00 Hz, 2H), 4.17 (t, J=6.8 Hz, 2H), 2.95 (t, J=6.6 Hz, 2H), 2.43 (d, J=7.3 Hz, 2H), 2.36 (s, 3H), 1.96-1.89 (m, 1H), 1.53 (s, 6H), 1.26 (t, J=5.9 Hz, 3H), 0.89 (d, J=7 Hz, 6H); MS (ES) m/e 466 (M+1).

[4-[2-(5-Methyl-2-phenyloxazol-4-yl)ethoxy]-2-(5-phenylpentyl)phenoxy]acetic acid ethyl ester, $^1$H NMR (400 MHz, CDCl$_3$) δ 7.98 (dd, J=8.3, 2.9 Hz, 2H), 7.45-7.38 (m, 3H), 7.31-7.21 (m, 2H), 7.17-7.14 (m, 3H), 6.72 (d, J=1.5 Hz, 1H), 6.64 (d, J=1.5 Hz, 2H), 4.55 (s, 2H), 4.21 (q, J=7.2 Hz, 2H), 4.13 (t, J=7.1 Hz, 2H), 3.00 (t, J=6.6 Hz, 2H), 2.64-2.58 (m, 4H), 2.37 (s, 3H), 1.67-1.49 (m, 4H), 1.25-1.35 (m, 2H), 1.28 (t, J=7.2 Hz, 3H); MS (ES) m/e 528 (M+1).

2-Methyl-2-[4-[2-(5-methyl-2-phenyloxazol-4-yl)ethoxy]-2-(5-phenylpentyl)phenoxy]propionic acid ethyl ester, $^1$H NMR (400 MHz, CDCl$_3$) δ 7.97 (dd, J=7.8, 2.4 Hz, 2H), 7.44-7.39 (m, 3H), 7.28-7.25 (m, 3H), 7.18-7.14 (m, 3H), 6.69 (d, J=2.9 Hz, 1H), 6.63-6.56 (m, 2H), 4.22 (q, J=7.0 Hz, 2H), 4.17 (t, J=6.6 Hz, 2H), 2.95 (t, J=6.6 Hz, 2H), 2.62-2.53 (m, 4H), 2.36 (s, 3H), 1.68-1.47 (m, 4H), 1.51 (s, 6H), 1.27-1.42 (m, 2H), 1.12 (t, J=7.0 Hz, 3H); MS (ES) m/e 556 (M+1).

{2-Butyl-4-[2-(5-methyl-2-phenyloxazol-4-yl)ethoxy]phenoxy}acetic acid ethyl ester, $^1$H NMR (400 MHz, CDCl$_3$) δ 7.98 (dd, J=7.8, 2.4 Hz, 2H), 7.45-7.38 (m, 3H), 6.73 (s, 1H), 6.67-6.58 (m, 2H), 4.56 (s, 2H), 4.25 (q, J=7.0 Hz, 2H), 4.18 (t, J=6.6 Hz, 2H), 2.95 (t, J=6.8 Hz, 2H), 2.63 (t, J=7.6 Hz, 2H), 2.37 (s, 3H), 1.61-1.54 (m, 2H), 1.35 (q, J=7 Hz, 2H), 1.28 (t, J=7 Hz, 3H), 0.95 (t, J=7.0 Hz, 3H); MS (ES) m/e 438 (M+1).

2-{2-Butyl-4-[2-(5-methyl-2-phenyloxazol-4-yl)ethoxy]phenoxy}-2-methylpropionic acid ethyl ester, $^1$H NMR (400 MHz, CDCl$_3$) δ 7.97 (dd, 8.3, 2.0 Hz, 2H), 7.45-7.39 (m, 3H), 6.70 (d, J=2.9 Hz, 1H), 6.61 (t, J=9.5 Hz, 1H), 6.57 (dd, J=8.8, 2.9 Hz, 1H), 4.23 (q, J=7.2 Hz, 2H), 4.17 (t, J=6.8 Hz, 2H), 2.95 (t, J=6.8 Hz, 2H), 2.56 (t, J=7.8 Hz, 2H), 2.36 (s, 3H), 1.58-1.48 (m, 8H), 1.28 (t, J=7 Hz, 3H), 0.90 (t, J=7.2 Hz, 3H); MS (ES) m/e 466 (M+1).

2-{2-Cyclohexylmethyl-4-[2-(5-methyl-2-phenyl-oxazol-4-yl)-ethoxy]-phenoxy}-2-methyl-propionic acid ethyl ester, MS (ES) m/e 506.3 (M+1).

2-{4-[(2-(2-Biphenyl-4-yl-5-methyl-oxazol-4-yl)-ethoxy]-2-cyclohexylmethyl-phenoxy}-2-methyl-propionic acid ethyl ester, MS (ES) m/e 582.3 (M+1).

2-{4-[2-(2-Biphenyl-3-yl-5-methyl-oxazol-4-yl)-ethoxy]-2-cyclohexylmethyl-phenoxy}-2-methyl-propionic acid ethyl ester, MS (ES) m/e 582.3 (M+1).

2-{2-Cyclohexylmethyl-4-[2-(5-methyl-2-thiophen-2-yl-oxazol-4-yl)-ethoxy]-phenoxy}-2-methyl-propionic acid ethyl ester, $^1$H NMR (400 MHz, CDCl$_3$) δ 7.56 (d, 1H, J=3.9 Hz), 7.36 (d, 1H, J=4.9 Hz), 7.08 (dd, 1H, J=3.7 Hz, J=4.9 Hz), 6.57-6.64 (m, 3H), 4.23 (q, 2H, J=7.0), 4.15 (t, 2H, J=6.8 Hz), 2.92 (t, 2H, J=6.6 Hz), 2.43 (d, 2H, J=6.8), 2.34 (s, 3H), 1.56-1.67 (m, 6H), 1.53 (s, 6H), 1.25 (t, 3H, J=7.0 Hz), 1.12-1.19 (m, 3H), 0.89-0.98 (m, 2H), MS (ES) m/e 512.3 (M+1).

2-{2-Cyclohexylmethyl-4-[2-(2-cyclohexyl-5-methyloxazol-4-yl)-ethoxy]-phenoxy}-2-methyl-propionic acid ethyl ester, MS (ES) m/e 512.4 (M+1).

2-Methyl-2-{4-[2-(5-methyl-2-phenyloxazol-4-yl)ethoxy]-2-phenethylphenoxy}propionic acid ethyl ester, MS (ES) m/e 515 (M+1).

2-{4-[2-(2-Cyclohexyl-5-methyloxazol-4-yl)ethoxy]-2-phenethylphenoxy}-2-methylpropionic acid ethyl ester, MS (ES) m/e 520 (M+1).

2-{4-[2-(2-Biphenyl-4-yl-5-methyloxazol-4-yl)ethoxy]-2-phenethylphenoxy}-2-methylpropionic acid ethyl ester, MS (ES) m/e 590 (M+1).

2-{4-[2-(2-Biphenyl-3-yl-5-methyloxazol-4-yl)ethoxy]-2-phenethylphenoxy}-2-methylpropionic acid ethyl ester, MS (ES) m/e 590 (M+1).

Step E

{2-Ethyl-4-[2-(5-methyl-2-phenyloxazol-4-yl)ethoxy]phenoxy}acetic acid

A solution of {2-ethyl-4-[2-(5-methyl-2-phenyloxazol-4-yl)ethoxy]phenoxy}acetic acid ethyl ester (0.22 g, 0.54 mmol) in ethanol (10 mL) was treated with 2.5 N aqueous NaOH (0.4 mL), and heated at 55° C. for 2 h. The reaction was cooled to ambient temperature and concentrated down to near dryness. The residue was then diluted with EtOAc (40 mL) and water (20 mL) and acidified to pH=1 with 1N aqueous HCl. The organic layer was washed with brine (20 mL), dried (Na$_2$SO$_4$) and concentrated in vacuo to give a white solid (0.18 g, 87%). $^1$H NMR (400 MHz, CDCl$_3$) δ 7.97 (dd, J=8.3, 2.9 Hz, 2H), 7.44-7.41 (m, 3H), 6.75 (d, J=2.9 Hz, 1H), 6.69-6.60 (m, 2H), 4.60 (s, 2H), 4.14 (t, J=6.6 Hz, 2H), 2.98 (t, J=6.60 Hz, 2H), 2.65 (q, J=7.5 Hz, 2H), 2.38 (s, 3H), 1.19 (t, J=7.6 Hz, 3H); MS (FIA) m/e 382 (M+1).

The following compounds were also prepared from their corresponding esters:

Example 30A

2-{2-Ethyl-4-[2-(5-methyl-2-phenyloxazol-4-yl)ethoxy]phenoxy}2-methylpropionic acid

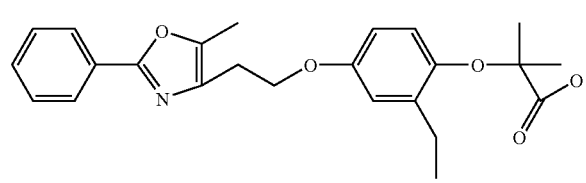

$^1$H NMR (400 MHz, CDCl$_3$) δ (dd, J=7.8, 2.4 Hz, 2H), 7.45-7.40 (m, 3H), 6.79-6.58 (m, 3H), 4.16 (t, J=6.6 Hz, 2H), 2.98 (t, J=6.4 Hz, 2H), 2.59 (q, J=7.5 Hz, 2H), 2.38 (s, 3H), 1.55 (s, 6H), 1.18 (t, J=7.6 Hz, 3H); MS (FIA) m/e 410 (M+1).

Example 30B

{2-Isobutyl-4-[2-(5-methyl-2-phenyloxazol-4-yl)ethoxy]phenoxy}acetic acid

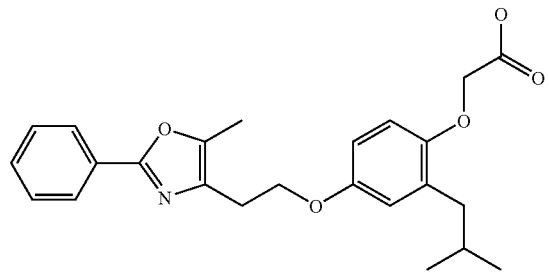

$^1$H NMR (400 MHz, CDCl$_3$) δ 7.97 (dd, J=7.8, 2.9 Hz, 2H), 7.46-7.39 (m, 3H), 6.69-6.61 (m, 3H), 4.58 (s, 2H), 4.14 (t, J=6.6 Hz, 2H), 2.97 (t, J=6.8 Hz, 2H), 2.48 (d, J=7.3 Hz, 2H), 2.38 (s, 3H), 1.95-1.86 (m, 1H), 0.90 (d, J=6.8 Hz, 6H); MS (ES) m/e 410 (M+1).

Example 30C

2-{2-Isobutyl-4-[2-(5-methyl-2-phenyloxazol-4-yl)ethoxy]phenoxy}-2-methylpropionic acid

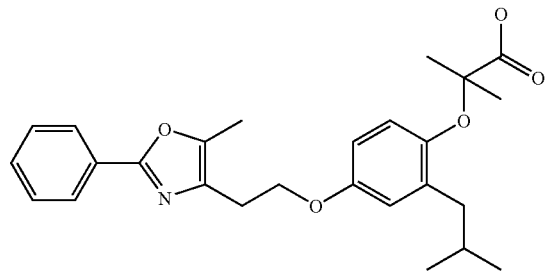

$^1$H NMR (400 MHz, CDCl$_3$) δ 7.97 (dd, J=7.3, 2.4 Hz, 2H), 7.44-7.40 (m, 3H), 6.76 (d, J=8.8 Hz, 1H), 6.67 (d, J=3.4 Hz, 1H), 6.59 (dd, J=8.8, 2.9 Hz, 1H), 4.15 (t, J=6.6 Hz, 2H), 2.98 (t, J=6.6 Hz, 2H), 2.42 (d, J=6.8 Hz, 2H), 2.37 (s, 3H), 1.93-1.86 (m, 1H), 1.55 (s, 6H), 0.89 (d, J=6.4 Hz, 6H); MS (FIA) m/e 424 (M+1).

Example 30D

[4-[2-(5-Methyl-2-phenyloxazol-4-yl)ethoxy]-2-(5-phenylpentyl)phenoxy]acetic acid

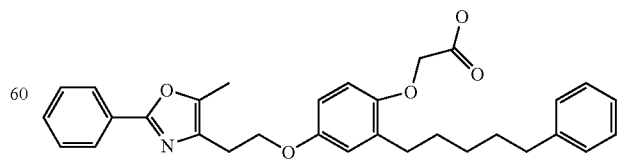

$^1$H NMR (400 MHz, CDCl$_3$) δ 7.97 (dd, J=7.8, 2.9 Hz, 2H), 7.44-7.40 (m, 3H), 7.27-7.21 (m, 2H), 7.17-7.14 (m, 3H), 6.71 (d, J=2.4 Hz, 1H), 6.66 (d, J=8.8 Hz, 1H), 6.60 (dd, J=2.9, 2.9 Hz, 1H), 4.57 (s, 2H), 4.13 (t, J=6.8 Hz, 2H),

Example 30E

2-Methyl-2-[4-[2-(5-methyl-2-phenyloxazol-4-yl)ethoxy]-2-(5-phenylpentyl)phenoxy]propionic acid

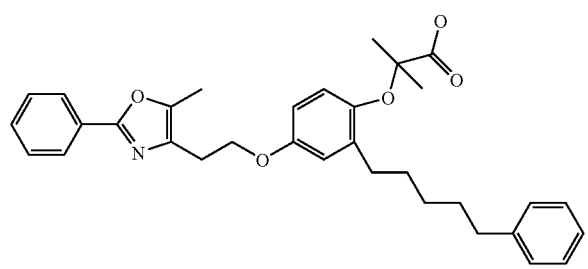

$^1$H NMR (400 MHz, CDCl$_3$) δ 7.97 (dd, J=8.3, 2.9 Hz, 2H), 7.45-7.38 (m, 3H), 7.31-7.28 (m, 2H), 7.25-7.15 (m, 3H), 6.77 (d, J=8.8 Hz, 1H), 6.66 (d, J=2.9 Hz, 1H), 6.59 (dd, J=8.8, 3.4 Hz, 1H), 4.16 (t, J=6.6 Hz, 2H), 2.98 (t, J=6.6 Hz, 2H), 2.61-2.52 (m, 4H), 2.37 (s, 3H), 1.70-1.50 (m, 8H), 1.23-1.33 (m, 2H); MS (ES) m/e 528 (M+1).

Example 30F

{2-Butyl-4-[2-(5-methyl-2-phenyloxazol-4-yl)ethoxy]phenoxy}acetic acid

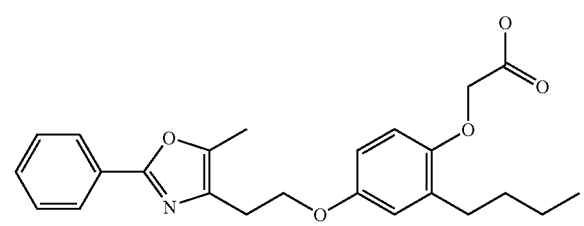

$^1$H NMR (400 MHz, CDCl$_3$) δ 7.97 (dd, J=7.8, 2.9 Hz, 2H), 7.45-7.39 (m, 3H), 6.72 (d, J=2.4 Hz, 1H), 6.66 (d, J=8.3 Hz, 1H), 6.60 (d, J=8.3 Hz, 1H), 4.56 (s, 2H), 4.13 (t, J=6.6 Hz, 2H), 2.97 (t, J=6.6 Hz, 2H), 2.60 (t, J=7.6 Hz, 2H), 2.37 (s, 3H), 1.55 (quintet, J=7.5 Hz, 2H), 1.36 (quintet, J=7.5 Hz, 2H), 0.89 (t, J=7.3 Hz, 3H); MS (ES) m/e 410 (M+1).

Example 30G

2-{2-Butyl-4-[2-(5-methyl-2-phenyloxazol-4-yl)-ethoxy]phenoxy}-2-methylpropionic acid

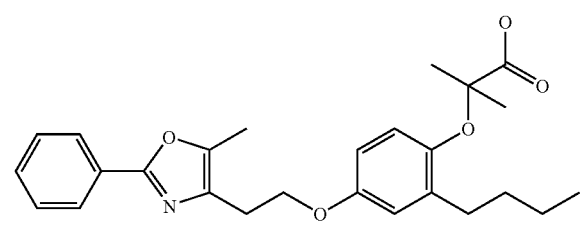

$^1$H NMR (400 MHz, CDCl$_3$) δ 7.97 (dd, J=7.8, 2.4 Hz, 2H), 7.45-7.40 (m, 3H), 6.77 (d, J=9.3 Hz, 1H), 6.71 (d, J=3.4 Hz, 1H), 6.59 (dd, J=8.8, 2.9 Hz, 1H), 4.16 (t, J=6.6 Hz, 2H), 4.16 (t, J=6.6 Hz, 2H), 2.98 (t, J=6.6 Hz, 2H), 2.55 (t, J=7.8 Hz, 2H), 2.38 (s, 3H), 1.58-1.50 (m, 8H), 1.34 (quintet, J=7.5 Hz, 2H), 0.92 (t, J=7.3 Hz, 3H); MS (ES) m/e 438 (M+1).

Example 30H

2-{2-Cyclohexylmethyl-4-[2-(5-methyl-2-phenyl-oxazol-4-yl)-ethoxy]-phenoxy}-2-methyl-propionic acid

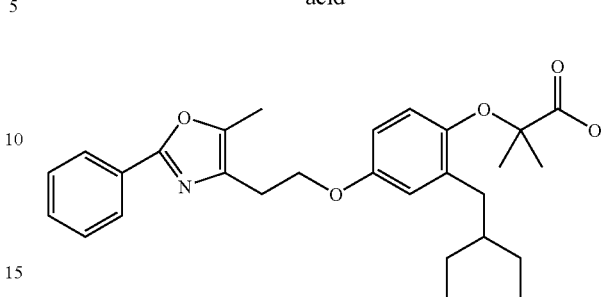

$^1$H NMR (400 MHz, CDCl$_3$) δ 7.94-7.96 (m, 2H), 7.41-7.45 (m, 3H), 6.73 (d, 1H, J=8.8 Hz), 6.61 (d, 1H, J=3.4 Hz), 6.57 (dd, 1H, J=8.8 Hz, J=2.9 Hz), 4.13 (t, 2H, J=6.4 Hz), 3.00 (t, 2H, J=6.1 Hz), 2.37 (s, 3H), 1.59-1.61 (m, 4H), 1.49 (s, 6H), 1.21 (s, 2H), 1.10-1.14 (m, 5H), 0.84-0.90 (m, 2H), MS (ES) m/e 478.2 (M+1).

Example 30I

2-{2-Cyclohexylmethyl-4-[2-(2-cyclohexyl-5-methyl-oxazol-4-yl)-ethoxy]-phenoxy}-2-methyl-propionic acid

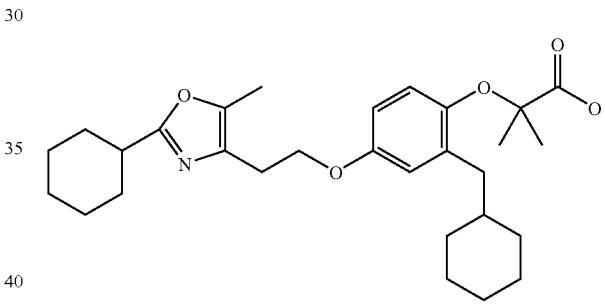

$^1$H NMR (400 MHz, CDCl$_3$) δ 6.74 (d, 1H, J=8.8 Hz), 6.61 (d, 1H, J=2.9 Hz), 6.57 (dd, 1H, J=8.8 Hz, J=2.9 Hz), 4.11 (t, 2H, J=5.9 Hz), 2.99 (t, 2H, J=5.6 Hz), 2.39 (d, 2H, J=7.3 Hz), 2.33 (s, 3H), 2.01-2.04 (m, 1H), 1.80-1.83 (m, 1H), 1.58-1.64 (m, 5H), 1.51 (s, 6H), 0.85-1.41 (m, 15H), MS (ES) m/e 484.3 (M+1).

Example 30J

2-Methyl-2-{4-[2-(5-methyl-2-phenyloxazol-4-yl)ethoxy]-2-phenethylphenoxy}propionic acid)

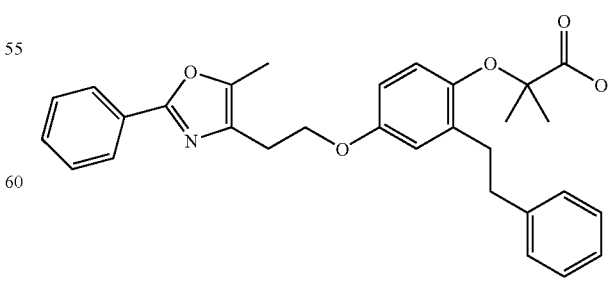

$^1$H NMR (400 MHz, CDCl$_3$) δ 7.99 (dd, J=6.8, 2.9 Hz, 2H), 7.47-7.46 (m, 3H), 7.31-7.14 (m, 5H), 6.75-6.71 (m, 2H), 6.62 (dd, J=8.8, 2.9 Hz, 1H), 4.16 (t, J=6.1 Hz, 2H), 3.02 (t, J=6.1 Hz, 2H), 2.85 (s, 4H), 2.41 (s, 3H), 1.53 (s, 6H), MS (ES) m/e 486 (M+1).

Example 30K

2-{4-[2-(2-Cyclohexyl-5-methyloxazol-4-yl)ethoxy]-2-phenethylphenoxy}-2-methylpropionic acid)

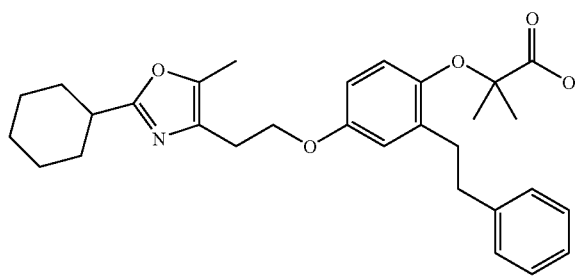

$^1$H NMR (400 MHz, CDCl$_3$) δ 7.31-7.15 (m, 5H), 6.74-6.68 (m, 3H), 6.58 (dd, J=8.8, 2.9 Hz, 1H), 4.08 (t, J=6.1 Hz, 2H), 2.95 (t, J=6.1 Hz, 2H), 2.86 (s, 4H), 2.31 (s, 3H), 2.26-2.02 (m, 2H), 1.84-1.81 (m, 2H), 1.74-1.71 (m, 1H), 1.61-1.58 (m, 7H), 1.49-1.25 (m, 4H), MS (ES) m/e 492 (M+1).

EXAMPLE 31

{3-Ethyl-4-[2-(5-methyl-2-phenyloxazol-4-yl)ethoxy]phenoxy}acetic acid

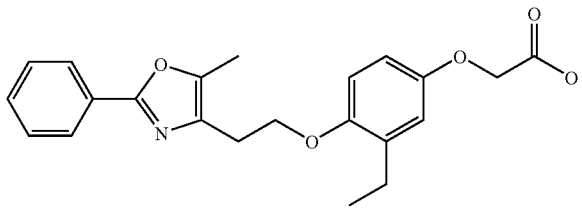

Step A

4-[2-(4-Benzyloxy-2-vinylphenoxy)ethyl]-5-methyl-2-phenyloxazole

A mixture of 4-benzyloxy-2-vinylphenol (0.88 g. 3.89 mmol), toluene-4-sulfonic acid 2-(5-methyl-2-phenyloxazol-4-ly)ethyl ester (1.67 g (4.67 mmol) and cesium carbonate (1.65 g (5.06 mmol) in anhydrous DMF (8 mL) was heated for 18 h at 55° C. The mixture was concentrated in vacuo, and the residue was partitioned between EtOAc (100 mL) and water (50 mL), washed with brine (50 mL), dried (Na$_2$SO$_4$), and removed in vacuo to give a crude oil which was purified using the Biotage FlashElute chromatography system using a 40 L normal phase cartridge, eluting with 10-15% EtOAc/Hexanes to give a white solid (1.35 g, 84%): $^1$H NMR (400 MHz, CDCl$_3$) δ 7.97 (dd, J=8.3, 2.4 Hz, 2H), 7.45-7.30 (m, 8H), 7.11 (d, J=2.0 Hz, 1H), 7.10-6.95 (m, 1H), 6.82 (d, J=1.5 Hz, 2H), 5.68 (dd, J=18.1, 1.5 Hz, 1H), 5.22 (dd, J=11.2, 1.5 Hz, 1H), 5.02 (s, 2H), 4.23 (t, J=6.6 Hz, 2H), 2.98 (t, J=6.6 Hz, 2H), 2.37 (s, 3H); MS (FD) m/e 411 (M+).

Step B

3-Ethyl-4-[2-(5-methyl-2-phenyloxazole-4-yl)ethoxy]phenol

A solution of 4-[2-(4-benzyloxy-2-vinylphenoxy)ethyl]-5-methyl-2-phenyloxazole (1.30 g, 3.16 mmol) in ethanol (100 mL) was treated with 5% Pd/C (160 mg) and hydrogen (60 psi) at ambient temperature for 18 h. The mixture was filtered and concentrated in vacuo to give a tan solid (0.65 g, 64%):
$^1$H NMR (400 MHz, CDCl$_3$) δ 7.99 (dd, J=8.3 Hz, 2.0 Hz, 2H), 7.45-7.38 (m, 3H), 6.63 (d, J=2.4 Hz, 1H), 6.50-6.41 (m, 2H), 5.98 (br s, 1H), 4.10 (t, J=6.4 Hz, 2H), 2.95 (t, J=6.4 Hz, 2H), 2.85-2.51 (m, 2H), 2.39 (s, 3H), 1.08 (t, J=7 Hz, 3H); HRMS: Calc'd=324.1599; Found=324.1597.

Step C

{3-Ethyl-4-[2-(5-methyl-2-phenyl-oxazol-4-yl)ethoxy]phenoxy}acetic acid ethyl ester A mixture of 3-ethyl-4-[2-(5-methyl-2-phenyloxazole-4-yl)ethoxy]phenol (0.29 g. 0.90 mmol), ethyl bromoacetate (0.25 mL, 2.25 mmol) and cesium carbonate (0.45 g, (1.38 mmol) in anhydrous DMF (4 mL) was heated for 24 h at 55° C. The mixture was concentrated in vacuo, and the residue was partitioned between EtOAc (50 mL) and water (40 mL), washed with brine, dried (Na$_2$SO$_4$), and removed in vacuo to give a crude oil which was purified using radial chromatography eluting with 2% EtOAc/MeCl$_2$ to give a white solid (0.25 g, 68%): $^1$H NMR (400 MHz, CDCl$_3$) δ 7.97 dd, J=8.3, 2.4 Hz, 2H), 7.45-7.39 (m, 3H), 6.75 (dd, J=8.3, 2.0 Hz, 2H), 2H), 6.64 (dd, J=8.8, 3.4 Hz, 1H), 4.55 (s, 2H), 4.24 (q, J=6.5 Hz, 2H), 4.10 (t, J=6.4 Hz, 2H), 2.97 (t, J=6.6 Hz, 2H), 2.57 (t, J=7.3 Hz, 2H), 2.37 (s, 3H), 1.29 (t, J=7.3 Hz, 3H), 1.12 (t, J=6.5 Hz, 3H); MS (ES) m/e 410 (M+1).

The following compounds were also prepared by this procedure:

2-{3-Ethyl-4-[2-(5-methyl-2-phenyloxazol-4-yl)ethoxy]phenoxy}2-methylpropionic acid ethyl ester: $^1$H NMR (400 MHz, CDCl$_3$) δ 7.97 (dd, J=7.3, 2.9 Hz, 2H), 7.45-7.39 (m, 3H), 6.72-6.61 (m, 3H), 4.25-4.17 (m, 4H), 2.96 (t, J=6.4 Hz, 2H), 2.53 (q, J=7.5 Hz, 2H), 1.52 (s, 6H), 1.27 (t, J=7.1 Hz, 3H), 1.08 (t, J=7.3 Hz); MS (FIA) m/e 438 (M+1).

{3-Isobutyl-4-[2-(5-methyl-2-phenyloxazol-4-yl)ethoxy]phenoxy}acetic acid ethyl ester: $^1$H NMR (400 MHz, CDCl$_3$) δ 7.97 (dd, J=8.3 Hz, 2H), 7.45-7.39 (m, 3H), 6.77 (d, J=8.8 Hz, 1H), 6.70-6.64 (m, 2H), 4.54 (s, 2H), 4.26 (q, J=7.2 Hz, 2H), 4.19 (t, J=6.4 Hz, 2H), 2.95 (t, J=6.4 Hz, 2H), 2.38 (s, 3H), 1.84-1.77 (m, 1H), 1.32-1.28 (m, 5H), 0.82 (d, J=7 Hz, 6H); MS (ES) m/e 438 (M+1).

2-{3-Isobutyl-4-[2-(5-methyl-2-phenyloxazol-4-yl)ethoxy]phenoxy}-2-methylpropionic acid ethyl ester, $^1$H NMR (400 MHz, CDCl$_3$) δ 7.97 (dd, J=7.8, 2.0 Hz, 2H), 7.45-7.40 (m, 3H), 6.72-6.65 (m, 3H), 4.23 (q, J=7.1, 2.0 Hz, 2H), 2.95 (t, J=6.4 Hz, 2H), 2.37-2.35 (m, 5H), 1.82-1.75 (m, 1H), 1.51 (s, 6H), 1.27 (t, 6.8 Hz, 3H), 0.81 (d, J=6.8 Hz, 6H); MS (ES) m/e 466 (M+1).

[4-[2-(5-Methyl-2-phenyloxazol-4-yl)ethoxy]-3-(5-phenylpentyl)phenoxy]acetic acid ethyl ester, $^1$H NMR (400 MHz, CDCl$_3$) δ 7.96 (dd, J=7.8, 2.4 Hz, 2H), 7.43-7.38 (m, 3H), 7.28-7.21 (m, 2H), 7.19-7.12 (m, 3H), 6.76 (d, J=8.8

Hz, 1H), 6.50 (d, J=3.4 Hz, 1H), 6.66-6.63 (m, 1H), 4.54 (s, 2H), 4.27 (q, J=7.2 Hz, 2H), 4.19 (t, J=6.6 Hz, 2H), 2.95 (t, J=7 Hz, 2H), 2.58-2.48 (m, 4H), 2.33 (s, 3H), 1.63-1.45 (m, 4H), 1.35-1.03 (m, 5H); MS (ES) m/e 528 (M+1).

2-Methyl-2-[4-[2-(5-methyl-2-phenyloxazol-4-yl)ethoxy]-3-(5-phenyl-pentyl)phenoxy]propionic acid ethyl ester, $^1$H NMR (400 MHz, CDCl$_3$) δ 7.96 (dd, J=7.3, 2.4 Hz, 2H), 7.42-7.38 (m, 3H), 7.28-7.24 (m, 2H), 7.17 (d, J=7.3 Hz, 1H), 7.13 (d, J=7.3 Hz, 2H), 6.71-6.62 (m, 3H), 4.22 (q, J=7.1 Hz, 2H), 4.19 (t, J=6.4 Hz, 2H), 2.95 (t, J=6.4 Hz, 2H), 2.56-2.46 (m, 4H), 2.33 (s, 3H), 1.61 (s, 6H), 1.38-1.23 (m, 5H); MS (FIA) m/e 556 (M+1).

{3-Butyl-4-[2-(5-methyl-2-phenyloxazol-4-yl)ethoxy]phenoxy}acetic acid ethyl ester, $^1$H NMR (400 MHz, CDCl$_3$) δ 7.97 (dd, J=7.8, 2.0 Hz, 2H), 7.45-7.37 (m, 3H), 6.77-6.72 (m, 2H), 6.64 (dd, J=8.8, 3.4 Hz, 1H), 4.54 (s, 2H), 4.26 (q, J=7.0 Hz, 2H), 4.21 (t, J=6.6 Hz, 2H), 2.96 (t, J=6.4 Hz, 2H), 2.52 (t, J=7.6 Hz, 2H), 2.37 (s, 3H), 1.50-1.43 (m, 2H), 1.35-1.23 (m, 5H), 0.85 (t, J=7.0 Hz, 3H); MS (ES) m/e 438 (M+1).

2-{3-Butyl-4-[2-(5-methyl-2-phenyloxazol-4-yl)ethoxy]phenoxy}-2-methylpropionic acid ethyl ester, $^1$H NMR (400 MHz, CDCl$_3$) δ 7.97 (dd, J=8.3, 2.4 Hz, 2H), 7.44-7.39 (m, 3H), 6.69 (d, J=2.4 Hz, 2H), 6.63 (dd, J=8.8, 2.9 Hz, 1H), 4.22 (q, J=7.2 Hz, 2H), 4.19 (t, J=6.4 Hz, 2H), 2.96 (t, J=6.4 Hz, 2H), 2.49 (t, J=7.6 Hz, 2H), 1.32-1.25 (m, 5H), 0.85 (t, J=7.2 Hz, 3H); MS (ES) m/e 466 (M+1).

2-Methyl-2-{4-[2-(5-methyl-2-phenyloxazol-4-yl)ethoxy]-3-phenethylphenoxy}propionic acid ethyl ester, $^1$H NMR (400 MHz, CDCl$_3$) δ 7.96 (d, J=5.9 Hz, 2H), 7.41 (d, J=5.9 Hz, 3H), 7.22 (d, J=7.3 Hz, 2H), 7.16 (d, J=7.8 Hz, 1H), 7.11 (d, J=7.3 Hz, 2H), 6.73 (d, J=9.3 Hz, 1H), 6.67 (d, J=7.8 Hz, 2H), 4.24-4.11 (m, 4H), 2.96 (t, J=6.4 Hz, 2H), 2.80 (s, 4H), 2.31 (s, 3H), 1.47 (s, 6H), 1.27 (t, J=7.1 Hz, 3H), MS (ES) m/e 514 (M+1).

2-{3-Cyclohexylmethyl-4-[2-(5-methyl-2-phenyloxazol-4-yl)ethoxy]phenoxy}-2-methylpropionic acid ethyl ester, $^1$H NMR (400 MHz, CDCl$_3$) δ 7.97 (dd, J=5.4, 2.4 Hz, 2H), 7.43-7.39 (m, 3H), 6.72-6.63 (m, 3H), 4.25-4.17 (m, 4H), 2.95 (t, J=6.4 Hz, 2H), 2.97-2.93 (m, 5H), 1.59-1.52 (m, 10H), 1.46-1.38 (m, 2H), 1.27 (t, J=7.1 Hz, 3H), 1.10-1.03 (m, 3H), 0.90-0.73 (m, 2H), MS (ES) m/e 506 (M+1).

2-{4-[2-(2-Cyclohexyl-5-methyl-oxazol-4-yl)ethoxy]phenoxy}-2-methyl-propionic acid ethyl ester. MS (ES) m/e 416.3 (M+1).

Step D

{3-Ethyl-4-[2-(5-methyl-2-phenyloxazol-4-yl)ethoxy]phenoxy}acetic acid

A solution of {3-ethyl-4-[2-(5-methyl-2-phenyloxazol-4-yl)ethoxy]phenoxy}acetic acid ethyl ester (0.23 g, 0.57 mmol) in ethanol (10 mL) was treated with 2.5 N aqueous NaOH (1.1 mL), and heated at 55° C. for 2 h. The reaction was cooled to ambient temperature and concentrated down to near dryness. The residue was then diluted with EtOAc (40 mL) and water (20 mL) and acidified to pH=1 with 1N aqueous HCl. The organic layer was washed with brine (20 mL), dried (Na$_2$SO$_4$) and concentrated in vacuo to give a white solid (0.18 g, 81%). $^1$H NMR (400 MHz, CDCl$_3$) δ 7.98 (dd, J=7.8, 2.9 Hz, 2H), 7.46-7.40 (m, 3H), 6.79 (d, J=2.9 Hz, 1H), 6.70 (d, J=8.8 Hz, 1H), 6.63 (dd, J=8.8, 2.9 Hz, 1H), 4.58 (s, 2H), 4.14 (t, J=6.4 Hz, 2H), 3.01 (t, J=6.4 Hz, 2H), 2.56 (q, J=7.5 Hz, 2H), 2.39 (s, 3H), 1.11 (t, J=7.6 Hz, 3H); MS (ES) m/e 382 (M+1).

The following compounds were also prepared from their corresponding esters:

Example 31A

2-{3-Ethyl-4-[2-(5-methyl-2-phenyloxazol-4-yl)ethoxy]phenoxy}-2-methylpropionic acid

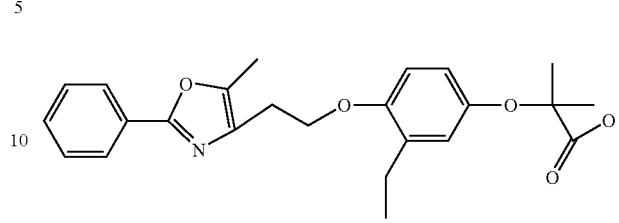

$^1$H NMR (400 MHz, CDCl$_3$) δ 7.98 (dd, J=7.8, 2.4 Hz, 2H), 7.44-7.41 (m, 3H), 6.77-6.69 (m, 3H), 4.18 (t, J=6.4 Hz, 2H), 3.01 (t, J=6.4 Hz, 2H), 2.55 (q, J=7.4 Hz, 2H), 2.39 (s, 3H), 1.53 (s, 6H), 1.10 (t, J=7.6 Hz, 3H); MS (ES) m/e 410 (M+1).

Example 31B

{3-Isobutyl-4-[2-(5-methyl-2-phenyloxazol-4-yl)ethoxy]phenoxy}acetic acid

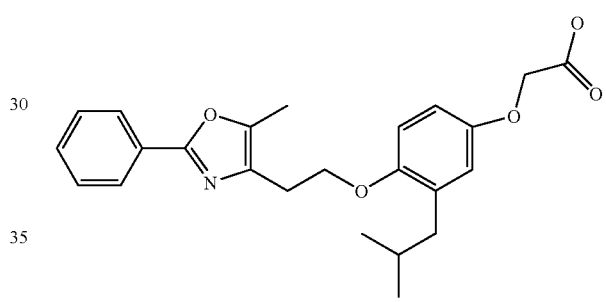

$^1$H NMR (400 MHz, CDCl$_3$) δ 7.97 (dd, J=7.3, 2.4 Hz, 2H), 7.45-7.42 (m, 3H), 6.74-6.63 (m, 3H), 4.57 (s, 2H), 4.15 (t, J=6.4 Hz, 2H), 3.00 (t, J=6.4 Hz, 2H), 2.45-2.38 (m, 5H), 1.83-1.75 (m, 1H), 0.82 (d, J=6.4 Hz, 6H); MS (ES) m/e 410 (M+1).

Example 31C

2-{3-Isobutyl-4-[2-(5-methyl-2-phenyoxazol-4-yl)ethoxy]phenoxy}-2-methylpropionic acid

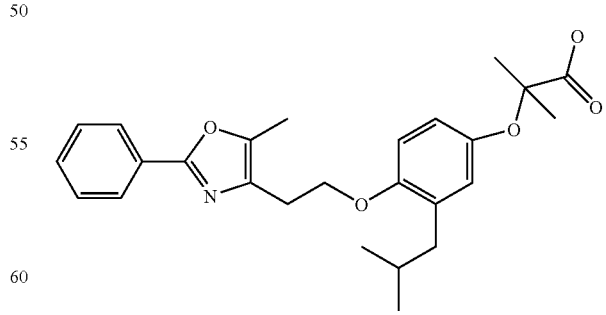

$^1$H NMR (400 MHz, CDCl$_3$) δ 7.97 (dd, J=7.8, 2.8 Hz, 2H), 7.45-7.40 (m, 3H), 6.78-6.70 (m, 3H), 4.19 (t, J=6.4 Hz, 2H), 2.99 (t, J=6.4 Hz, 2H), 2.39-2.34 (m, 5H), 1.83-1.76 (m, 1H), 1.51 (s, 6H), 0.81 (d, J=6.8 Hz, 6H); MS (ES) m/e 438 (M+1).

Example 31D

[4-[2-(5-Methyl-2-phenyloxazol-4-yl)ethoxy]-3-(5-phenylpentyl)phenoxy]acetic acid

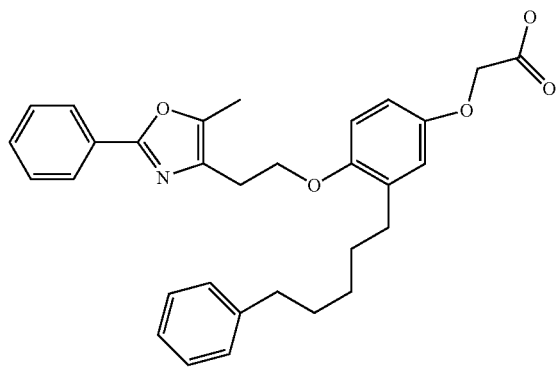

$^1$H NMR (400 MHz, CDCl$_3$) δ 0.96 (dd, J=7.8, 2.0 Hz, 2H), 7.43-7.39 (m, 3H), 7.28-7.24 (m, 2H), 7.18-7.12 (m, 3H), 6.74 (d, J=3.4 Hz, 1H), 6.71 (s, 1H), 6.64 (dd, J=8.8, 2.9 Hz, 1H), 4.56 (s, 2H), 4.15 (t, J=6.4 Hz, 2H), 2.98 (t, J=6.4 Hz, 2H), 2.56-2.51 (m, 4H), 2.49 (s, 3H), 1.61-1.48 (m, 4H), 1.38-1.25 (m, 2H); MS (ES) m/e 500 (M+1).

Example 31E

2-Methyl-2-[4-[2-(5-methyl-2-phenyloxazol-4-yl)ethoxy]-3-(5-phenylpentyl)phenoxy]propionic acid

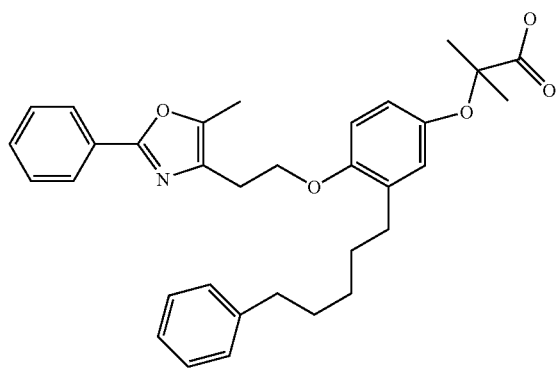

$^1$H NMR (400 MHz, CDCl$_3$) δ 0.96 (dd, J=7.3, 2.4 Hz, 2H), 7.41 (dd, J=8.8, 4.9 Hz, 3H), 7.28-7.24 (m, 2H), 7.17 (d, J=6.8 Hz, 1H), 7.14 (d, J=5.9 Hz, 2H), 6.73 (s, 3H), 4.19 (t, J=6.1 Hz, 2H), 3.00 (t, J=5.9 Hz, 2H), 2.52 (quintet, J=8.1 Hz, 4H), 2.35 (s, 3H), 1.61-1.46 (m, 10H), 1.34-1.25 (m, 2H); MS (ES) m/e 528 (M+1).

Example 31F

2-{3-Butyl-4-[2-(5-methyl-2-phenyloxazol-4-yl)ethoxy]phenoxy}-2-methylpropionic acid

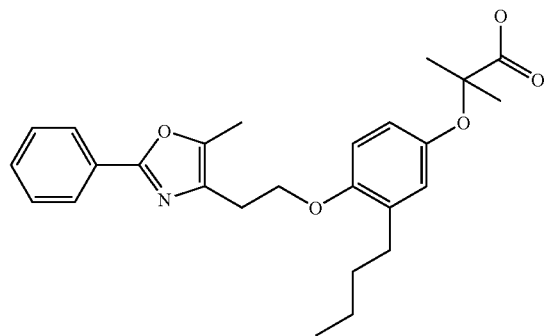

$^1$H NMR (400 MHz, CDCl$_3$) δ 7.97 (dd, J=7.8, 2.4 Hz, 2H), 7.45-7.40 (m, 3H), 6.74-6.69 (m, 3H), 4.19 (t, J=6.1 Hz, 2H), 3.00 (t, J=6.1 Hz, 2H), 2.51 (t, J=7.6 Hz, 2H), 2.38 (s, 3H), 1.52 (s, 6H), 1.46 (q, J=7.5 Hz, 2H), 1.29 (q, J=7.3 Hz, 2H), 0.86 (t, J=7.3 Hz, 3H); MS (ES) m/e 438 (M+1).

Example 31G

{3-Butyl-4-[2-(5-methyl-2-phenyloxazol-4-yl)ethoxy]phenoxy}acetic acid

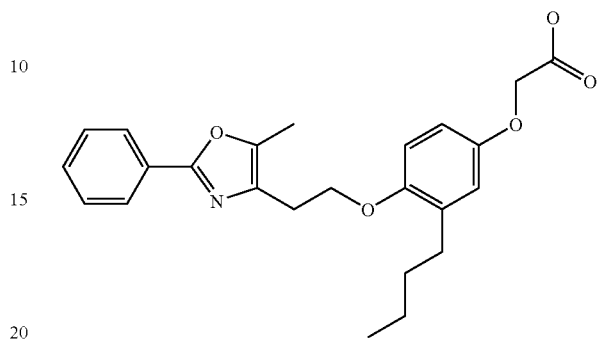

$^1$H NMR (400 MHz, CDCl$_3$) δ 7.96 (dd, J=7.8, 2.9 Hz, 2H), 7.45-7.40 (m, 3H), 6.76 (d, J=3.4 Hz, 1H), 6.71 (d, J=8.8 Hz, 1H), 6.63 (dd, J=8.8, 2.9 Hz, 1H), 4.57 (s, 2H), 4.14 (t, J=6.4 Hz, 2H), 3.00 (t, J=6.1 Hz, 2H), 2.52 (t, J=7.8 Hz, 2H), 2.38 (s, 3H), 1.45 (q, J=7.8 Hz, 2H), 1.28 (q, J=7.3 Hz, 2H), 0.85 (t, J=7 Hz, 3H); MS (ES) m/e 410 (M+1).

Example 31H

2-Methyl-2-{4-[2-(5-methyl-2-phenyloxazol-4-yl)ethoxy]-3-phenethylphenoxy}propionic acid)

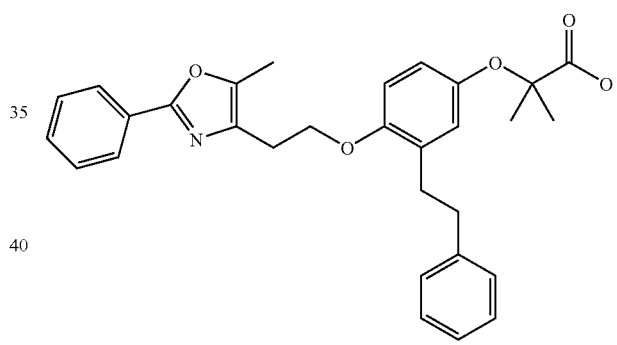

$^1$H NMR (400 MHz, CDCl$_3$) δ 7.96 (d, J=4.9 Hz, 2H), 7.42-7.40 (m, 3H), 7.26-7.22 (m, 2H), 7.15 (t, J=6.6 Hz, 1H), 7.08 (d, J=7.3 Hz, 2H), 6.75 (s, 2H), 6.63 (s, 1H), 4.22 (t, J=6.4 Hz, 2H), 3.00 (t, J=6.4 Hz, 2H), 2.86-2.79 (m, 4H), 2.33 (s, 3H), 1.43 (s, 6H), MS (ES) m/e 486 (M+1).

Example 31I

2-{3-Cyclohexylmethyl-4-[2-(5-methyl-2-phenyloxazol-4-yl)ethoxy]phenoxy}-2-methylpropionic acid

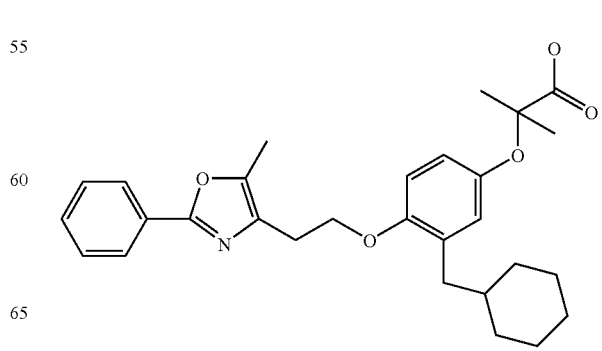

¹H NMR (400 MHz, CDCl₃) δ 7.97 (dd, J=5.6, 2.7 Hz, 2H), 7.45-7.38 (m, 3H), 6.74 (d, J=2.0 Hz, 2H), 6.69 (d, J=2.0 Hz, 1H), 4.20 (t, J=6.1 Hz, 2H), 2.99 (t, J=6.4 Hz, 2H), 2.40-2.34 (m, 5H), 1.60-1.51 (m, 10H), 1.46-1.39 (m, 1H), 1.30-1.27 (m, 2H), 1.08-1.06 (m, 2H), 0.98-0.82 (m, 2H), MS (ES) m/e 478 (M+1).

Example 31J

2-{4-[2-(2-Cyclohexyl-5-methyl-oxazol-4-yl)ethoxy]phenoxy}-2-methyl-propionic acid

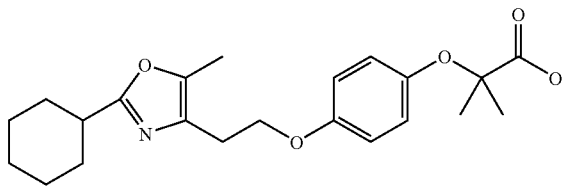

¹H NMR (400 MHz, CDCl₃) δ 6.85 (d, 2H, J=8.8 Hz), 6.74 (d, 2H, J=9.3 Hz), 4.11 (t, 2H, J=6.1 Hz), 2.97 (t, 2H, J=5.9 Hz), 2.31 (s, 3H), 1.99-2.29 (m, 2H), 1.78-1.81 (m, 2H), 1.68-1.71 (m, 1H), 1.48-1.59 (m, 3H), 1.47 (s, 6H), 1.21-1.39 (m, 3H), MS (ES) m/e 388.4 (M+1).

EXAMPLE 32

2-{2-Benzyl-4-[2-(5-methyl-2-phenyloxazol-4-yl)ethoxy]phenoxy}-2-methylpropionic acid

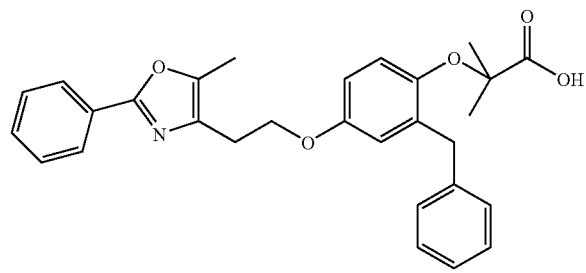

Step A

4-Benzyloxy-2-(hydroxy-phenyl-methyl)-phenol

A solution of phenol (Kappe, T.; Witoszynskyj, T. Arch. Pharm., 1975, 308 (5), 339-346) (1.14 g, 5.00 mmol) in THF (15 mL) was cooled in a dry ice/acetone bath and treated dropwise with phenyllithium (7.5 mL, 13.5 mmol, 1.8M in cyclohexane/ethyl ether 70/30). The reaction mixture was allowed to warm gradually to ambient temperature. After 18 h, the reaction was quenched with aqueous saturated NH₄Cl solution (1 mL) and partitioned between EtOAc (50 mL) and 1N HCl (20 mL). The organic layer was washed with brine (75 mL), dried (Na₂SO₄), and concentrated to a brown oil (2.3 g). The crude product was purified by flash chromatography using hexanes:ethyl acetate (3:1 to 2:1) to give a pale yellow oil (1.42 g, 93%): ¹H NMR (400 MHz, CDCl₃) δ 2.79 (s, 1H), 4.92 (s, 2H), 5.95, (s, 1H), 6.51 (s, 1H), 6.81 (d, 3H, J=1.5 Hz), 7.28-7.38 (s, 10H); MS (ES) m/e 305 [M−1].

Step B

2-[4-Benzyloxy-2-(hydroxy-phenyl-methyl)-phenoxy]-2-methyl-propionic acid ethyl ester 4-Benzyloxy-2-(hydroxy-phenyl-methyl)-phenol (690 mg, 2.25 mmol) and Cs₂CO₃ (734 mg, 2.25 mmol) in DMF (7 mL) was treated with ethyl bromoisobutyrate (0.66 mL, 4.5 mmol) and heated at 55° C. for 16 h. Additional bromo ester (0.40 mL, 1.23 mmol) and Cs₂CO₃ (400 mg, 1.23 mmol) were added and the reaction mixture was heated for 40 h. The mixture was cooled and partitioned between EtOAc (30 mL) and H₂O (10 mL). The organic layer was washed with brine (10 mL), dried (Na₂SO₄), and concentrated. The crude product was purified by flash chromatography using hexanes:ethyl acetate to give a pale yellow oil (615 mg, 65%): ¹H NMR (400 MHz, CDCl₃) δ 1.21 (t, 3H, J=7.3 Hz), 1.39 (s, 3H), 1.43 (s, 3H), 4.19 (q, 2H, J=7.3 Hz), 4.97 (s 2H), 6.00 (s, 1H), 6.61 (d, 1H, J=8.8 Hz), 6.74 (dd, 2H, J=3.2, 9.0 Hz), 6.96 (d, 1H, J=2.9 Hz), 7.22-7.39 (m, 10).

Step C 2-(2-Benzyl-4-hydroxy-phenoxy)-2-methyl-propionic acid ethyl ester

A solution of 2-[4-benzyloxy-2-(hydroxy-phenyl-methyl)-phenoxy]-2-methyl-propionic acid ethyl ester (1.67 g, 3.97 mmol maximum) in ethanol (50 mL) was treated with 5% Pd/C (0.42 g) and hydrogen (60 psi, rt, 18 h). The mixture was filtered and concentrated to a viscous colorless oil (1.15 g, 91%): ¹H NMR (400 MHz, CDCl₃) δ 1.32 (t, 3H, J=7.1 Hz), 1.51 (s, 6H), 3.99 (s, 2H), 4.30 (q, 2H, J=7.0 Hz), 4.93 (brs, 1H), 6.58-6.66 (m, 3H), 7.22-7.34 (m, 5H); MS (ES) m/e 315 [M+1].

Step D

2-{2-Benzyl-4-[2-(5-methyl-2-phenyloxazol-4-yl)ethoxy]phenoxy}-2-methylpropionic acid ethyl ester A mixture of 2-(2-benzyl-4-hydroxy-phenoxy)-2-methyl-propionic acid ethyl ester (1.14 g, 3.63 mmol), toluene-4-sulfonic acid 2-(5-methyl-2-phenyl-oxazol-4-yl)ethyl ester (Japan Tobacco Inc WO 9518125) (1.68 g, 4.71 mmol), and Cs₂CO₃ (1.77 g, 5.45 mmol) was heated at 55° C. in DMF (10 mL) for 72 h. The reaction mixture cooled and partitioned between EtOAc (30 mL) and H₂O (10 mL). The organic layer was washed with brine (15 mL). The organic layer was dried (Na₂SO₄) and concentrated. The crude product was purified by flash chromatography using hexanes:ethyl acetate (8:1) to give an oil (1.2 g, 66%): ¹H NMR (400 MHz, CDCl₃) δ 7.96 (dd, 2H, J=7.8, 2.9 Hz), 7.45-7.37 (m, 3H), 7.26-7.37 (m, 5H), 6.66 (s, 1H), 6.65 (d, 2H, J=1.5 Hz), 4.23 (q, 2H, J=7.1 Hz), 4.14 (t, 2H J=6.8 Hz), 3.94 (s, 2H), 2.91 (t, 2H, J=6.6 Hz), 2.33 (s, 3H), 1.42 (s, 6H), 1.25 (t, 3H, J=7.1 Hz); MS (ES) m/e 500 [M+1].

The following compound was prepared by the same procedure:

2-{2-Benzyl-4-[2-(2-cyclohexyl-5-methyl-oxazol-4-yl)ethoxy]-phenoxy}-2-methyl-propionic acid ethyl ester, MS (ES) m/e 506 (M+1).

Step E

2-{2-Benzyl-4-[2-(5-methyl-2-phenyloxazol-4-yl)ethoxy]phenoxy}-2-methylpropionic acid A solution of 2-{2-benzyl-4-[2-(5-methyl-2-phenyloxazol-4-yl)ethoxy]phenoxy}-2-methylpropionic acid ethyl ester (1.15 g, 2.30 mmol) in THF (15 mL) and MeOH (30 mL) was treated with 2.5N aqueous NaOH (10 mL). The solution was heated at 55° C. for 2 h, cooled to ambient temperature, and concentrated in vacuo. The residue was acidified with 5N aqueous HCl (5 mL) and partitioned between EtOAc (125 mL) and $H_2O$ (25 mL). The organic layer was washed with brine (50 mL), dried ($Na_2SO_4$), and concentrated to a colorless oil (1.1 g, 100%): $^1$H NMR (400 MHz, $CDCl_3$) δ 7.97 (dd, 2H, J=7.6, 2.2 Hz), 7.44-7.40 (m, 3H), 7.27-7.15 (m, 5H), 6.77 (d, 1H, J=8.8 Hz), 6.69 (d, 1H, J=2.9 Hz), 6.62 (dd, 1H, J=8.8, 2.9 Hz), 4.12 (t, 2H, J=6.4 Hz), 3.93 (s, 2H), 2.96 (t, 2H, J=6.6 Hz), 2.35 (s, 3H), 1.45 (s, 6H); MS (ES) m/e 472 [M+1].

The following compound was prepared by the same procedure from their corresponding ester:

Example 32A

2-{2-Benzyl-4-[2-(2-cyclohexyl-5-methyl-oxazol-4-yl)-ethoxy]-phenoxy}-2-methyl-propionic acid

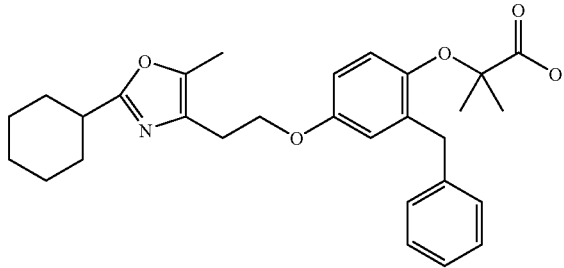

$^1$H NMR (400 MHz, $CDCl_3$) δ 7.22-7.24 (m, 2H), 7.10-7.17 (m, 3H), 6.75 (d, 1H, J=8.8 Hz), 6.64 (d, 1H, J=2.9 Hz), 6.61 (dd, 1H, J=8.8 Hz, J=2.9 Hz), 4.08 (t, 2H, J=5.9 Hz), 3.90 (s, 2H), 2.96 (t, 2H, J=6.1 Hz), 2.30 (s, 3H), 2.02 (m, 2H), 1.81 (m, 2H), 1.71 (m, 1H), 1.48-1.60 (m, 2H), 1.44 (s, 6H), 1.23-1.40 (m, 4H), MS (ES) m/e 478.3 (M+1).

EXAMPLE 33

2-{4-Butyl-3-[2-(5-methyl-2-phenyloxazol-4-yl)ethoxy]phenoxy}-2-methylpropionic acid

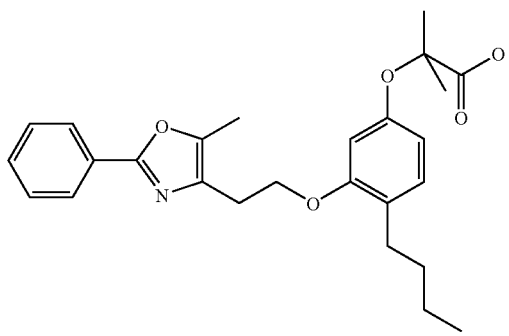

Step A

5-Benzyloxy-2-but-1-enylphenol

To a flame dried 500 mL 3-neck flask under an atmosphere of argon, was charged n-propyltriphenyl-phosphonium bromide (12.66 g, 32.85 mmol) dissolved in anhydrous THF (85 mL), followed by the dropwise addition of n-butyllithium 16.4 mL, 26.28 mmol). The dark red mixture was stirred at ambient temperature for 1 h. 15 min. Next 4-benzyloxy-2-hydroxybenzaldehyde (1.5 g, 6.57 mmol) (Synth. Commun., 26(3), 593-601, (1996) was added followed by the addition of anhydrous dichloromethane (27 mL). The mixture was stirred at ambient temperature for 18 h. The solvents were removed in vacuo, and the residue was partitioned between EtOAc and water (500 mL each). The organic layer was washed with brine (500 mL), dried ($Na_2SO_4$), and concentrated in vacuo. The crude product was purified using the Biotage FlashElute chromatography system using a 65M normal phase cartridge, eluting with 15% EtOAc/Hex to give a yellow solid (1.50 g, 90%). $^1$H NMR (400 MHz, $CDCl_3$) δ 7.43-7.30 (m, 5H), 7.19 (d, J=8.3 Hz, 1H), 6.52 (dd, J=8.8, 2.4 Hz, 1H), 6.46 (d, J=2.4 Hz, 1H), 6.43 (s, 1H), 6.14-6.07 (m, 1H), 5.03 (s, 2H), 4.98 (s, 1H), 2.25 (quintet, J=7.6 Hz, 2H), 1.09 (t, J=7.3 Hz, 3H), MS (ES) m/e 255 (M+1).

Step B

4-[2-(5-Benzyloxy-2-but-1-enylphenoxy)ethyl]-5-methyl-2-phenyloxazole

A mixture of 5-benzyloxy-2-but-1-enylphenol (0.090 g, 0.35 mmol), toluene-4-sulfonic acid 2-(5-methyl-2-phenyloxazol-4-ly)ethyl ester (0.164 g, 0.46 mmol) and cesium carbonate (0.173 g, 0.53 mmol) in anhydrous DMF (0.5 mL) was heated for 18 h at 55° C. The mixture was concentrated in vacuo, and the residue was partitioned between EtOAc (60 mL) and water (40 mL), washed with brine (50 mL,), dried ($Na_2SO_4$), and removed in vacuo to give a crude oil which was purified using radial chromatography eluting with 5% EtOAc/Hex to give a white solid (0.11 g, 72%). $^1$H NMR (400 MHz, $CDCl_3$) δ 7.97 (dd, J=6.8, 2.9 Hz, 2H), 7.44-7.25 (m, 9H), 6.58-6.50 (m, 3H), 6.13-6.06 (m, 1H), 5.03 (s, 2H), 4.24 (t, J=6.6 Hz, 2H), 3.00 (t, J=6.4 Hz, 2H), 2.38 (s, 3H), 2.20 (quintet, J=7.2 Hz, 2H), 1.06 (t, J=7.3 Hz, 3H).

Step C

4-Butyl-3-[2-(5-methyl-2-phenyloxazol-4-yl)ethoxy]phenol

A solution of 4-[2-(5-benzyloxy-2-but-1-enylphenoxy)ethyl]-5-methyl-2-phenylox (0.15 g, 0.34 mmol) in ethanol (10 mL) was treated with 5% Pd/C (30 mg) under a balloon containing hydrogen at ambient temperature for 24 h. The mixture was filtered and concentrated in vacuo to give a white solid (0.12 g, quantitative). $^1$H NMR (400 MHz, $CDCl_3$) δ 7.98 (dd, J=7.8, 2.0 Hz, 2H), 7.44-7.39 (m, 3H), 6.91 (d, J=6.9 Hz, 1H), 6.42 (d, J=2.4 Hz, 1H), 6.32 (dd, J=7.8, 2.4 Hz, 1H), 5.54 (br s, 1H), 4.19 (t, J=6.4 Hz, 2H), 2.97 (t, J=6.4 Hz, 2H), 2.47 (t, J=7.6 Hz, 2H), 2.39 (s, 3H), 1.43 (quintet, J=7.5 Hz, 2H), 1.28 (sextet, J=7.3 Hz, 2H), 0.86 (t, J=7.3 Hz, 3H).

Step D

2-{4-Butyl-3-[2-(5-methyl-2-phenyloxazol-4-yl)ethoxy]phenoxy}-2-methylpropionic acid ethyl ester A mixture of 4-butyl-3-[2-(5-methyl-2-phenyloxazol-4-yl)ethoxy]phenol (0.11 g, 0.313 mmol), ethyl bromoisobutyrate (0.18 mL, 1.25 mmol) and cesium carbonate (0.41 g, 1.25 mmol) in anhydrous DMF (2 mL) was heated for 18 h at 55° C. The mixture was concentrated in vacuo, and the residue was partitioned between EtOAc (50 mL) and water (40 mL), washed with brine, dried ($Na_2SO_4$), and removed in vacuo to give a crude oil which was purified using radial chromatography eluting with 5-15% EtOAc/Hex to give a yellow oil (0.12 g, 68%). $^1$H NMR (400 MHz, CDCl$_3$) δ 7.97 (dd, J=7.6, 1.7 Hz, 2H), 7.45-7.39 (m, 3H), 6.90 (d, J=7.8 Hz, 1H), 6.45 (d, J=2.4 Hz, 1H), 6.29 (dd, J=8.3, 2.0 Hz, 1H), 4.25-4.17 (m, 4H), 2.97 (t, J=6.4 Hz, 2H), 2.47 (t, J=7.6 Hz, 2H), 2.37 (s, 3H), 1.56 (s, 6H), 1.43 (quintet, J=7.7 Hz, 2H), 1.30-1.22 (m, 5H), 0.86 (t, J=7.3 Hz, 3H), MS (ES) m/e 466 (M+1).

Step E

2-{4-Butyl-3-[2-(5-methyl-2-phenyloxazol-4-yl)ethoxy]phenoxy}-2-methylpropionic acid A solution of 2-{4-butyl-3-[2-(5-methyl-2-phenyloxazol-4-yl)ethoxy]phenoxy}-2-methylpropionic acid ethyl ester (0.12 g, 0.258 mmol) in ethanol (3 mL) was treated with 2 N aqueous NaOH (0.64 mL), and heated at 55° C. for 8 h. The reaction was cooled to ambient temperature and concentrated down to near dryness. The residue was then diluted with EtOAc (25 mL) and water (20 mL) and acidified to pH=1 with 1N aqueous HCl. The organic layer was washed with brine (20 mL), dried (Na$_2$SO$_4$) and concentrated in vacuo to give a white solid (0.10 g, 88%). $^1$H NMR (400 MHz, CDCl$_3$) δ 7.99-7.97 (m, 2H), 7.00 (d, J=7.8 Hz, 1H), 6.79 (d, J=2.0 Hz, 1H), 6.49 (dd, J=8.3, 2.0 Hz, 1H), 4.23 (t, J=7.6 Hz, 2H), 2.92 (t, J=7.6 Hz, 2H), 2.52 (t, J=7.6 Hz, 2H), 2.38 (s, 3H), 1.59 (s, 6H), 1.50 (quintet, J=7.8 Hz, 2H), 1.32 (sextet, J=7.5 Hz, 2H), 0.90 (t, J=7.3 Hz, 3H), MS (ES) m/e 438 (M+1).

EXAMPLE 34

2-{2-Butyl-5-[2-(5-methyl-2-phenyloxazol-4-yl)ethoxy]phenoxy}-2-methylpropionic acid (507310)

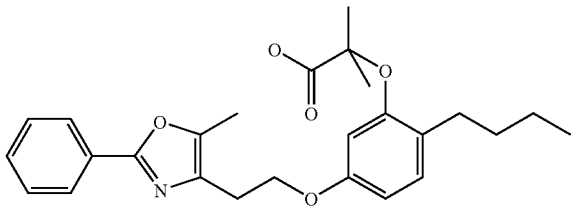

Step A 2-(5-Benzyloxy-2-but-1-enylphenoxy)-2-methylpropionic acid ethyl ester

5-Benzyloxy-2-but-1-enylphenol (0.70 g, 2.75 mmol) was dissolved in anhydrous DMF (12 mL), followed by the addition of ethyl bromoisobutyrate (1.62 mL, 11.0 mmol), and cesium carbonate (3.58 g, 11.0 mmol). The mixture was then heated for 18 h (55° C.). The reaction mixture was then cooled and concentrated in vacuo. The crude residue was partitioned between EtOAc (70 mL) and water (40 mL). The organic layer was washed with brine, dried (Na$_2$SO$_4$), and removed in vacuo. The crude residue was purified using radial chromatography, eluting with 5% EtOAc/Hex to give 0.77 g (76%) of a colorless oil. $^1$H NMR (400 MHz, CDCl$_3$) δ 7.41-7.28 (m, 6H), 6.65-6.59 (m, 2H), 6.40 (d, J=2.4 Hz, 1H), 6.14-6.07 (m, 1H), 4.99 (s, 2H), 4.22 (q, J=7.2 Hz, 2H), 2.22 (quintet, J=7.6 Hz, 2H), 1.56 (s, 6H), 1.26 (t, J=7.1 Hz, 3H), 1.08 (t, J=7.6 Hz, 3H), MS (ES) m/e 369 (M+1).

Step B 2-(2-Butyl-5-hydroxyphenoxy)-2-methylpropionic acid ethyl ester

A solution of 2-(5-Benzyloxy-2-but-1-enylphenoxy)-2-methylpropionic acid ethyl ester (0.76 g, 2.06 mmol) in ethanol (50 mL) was treated with 5% Pd/C (0.10 g) and hydrogen (60 psi) at ambient temperature for 6 h. The mixture was filtered and concentrated in vacuo to give a colorless oil (0.52 g, 90%). $^1$H NMR (400 MHz, CDCl$_3$) δ 6.96 (d, J=7.8 Hz, 1H), 6.37 (dd, J=8.3, 2.4 Hz, 1H), 6.20 (s, 1H), 4.66 (br s, 1H), 4.24 (q, J=7.2 Hz, 2H), 2.53 (t, J=7.8 Hz, 2H), 1.60 (s, 6H), 1.53 (quintet, J=7.6 Hz, 2H), 1.34 (sextet, J=7.3 Hz, 2H), 1.25 (t, J=7.1 Hz, 3H), 0.92 (t, J=7.3 Hz, 3H), MS (ES) m/e 281 (M+1).

Step C

2-{2-Butyl-5-[2-(5-methyl-2-phenyloxazol-4-yl)ethoxy]phenoxy}-2-methylpropionic acid The following example exemplifies the general procedure for the parallel synthesis of analogs utilizing the DynaVac carousel. To a 50 mL glass tube with screw cap and nitrogen inlet were charged 2-(2-butyl-5-hydroxyphenoxy)-2-methylpropionic acid ethyl ester, (0.050 g, 0.178 mmol), toluene-4-sulfonic acid 2-(5-methyl-2-phenyloxazol-4-yl)ethyl ester (0.067 g, 0.187 mmol), and powdered potassium carbonate (0.050 g, 0.36 mmol) in 1 mL of absolute ethanol. The mixture was heated to reflux for 18 h. MS analysis of the reaction indicated that 2-{2-Butyl-5-[2-(5-methyl-2-phenyloxazol-4-yl)ethoxy]phenoxy}-2-methylpropionic acid ethyl ester, MS (ES) m/e 466 (M+1) had formed. Next 0.4 mL of 5N sodium hydroxide was added and the reaction was heated for 3 h at 55° C. The ethanol was removed in vacuo and the residue was treated with 1 mL of 5N hydrochloric acid and 1 mL of dichloromethane and poured into a 3 mL ChemElute column to remove the aqueous layer. The column was eluted with additional dichloromethane until nothing UV active remained on the column. The solvent was removed in vaco. The crude residue was purified by mass-directed reverse phase HPLC to provide 0.038 g (49%) of 2-{2-Butyl-5-[2-(5-methyl-2-phenyloxazol-4-yl)ethoxy]phenoxy}-2-methylpropionic acid,
$^1$H NMR (400 MHz, CDCl$_3$) δ 7.99 (dd, J=6.4, 2.4 Hz, 2H), 7.46 (dd, J=5.9, 2.4 Hz, 3H), 7.03 (d, J=8.3 Hz, 1H), 6.62 (d, J=2.4 Hz, 1H), 6.51 (dd, J=8.3, 2.4 Hz, 1H), 4.18 (t, J=7.3 Hz, 2H), 2.95 (t, J=7.3 Hz, 2H), 2.54 (t, J=7.6 Hz, 2H), 2.38 (s, 3H), 1.63 (s, 6H), 1.53 (quintet, J=7.6 Hz, 2H), 1.35 (sextet, J=7.3 Hz, 2H), 0.92 (t, J=7.1 Hz, 3H), MS (ES) m/e 438 (M+1). The following compounds were also prepared by this procedure: 2-{2-Butyl-5-[2-(5-methyl-2-phenyloxazol-4-yl)ethoxy]phenoxy}-2-methylpropionic acid ethyl ester, MS (ES) m/e 472 (M+1).

Example 34A

2-{2-Butyl-5-[2-(5-methyl-2-phenyloxazol-4-yl)ethoxy]phenoxy}-2-methylpropionic acid

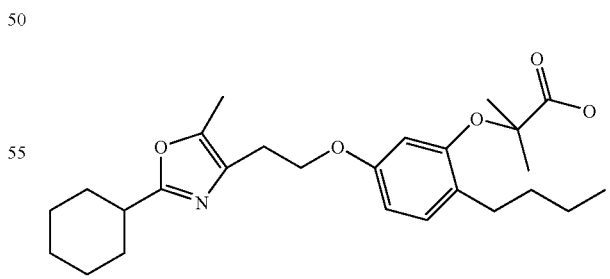

$^1$H NMR (400 MHz, CDCl$_3$) δ 6.98 (d, J=8.3 Hz, 1H), 6.43 (dd, J=7.1, 2.4 Hz, 1H), 6.39 (d, J=2.4 Hz, 1H), 4.18 (t, J=5.9 Hz, 2H), 3.06-3.00 (m, 1H), 2.96 (t, J=6.1 Hz, 2H), 2.51 (t, J=7.6 Hz, 2H), 2.33 (s, 3H), 2.08-2.05 (m, 2H), 1.86-1.82 (m, 2H), 1.75-1.72 (m, 1H), 1.63-1.40 (m, 10H), 1.37-1.25 (m, 5H), 0.92 (t, J=7.3 Hz, 3H), MS (ES) m/e 444 (M+1).

2-{5-[2-(2-Cyclohexyl-5-methyloxazol-4-yl)ethoxy]-2-propylphenoxy}-2-methylpropionic acid ethyl ester, MS (ES) m/e 558 (M+1).

Example 34B

2-{5-[2-(2-Cyclohexyl-5-methyloxazol-4-yl)ethoxy]-2-propylphenoxy}-2-methylpropionic acid

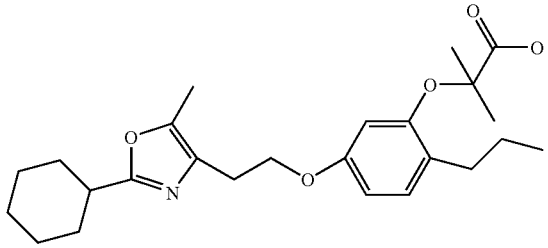

$^1$H NMR (400 MHz, CDCl$_3$) δ 6.98 (d, J=8.3 Hz, 1H), 6.43 (d, J=7.3 Hz, 2H), 4.17 (t, J=6.1 Hz, 2H), 3.02-2.99 (m, 1H), 2.93 (t, J=5.9 2H), 2.31 (s, 3H), 2.18-2.05 (m, 2H), 1.85-1.87 (m, 2H), 1.75-1.72 (m, 1H), 1.63-1.51 (m, 9H), 1.43-1.26 (m, 4H), 0.91 (t, J=7.1 Hz, 3H), MS (ES) m/e 430 (M+1).

2-Methyl-2-{5-[2-(5-methyl-2-phenyloxazol-4-yl)ethoxy]-2-propylphenoxy}propionic acid ethyl ester, MS (ES) m/e 452 (M+1).

Example 34C

2-Methyl-2-{5-[2-(5-methyl-2-phenyloxazol-4-yl)ethoxy]-2-propylphenoxy}propionic acid

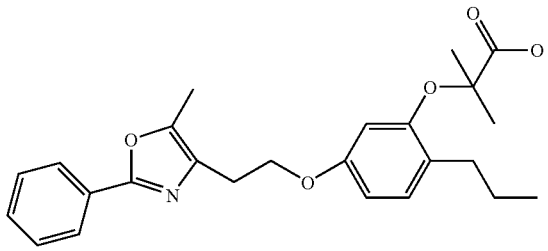

$^1$H NMR (400 MHz, CDCl$_3$) δ 8.01-7.98 (m, 2H), 7.49-7.46 (m, 3H), 7.02 (d, J=8.3 Hz, 1H), 6.60 (d, J=2.4 Hz, 1H), 6.51 (dd, J=8.3, 2.4 Hz, 1H), 4.19 (t, J=7.3 Hz, 2H), 2.97 (t, J=7.3 Hz, 2H), 2.39 (s, 3H), 1.62 (s, 6H), 1.58 (sextet, J=7.3 Hz, 2H), 0.93 (t, J=7.6 Hz, 3H), MS (ES) m/e 424 (M+1).

EXAMPLE 35

2-Methyl-2-{4-[2-(5-methyl-2-phenyl-thiazol-4-yl)-ethoxy]phenoxy}-2-methyl-propionic acid

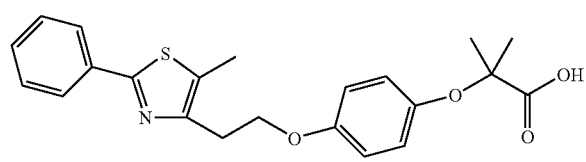

Step A (5-methyl-2-phenyl-thiazol-4-yl)-acetic acid methyl ester

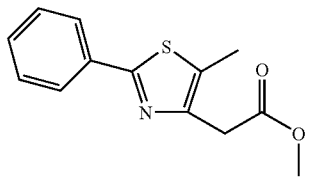

Thiobenzamide (7.3 g) in toluene was heated at reflux for 1 h in a flask equipped with a Dean-Stark trap. After 1.2 mL water was obtained, the dry thioamide (6.0 g, 28 mmol) and 4-bromo-3-oxo-pentanoic acid methyl ester (9.0 g, 43 mmol) were heated in toluene (200 mL) for 3 h. The cooled reaction was concentrated and purified by short path chromatography (400 g silica gel, 15% EtOAc/hexanes, then 20% EtOAc/hexanes). The fractions that contained pure product were concentrated to yield 3.53 g (39%) ester as a yellow oil: $^1$H NMR (CDCl$_3$) δ 2.40 (s, 3H), 3.70 (s, 3H), 3.78 (s, 2H), 7.34-7.39 (m, 3H), 7.85 (d, 2H); MS (m/e) 248 (M+H).

Step B 2-(5-Methyl-2-phenyl-thiazol-4-yl)-ethanol

According to the general method of Collins et al, J. Med. Chem. 41 5037-5054 (1998), a THF (100 mL) solution of 2-(5-methyl-2-phenyl-thiazol-4-yl)-acetic acid methyl ester (3.5 g, 16 mmol) was cooled to 0° C. and a 1M LiAlH$_4$ (16 mL, 16 mmol) was added slowly. After stirring at room temperature for 45 min, tlc (15% EtOAc/hexane) showed that all the starting ester had been consumed. The reaction was cooled and carefully quenched with 4 mL water, 2.6 mL 5N NaOH and 2 mL water. The light tan solid was filter and dried to give 3.29 g crude product. Recrystallization (60 mL toluene) gave 2.36 g (50%) alcohol as a light tan oil: $^1$H NMR (CDCl$_3$) δ 2.42 (s, 3H), 2.94 (t, 2H), 4.03 (t, 2H), 7.39-7.47 (m, 3H), 7.85-7.93 (m, 2H).

Step C

2-Methyl-2-{4-[2-(5-methyl-2-phenyl-thiazol-4-yl)-ethoxy]-phenoxy}-propionic acid ethyl ester As described in Example 9, Part E, 2-(5-methyl-2-phenyl-thiazol-4-yl)-ethanol (2.0 g, 6.77 mmol) was converted to the tosylate derivative 2.87 g (94%) with a crude product (MS (m/e) 375 (MH)) and used without further purification. A mixture of toluene-4-sulfonic acid 2-(5-methyl-2-phenyl-thiazol-4-yl)-ethyl ester (2.8 g, 6.2 mmol), Cs$_2$CO$_3$ (1.8 g, 5.5 mmol) phenol (1.0 g, 4.4 mmol) in DMF (100 mL) was warmed at 55° C. for 18 h. The reaction was partitioned between EtOAc/water. The organic solution was washed a second time with water and then dried (MgSO$_4$). After concentration, 3.2 g crude product was obtained. Purification by flash column chromatography (15% EtOAc/hexane) gave 420 mg (19%) ester as a colorless oil:

Toluene-4-sulfonic acid 2-(5-methyl-2-phenyl-thiazol-4-yl)-ethyl ester, 90% as a white semi-solid: $^1$H NMR (CDCl$_3$)

δ 2.24 (s, 3H), 2.40 (s, 3H), 3.07 (t, 2H), 4.42 (t, 2H), 7.18 (d, 2H), 7.35-7.47 (m, 3H), 7.66 (d, 2H), 7.75-7.84 (m, 2H); MS (m/e) 374 (M+H).

2-Methyl-2-{4-[2-(5-methyl-2-phenyl-thiazol-4-yl)-ethoxy]-phenoxy}-propionic acid ethyl ester 19% yield as a colorless oil: $^1$H NMR (CDCl$_3$) δ 1.31 (t, 3H), 1.54 (s, 6H), 2.47 (s, 3H), 3.22 (t, 2H), 4.27 (q, 2H), 4.31 (t, 2H), 6.78-6.88 (m, 4H), 7.40-7.45 (m, 3H), 7.87-7.94 (m, 2H); MS (m/e) 426 (M+H).

Step D

2-Methyl-2-{4-[2-(5-methyl-2-phenyl-thiazol-4-yl)-ethoxy]-phenoxy}-2-methyl-propionic acid A sample of ester (400 mg, 0.8 mmol) was dissolved in EtOH (15 mL) and 5N NaOH (5 mL) added. The reaction was warmed at 40° C. for 1.5 h and then cooled to room temperature. After removing some of the EtOH, the reaction was acidified with HCl. After stirring in an ice-bath for 1 h, the yellow solid was collected and dried to give 328 mg (76%) yield as a pale yellow solid: mp 163.5° C.; $^1$H NMR (CDCl$_3$) δ 1.53 (s, 6H), 2.49 (s, 3H), 3.24 (t, 2H), 4.32 (t, 2H), 6.82-6.95 (m, 4H), 7.40-7.47 (m, 3H), 7.88-7.95 (m, 2H); MS (m/e) 398 (M+H).

EXAMPLE 36

2-Methyl-2-{4-[2-(5-methyl-2-phenyloxazol-4-yl) ethylsulfanyl]phenoxy}propionic acid

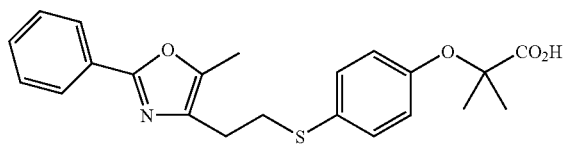

Step A 2-(4-Dimethylthiocarbamoyloxy-phenoxy)-2-methyl-propionic acid ethyl ester A DMF (100 mL) solution of 2-(4-hydroxyphenoxy)-2-methyl propionic acid ethyl ester (15.2 g, 67.7 mmol) and DABCO (15.2 g, 135.5 mmol) was charged dropwise with N,N-dimethylthiocarbamoyl chloride (16.7 g, 135.5 mmol) in 20 mL DMF over 15 min. The reaction was stirred at rt for 18 h and then quenched with water. The reaction was partitioned between water (1 L) and EtOAc (500 mL) and the organic layer washed with 1N HCl (500 mL). After drying (MgSO$_4$) and concentration, the crude product was obtained as a tan oil. Purification by flash chromatography (15% EtOAc/hexane) provided the product (15.8 g, 75%) as a pale yellow oil: $^1$H NMR (CDCl$_3$) δ 1.32 (t, 3H), 1.65 (s, 6H), 3.37 (s, 3H), 3.50 (s, 3H), 4.30 (q, 2H), 6.93 (dd, 4H); MS (m/e) 312.

Step B 2-(4-Dimethylcarbamoylsulfanyl-phenoxy)-2-methyl-propionic acid ethyl ester Neat (2-(4-dimethylthiocarbamoyloxyphenoxy)-2-methyl propionic acid ethyl ester (15 g, 48.2 mmol) was heated at 200° C. for 1 h. TLC (20% EtOAc/hexane) showed that no reaction had occurred. The temperature was raised to 240° C. for 30 min. By TLC, all starting material was gone and there was significant decomposition. Purification by short plug column (20% EtOAc/hexane) followed by prep HPLC gave the product (2.6 g) as a pale yellow oil: $^1$H NMR (CDCl$_3$) δ 1.27 (t, 3H), 1.63 (s, 6H), 3.05 (br s, 6H), 4.24 (q, 2H), 6.86 (d, 2H), 7.35 (d, 2H); MS (m/e) 312.

Step C

2-Methyl-2-{4-[2-(5-methyl-2-phenyloxazol-4-yl) ethylsulfanyl]phenoxy}propionic acid ethyl ester Freshly prepared NaOEt (from 50 mg (2.2 mmol) Na) was charged with 2-(4-dimethylcarbamoylsulfanyl-phenoxy)-2-methyl-propionic acid ethyl ester (420 mg, 1.35 mmol) and refluxed for 3 h. Toluene-4-sulfonic acid 2-(5-methyl-2-phenyloxazol-4-yl)-ethyl ester (572 mg, 2.2 mmol) was added and the mixture was refluxed for another 3 h. The reaction was cooled and concentrated. The residue was shaken with EtOAc/water. After a second water wash, the organic layer was dried (MgSO$_4$) and concentrated to give 500 mg crude product. Purification by flash chromatography (15% EtOAc/hexane) provided the product (98 mg, 17%): R$_f$=0.32 in 15% EtOAc/hexane; MS m/e 426 (MH$^+$).

Step D

2-Methyl-2-{4-[2-(5-methyl-2-phenyloxazol-4-yl) ethylsulfanyl]phenoxy}propionic acid 2-Methyl-2-{4-[2-(5-methyl-2-phenyl-oxaz-4-yl)ethyl-sulfanyl]phenoxy}propionic acid ethyl ester (98 mg, 0.23 mmol) was dissolved in EtOH (10 mL) and 5N NaOH (0.5 mL) was added. The reaction was stirred overnight at rt. The reaction was acidified with 5N HCl and the product was extracted into EtOAc, dried (MgSO$_4$) and concentrated to give 96 mg crude product. Purification by reverse phase HPCL gave 47.5 mg (52%) as a light tan solid: mp 104-106° C., $^1$H NMR (DMSO-d$_6$) δ 1.47 (s, 6H), 2.26 (s, 3H), 2.71 (t, 2H), 3.16 (t, 2H), 6.78 (d, 2H), 7.30 (d, 2H), 7.48 (m, 3H), 7.90 (m, 2H), 13.08 (br s, 1H).

EXAMPLE 37

2-Methyl-2-{4-[2-(5-methyl-2-phenyl-oxazol-4-yl)-ethoxy]-naphthalen-1-yloxy}-propionic acid

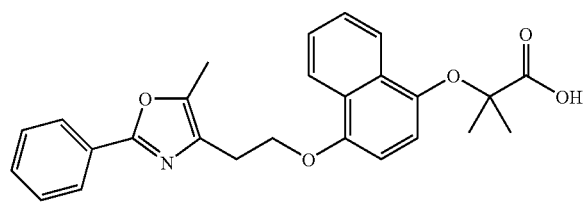

Step A 2-(4-Hydroxy-naphthalen-1-yloxy)-2-methyl-propionic acid ethyl ester

A solution of naphthalene-1,4-diol (30.0 g, 187 mmol) was prepared in DMF (60 mL, anhydrous), cooled to 0° C., and treated with NaH (7.50 g of a 60% solution in oil, 188 mmol) in portions, over a 5 min period. The ice bath was removed and the mixture stirred for 30 min. The resulting black suspension was treated with ethyl 2-bromoisobutyrate (27.6 mL, 188 mmol) and stirred at 95° C. for 18 h. The mixture was cooled to rt, then poured into cracked ice containing HCl (1 N aqueous, 200 mL). The aqueous layer was extracted with ethyl ether (3×500 mL) and the organic layers washed with brine (100 mL), dried (MgSO$_4$), filtered, and the filtrate evaporated (40° C., 20 mm Hg). The residue was chromatographed on SiO$_2$ (Biotage, 65M column; 18% EtOAc/hexanes) to afford a total of 19.2 g of 2-(4-hydroxy-naphthalen-1-yloxy)-2-methyl-propionic acid ethyl ester as a black oil 37% yield: R$_f$=0.31 (20% EtOAc/hexanes); $^1$H NMR (CDCl$_3$) δ 8.2 (m, 1H), 8.1 (m, 1H), 7.5 (m, 2H), 6.62 (dd, J=15.4, 8.4 Hz, 2H), 4.22 (q, J=7.2 Hz, 2H), 1.60 (s, 6H), 1.21 (t, J=7.2 Hz, 3H); MS (ES+) m/e (% relative intensity) 275.1 (M$^+$+1, 21), 230.1 (33), 229.0 (100), 201.0 (60).

Step B

2-Methyl-2-{4-[2-(5-methyl-2-phenyl-oxazol-4-yl)-ethoxy]-naphthalen-1-yloxy}-propionic acid ethyl ester A solution of 2-(4-hydroxy-naphthalen-1-yloxy)-2-methyl-propionic acid ethyl ester (450 mg, 1.64 mmol) and toluene-4-sulfonic acid 2-(5-methyl-2-phenyl-oxazol-4-yl)-ethyl ester (700 mg, 1.96 mmol) was prepared in DMF (4 mL, anhydrous) under N$_2$, treated with Cs$_2$CO$_3$ (638 mg, 1.96 mmol), and stirred at 60° C. for 18 h. The solution was poured into 1/1 H$_2$O/brine and extracted twice with 2/1 EtOAc/toluene. The organic layers were washed with brine, dried (MgSO$_4$), filtered, and the filtrate evaporated (40° C., 20 mm Hg) to a residue. The residue was chromatographed on SiO$_2$ (Biotage, 40 L column; 20% EtOAc/hexanes) to afford 440 mg of 2-methyl-2-{4-[2-(5-methyl-2-phenyl-oxazol-4-yl)-ethoxy]-naphthalen-1-yloxy}propionic acid ethyl ester as a colorless solid, 58% yield: $^1$H NMR (400 MHz, CDCl$_3$) δ 8.1 (m 2H), 7.94 (dd, J=8.0, 1.6 Hz, 2H), 7.4 (m, 5H), 6.68 (d, J=8.6 Hz, 1H), 6.62 (d, J=8.6 Hz, 1H), 4.33 (t, J=6.4 H, 2H), 4.21 (q, J=7.2 Hz, 2H), 3.06 (t, J=6.4 Hz, 2H), 2.36 (s, 3H), 1.59 (s, 6H), 1.20 (t, J=7.2 Hz, 3H); MS (ES+) m/e (% relative intensity) 462.2 (16), 461.2 (72), 460.1 (M$^+$+1, 100).

Step C

2-Methyl-2-{4-[2-(5-methyl-2-phenyloxazol-4-yl)ethoxy]naphthalen-1-yloxy}propionic acid A solution of 2-methyl-2-{4-[2-(5-methyl-2-phenyl-oxazol-4-yl)-ethoxy]-naphthalen-1-yloxy}-propionic acid ethyl ester (440 mg, 91 μmol) was prepared in THF (10 mL) and methanol (2 mL), treated with NaOH (2.0 mL of a 1 N aqueous solution, 2.0 mmol), and stirred for 4 h. The solution was acidified with HCl (400 μL, 5 N aqueous, 2.0 mmol), and partitioned between water and EtOAc. The layers were separated and the organic layer dried (MgSO$_4$), filtered, and the filtrate evaporated (40° C., 20 mm Hg). The residue was triturated with ethyl ether to afford 260 mg (2 crops) of 2-methyl-2-{4-[2-(5-methyl-2-phenyl-oxazol-4-yl)-ethoxy]-naphthalen-1-yloxy}-propionic acid as a pink powder, 63% yield: $^1$H NMR (400 MHz, CDCl$_3$) δ 8.1 (m 2H), 8.00 (d, J=8.8 Hz, 2H), 7.4 (m, 5H), 6.87 (d, J=8.4 Hz, 1H), 6.58 (d, J=8.4 Hz, 1H), 4.27 (t, J=6.1 Hz, 2H), 3.12 (t, J=6.1 Hz, 2H), 2.42 (s, 3H), 1.62 (s, 6H); MS (ES+) m/e (% relative intensity) 433.2 (50), 432, 1.20 (t, J=7.2 Hz, 3H). 2 (M$^+$+1, 100).

EXAMPLE 38

2-Methyl-2-{4-[2-(5-methyl-2-phenyl-oxazol-4-yl)-ethoxy]-5,6,7,8-tetrahydro-naphthalen-1-yloxy}-propionic acid

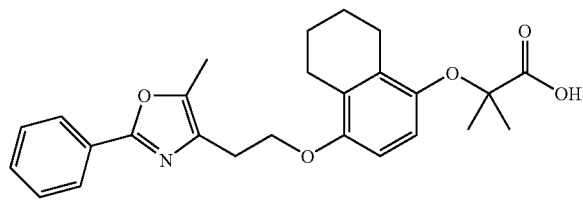

Step A 5,6,7,8-Tetrahydronaphthyl-1,4-diol

A solution of naphthalene-1,4-diol (4.00 g, 25.0 mmol) was prepared in ethanol (95 mL) and acetic acid (25 mL), treated with PtO$_2$ (0.60 g, 2.6 mmol), charged with H$_2$ (60 psig), and shaken for 18 h at 40° C. The catalyst was filtered off and the filtrate evaporated (40° C., 20 mm Hg). The residue was dissolved in EtOAc (100 mL) and washed with NaHCO$_3$ (saturated aqueous, 100 mL), brine (100 mL), dried (MgSO$_4$), filtered, and the filtrate evaporated (40° C., 20 mm Hg) to afford a total of 2.6 g of 5,6,7,8-tetrahydronaphthalene-1,4-diol as a black solid, 63% yield: 1H NMR (CDCl$_3$) δ 6.45 (s, 2H), 2.6 (m, 4H), 1.9 (m, 4H); MS (ES+) m/e (% relative intensity) 327.2 (100), 165.1 (M$^+$1, 26).

Step B 2-(4-Hydroxy-5,6,7,8-tetrahydronaphthalen-1-yloxy)-2-methyl propionic acid ethyl ester A solution of 5,6,7,8-tetrahydronaphthalene-1,4-diol (2.60 g, 15.8 mmol) was prepared in DMF (20 mL, anhydrous), cooled to 0° C., and treated with NaH (0.63 g of a 60% solution in oil, 15.8 mmol) in one portion. The ice bath was removed and the mixture stirred for 30 min. The resulting black suspension was treated with ethyl 2-bromoisobutyrate (2.33 mL, 15.9 mmol) and stirred at 100° C. for 18 h. The mixture was cooled to rt, then poured into cracked ice containing HCl (1 N aqueous, 20 mL). The aqueous layer was extracted with ethyl ether (3×50 mL) and the organic layers washed with brine (100 mL), dried (MgSO$_4$), filtered, and the filtrate evaporated (40° C., 20 mm Hg). The residue was chromatographed on SiO$_2$ (Biotage, 40 L column; 15% EtOAc/hexanes) to afford a total of 1.2 g of 2-(4-hydroxy-5,6,7,8-tetrahydro-naphthalen-1-yloxy)-2-methyl-propionic acid ethyl ester as a black oil 27% yield: R$_f$=0.27 (15% EtOAc in hexanes); $^1$H NMR (CDCl$_3$) δ 6.42 (d, J=8.6 Hz, 2H), 6.38 (d, J=8.6 Hz, 2H), 4.20 (q, J=7.2 Hz, 2H), 2.61 (t, J=6.0 Hz, 2H), 2.55 (t, J=6.0 Hz, 2H), 1.6 (m, 9H), 1.49 (s, 6H), 1.23 (t, J=7.2 Hz, 3H); MS (ES+) m/e (% relative intensity) 301.1 (28), 279.2 (M$^+$+1, 49), 233.1 (100), 205.1 (470), 165.1 (88).

Step C

2-Methyl-2-{4-[2-(5-methyl-2-phenyloxazol-4-yl)-ethoxy]-5,6,7,8-tetrahydronaphthalen-1-yloxy}propionic acid ethyl ester A solution of 2-(4-hydroxy-5,6,7,8-tetrahydronaphthalen-1-yloxy)-2-methyl propionic acid ethyl ester (400 mg, 1.44 mmol) and toluene-4-sulfonic acid 2-(5-methyl-2-phenyloxazol-4-yl)ethyl ester (608 mg, 1.70 mmol) was prepared in DMF (4 mL, anhydrous) under $N_2$, treated with $Cs_2CO_3$ (555 mg, 1.70 mmol), and stirred at 55° C. for 24 h, then stirred over the week end at rt. The solution was poured into dilute aqueous HCL and extracted twice with EtOAc. The organic layers were washed with brine, dried ($MgSO_4$), filtered, and the filtrate evaporated (40° C., 20 mm Hg) to a residue. The residue was chromatographed on $SiO_2$ (Biotage, 40S column; 15% EtOAc/hexanes) to afford 350 mg of 2-methyl-2-{4-[2-(5-methyl-2-phenyl-oxazol-4-yl)-ethoxy]-5,6,7,8-tetrahydronaphthalen-1-yloxy}propionic acid ethyl ester as a colorless solid, 52% yield: $^1H$ NMR (400 MHz, $CDCl_3$) δ 7.92 (dd, J=7.8, 1.8 Hz, 2H), 7.3 (m, 3H), 6.4 (m, 2H), 4.19 (q, J=7.0 Hz, 2H), 4.11 (t, J=6.4 Hz, 2H), 2.91 (t, J=6.4 Hz, 2H), 2.6 (m, 4H), 2.32 (s, 3H), 1.7 (m, 4H), 1.48 (s, 6H), 1.22 (t, J=7.0 Hz, 3H); MS (ES+) m/e (% relative intensity) 466.3 (16), 465.3 (70), 464.3 ($M^+$+1, 100).

Step D

2-Methyl-2-{4-[2-(5-methyl-2-phenyloxazol-4-yl)-ethoxy]-5,6,7,8-tetrahydronaphthalen-1-yloxy}propionic acid A solution of 2-methyl-2-{4-[2-(5-methyl-2-phenyloxazol-4-yl)-ethoxy]-5,6,7,8-tetrahydronaphthalen-1-yloxy}propionic acid ethyl ester (350 mg, 755 µmol) was prepared in THF (10 mL) and methanol (3 mL), treated with NaOH (3.0 mL of a 1 N aqueous solution, 3.0 mmol), and stirred for 18 h. The solution was acidified with HCl (1.0 mL, 5 N aqueous, 5.0 mmol), and partitioned between water and EtOAc. The layers were separated and the organic layer was washed with brine, dried ($MgSO_4$), filtered, and the filtrate evaporated (40° C., 20 mm Hg). The resulting solid was recrystallized from EtOAc/hexanes to afford 179 mg (2 crops) of 2-methyl-2-{4-[2-(5-methyl-2-phenyl-oxazol-4-yl)-ethoxy]-5,6,7,8-tetrahydro-naphthalen-1-yloxy}-propionic acid as a colorless powder, 54% yield: 1H NMR (400 MHz, $CDCl_3$) δ 7.9 (m 2H), 7.4 (m, 3H), 6.63 (d, J=8.8 Hz, 1H), 6.50 (d, J=8.8 Hz, 1H), 4.11 (t, J=6.0 Hz, 2H), 2.98 (t, J=6.0 Hz, 2H), 2,57 (m, 4H), 2.35 (s, 3H), 1.7 (m, 4H), 1.51 (s, 6H); MS (ES+) m/e (% relative intensity) 437.3 (52), 436.2 ($M^+$+1, 100).

Additional compounds of the present invention, having the structural formula shown below, were synthesized by similar to those described in the previous examples.

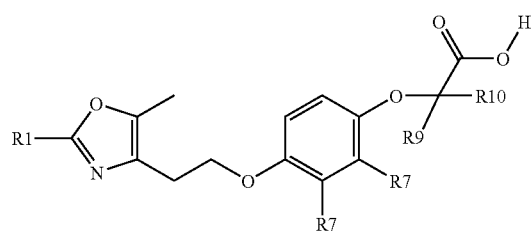

These additional compounds are further exemplified in the following table.

TABLE I

| Ex. | R1 | o-R7 | m-R7 | R9 | R10 |
|---|---|---|---|---|---|
| 39A | phenyl | H | H | H | benzyl |
| 39B | phenyl | pentyl | H | Me | Me |
| 39C | phenyl | H | pentyl | Me | Me |
| 39D | cyclohexyl | pentyl | H | Me | Me |
| 39E | phenyl | H | H | Et | Et |
| 39F | cyclohexyl | butyl | H | Me | Me |
| 39G | 2-thienyl | H | H | Me | Me |
| 39H | 2-thienyl | H | benzyl | Me | Me |
| 39I | 2-thienyl | H | $C_6H_{11}CH_2$ | Me | Me |
| 39J | phenethyl | H | H | Me | Me |
| 39K | benzyl | H | H | Me | Me |
| 39L | phenyl-propyl | H | H | Me | Me |
| 39M | phenethyl | H | H | Me | benzyl |
| 39N | phenethyl | H | benzyl | Me | Me |
| 39O | phenethyl | H | H | Me | benzyl |
| 39P | phenethyl | H | benzyl | Me | Me |
| 39Q | 2-thienyl | H | H | Me | benzyl |
| 39R | phenyl-propyl | H | H | Me | benzyl |
| 39S | cyclohexyl | H | H | Me | benzyl |
| 39T | 1-methyl-cyclohexyl | H | H | Me | benzyl |
| 39U | phenyl | H | benzoyl | Me | Me |
| 39V | 2-thienyl | H | benzoyl | Me | Me |
| 39W | cyclohexyl | H | H | Me | 4-trifluoromethylbenzyl |
| 39X | cyclohexyl | H | H | Me | 4-trifluoromethyloxybenzyl |
| 39Y | cyclohexyl | H | H | Me | 4-phenylbenzyl |
| 39Z | cyclohexyl | H | H | Me | 4-trifluoromethyloxybenzyl |
| 39AA | cyclohexyl | H | H | Me | 4-methylbenzyl |
| 39BB | cyclohexyl | H | H | Me | 3-methylbenzyl |
| 39CC | cyclohexyl | H | H | Me | 4-methoxybenzyl |
| 39DD | cyclohexyl | H | H | Me | 3-methoxybenzyl |
| 39EE | cyclohexyl | H | H | Me | 2-methylbenzyl |
| 39FF | cyclohexyl | H | H | Me | 4-trifluoromethylbenzyl |
| 39GG | cyclohexyl | H | H | Me | 2-methyloxybenzyl |
| 39HH | cyclohexyl | H | H | Me | 2-trifluoromethylbenzyl |

EXAMPLE 40

{4-[5-Methyl-2-(4-trifluoromethyl-phenyl)-oxazol-4-ylmethylsulfanyl]-2-propyl-phenoxy}-acetic acid

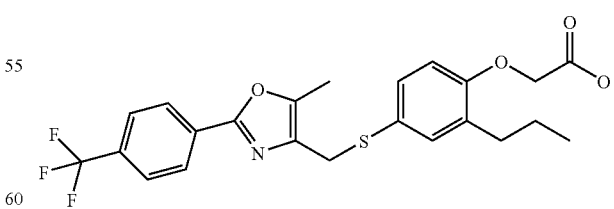

Step A

(2-Allyl-phenoxy)-acetic acid ethyl ester

A mixture of 2-allyl-phenol (10 g, 74.5 mmol), ethyl 2-bromoacetate (12.4 mL, 112 mmol) and cesium carbonate (36.5 g, 112 mmol) in DMF (180 mL) was heated at 60° C. overnight. The mixture was cooled and filtered through a pad of celite. The filtrate was diluted with water and extracted with ethyl acetate. The combined organic layers were washed with water, dried over sodium sulfate, filtered, and concentrated. The crude material was purified by column chromatography on silica gel to give 14.5 g of title compound. $^1$H NMR (400 MHz, CDCl$_3$) • 7.19~7.14 (m, 2H), 6.97~6.92 (m, 1H), 6.73 (d, J=8.1 Hz, 1H), 6.09~5.95 (m, 1H), 5.11~5.02 (m, 2H), 4.54 (s, 2H), 4.26 (q, J=7.2 Hz, 2H), 3.46 (d, J=6.8 Hz, 2H), 1.29 (t, J=7.2 Hz, 3H).

Step B

(2-Propyl-phenoxy)-acetic acid ethyl ester

A solution of (2-allyl-phenoxy)-acetic acid ethyl ester (5.8 g, 26.3 mmol) in ethanol (200 mL) was treated with 5% Pd/C (59 mg) and hydrogen at ambient temperature for overnight. The mixture was filtered and concentrated to give the title compound (5.7 g, 98%). $^1$H NMR (400 MHz, CDCl$_3$) • 7.16~7.10 (m, 2H), 6.94~6.89 (m, 1H), 6.71 (d, J=8.1 Hz, 1H), 4.53 (s, 2H), 4.26 (q, J=7.2 Hz, 2H), 2.65 (t, J=7.7 Hz, 2H), 1.71~1.60 (m, 2H), 1.29 (t, J=7.0 Hz, 2H), 0.96 (t, J=7.0 Hz, 3H); MS (ES) m/e 406.18 (M$^+$+1).

Step C

(4-Chlorosulfonyl-2-propyl-phenoxy)-acetic acid ethyl ester (2-Propyl-phenoxy)-acetic acid ethyl ester (5.0 g, 22.4 mmol) was added to chlorosulfonic acid (6.6 mL) at 0° C. dropwise. After addition, the mixture was warmed to room temperature slowly and stirred for 2 h. The reaction mixture was poured into ice and stirred for 1 h, filtered and the solid product was washed with water, dried in vacuum oven over night giving the title compound (6.0 g, 83.5%).
$^1$H NMR (400 MHz, DMSO) • 7.35 (s, 1H), 7.34 (d, J=8.0 Hz, 1H), 6.75 (d, J=8.1 Hz, 1H), 4.78 (s, 2H), 4.13 (q, J=7.3 Hz, 2H), 2.54 (t, J=7.3 Hz, 2H), 1.60~1.50 (m, 2H), 1.18 (t, J=7.3 Hz, 2H), 0.88 (t, J=7.3 Hz, 3H).

Step D

(4-Mercapto-2-propyl-phenoxy)-acetic acid ethyl ester

A mixture of (4-chlorosulfonyl-2-propyl-phenoxy)-acetic acid ethyl ester (1.12 g, 3.5 mmol), tin powder (2.1 g) and HCl (4.0 M in dioxane, 4.4 mL) in ethanol (4.4 mL) was refluxed for 4 h, the mixture was poured into ice, extracted with methylene chloride. The combined organic layers were washed with brine, dried over sodium sulfate, concentrated to give the title compound, which was used for next step without purification.

Step E

{b 4-[5-Methyl-2-(4-trifluoromethyl-phenyl)-oxazol-4-ylmethylsulfanyl]-2-propyl-phenoxy}-acetic acid To a mixture of (4-mercapto-2-propyl-phenoxy)-acetic acid ethyl ester (127 mg, 0.5 mmol) and 4-Chloromethyl-5-methyl-2-(4-trifluoromethyl-phenyl)-oxazole (131 mg, 0.48 mmol) in acetonitrile (2 mL) was added cesium carbonate (326 mg, 1 mmol). After 4 h at room temperature, the reaction was quenched by water, extracted with ethyl acetate. Combined organic layers were washed with brine, dried (sodium sulfate) and concentrated. The residue was taken into THF (2 mL) and treated with lithium hydroxide (1N, 0.5 mL) at room temperature for 2 h. THF was evaporated, the residue was treated with water (0.5 mL) and extracted with ether. The aqueous was acidified with 5 N HCl, extracted with ether, dried over sodium sulfate and concentrated. The crude product was purified by reversed phase HPLC to give the title compound (125 mg, 53.7%)
$^1$H NMR (400 MHz, DMSO) • 8.08 (d, J=8.4 Hz, 2H), 7.85 (d, J=8.4 Hz, 2H), 7.15~7.12 (m, 1H), 7.10~7.08 (m, 1H), 6.76 (d, J=8.4 Hz, 1H), 4.57 (s, 2H), 3.94 (s, 2H), 2.50~2.42 (m, 2H), 2.00 (s, 3H), 1.52~1.41 (m, 2H), 0.79 (t, J=8.0 Hz, 3H); MS (ES) m/e: 466.07 (M$^+$+1).

The following compounds were made in a substantially similar manner

EXAMPLE 41

[4-(5-Methyl-2-phenyl-oxazol-4-ylmethylsulfanyl)-2-propyl-phenoxy]-acetic acid

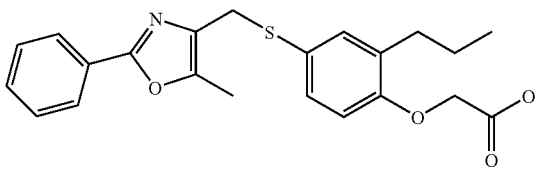

$^1$H NMR (400 MHz, DMSO) • 7.89~7.85 (m, 2H), 7.49~7.47 (m, 3H), 7.14 (dd, J=2.4, 8.2 Hz, 1H), 7.1 (d, J=2.3 Hz, 1H), 6.76 (d, J=8.4 Hz, 1H), 4.67 (s, 2H), 3.92 (s, 2H), 2.55~2.41 (m, 2H), 1.98 (s, 3H), 1.52~1.40 (m, 2H), 0.81 (t, J=7.2 Hz, 3H); MS (ES) m/e 398.12 (M$^+$+1).

Example 42A

{4-[2-(4-Benzyloxy-phenyl)-5-methyl-oxazol-4-ylmethylsulfanyl]-2-propyl-phenoxy}-acetic acid

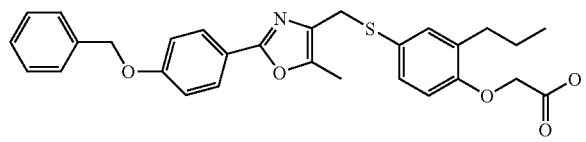

$^1$H NMR (400 MHz, DMSO) • 12.93 (br, 1H), 7.84~7.78 (m, 2H), 7.47~7.30 (m, 5H), 7.16~7.08 (m, 4H), 6.75 (d, J=7.9 Hz, 1H), 5.15 (s, 2H), 4.67 (s, 2H), 3.89 (s, 2H), 2.50~2.44 (m, 2H), 1.96 (s, 3H), 1.52~1.43 (m, 2H), 0.81 (t, J=7.8 Hz, 3H); MS (ES) m/e: 504.11 (M$^+$+1)

EXAMPLE 42

{4-[2-(4-Bromo-phenyl)-5-methyl-oxazol-4-ylmethylsulfanyl]-2-propyl-phenoxy}-acetic acid

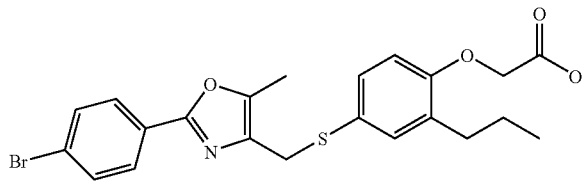

$^1$H NMR (400 MHz, DMSO) • 12.91 (br, 1H), 7.81 (d, J=8.4 Hz, 2H), 7.59 (d, J=8.4 Hz, 2H), 7.16~7.11 (m, 1H), 7.10~7.07 (m, 1H), 6.76 (d, J=8.4 Hz, 1H), 4.67 (s, 2H), 3.92

(s, 2H), 2.51~2.44 (m, 2H), 1.98 (s, 3H), 1.53~1.44 (m, 2H), 0.80 (t, J=8.0 Hz, 3H); MS (ES) m/e: 476.02 (M$^+$+1, $^{79}$Br), 478.03 (M$^+$+1, $^{81}$Br).

EXAMPLE 43

{4-[2-(4-Benzyloxy-phenyl)-5-methyl-oxazol-4-ylmethoxy]-2-methyl-phenoxy}-acetic acid

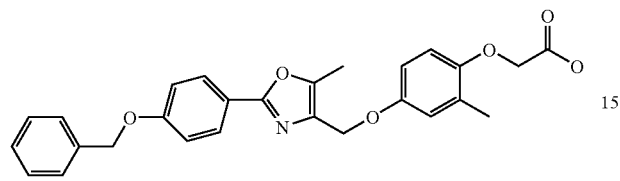

$^1$H NMR (400 MHz, DMSO) • 12.91 (br, 1H), 7.85 (d, J=8.4 Hz, 2H), 7.49~7.29 (m, 5H), 7.13 (d, J=8.4 Hz, 2H), 6.83 (m, 1H), 6.79~6.71 (m, 2H), 5.15 (s, 2H), 4.86 (s, 2H), 4.59 (s, 2H), 2.38 (s, 3H), 2.16 (s, 3H); MS (ES) m/e: 460.2 (M$^+$+1).

EXAMPLE 44

{4-[2-(4-Benzyloxy-phenyl)-5-methyl-oxazol-4-ylmethylsulfanyl]-phenoxy}-acetic acid

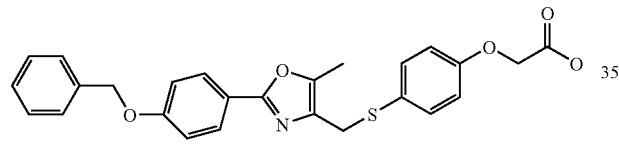

$^1$H NMR (400 MHz, DMSO) • 12.93 (br, 1H), 7.81 (d, J=8.4 Hz, 2H), 7.47~7.25 (m, 7H), 7.11 (d, J=8.4 Hz, 2H), 6.85 (d, J=8.4 Hz, 2H), 5.15 (s, 2H), 4.65 (s, 2H), 3.91 (s, 2H), 1.99 (s, 3H); MS (ES) m/e: 462.09 (M$^+$+1).

EXAMPLE 45

{4-[2-(4-Benzyloxy-phenyl)-5-methyl-oxazol-4-ylmethoxy]-phenoxy}-acetic acid

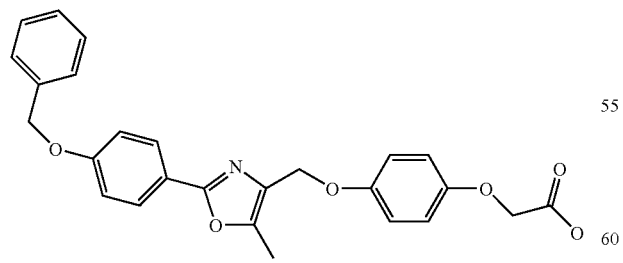

$^1$H NMR (400 MHz, DMSO-d6) • 7.85 (d, J=8.8 Hz, 2H) 7.45 (d, J=7.8 Hz, 2H), 7.38-7.34 (m, 2H), 7.32-7.30 (m, 1H), 7.13 (d, J=8.8 Hz, 2H), 6.94 (d, J=8.8 Hz, 2H), 6.84 (d, J=8.8 Hz, 2H), 5.15 (s, 2H), 4.88 (s, 2H), 4.57 (s, 2H), 2.38 (s, 3H); MS (ES) m/e 446.2 (M$^+$+1), 444.1 (M$^+$-1).

EXAMPLE 46

4-[4-(4-Carboxymethoxy-3-methyl-phenoxymethyl)-5-methyl-oxazol-2-yl]-benzoic acid

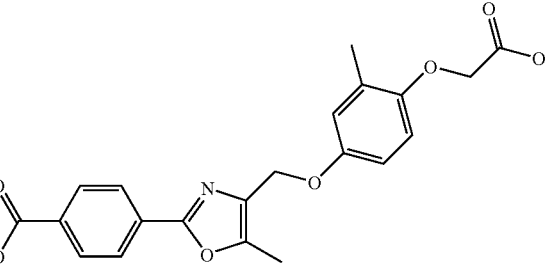

$^1$H NMR (400 MHz, DMSO-d$_6$) • 8.04 (s, 4H), 6.75 (m, 3H), 4.91 (s, 2H), 4.59 (s, 2H), 2.43 (s, 3H), 2.16 (s, 3H); ESMS m/e 398.2 (M+H$^+$, 100).

EXAMPLE 47

(4-{2-[2-(4-Butoxy-phenyl)-5-methyl-oxazol-4-yl]-ethylsulfanyl}-2-methyl-phenoxy)-acetic acid

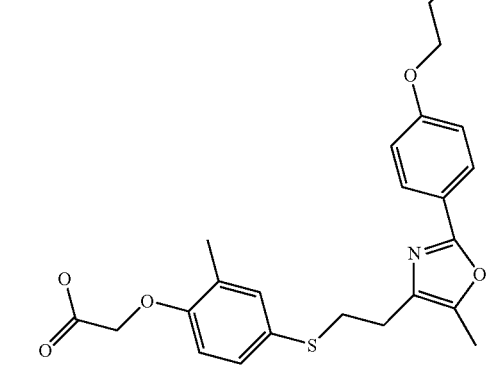

$^1$H NMR (DMSO-d$_6$, 400 MHz): δ 0.918 (t, J=7.34 Hz, 3H), 1.39-1.45 (m, 2H), 1.65-1.76 (m, 2H), 2.13 (s, 3H), 2.22 (s, 3H), 2.65 (t, J=7.09 Hz, 2H), 3.10 (t, J=7.09 Hz, 2H), 4.00 (t, J=6.36 Hz, 2H), 4.63 (s, 2H), 6.75 (d, J=8.31 Hz, 1H), 7.00 (d, J=9.18 Hz, 2H), 7.13-7.17 (m, 2H), 7.77 (d, J=9.28 Hz, 2H), 12.9 (br s, 1H); MS (ES, m/z): C$_{25}$H$_{29}$NO$_5$S: 456.2 (M$^+$+1), 454.1 (M$^+$-1).

EXAMPLE 48

Procedure 1

Scheme 1

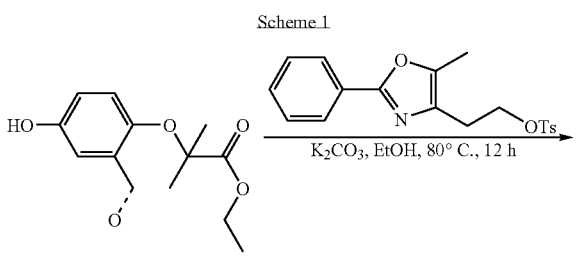

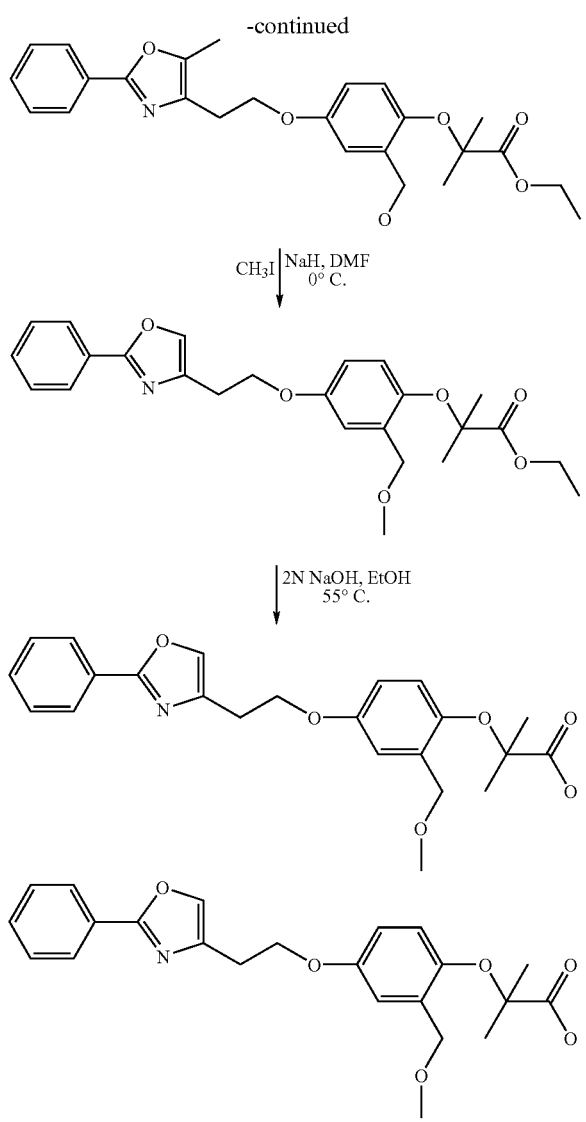

A.

2-{2-hydroxymethyl-4-[2-(5-methyl-2-phenyloxazol-4-yl)ethoxy]phenoxy}-2-methylpropionic acid ethyl ester To a 25 mL round bottom flask under a nitrogen atmosphere were charged 0.77 g (2.17 mmol) of toluene-4-sulfonic acid 2-(5-methyl-2-phenyloxazol-4-yl)ethyl ester, and 0.5 g (1.97 mmol) of 2-(4-hydroxy-2-hydroxymethylphenoxy)-2-methylpropionic acid ethyl ester dissolved in 10 mL of absolute ethanol. Next, 0.54 g (3.94 mmol) of potassium carbonate (325 mesh) was added and the reaction was heated to 80° C. for 12 h. The volatiles were removed in vacuo and the crude residue was dissolved in 75 mL EtOAc and washed twice with brine, dried over Na$_2$SO$_4$, and removed in vacuo to give a crude oil. This crude residue was purified using radial chromatography with a 2 mm normal phase silica gel plate, eluting with a step gradient of 5:95 EtOAc:Hex to 35:65 EtOAc:Hex to give a colorless oil (0.17 g, 20%). MS (ES) m/e 452 (M+1).

B.

2-{2-Methoxymethyl-4-[2-(5-methyl-2-phenyloxazol-4-yl)ethoxy]phenoxy}-2-methylpropionic acid ethyl ester To a 15 mL round bottom flask under a nitrogen atmosphere were charged 0.075 g (0.17 mmol) of 2-{2-hydroxymethyl-4-[2-(5-methyl-2-phenyloxazol-4-yl)ethoxy]phenoxy}-2-methylpropionic acid ethyl ester, dissolved in 1 mL of anhydrous DMF, followed by the addition of 0.16 mL (1.7 mmol) of methyl iodide. The reaction solution was cooled down in an ice bath and was treated with 0.014 g (0.34 mmol) of NaH. The reaction was stirred cold for 2 h. Next the reaction was poured into 6 mL of EtOAc and 10 mL of brine, and then acidified using dilute sulfuric acid. The organic layer was separated away, dried over Na$_2$SO$_4$, and removed in vacuo to give a crude oil. This crude residue was purified using radial chromatography with a 1 mm normal phase silica gel plate, eluting with 15:85 EtOAc:Hex to give a colorless oil (0.039 g, 51%). MS (ES) m/e 454 (M+1).

C.

2-{2-Methoxymethyl-4-[2-(5-methyl-2-phenyloxazol-4-yl)ethoxy]phenoxy}-2-methylpropionic acid To a 25 mL round bottom flask were charged 0.039 g (0.087 mmol) of 2-{2-methoxymethyl-4-[2-(5-methyl-2-phenyloxazol-4-yl)ethoxy]phenoxy}-2-methylpropionic acid ethyl ester dissolved in 2 mL of ethanol, followed by the addition of 0.22 mL (0.44 mmol) of 2N NaOH. The solution was heated to 55° C. for 1 h. The volatiles were removed in vacuo and the residue was taken up in 10 mL EtOAc and 5 mL of brine and acidified using 1N HCl to give a white solid (0.024 g, 66%). MS (ES) m/e 426 (M+1).

The following compound was also prepared by this procedure:

EXAMPLE 49

2-{2-Benzyloxymethyl-4-[2-(5-methyl-2-phenyloxazol-4-yl)ethoxy]phenoxy}-2-methylpropionic acid, MS (ES) m/e 530 (M+1).

EXAMPLE 50

Procedure 2

Scheme 2

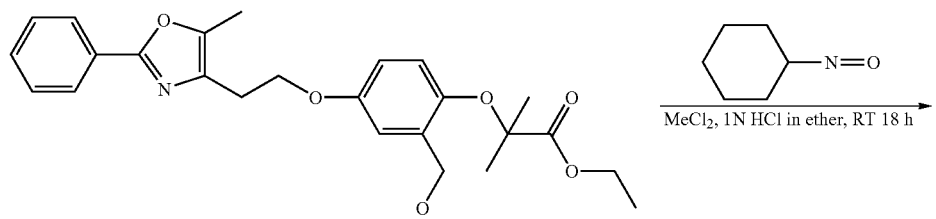

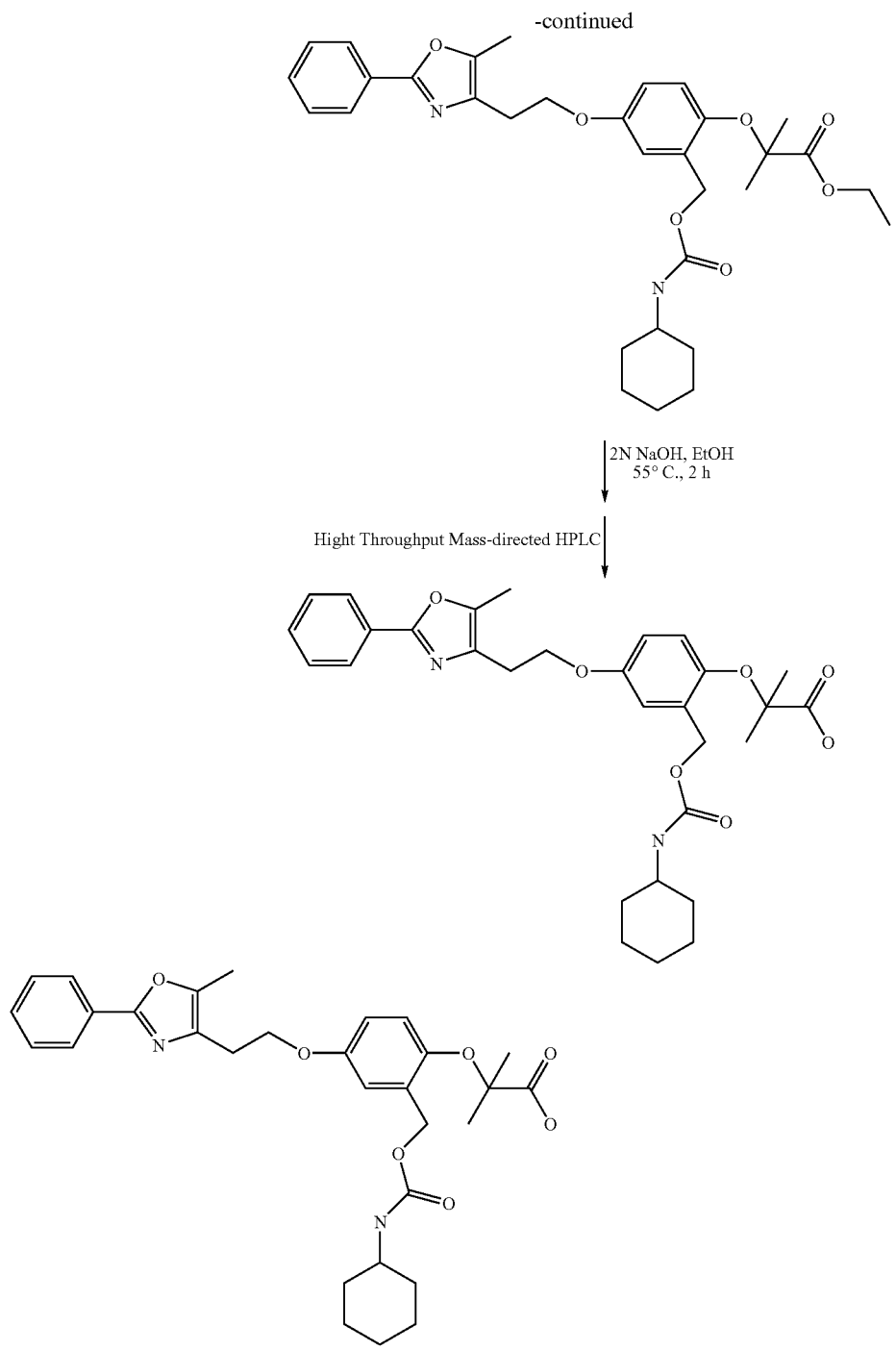

A.

3-{2-Cyclohexylcarbamoyloxymethyl-4-[2-(2-phenyloxazol-4-yl)ethoxy]phenyl}propionic acid ethyl ester To a 15 mL round bottom flask under $N_2$ were charged 0.075 g (0.17 mmol) of 2-{2-hydroxymethyl-4-[2-(5-methyl-2-phenyloxazol-4-yl)ethoxy]phenoxy}-2-methylpropionic acid ethyl ester, and 0.13 mL (1.0 mmol) of cyclohexylisocyanate dissolved in 0.5 mL of anhydrous $MeCl_2$, followed by the addition of 0.086 mL (0.086 mmol) of 1.0 N HCl in ether. The reaction was stirred at RT for 18 h. Next, the reaction was diluted with 10 mL $MeCl_2$, washed with brine, dried over $Na_2SO_4$ and removed in vacuo to give 0.10 g of a crude oil which was used directly in the next step. MS (ES) m/e 564 (M+1).

B.

3-{2-Cyclohexylcarbamoyloxymethyl-4-[2-(2-phenyloxazol-4-yl)ethoxy]phenyl}propionic acid To a 15 mL round bottom flask were charged 0.10 g (0.17 mmol) of 3-{2-cyclohexylcarbamoyloxymethyl-4-[2-(2- phenyloxazol-4-yl)ethoxy]phenyl}propionic acid ethyl ester dissolved in 2 mL of ethanol. Next this solution was treated with 0.48 mL (0.96 mmol) of 2N NaOH and then heated to 55° C. for 2 h. The volatiles were removed in vacuo and this crude residue was taken up in 20 mL of EtOAc and 10 mL brine and acidified with 1 mL of 5N HCl. The aqueous layer was discarded and the organic layer was dried over $Na_2SO_4$ and removed in vacuo. The crude residue was submitted for mass-directed HPLC purification to give a white solid (0.058 g, 63%). MS (ES) m/e 537 (M+1).

The following compounds were also prepared by this procedure:

EXAMPLE 51

2-{2-Isopropylcarbamoyloxymethyl-4-[2-(5-methyl-2-phenyloxazol-4-yl)ethoxy]phenoxy}-2-methylpropionic acid, MS (ES) m/e 497 (M+1).

EXAMPLE 52

2-{2-Benzylcarbamoyloxymethyl-4-[2-(5-methyl-2-phenyloxazol-4-yl)ethoxy]phenoxy}-2-methylpropionic acid, MS (ES) m/e 545 (M+1).

EXAMPLE 53

2-{2-(4-Fluorobenzylcarbamoyloxymethyl)-4-[2-(5-methyl-2-phenyloxazol-4-yl)ethoxy]phenoxy}-2-methylpropionic acid, MS (ES) m/e 563 (M+1).

EXAMPLE 54

Procedure 3

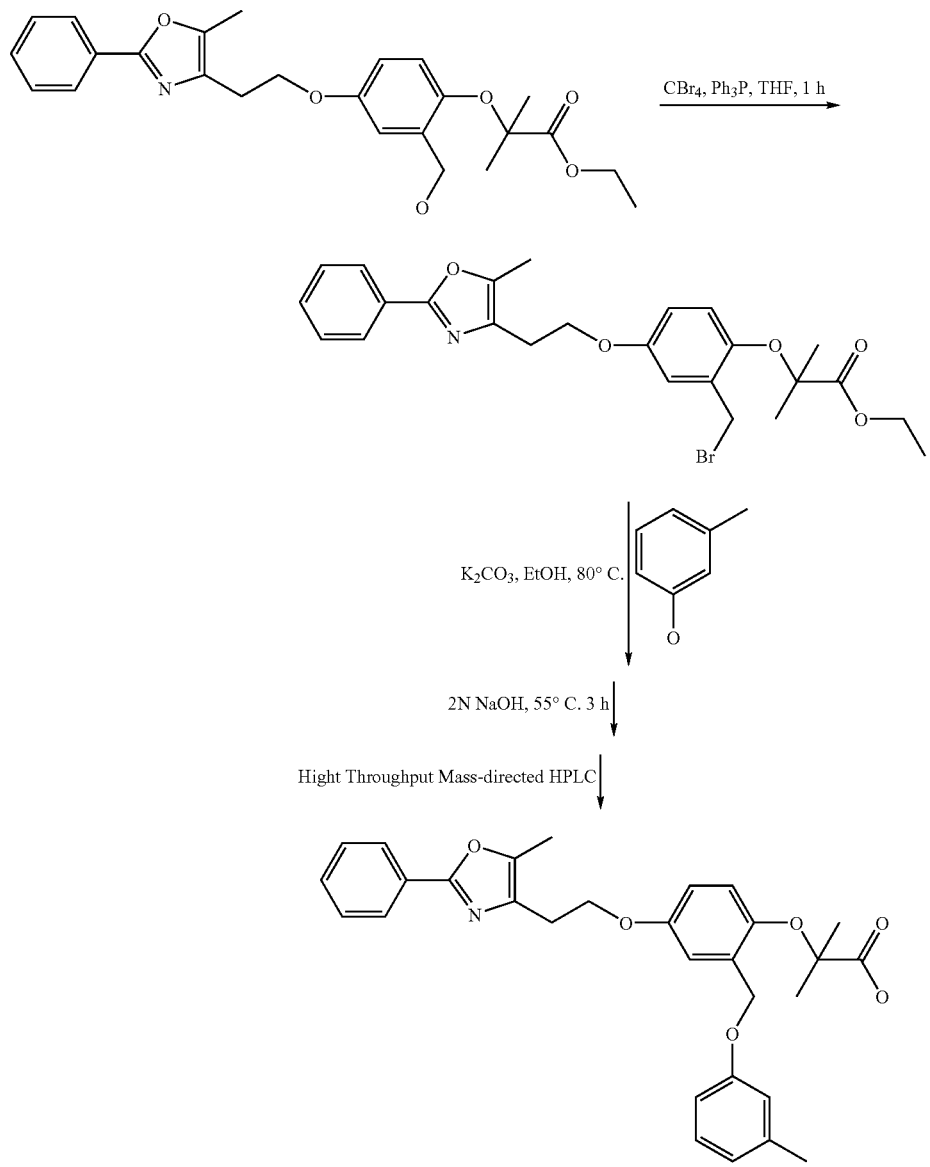

The following example exemplifies the general procedure for the parallel synthesis of analogs utilizing the DynaVac carousel. To a 50 mL glass tube with screw cap and nitrogen inlet were charged 2-{2-bromomethyl-4-[2-(5-methyl-2-phenyloxazol-4-yl)ethoxy]phenoxy}-2-methylpropionic acid ethyl ester (0.040 g, 0.080 mmol), and 0.012 mL (0.12 mmol) of m-cresol dissolved in 1 mL of absolute ethanol, followed by the addition of powdered potassium carbonate (325 mesh) (0.022 g, 0.16 mmol). The mixture was heated to 80° C. for 4 h. MS analysis of the reaction indicated that 2-methyl-2-{4-[2-(5-methyl-2-phenyloxazol-4-yl)ethoxy]-2-m-tolyloxymethylphenoxy}propionic acid ethyl ester, MS (ES) m/e 530 (M+1) had formed. Next 0.4 mL of 5N NaOH was added and the reaction was heated for 3 h at 55° C. The ethanol was removed in vacuo and the residue was treated with 0.75 mL of 5N HCl and 1 mL of MeCl$_2$ and poured into a 3 mL ChemElute column to remove the aqueous layer. The column was eluted with additional MeCl$_2$ until nothing UV active remained on the column. The solvent was removed in vacuo. The crude residue was purified by mass-directed reverse phase HPLC to provide 0.032 g (38%) of 2-{2-bromomethyl-4-[2-(5-methyl-2-phenyloxazol-4-yl)ethoxy]phenoxy}-2-methylpropionic acid, MS (ES) m/e 502 (M+1).

The following compounds were also prepared by this procedure:

EXAMPLE 55

2-{2-(4-Fluorophenoxymethyl)-4-[2-(5-methyl-2-phenyloxazol-4-yl)ethoxy]phenoxy}-2-methylpropionic acid, MS (ES) m/e 506 (M+1).

EXAMPLE 56

2-{2-(3-Fluorophenoxymethyl)-4-[2-(5-methyl-2-phenyloxazol-4-yl)ethoxy]phenoxy}-2-methylpropionic acid, MS (ES) m/e 506 (M+1).

EXAMPLE 57

2-{2-(2-Fluorophenoxymethyl)-4-[2-(5-methyl-2-phenyloxazol-4-yl)ethoxy]phenoxy}-2-methylpropionic acid, MS (ES) m/e 506 (M+1).

EXAMPLE 58

2-Methyl-2-{4-[2-(5-methyl-2-phenyloxazol-4-yl)ethoxy]-2-p-tolyloxymethylphenoxy}propionic acid, MS (ES) m/e 502 (M+1).

EXAMPLE 59

2-Methyl-2-{4-[2-(5-methyl-2-phenyloxazol-4-yl)ethoxy]-2-o-tolyloxymethylphenoxy}propionic acid, MS (ES) m/e 502 (M+1).

EXAMPLE 60

2-{2-(4-Methoxyphenoxymethyl)-4-[2-(5-methyl-2-phenyloxazol-4-yl)ethoxy]phenoxy}-2-methylpropionic acid, MS (ES) m/e 518 (M+1).

EXAMPLE 61

2-Methyl-2-[4-[2-(5-methyl-2-phenyloxazol-4-yl)ethoxy]-2-(4-trifluoromethylphenoxymethyl)phenoxy]propionic acid, MS (ES) m/e 556 (M+1).

EXAMPLE 62

2-{2-(Biphenyl-2-yloxymethyl)-4-[2-(5-methyl-2-phenyloxazol-4-yl)ethoxy]phenoxy}-2-methylpropionic acid, MS (ES) m/e 564 (M+1).

EXAMPLE 63

2-{2-(Biphenyl-4-yloxymethyl)-4-[2-(5-methyl-2-phenyloxazol-4-yl)ethoxy]phenoxy}-2-methylpropionic acid, MS (ES) m/e 564 (M+1).

Binding and Cotransfection Studies

The in vitro potency of compounds in modulating PPARα and PPARγ receptors were determined by the procedures detailed below. DNA-dependent binding (ABCD binding) was carried out using SPA technology with PPAR receptors. Tritium-labeled PPARα and PPARγ agonists were used as radioligands for generating displacement curves and IC$_{50}$ values with compounds of the invention. Cotransfection assays were carried out in CV-1 cells. The reporter plasmid contained an acylCoA oxidase (AOX) PPRE and TK promoter upstream of the luciferase reporter cDNA. Appropriate PPARs and RXRα were constitutively expressed using plasmids containing the CMV promoter. For PPARα and PPARβ, interference by endogenous PPARγ in CV-1 cells was an issue. In order to eliminate such interference, a GAL4 chimeric system was used in which the DNA binding domain of the transfected PPAR was replaced by that of GAL4, and the GAL4 response element was utilized in place of the AOX PPRE. Cotransfection efficacy was determined relative to PPARα agonist and PPARγ agonist reference molecules. Efficacies were determined by computer fit to a concentration-response curve, or in some cases at a single high concentration of agonist (10 μM). For binding or cotransfection studies with receptors other than PPARs, similar assays were carried out using appropriate ligands, receptors, reporter constructs, etc., for that particular receptor.

These studies were carried out to evaluate the ability of compounds of the invention to bind to and/or activate various nuclear transcription factors, particularly huPPARα ("hu" indicates "human") and huPPARγ. These studies provide in vitro data concerning efficacy and selectivity of compounds of the invention. Furthermore, binding and cotransfection data for compounds of the invention were compared with corresponding data for marketed compounds that act on either huPPARα or huPPARγ.

Binding and cotransfection data for representative compounds of the invention are compared with corresponding data for reference compounds in Table II.

TABLE II

| | huPPARα | | huPPARγ | |
|---|---|---|---|---|
| Example | IC$_{50}$ (nM) | CTF Eff. (%) | IC$_{50}$ (nM) | CTF Eff. (%) |
| 1 | 1677 | 72 | 2127 | 69 |
| 6 | 535 | 80 | 268 | 71 |
| 9A | 75 | 82 | 180 | 60 |
| 12 | 31 | 68 | 219 | 66 |
| 12A | 233 | 74 | 102 | 170 |
| 13 | 25 | 73 | 420 | 109 |
| 21 | 401 | 78 | 627 | 85 |
| 24 | 624 | 73 | 239 | 94 |
| 26 | 3277 | 35 | 1151 | 52 |
| 26A | 79 | 75 | 102 | 74 |

TABLE II-continued

| Example | huPPARα | | huPPARγ | |
|---|---|---|---|---|
| | IC$_{50}$ (nM) | CTF Eff. (%) | IC$_{50}$ (nM) | CTF Eff. (%) |
| 27A | 113 | 95 | 49 | 63 |
| 30A | 189 | 80 | 78 | 92 |
| 30C | 259 | 67 | 148 | 63 |
| 30J | 82 | 90 | 83 | 50 |
| 31F | 30 | 70 | 10 | 51 |
| 32 | 50 | 82 | 42 | 80 |
| 37 | 294 | 91 | 172 | 60 |
| 38 | 254 | 80 | 81 | 65 |
| 39C | 49 | 96 | 14 | 91 |
| 39I | 182 | 91 | 86 | 85 |
| 39N | 65 | 102 | 173 | 51 |
| Troglitazone | 94,500 | 0 | 1180 | 80 |
| Fenofibric acid | 68,000 | 16 | 125,000 | 0 |

Evaluation of Triglyceride and Cholesterol Level in HuapoAI Transgenic Mice

Five to six week old male mice, transgenic for human apoAI [C57Bl/6-tgn(apoa1)lrub, Jackson Laboratory, Bar Harbor, Me.] were housed five per cage (10"×20"×8" with aspen chip bedding) with food (Purina 5001) and water available at all times. After an acclimation period of 2 weeks, animals were individually identified by ear notches, weighed, and assigned to groups based on body weight. Beginning the following morning, mice were dosed daily by oral gavage for 7 days using a 20 gauge, 1½" curved disposable feeding needle (Popper & Sons). Treatments were test compounds (30 mg/kg), a positive control (fenofibrate, 100 mg/kg) or vehicle [1% carboxymethylcellulose (w/v)/0.25% Tween80 (w/v); 0.2 ml/mouse]. Prior to termination on day 7, mice were weighed and dosed. Three hours after dosing, animals were anesthetized by inhalation of isoflurane (2-4%; Abbott Laboratories, Chicago, Ill.) and blood obtained via cardiac puncture (0.7-1.0 ml). Whole blood was transferred to serum separator tubes (Vacutainer SST), chilled on ice, and permitted to clot. Serum was obtained after centrifugation at 4° C. and frozen until analysis for triglycerides, total cholesterol, compound levels, and serum lipoprotein profile by fast protein liquid chromatography (FPLC) coupled to an inline detection system. After sacrifice by cervical dislocation, the liver, heart and epididymal fat pads were excised and weighed.

The animals dosed with vehicle had average triglycerides values of 60-80 mg/dl, which were reduced by the positive control fenofibrate (33-58 mg/dl with a mean reduction of 37%). The animals dosed with vehicle had average total serum cholesterol values of 140-180 mg/dl, which were increased by fenofibrate (190-280 mg/dl, with a mean elevation of 41%). Triglyceride serum levels for animals receiving compounds of the invention are reported in Table III in mg/dl. When subject to FPLC analysis, pooled sera from vehicle-treated hu apoAI transgenic mice had a high density lipoprotein cholesterol (HDLc) peak area which ranged from 47 v-sec to 62 v-sec. Fenofibrate increased the amount of HDLc (68-96 v-sec with a mean percent increase of 48%). Test compounds are reported in terms of percent increase in the area under the curve as indicated in Table IV.

TABLE III

| Example | % Triglyceride Reduction |
|---|---|
| 1 | 79.2 |
| 3 | 66 |
| 6 | 35.4 |
| 9A | 67.1 |
| 12 | 74.3 |
| 13 | 44.8 |
| 24 | 75 |
| 26 | 25.5 |
| 26A | 35.9 |
| 27A | 29.5 |
| 30A | 51.8 |
| 30C | 6.2 |
| 31A | −6.4 |
| 31F | 35.7 |
| 37 | 29.9 |
| 38 | 39 |
| 39C | 37.2 |

TABLE IV

| Example | % HDLc Increase |
|---|---|
| 1 | 77 |
| 3 | 63 |
| 6 | 20 |
| 9A | 118 |
| 12 | 180 |
| 12A | 47 |
| 13 | 133 |
| 21 | 9 |
| 24 | 61 |
| 26 | 19 |
| 26A | 43 |
| 27A | 52 |
| 30A | 93 |
| 30C | 31 |
| 30J | 77 |
| 31A | 98 |
| 31F | 79 |
| 32 | 20 |
| 37 | 94 |
| 38 | 86 |
| 39C | 97 |
| 39I | 11 |
| 39N | 16 |

Evaluation of Glucose Levels in db/db Mice

Five week old male diabetic (db/db) mice [C57BlKs/j-m +/+ Lepr(db), Jackson Laboratory, Bar Harbor, Me.] or lean littermates (db+) were housed 6 per cage (10"×20"×8" with aspen chip bedding) with food (Purina 5015) and water available at all times. After an acclimation period of 2 weeks, animals were individually identified by ear notches, weighed, and bled via the tail vein for determination of initial glucose levels. Blood was collected (100 μl) from unfasted animals by wrapping each mouse in a towel, cutting the tip of the tail with a scalpel, and milking blood from the tail into a heparinized capillary tube (Fisher) balanced on the edge of the bench. Sample was discharged into a heparinized microtainer with gel separator (VWR) and retained on ice. Plasma was obtained after centrifugation at 4° C. and glucose measured immediately. Remaining plasma was frozen until the completion of the experiment, when glucose and triglycerides were assayed in all samples. Animals were grouped based on initial glucose levels and body weights. Beginning the following morning, mice were dosed daily by oral gavage for 7 days using a 20 gauge, 1½" curved disposable feeding needle. Treatments were test compounds (30 mg/kg), a positive control agent (30 mg/kg) or vehicle [1% carboxymethylcellulose (w/v)/0.25% Tween80 (w/v); 0.3 ml/mouse]. On day 7, mice were weighed and bled (tail vein) 3 hours after dosing. Twenty-four hours after the 7th dose (i.e., day 8), animals were bled again (tail vein). Samples obtained from conscious animals on days 0, 7 and 8 were assayed for glucose. After the 24 hour bleed, animals were weighed and dosed for the final time. Three hours after dosing on day 8, animals were anesthetized by inhalation of isoflurane and blood obtained via cardiac puncture (0.5-0.7 ml). Whole blood was transferred to serum separator tubes, chilled on ice and permitted to clot. Serum was obtained after centrifugation at 4° C. and frozen until analysis for compound levels. After sacrifice by cervical dislocation, the liver, heart and epididymal fat pads were excised and weighed.

The animals dosed with vehicle had average triglycerides values of 170-230 mg/dl, which were reduced by the positive PPARγ control (70-120 mg/dl with a mean reduction of 50%). Male db/db mice were hyperglycemic (average glucose of 680-730 mg/dl on the 7th day of treatment), while lean animals had average glucose levels between 190-230 mg/dl. Treatment with the positive control agent reduced glucose significantly (350-550 mg/dl with a mean decrease towards normalization of 56%). Test compounds are reported in Table V in terms of glucose normalization (i.e., 100% normalization would be glucose levels in treated db/db mice which did not differ from lean values.

Glucose was measured colorimetrically using commercially purchased reagents (Sigma #315-500). According to the manufacturers, the procedures were modified from published work (McGowan, M. W., Artiss, J. D., Strandbergh, D. R. & Zak, B. *Clin Chem*, 20:470-5 (1974) and Keston, A. Specific colorimetric enzymatic analytical reagents for glucose. *Abstract of papers 129th Meeting ACS*, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. *Ann Clin Biochem*, 6:24 (1969)). The absorbance of the dye produced is linearly related to the analyte in the sample. The assays were further modified in our laboratory for use in a 96 well format. Standards (Sigma #339-11, Sigma #16-11, and Sigma #CC0534 for glucose triglycerides and total cholesterol, respectively), quality control plasma (Sigma # A2034), and samples (2 or 5 µl/well) were measured in duplicate using 200 µl of reagent. An additional aliquot of sample, pipetted to a third well and diluted in 200 µl water, provided a blank for each specimen. Plates were incubated at room temperature (18, 15, and 10 minutes for glucose, triglycerides and total cholesterol, respectively) on a plate shaker (DPC Micormix 5) and absorbance read at 500 nm (glucose and total cholesterol) or 540 nm (triglycerides) on a plate reader (Wallac Victor 1420). Sample absorbances were compared to a standard curve (100-800, 10-500, and 100-400 mg/dl for glucose, triglycerides and total cholesterol, respectively). Values for the quality control sample were always within the expected range and the coefficient of variation for samples was below 10%. All samples from an experiment were assayed at the same time to minimize inter-assay variability.

Serum lipoproteins were separated and cholesterol quantitated with an in-line detection system. Sample was applied to a Superose® 6 HR 10/30 size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol was monitored in the flow stream at 505 nm and the analog voltage from the monitor was converted to a digital signal for collection and analysis. The change in voltage corresponding to change in cholesterol concentration was plotted vs time and the area under the curve corresponding to the elution of VLDL, LDL and HDL was calculated using Perkin Elmer Turbochrome software.

TABLE V

| Example | Glucose Normalization % |
|---------|------------------------|
| 1 | 38 |
| 6 | 65 |
| 9A | 86 |
| 12 | 101 |
| 12A | 51 |
| 13 | 65 |
| 21 | 23 |
| 24 | 72 |
| 26 | 42 |
| 26A | 77 |
| 27A | 62 |
| 30A | 76 |
| 30C | 48 |
| 30J | 58 |
| 31A | 19 |
| 31F | 77 |
| 32 | 47 |
| 37 | 56 |
| 38 | 38 |
| 39C | 62 |
| 39I | 26 |
| 39N | 37 |

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:

1. A compound represented by the following structural formula:

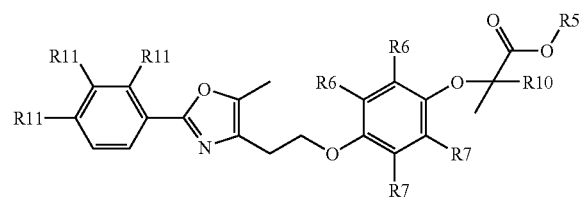

or a pharmaceutically acceptable salt, solvate and hydrate thereof, wherein:

R5 is H, C1-C4 alkyl or aminoalkyl;

R6 are each, independently, H, halo, C1-C6 alkyl, C1-C6 alkoxy, C1-C6 haloalkyl, C1-C6 haloalkoxy, cycloalkyl, cycloalkyl-C1-C4 alkyl, aryl-C1-C4 alkyl, or together with the phenyl to which they are bound form naphthyl or 1,2,3,4-tetrahydronaphthy;

R7 are each, independently, H, halo, C1-C6 alkyl, C1-C6 alkoxy, C1-C6 haloalkyl, C1-C6 haloalkoxy, cycloalkyl, cycloalkyl-C1-C4 alkyl, or aryl-C1-C4 alkyl;

R10 is C1-C10 alkyl, C1-C10 haloalkyl, or a substituted or unsubstituted benzyl; and R11 are each, independently, halo, hydroxy, carboxy, saturated or unsaturated C1-C4 alkyl, C1-C4 alkoxy, C1-C4 haloalkyl, C1-C4 haloalkoxy, cyano, carbamoyl, dioxaborolan-2-yl, benzoyl, or a substituted or unsubstituted group selected from aryl-C1-C4-alkyl, aryloxy, cycloalkyl, cycloalkyloxy or heterocyclo-oxy.

2. A compound represented by the following structural formula:

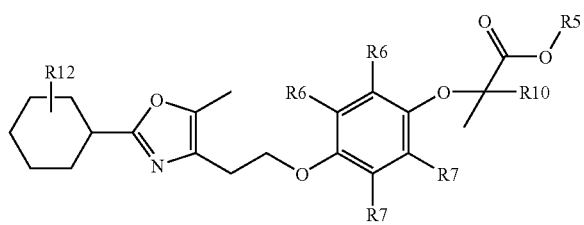

or a pharmaceutically acceptable salt, solvate and hydrate thereof, wherein:

R5 is H, C1-C4 alkyl or aminoalkyl;

R6 are each, independently, H, halo, C1-C6 alkyl, C1-C6 alkoxy, C1-C6 haloalkyl, C1-C6 haloalkoxy, cycloalkyl, cycloalkyl-C1-C4 alkyl, aryl-C1-C4 alkyl, or together with the phenyl to which they are bound form naphthyl or 1,2,3,4-tetrahydronaphthy;

R7 are each, independently, H, halo, C1-C6 alkyl, C1-C6 alkoxy, C1-C6 haloalkyl, C1-C6 haloalkoxy, cycloalkyl-C1-C4 alkyl, or aryl-C1-C4 alkyl;

R10 is C1-C10 alkyl, C1-C10 haloalkyl, or a substituted or unsubstituted benzyl; and R12 is H, aryl or C1-C4 alkyl.

3. A method of treating diabetes mellitus in a mammal, comprising the step of administering to the mammal a therapeutically effective amount of a compound of claim 1, or a pharmaceutically acceptable salt, solvate or hydrate thereof.

4. The method of claim 3 wherein the mammal is a human.

* * * * *